US009073829B2

(12) United States Patent
Myers et al.

(10) Patent No.: US 9,073,829 B2
(45) Date of Patent: Jul. 7, 2015

(54) SYNTHESIS OF TETRACYCLINES AND INTERMEDIATES THERETO

(75) Inventors: Andrew G. Myers, Boston, MA (US); David A. Kummer, La Jolla, CA (US); Derun Li, Roselle Park, NJ (US); Evan Hecker, Arlington, MA (US); Amelie Dion, Cambridge, MA (US); Peter M. Wright, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 485 days.

(21) Appl. No.: 13/266,788

(22) PCT Filed: Apr. 30, 2010

(86) PCT No.: PCT/US2010/001284
§ 371 (c)(1),
(2), (4) Date: Jan. 11, 2012

(87) PCT Pub. No.: WO2010/126607
PCT Pub. Date: Nov. 4, 2010

(65) Prior Publication Data
US 2012/0115818 A1    May 10, 2012

Related U.S. Application Data

(60) Provisional application No. 61/174,185, filed on Apr. 30, 2009, provisional application No. 61/322,613, filed on Apr. 9, 2010.

(51) Int. Cl.
| | | |
|---|---|---|
| *A61K 31/65* | (2006.01) | |
| *C07C 237/26* | (2006.01) | |
| *C07C 311/05* | (2006.01) | |
| *C07C 45/67* | (2006.01) | |
| *C07C 45/69* | (2006.01) | |
| *C07C 49/637* | (2006.01) | |
| *C07D 207/16* | (2006.01) | |
| *C07D 209/58* | (2006.01) | |
| *C07D 213/30* | (2006.01) | |
| *C07D 213/74* | (2006.01) | |
| *C07D 233/61* | (2006.01) | |
| *C07D 261/20* | (2006.01) | |
| *C07D 277/24* | (2006.01) | |
| *C07D 277/64* | (2006.01) | |
| *C07D 295/15* | (2006.01) | |
| *C07D 295/155* | (2006.01) | |
| *C07D 498/04* | (2006.01) | |
| *C07F 7/08* | (2006.01) | |

(52) U.S. Cl.
CPC ........... *C07C 311/05* (2013.01); *C07B 2200/07* (2013.01); *C07C 45/673* (2013.01); *C07C 45/69* (2013.01); *C07C 49/637* (2013.01); *C07C 237/26* (2013.01); *C07C 2101/02* (2013.01); *C07C 2101/08* (2013.01); *C07C 2103/46* (2013.01); *C07C 2103/66* (2013.01); *C07D 207/16* (2013.01); *C07D 209/58* (2013.01); *C07D 213/30* (2013.01); *C07D 213/74* (2013.01); *C07D 233/61* (2013.01); *C07D 261/20* (2013.01); *C07D 277/24* (2013.01); *C07D 277/64* (2013.01); *C07D 295/15* (2013.01); *C07D 295/155* (2013.01); *C07D 498/04* (2013.01); *C07F 7/0814* (2013.01)

(58) Field of Classification Search
CPC .. C07C 237/26; C07C 311/16; C07D 207/04; C07D 233/61; C07D 277/24; C07D 295/135
USPC .......................................... 552/203; 514/152
See application file for complete search history.

(56) References Cited

U.S. PATENT DOCUMENTS

| | | |
|---|---|---|
| 2,482,055 A | 9/1949 | Duggar et al. |
| 3,019,260 A | 1/1962 | McCormick et al. |
| 3,109,007 A | 10/1963 | Blackwood et al. |
| 3,219,671 A | 11/1965 | Hlavka |
| RE26,253 E | 8/1967 | Patisi et al. |
| 3,338,963 A | 8/1967 | Petisi et al. |
| 3,502,660 A | 3/1970 | Butler et al. |

(Continued)

FOREIGN PATENT DOCUMENTS

| | | |
|---|---|---|
| CN | 101 684 101 A | 3/2010 |
| EP | 1 241 160 A1 | 9/2002 |

(Continued)

OTHER PUBLICATIONS

Extended European Search Report for EP 12156059.3, mailed Jun. 27, 2012.
Extended European Search Report for EP 12156126.0, mailed Jul. 12, 2012.
International Preliminary Report on Patentability for PCT/US2010/001284, mailed Nov. 10, 2011.
International Preliminary Report on Patentability for PCT/US2011/054791, mailed Apr. 18, 2013.
Extended European Search Report for EP 07873526.3 mailed Sep. 29, 2009.

(Continued)

*Primary Examiner* — Barbara P Badio
(74) *Attorney, Agent, or Firm* — Wolf, Greenfield & Sacks, P.C.; C. Hunter Baker; Robin A. Weatherhead

(57) ABSTRACT

The tetracycline class of antibiotics has played a major role in the treatment of infectious diseases for the past 50 years. However, the increased use of the tetracyclines in human and veterinary medicine has led to resistance among many organisms previously thought susceptible to tetracycline antibiotics. The recent development of a modular synthesis of tetracycline analogs through a chiral enone intermediate has allowed for the efficient synthesis of novel tetracycline analogs never prepared before. The present invention provides more efficient routes for preparing the enone intermediate and allows for substituents at positions 4a, 5, 5a, and 12a of the tetracycline ring system.

20 Claims, 40 Drawing Sheets

(56) References Cited

U.S. PATENT DOCUMENTS

| | | | |
|---|---|---|---|
| 3,509,184 A | 4/1970 | Conover et al. |
| 3,697,552 A | 10/1972 | Conover et al. |
| 3,699,117 A | 10/1972 | Butler, et aL |
| 3,772,363 A | 11/1973 | Conover et al. |
| 3,829,453 A | 8/1974 | Conover et al. |
| 3,849,493 A | 11/1974 | Conover et al. |
| 3,862,225 A | 1/1975 | Conover et al. |
| 3,914,299 A | 10/1975 | Muxfeldt |
| 3,947,517 A | 3/1976 | Muxfeldt et al. |
| 3,962,330 A | 6/1976 | Cotti et al. |
| 3,983,173 A | 9/1976 | Hartung et al. |
| 4,052,467 A | 10/1977 | Mills et al. |
| 4,060,605 A | 11/1977 | Corti et al. |
| 4,066,694 A | 1/1978 | Blackwood et al. |
| 4,418,060 A | 11/1983 | Kahan nee Laszlo et al. |
| 4,597,904 A | 7/1986 | Page et al. |
| 5,362,754 A | 11/1994 | Raad et al. |
| 5,529,990 A | 6/1996 | Hlavka et al. |
| 5,538,954 A | 7/1996 | Koch et al. |
| 5,574,026 A | 11/1996 | Backer et al. |
| 5,589,470 A | 12/1996 | Levy et al. |
| 5,688,516 A | 11/1997 | Raad et al. |
| 5,811,412 A | 9/1998 | Levy et al. |
| 5,834,450 A | 11/1998 | Su et al. |
| 6,143,161 A | 11/2000 | Heggie et al. |
| 6,165,999 A | 12/2000 | Vu et al. |
| 6,506,740 B1 | 1/2003 | Ashley et al. |
| 6,509,319 B1 | 1/2003 | Raad et al. |
| 6,617,318 B1 | 9/2003 | Nelson et al. |
| 6,624,168 B2 | 9/2003 | Nelson et al. |
| 6,638,532 B2 | 10/2003 | Rudnic et al. |
| 6,642,270 B2 | 11/2003 | Nelson et al. |
| 6,683,068 B2 | 1/2004 | Nelson et al. |
| 6,818,634 B2 | 11/2004 | Nelson et al. |
| 6,818,635 B2 | 11/2004 | Nelson et al. |
| 6,841,546 B2 | 1/2005 | Draper et al. |
| 6,846,939 B2 | 1/2005 | Nelson et al. |
| 6,849,615 B2 | 2/2005 | Nelson et al. |
| 7,001,918 B2 | 2/2006 | Huss et al. |
| 7,763,735 B2 | 7/2010 | Myers et al. |
| 7,807,742 B2 | 10/2010 | Tanaka et al. |
| 7,807,842 B2 | 10/2010 | Myers et al. |
| 7,960,559 B2 | 6/2011 | Myers et al. |
| 8,293,920 B2 | 10/2012 | Myers et al. |
| 8,486,921 B2 | 7/2013 | Myers et al. |
| 8,580,969 B2 | 11/2013 | Myers et al. |
| 8,598,148 B2 | 12/2013 | Myers et al. |
| 2002/0045602 A1 | 4/2002 | Nelson et al. |
| 2002/0103171 A1 | 8/2002 | Nelson et al. |
| 2002/0111335 A1 | 8/2002 | Nelson et al. |
| 2002/0128237 A1 | 9/2002 | Nelson et al. |
| 2002/0128238 A1 | 9/2002 | Nelson et al. |
| 2002/0132798 A1 | 9/2002 | Nelson et al. |
| 2002/0136766 A1 | 9/2002 | Rudnic et al. |
| 2002/0193354 A1 | 12/2002 | Nelson et al. |
| 2003/0055025 A1 | 3/2003 | Nelson et al. |
| 2003/0096008 A1 | 5/2003 | Rudnic et al. |
| 2003/0100017 A1 | 5/2003 | Draper et al. |
| 2003/0153537 A1 | 8/2003 | Levy et al. |
| 2003/0166585 A1 | 9/2003 | Draper et al. |
| 2004/0048835 A1 | 3/2004 | Nelson et al. |
| 2004/0063674 A1 | 4/2004 | Levy et al. |
| 2004/0067912 A1 | 4/2004 | Hlavka et al. |
| 2005/0282782 A1 | 12/2005 | Martin |
| 2007/0066253 A1 | 3/2007 | Sorrells et al. |
| 2010/0130451 A1 | 5/2010 | Myers et al. |
| 2011/0009371 A1 | 1/2011 | Myers et al. |
| 2012/0029199 A1 | 2/2012 | Myers et al. |

FOREIGN PATENT DOCUMENTS

| | | |
|---|---|---|
| FR | 2 279 720 A1 | 2/1976 |
| GB | 973022 A | 10/1964 |
| GB | 1013576 A | 12/1965 |
| GB | 1013906 A | 12/1965 |
| GB | 1019562 A | 2/1966 |
| GB | 1019563 A | 2/1966 |
| GB | 1100885 A | 1/1968 |
| WO | WO 95/22529 A1 | 8/1995 |
| WO | WO 01/98236 A2 | 12/2001 |
| WO | WO 01/98259 A1 | 12/2001 |
| WO | WO 01/98260 A1 | 12/2001 |
| WO | WO 02/04404 A1 | 1/2002 |
| WO | WO 02/04406 A2 | 1/2002 |
| WO | WO 02/04407 A2 | 1/2002 |
| WO | WO 02/12170 A1 | 2/2002 |
| WO | WO 02/072532 A1 | 9/2002 |
| WO | WO 02/085303 A2 | 10/2002 |
| WO | WO 03/005971 A2 | 1/2003 |
| WO | WO 03/057169 A2 | 7/2003 |
| WO | WO 03/076424 A1 | 9/2003 |
| WO | WO 2004/038001 A2 | 5/2004 |
| WO | WO 2004/064728 A2 | 8/2004 |
| WO | WO 2005/030149 A2 | 4/2005 |
| WO | WO 2005/056538 A1 | 6/2005 |
| WO | WO 2005/112945 A2 | 12/2005 |
| WO | WO 2005/112985 A2 | 12/2005 |
| WO | WO 2007/067807 A1 | 6/2007 |
| WO | WO 2007/112121 A2 | 10/2007 |
| WO | WO 2007/117639 A2 | 10/2007 |
| WO | WO 2007/118237 A2 | 10/2007 |
| WO | WO 2008/127361 A2 | 10/2008 |
| WO | WO 2010/126607 A2 | 11/2010 |
| WO | WO 2012/047907 A1 | 4/2012 |

OTHER PUBLICATIONS

Invitation to Pay Additional Fees for PCT/US2007/081076 mailed Sep. 30, 2008.

International Search Report and Written Opinion for PCT/US2007/081076 mailed Dec. 15, 2008.

International Preliminary Report on Patentability for PCT/US2007/081076 mailed Apr. 23, 2009.

Supplementary European Search Report for EP05779988.4 mailed Jun. 9, 2009.

International Search Report and Written Opinion for PCT/US2005/017831 mailed May 4, 2006.

International Preliminary Report on Patentability for PCT/US2005/017831 mailed Nov. 30, 2006.

International Search Report and Written Opinion for PCT/US2007/008647 mailed Mar. 14, 2008.

International Preliminary Report on Patentability for PCT/US2007/008647 mailed Oct. 16, 2008.

Invitation to Pay Additional Fees for PCT/US2010/001284 mailed Feb. 10, 2011.

International Search Report and Written Opinion for PCT/US2010/001284 mailed May 24, 2011.

International Search Report and Written Opinion for PCT/US2011/054791 mailed Jan. 19, 2012.

Notice of Allowance mailed Apr. 7, 2010 for U.S. Appl. No. 11/870,772.

Notice of Allowance mailed Nov. 23, 2010 for U.S. Appl. No. 12/833,628.

Office Communication mailed Oct. 27, 2009 for U.S. Appl. No. 11/133,789.

Notice of Allowance mailed Feb. 22, 2010 for U.S. Appl. No. 11/133,789.

[No Author Listed] March's Advanced Organic Chemistry 4th Ed., p. 1062-75. 1992.

[No Author Listed] March's Advanced Organic Chemistry 4th Ed., p. 518-19. 1992.

[No Author Listed] Organomagnesium in Organic Synthesis, Academic Press, Inc.: San Diego, p. 51-59. 1995.

Akgun et al., Metalation of 0-Halostyrenes Oxides. Preparation of Benzocyclobutenols. J. Org. Chem. 1981;46:2730-2734.

Allen et al., A Powerful o-Quinone Dimethide Strategy for Intermolecular Diels—Alder Cycloadditions. J. Am. Chem. Soc. 2000;122:571-575.

(56) References Cited

OTHER PUBLICATIONS

Allen et al., The Total Synthesis of (±)-Rishirilide B. Am. Chem. Soc. 2001;123:351-352.
Amaro et a., Synthesis of Tetracyclic Hydroxyquinones by Cycloaddition Reactions With Dienols. Tetrahedron Lett. 1979:3983-3986.
Ballard et al., A Biotech Route to Polyphenylene. J. Chem. Soc. Chem. Commun. 1983:954955.
Barr et al., Zirconocene(iso-butyl) Chloride: In Situ Generation of a Zirconocene(methyl) Chloride Equivalent for Use In Organic Synthesis. Tetrahedron Lett. 1991;32:5465-5468.
Beard et al., Inhibition of Mammalian Protein Synthesis by Antibiotics. Pharmacol. Revs. 1969;21: 213-245.
Becker et al., Oxidative Formation and Photochemical Isomerization of Spiro-Epoxy-2,4-Cyclohexadienones. Tetrahedron Lett. 1972;13:4205-4208.
Beereboom et al., Further 6-Deoxytetracycline Studies: Effect of Aromatic Substituents on Biological Activity. J. Am. Chem. Soc. 1960;82:1003-1004.
Berge et al., Pharmaceutical Salts. J. Pharmaceutical Sciences 1977;66:1-19.
Berk et al., Preparations and Reactions of Functionalized Benzylic Organometallics of Zinc and Copper. Organometallics. 1990;9:3053-3064.
Boothe et al., Identification of an Antibiotic Polyacetylene From Clitocybe Diatreta As A Suberamic Acid Ene-Diyne. J. Am. Chem. Soc.1953;75:4621.
Boudier et al., New Applications of Polyfunctional Organometallic Compounds in Organic Synthesis Frequently used abbreviations are defined at the end of the article. Angew Chem Int Ed Engl. 2000 Dec 15;39(24):4414-4435.
Brodersen et al,The Structural Basis for the Action of the Antibiotics Tetracycline, Pactamycin, and Hygromycin B on the 30S Ribosomal Subunit. Cell. 2000;103:1143-1154.
Brown et al., Activities of the Glycylcyclines N, N-Dimethylglycylamido-Minocycline and N,N-Dimethylglycylamido-6-Deoxytetracycline Against Nocardia spp. And Tetracycline-Resistant Isolates of Rapidly Growing Mycobacteria. Antimicrob. Agents Chemother. 1996;40:874-878.
Brubaker et al., A practical, enantioselective synthetic route to a key precursor to the tetracycline antibiotics. Org Lett. 2007 Aug 30;9(18):3523-5. Epub 2007 Aug 11.
Burdett, Purification and Characterization of Tet(M), a Protein That Renders Ribosomes Resistant to Tetracycline. J. Biol. Chem. 1991;266:2872-2877.
Burke, Flexible tetracycline synthesis yields promising antibiotics. Nat Chem Biol. 2009 Feb;5(2):77-9.
Bush et al., Taking Inventory: Antibacterial Agents Currently At or Beyond Phase 1. Curr. Opin. Microbiol. 2004;7:466-476.
Cane et al., Harnessing the Biosynthetic Code: Combinations, Permutations, and Mutations. Science 1998;282:63-68.
Carless, The Use of Cyclohexa-3,5-Diene-1,2-Diols in Enantiospecific Synthesis. Tetrahedron Asymmetry. 1992;3:795-826.
Charest et al., A convergent enantioselective route to structurally diverse 6-deoxytetracycline antibiotics. Science. 2005;308:395-398.
Charest et al., Synthesis of (-)-Tetracycline. J. Am. Chem. Soc. 2005;127: 8292-93.
Charette et al., Spectroscopic studies of the electrophilic activation of amides with triflic anhydride and pyridine. CA J Chem. 2001;79:1694-1703.
Col et al., Estimating Worlwide Current Antibiotic Usage: Report of Task Force 1. Reviews of Infectious Diseases. 1987;3: S232-43.
Conover et al., Terramycin. XI. Tetracycline. J. Am. Chem. Soc. 1953;75:4622-23.
Conover et al., The Total Synthesis of 6-Demethyl-6-Deoxytetracycline. J. Am. Chem. Soc. 1962;84:3222-24.
Corey et al., Dimethyloxosulfonium Methylide ((CH3)2SOCH2) and Dimethylsulfonium Methylide ((CH3)2SOCH2). Formation and Applicaton to Organic Synthesis. J. Am. Chem. Soc. 1965;87:1353-1364.

Corey et al., Highly Enantioselective Borane Reduction of Ketones Catalyzed by Chiral Oxaborolidines. Mechanism and Synthetic Implications. J. Am. Chem. Soc. 1987;109:5551-5553.
Corey et al., Practical Enantioselective Diels-Alder and Aldol Reactions Using a New Chiral Controller System. J. Am. Chem. Soc. 1989;111:5493-5495.
Corey et al., Reduction of Carbonyl Compounds With Chiral Oxaborolidine Catalysts: a New Paradigm for Enantioselective Catalysis and a Powerful New Synthetic Method. Angew. Chem. Int. Ed Engl.1988;37:1986-2012.
Corey et al., Studies With Trialkylsityltrifiates: New Synthesis and Applications. Tetrahedron Lett. 1981;22:3455-3458.
Curtis et al., A nitrogen-15 nuclear magnetic resonance study of the tetracycline antibiotics. Can J Chem. 1991;69:834-38.
Dale et al., Nuclear Magnetic Resonance Enantiomer Reagents. Configurational Correlations via Nuclear Magnetic Resonance Chemical Shifts of Diastereomeric Mandelate, O-Methylmandelate and α-Methoxy-α-trifluoromethylphenylacetate (MTPA) Esters. J Am Chem Soc. 1973;95:512-19.
Dale et al., α-Methoxy-αTrifluoromethylphenylacetic Acid, A Versatile Reagent for the Determination of Enantiometric Composition of Alcohols and Amines. J. Org. Chem. 1969;34:2543-2549.
Danishefsky et al., Functionalized Alanes for the Conversion of Epoxides to Trans-Fused γ-Lactones. J Org Chem. 1976;41:1669-71.
Davis et al., Chemistry of Oxaziridines. 18. Synthesis and Enantioselective Oxidations of the [(88-Dihalocamphoryl) Sulfonyl] Oxaziridines. J. Org. Chem. 1992;57:7274-7285.
De Silva at al., Directed Lithiation of N,N-Diethylbenzamides. Tetrahedron Lett. 1978;51:50995102.
De Silva et al., General Route to Anthraquinone Natural Products via Directed Metalation of N,N-Diethylbenzamides. J. Org. Chem. 1979;44:4802-4808.
Deity, Electrophilic Conversion of Oxiranes to Allylic Alcohols with tert-Butyldimethylsilyl Iodide. J. Org. Chem. 1980;45:924-926.
Devasthale et al., Dactylocyclines Novel Tetracycline Derivatives Produced by a Dactylosporangium. Antibiotics. 1992;45:1907-1913.
Ditrich et al., Synthesis of a Protected C-11/C-17 Segment of Mycinolide-V. Liebigs Ann. Chem. 1990:15-21.
Dodd et al., Synthesis of the Carbon Framework of Olivin. Tetrahedron Lett. 1979;20:35933596.
Duggar, Aureomycin: A Product of the Continuing Search for New Antibiotics. Ann. N.Y. Acad. Sci. 1948;51:177-181.
Duhamel et al., A Method for Simple Titration of Organolithium Reagents in Ethers or HydrocarbonsUsing Metalation of N-Benzylidenebenzylamine As Colored Reaction. J. Org. Chem. 1979;44:3404-3405.
Eckert et al., Topology of the Transposon Tn10-Encoded Tetracycline Resistance Protein Within the Inner Membrane of Escheria coli. J. Biol. Chem. 1989;264:11663-11670.
Epe et al., Competition Between Tetracycline and tRNA At Both P And A Sites of the Ribosome of Escheria coil. FEBS Lett. 1987;213:443-47.
Epe et al., The Binding of 6Demethylchlorotetracyline to 70S, 50S, and 30S Ribosomal Particles-A Quantitative Study by Fluorescence Anisotropy. EMBO J. 1984;3:121-26.
Ettner et al., Proximity Mapping of the Tet Repressor-Tetracycline-Fe2+ Complex by Hydrogen Peroxide Mediated Protein Cleavage. Biochemistry. 1995;34:22-31.
Finlay et al., Terramycin, a New Antibiotic. Science 1950;111:85.
Franklin et al., Resistance of Escherichia coli to Tetraclines. Biochem J. 1965;94:54-60.
Franklin, The Inhibition of Incorporation of Leucine Into Protein of Cell-Free Systems From Rat Liver and Escherichia Coll by Chlortetracycline. Biochem. J. 1963;87:449-453.
Frigerio et al., A Mild Oxidizing Reagent for Alcohols and, 1,2-Diols: o-Iodoxybenzoic Acid (IBX) in DMSO. Tetrahedron Lett. 1994;35:8019-8022.
Gibson et al., Oxidative Degradation of Aromatic Hydrocarbons by Microorganisms. II. Metabolism of Halogenated Aromatic Hydrocarbons. Biochemistry 1968;7:3795-3802.
Glatz et al., Tetracyclines. A total synthesis and structural aspects of racemic 8-oxygenated tetracyclines. J Am Chem Soc. 1979;101:2171-81.

(56) References Cited

OTHER PUBLICATIONS

Goldman et at, Photoincorporation of Tetracycline Into *Escherichia coil* Ribosomes. Identification of the Major Proteins Photolabeled by Native Tetracycline and Tetracycline Photoproducts and Implications for the Inhibitory Action of Tetracycline on Protein Synthesis. Biochemistry. 1983;22:359-368.

Goldstein et al., N,N-Dimethylglycyl-Amido Derivative of Minocycline and 6-Demethyl-6- Desoxytetracycline, Two New Glycylcyclines Highly Effective Against Tetracycline-Resistant Gram-Positive Cocci. Antimicrob. Agents Chemother. 1994;38:2218-2220.

Gurevich et al., Synthesis of 12a-Deoxy-5a,6-Anhydrotetracycline. The First Total Synthesis of the Naturally Occurring Tetracycline. Tetrahedron Lett. 1967;8:131-134.

Hauser et al., New Synthetic Methods for the Regioselective Annelation of Aromatic Rings: 1-Hydroxy-2,3-disubstituted Naphthalenes and 1,4-Dihydrocy-2,3-disubstituted Naphthalenes. J Org Chem. 1978;43:178-180.

Hauser et al., ortho-Toluate Carbanion Chemistry: Sulfenylation and Selenation. Synthesis. 1980: 72-74.

He et al., Pyrrocidines A and B, New Antibiotics Produced by a Filamentous Fungus. Tetrahedron Letters. 2002;43:1633-36.

Hiilen et al., Control of the Expression of the Tn10-Encoded Tetracycline Resistance Genes. Equilibrium and Kinetic Investigation of the Regulatory Reactions. J. Mol. Biol. 1983;169:707721.

Hinrichs et al., Structure of the Tet Repressor-Tetracycline Complex and Regulation of Antibiotic Resistance. Science. 1994;264:418-420.

Hochstein et al., Terramycin. VII. The Structure of Terramycin. J. Am. Chem. Soc. 1952;74:3708-3709.

Hochstein et al., The Structure of Terramycin. J. Am. Chem Soc. 1953;75:5455-75.

Hollinshead et al., Two Practical Syntheses of Sterically Congested Benzophenones. J. Org. Chem. 1994;59:6703-6709.

Holmlund et al., Chemical Hydroxylation of 12a-Dexytetracycline. J. Am. Chem. Soc. 1959;81: 4748-4749.

Hong et al., Lewis acid-promoted alpha-hydroxy beta-dicarbonyl to alpha-ketol ester rearrangement. Tetrahedron Lett. 2006 Nov 20;47(47):8387-8390.

Hudlicky et al., A Short Synthesis of (+)-Lycoricidne. J. Am. Chem. Soc. 1992;114: 9694-9696.

Hudlicky et al., Enantioselective Synthesis Through Microbial Oxidation of Arenes. Efficient Preparation of Terpene and Prostanoid Synthons. J. Am. Chem. Soc. 1988;110:4735-4741.

Hudlicky et al., Enzymatic Dihydroxylation of Aromatics in Enantioselective Synthesis: Expanding Asymmetric Methodology. Aldrichimica Acta. 1999;32:35-62.

Hudlicky et al., Microbial Oxidation of Aromatics in Enantiocontrolled Synthesis. Rational DesignsOf Aza Sugars (endo-Nitrogenous). Total Synthesis of (+)-Kifunensine, Mannorjirimycin, and Other Glycosidase Inhibitors. J. Am. Chem. Soc. 1994;116:5099-5107.

Hudlicky et al., Toluene Dioxygenase-Mediated cis-Dihydroxylation of Aromatics in Enantioselective Synthesis. Asymmetric Total Synthesis of Pancratistatin and 7- Deoxpancratistatin, Promising Antitumor Agents. J. Am. Chem. Soc. 1996;118:10752-10765.

Hyatt et al., Thermal Decomposition of 2,2,6-Trimethyl-4H-1,3-Dioxin-4-One and 1-Ethoxybutyn-3-One. Acetylketene. J. Org. Chem. 1984;49:5105-5108.

Jacouinet et al., Synthesis of Heparin Fragments . A Chemical Synthesis of the Trisaccharide 0-(2-Deoxy-2-Sulfamido-3.6-Ii-O-Sulfo-a-D-Glucopyranosyl)-(1—>4)-0-(2-0- Sulfo-a-L-Idopyranosyl-Uronic Acid)-(1—>4)-2-Deoxy-2-Sulfamido-6-0-Sulfo-D-Gluco-Pyranose Heptasodium Salt. Carbohydr. Res. 1984;130:221-241.

Jenkins et al., Synthetic application of biotransformations: absolute stereochemistry and Diels-Alder reactions of the (1S,2R)-1,2-dihydroxycyclohexa-3,5-diene-1-carboxylic acid from Pseudomonas putida. J Chem Soc Perkin Trans. 1995;1:2647-55.

Jensen et al., Unsaturated Four-Membered Ring Compounds. II. 1,2-Diphenylbenzocyclobutene, A Compound Having Unusual Reactivity. J. Am. Chem. Soc.1958; 80:6149.

Johns et al., Synthesis and Biological Evaluation of Aza-C-Disaccharides: (I—>6), (1-44), and (1—>1) Linked Sugar Mimics. J. Am. Chem. Soc. 1997;119:4856-4865.

Johnson et al., Triply Convergent Synthesis of (-)-Prostaglandin E2 Methyl Ester. J Am Chem Soc. 1988;110:4726-4735.

Johnson, Biotransformations in the Synthesis of Enantiopure Bioactive Molecules. Acc Chem Res. 1998;31:333-341.

Katz, Manipulation of Modular Polyketide Synthases. Chem. Rev. 1997;97:2557-2575.

Kenny et al., Susceptibilities of Mycoplasma Hominis, Mycoplasma Pneumoniae, and Ureaplasma Urealyticum to New Glycylcyclines in Comparison With Those to Older Tetracyclines. Antimicrob. Agents Chemother. 1994;38:2628-2632.

Khosla et al., Chemistry. A new route to designer antibiotics. Science. 2005 Apr 15;308(5720):367-8.

Kofron et al., A Convenient Method for Estimation of Alkyllithium Concentrations. J Org Chem. 1976;41:1879-80.

Konno et al., A Practical Preparation of Versatile Cyclohexenoid Chiral Building Blocks. Synthesis. 1999:1135-40.

Korst et al., The Total Synthesis of d/-6-Demethyl-6-Deoxytetracycline. J. Am. Chem. Soc. 1968;90: 439-457.

Koza et al., Synthesis and Biological Evaluation of 9-Substituted Tetracycline Derivatives. Bioorgan. & Med. Chem. Letters. 2002;12: 2163-2165.

Koza et al., Synthesis of 7-Substituted Tetracycline Derivatives. Organic Letters. 2000;2:815-817.

Koza, The Synthesis of 8-Substituted Tetracycline Derivatives, The First 8-Position Carbon-Carbon Bond. Tetrahedron Lett. 2000;41:5017-5020.

Landais et al., Studies on the Mercury-desilylation of Chiral Cyclopropylmethylsilanes. A Stereocontrolled Access to Carba-sugars.. Eur. J. Org. Chem. 2000;2:401-18.

Laskin et al., Inhibition by Tetracyclines of Polyuridylic Acid Directed Phenylalanine Incorporation in *Escherichia coli* Cell- Free Systems. Biochem Biophys. Res. Conunun. 1964;14:137-142.

Lederer et al., Thermodynamic Analysis of Tetracycline-Mediated Induction of Tet Repressor by a Quantitative Methylation Protection Assay. Anal. Biochem. 1995;232:190-196.

Leeb, A Shot in the Arm. Nature. 2004;431:892-893.

Leeper et aL, Biomimetric Synthesis of Heptaketide Metabolites: Alternariol and a Derivative of Rubrofusarin. J.C.S. Chem. Comm. 1978:406-407.

Levy, Tetracycline Resistance Determinants Are Widespread. Amer. Soc. Microbial News. 1988;54: 418-421.

Ley et al., Microbial Oxidation in Synthesis: a Six Step Preparation of (+)-Pinitol From Benzene. Tetrahedron Lett. 1987;28:225-226.

Magnus et al., Trimethylsilyl accelerated retro-Diels-Alder reaction: a quantitative measure of the .beta.-effect. J Am Chem Soc. 1987;109(8):2469-2471.

Mao et al., Mode of Action Of β-Chelocardin. Biochim. Biophys. Acta. 1971;238: 157-160.

Marchand et al., Facile Stereoselective Reductions of Enediones and Cage Diketones Using NaBH4—CeC13. J Org Chem. 1986;51:1622-25.

Marger et al., A Major Superfamily of Transmembrane Facilitators That Catalyse Uniport, Symport and Antiport. Trends Biochem Sci. 1993;18:13-20.

Martell et al., The 6-Deoxytetracyclines. IX. Imidomethylation. J. Med. Chem. 1967;10:359363.

Martell et al., The 6-Deoxytetracyclines. VII. Alkylated Aminotetracyclines Possessing Unique Antibacterial Activity. J. Med. Chem. 1967;10: 44-46.

Martin et al., Totalsynthese von d, 1-7-Chlor-6-desoxytetracylinen und d, 1-7-Chlor-6- desmethyl-6-desoxytetracylinen der naturlichen, der 5a-epi- und der 6-epi-Reihe. Tetrahedron Lett. 1973:36:3513-16. German. N.

McComsey et al., Improved Synthesis of Pseudo-13-D-Fructopyranose, a Carbocyclic Monosaccharide, From (-)-Quinic Acid. J. Org. Chem. 1994;59:2652-2654.

(56) References Cited

OTHER PUBLICATIONS

McCormick et al., the 6-Deoxytetracyclines. Further Studies on the Relationship Between Structure and Antibacterial Activity in the Tetracycline Series. J. Am. Chem. Soc. 1960;82: 3381- 3386.
Meister et al., Synthese von 3(2H)-Furanonen and 3-Methoxyfuranen. Synthesis; 1981:737-39.
Mendez et al., Heterogeneity of Tetracycline Resistance Determinants. Plasmid. 1980;3:99-108.
Mercier et al., In Vitro Activities of an Investigational Quinolone, Glycylcycline, Glycopeptide, Streptogramin, and Oxazolidinone Tested Alone and in Combinations Against Vancomycin-Resistant Enterococcus Faecium. Antimicrob Agents Chemother. 1997;41: 2573-2575.
Movassaghi et al., Direct synthesis of pyridine derivatives. J Am Chem Soc. 2007 Aug 22;129(33):10096-7. Epub 2007 Jul 31.
Movassaghi et al., Single-step synthesis of pyrimidine derivatives. J Am Chem Soc. 2006 Nov 8;128(44):14254-5.
Movassaghi et al., Synthesis of substituted pyridine derivatives via the ruthenium-catalyzed cycloisomerization of 3-azadienynes. J Am Chem Soc. 2006 Apr 12;128(14):4592-3.
Muxfeldt et al., Tetracyclines. 9. Total Synthesis of dl-Terramycin. J. Am. Chem. Soc. 1979;101:689-701.
Muxfeldt et al., Tetracyclines. V. A Total Synthesis of (±)-6-Deoxy-6-Demethyltetracycline. J. Am. Chem. Soc. 1965;87:933-934.
Muxfeldt et al., Total Synthesis of Anhydroaureomycin. Angew Chem. Intl. Ed. EngL 1973;12: 497-499.
Myers et al., A Convergent Synthetic Route to (+)-Dynemicin a and Analogs of Wide Structural Variability. J. Am. Chem. Soc. 1997;119:6072-6094.
Myers et al., An Efficient Method for the Reductive Transposition of Allylic Alcohols. Tetrahedron Lett. 1996;37:4841-4844.
Myers et al., Synthesis of a Broad Array of Highly Functionalized, Enantiomerically Pure Cyclohexanecarboxylic Acid Derivative by Microbal Dihydroxylation of Benzoic Acid and Subsequent Oxidative and Rearrangement Reactions. Organic Letters. 2001;3(18):2923-26.
Nakashima et al., a Stereocontrolled Route to (—)-Epibatidine Using a Chiral cisCyclohexadiene-1,4-diol Equivalent. Synlett. 1999:1405-6.
Nelson et al., Molecular requirements for the inhibition of the tetracycline antiport protein and the effect of potent inhibitors on the growth of tetracycline-resistant bacteria. J Med Chem. 1994 Apr 29;37(9):1355-61.
Nelson et al., Versatile and Facile Synthesis of Diverse. Semisynthetic Tetracycline Derivatives Via Pd-Catalyzed Reactions. J. Org. Chem. 2003;68: 5838-5851.
Nicolaou et al., Recent advances in the chemistry and biology of naturally occurring antibiotics. Angew Chem Int Ed Engl. 2009;48(4):660-719.
Oda et al., 2-Cyclohexene-1,4-Dione. Org Syntheses. 1996;73:253.
Oikawa et al., Biosynthesis of Structurally Unique Fungal Metabolite GKK1032A2: Indication of Novel Carbocyclic Formation Mechanism in Polyketide Biosynthesis. J. Org. Chem. 2003;68: 3552-3557.
Oikawa et al., Kinetic Acetalization for 1, 2- and 1, 3-Diol Protection by the Reaction of pMethoxyphenylmethyl Methyl Ether With DDQ. Tetrahedron Lett. 1983;24:4037-4040.
Okamoto et al., Mechanism of Chloramphenicol and Tetracycline Resistance in *Escherichia coli*. J Gen. Microb. 1964;35:125-133.
Oliva et al., Evidence That Tetracycline Analogs Whose Primary Target Is Not the Bacterial Ribosome Cause Lysis of *Escherichia* cox Antimicrob. Agents Chemother. 1992;36:913-919.
Osman et al., Synthesis and Biological Activity of Certain Nicotinic Acid Derivatives. Revue Roumaine de Chime. 1986;31:615-624.
Palenik et al., Structural Studies of Tetracylcines. Crystal and Molecular Structures of Anhydrotetracycline Hydrobromide Monohydrate and 6-Demethyl-7-chlorotetracycline Hydrochloride Trihydrate. J Am Chem Soc. 1978;100(14):4458-64.
Pangborn et al., Safe and Convenient Procedure for Solvent Purification. Organometallics. 1996;15:1518-1520.

Paradies et al., A New Method for the Preparation of Organomagnesium Compounds of Pyridine. Angew. Chem. Int. Ed. Engl. 1969;8:279.
Parham et al., Selective Halogen—Lithium Exchange in Bromophenylalkyl Halides. J. Org. Chem. 1976; 41: 1184-1186.
Patel et al., A New Tetracycline Antibiotic From a Dactylosporangium Species. Antibiotics. 1987;40:1414-1418.
Pelaez, The historical delivery of antibiotics from microbial natural products—can history repeat? Biochem Pharmacol. 2006 Mar 30;71(7):981-90. Epub 2005 Nov 14.
Pelter et al., Phenolic Oxidation With (Diacetoxyiodo) Benzene. Tetrahedron Lett. 1988;29: 677680.
Pevarello et al., An Improved Synthesis of Muscimol. Synth. Commun. 1992;22:1939-1948.
Pickens et al., Decoding and engineering tetracycline biosynthesis. Metab Eng. 2009 Mar;11(2):69-75. Epub 2008 Oct 22.
Pierce et al., Practical Asymmetric Synthesis of Efavirenz (DMP 266), an Hiv-1 Reverse Transcriptase Inhibitor. J Org Chem. 1998;63:8536-43.
Pine, The Base-Promoted Rearrangements of Quaternary Ammonium Salts. Organic Reactions. 1970;18:403-465.
Pioletti et al., Crystal Structures of Complexes of the Small Robosomal Subunit With Tetracycline, Edeine, and IF3. EMBO J. 2001;20:1829-1839.
Prilezhaeva, Rearrangements of Sulfoxides and Sulfones in the Total Synthesis of Natural Compounds. Russ. Chem. Rev. 2001;70: 897-920.
Rasmussen et al., Molecular Basis of Tetracycline Action: Identification of Analogs Whose Primary Target Is Not the Bacterial Ribosome. Antimicrob. Agents Chemother. 1991;35:2306-11.
Rassmussen et al., Inhibition of Protein Synthesis Occurring on Tetracycline-Resistant, TetMProtected Ribosomes by a Novel Class of Tetracyclines, the Glycylcyclines. Antimicrob. Agents Chemother. 1994;38:1658-1660.
Reineke et al., cis-Dihydrodiols Microbially Produced From Halo- and Methylbenzoic Acids. Tetrahedron. 1978;34:1707-1714.
Reiner et al., Metabolism of Benzoic Acid by Bacteria, Accumulation of (-)-3,5- Cyclohexadiene-1,2—Diol-1-Carboxylic Acid by a Mutant Strain of Alcaligenes Eutrophus. Biochemistry. 1971;10:2530-2536.
Rendi et al., Effect of Chloramphenicol on Protein Synthesis in Cell-free Preparations of *Escherichia coli*. J. Biol. Chem. 1962;237:3711-3713.
Mess et al., Evaluation of Protecting Groups for 3-Hydroxyisoxazoles—Short Access to 3- Alkoxyisoxazole-5-Carbaldehydes and 3-Hydroxyisoxazole-5-Carbaldehyde, the Putative Toxic Metabolite of Muscimol. Eur. J. Org. Chem. 1998:473-479.
Rogalski, Chapter 5. Chemical Modification of Tetracyclines. Handbook of Experimental Pharmacology. 1985:179-316.
Rossiter et al., Aromatic Biotransformations 2: Production of Novel Chiral Fluorinated 3,5- Cycloheadiene-Cis-1,2-Diol-1-Carboxylates. Tetrahedron Lett. 1987;28:5173-5174.
Saenger et al.,Tthe Tetracycline Repressor—A Paradigm for a Biological Switch. Angew. Chem. Int. Ed. 2000;39:2042-2052.
Sanchez-Pescador et al., Homology of the TetM With Translational Elongation Factors: Implications for Potential Modes of tetM Conferred Tetracycline Resistance. Nucl. Acids. Res. 1988;16:1218.
Sato et aL, Synthesis of 1,3-Dioxin-4-One Deirvatives. Chem. Pharm. Bull. 1983;31:1896-1901.
Schach Von Wittenau et al., Proton Magnetic Resonance Spectra of Tetracyclines. J Chem Soc. 1966;31:613-15.
Schnappinger et al., Tetracyclines: Antibiotic Action, Uptake, and Resistance Mechanisms. Arch. Microbiol. 1996;165:359-369.
Scott et al., Simulation of the Biosynthesis of Tetracyclines . A Partial Syntheis of Tetracycline From Anhydroaureomycin. J Am. Chem. Soc. 1962;84:2271-2272.
Shu et al., BMA-192548, a tetracyclic binding inhibitor of neuropeptide Y receptors, from *Aspergillus niger* WB2346. II. Physico-chemical properties and structural characterization. J Antibiot (Tokyo). 1995 Oct;48(10):1060-5.

(56) References Cited

OTHER PUBLICATIONS

Singer et al., Catalytic, Enantioselective Dienolate Additions to Aldehydes: Preparation of Optically Active Acetoacetate Aldol Adducts. J. Am. Chem. Soc. 1995;117:12360-12361.

Stephens et al., 6-Deoxytetracyclines. IV. Preparation, c-6 Stereochemistry, and Reactions. J. Am. Chem. Soc. 1963;85:2643-2652.

Stephens et al., Terramycin. VIII. Structure of Aureomycin and Terramycin. J. Am. Chem. Soc. 1952;74: 4976-77.

Stephens et al., The Structure of Aureomycin. J. Am. Chem. Soc. 1954;76:3568-75.

Stevens et al., Degradation of Quaternary Ammonium Salts. Part I. J. Chem. Soc. 1928: 31933197.

Stevens, Degradation of Quaternary Ammonium Salts. Part II. J Chem. Soc. 1930:2107-2125.

Still et al., Rapid Chromatographic Technique for Preparative Separations With Moderate Resolution. J. Org. Chem. 1978;43:2923-2925.

Stork et al., 3-Benzyloxyisoxazole System in Construction of Tetracyclines. J Am Chem Soc. 1978;100(1 0:3609-11.

Stork et al., Stereocontrolled Synthesis of (±)-12a-Deoxytetracycline. J. Am. Chem. Soc. 1996;118:5304-5305.

Strohl, Biochemical Engineering of Natural Product Biosynthesis Pathways. Metabolic Engineering. 2001;3:4-14.

Sum et al., Glycylcylines. 1. A New Generation of Potent Antibacterial Agents Through Modification of (-Aminotetracyclines. J. Med. Chem. 1994;37:184-188.

Sum et al., Recent developments in tetracycline antibiotics. Curr Pharm Des. 1998 Apr;4(2):119- 32.

Sum et al., Synthesis and Structure—Activity Relationship of Novel Glycylcycline Derivatives Leading to the Discovery of Gar-936. Bioorg. Med. Chem. Lett. 1999;9:1459-1462.

Sum et al., Synthesis of Novel Tetracycline Derivatives With Substitution At the C-8 Position. Tetrahedron Lett. 1994;35:1835-1836.

Sum et al., The Design, Synthesis and Structure-Activity Relationships of Novel Glycylcycline Derivatives: A New Generation of Tetracycline Antibacterial Agents. 24th National Medicinal Chemistry Symposium Utah. 1994; 83:119. (Abstract Only).

Sun et al., A robust platform for the synthesis of new tetracycline antibiotics. J Am Chem Soc. 2008 Dec 31;130(52):17913-27.

Suzuki et al., Palladium(0) Catalyzed Reaction of 1,3-Diene Epoxides. A Useful Method for the Site Specific Oxygenation of 1,3-Dienes. J. Am. Chem. Soc. 1979;101:1623-1625.

Takano et al., Enantiodivergent Preparation of Chiral 2,5-Cyclohexadienone Synthons. Synthesis. 1993;(7): 948-50.

Tatsuta, Total synthesis and development of bioactive natural products. Proc Jpn Acad Ser B Phys Biol Sci. 2008;84(4):87-106.

Tatsuta et al., The First Total Synthesis of Natural (-)-Tetracycline. Chem. Lett. 2000:646-47.

Tatsuta et al., Total syntheses of bioactive natural products from carbohydrates. Sci Tech Adv Mater. 2006;7:397-410.

Tatsuta et al., Total syntheses of polyketide-derived bioactive natural products. Chem Rec. 2006;6(4):217-33.

Tatsuta et al., Total synthesis of selected bioactive natural products: illustration of strategy and design. Chem Rev. 2005 Dec;105(12):4707-29.

Taylor, Reactions of Epoxides With Ester, Ketone and Amide Enolates. Tetrahedron. 2000;56:1149-1163.

Testa et al., In Vitro and in Vivo Antibacterial Activities of the Glycylcyclines, A New Class of Semisynthetic Tetracyclines. Antimicrob. Agents Chemother. 1993;37:2270-2277.

Tolchin et al., Synthesizing New Antibiotics. Drug Discov & Develop: Reed Life Science News. Apr. 14, 2005.

Tovar et al., Identification and Nucleotide Sequence of the Class E tet Regulatory Elements and Operator and Inducer Binding of the Encoded Purified Tet Repressor. Mol. Gen. Genet. 1988;215:76-80.

Travis, Receiving the Antibiotic Miracle? Science. 1994;264:360-362.

Tymiak et al., Dactylocyclines, Novel Tetracycline Derivatives Produced by a Dactylosporangium sp. J. Antibiotics. 1992;45:1899-1906.

Tymiak et al., Dactylocyclines: Novel Tetracyclines Glycosides Active Against Tetracycline-Resistant Bacteria. J. Org. Chem. 1993;58:535-537.

Urbach et al., Totalsynthese von d,1 4-Amino-7-chlor-2-N-methylcarbamyl-2-descarbamyl-4- des-dimethylamino-6-desmethyl-6-desoxytetracyclin. Tetrahedron Lett. 1973;49:4907-10. German. N.

Verma et al., Antibiotic and non-antibiotic tetracycline patents: 2002-2007. Expert Opin Thera Pat. 2008;18(1):69-82.

Vishwakarma et al., (±)-trans-2-(Phenylsulfonyl)-3-Phenyloxaziridine. Org Syntheses. 1988;66:203.

Vu et al., New Functionalized Alkenylmagnesium Reagents Bearing an Oxygen Function in the 13-Position. Preparation and Reaction of 5-Magnesiated-1,3-Dioxin-4-One Derivatives. Tetrehedron Lett. 2001;42:6847-6850.

Vyas et al., A Short, Efficient Total Synthesis of (±) Acivicin and (±) Bromo-Acivicin. Tetrahedron Lett. 1984;25:487-490.

Wang et al., Identification of OxyE as an ancillary oxygenase during tetracycline biosynthesis. Chembiochem. 2009 Jun. 15;10(9):1544-50.

Wasserman et al., On the Total Synthesis of tetracycline. J. Am. Chem. Soc. 1986;108:42374238.

Weiss et al., Susceptibility of Enterococci, Methicillin—Resistant *Staphylococcus aureus* and *Steptococcus pneumoniae* to the Glycylcyclines. J Antimicrob. Agents Chemother. 1995;36:225230.

Wells et al., Dactylocyclines, novel Tetracycline Derivatives Produced by a Dactylosporangium sp. Antibiotics. 1992;45:1892-1898.

White et al., Stereochemical Transcription Via the Intramolecular Diels-Alder Reaction. Enantioselective Synthesis of (+)-Pillaromycinone. J. Org. Chem. 1986;51:1150-1152.

Wilson et al., Selective Reduction of 2-Ene-1,4-diones and 2-En-I-ones with Di-ibutylaluminium Hydride. J Chem Soc Chem Commun. 1970;(4):213-14.

Wissmann et al., Tetracyclin-Resistenzdeterminanten: Machanismen der Resistenz and Regulation ihrer Epression. Forum Mikrobiol. 1998:292-299.

Woodward, The Total Synthesis of a Tetracycline. Pure Appl Chem. 1963;6:561-573.

Wu et al., [A new era for organic synthesis—Highlights of the recent progress.] Progress in Chemistry. 2007;19(1):6-34. Chinese. Translated copy from Front Chem China, 2007, 2(3): 277-64.

Yarnell et al., Synthetic Route to Tetracyclines: Modular, flexible synthesis yields structurally diverse antibiotics. Chem & Eng News. 2005;83(16):9. 2 pp.

Yersin et al., Polarized Emission of [Ru(bpy)3] (PF5)2Single Crystals. J. Am. Chem. Soc. 1983;48: 4155-4156.

Zakeri et al., Chemical biology of tetracycline antibiotics. Biochem Cell Biol. 2008 Apr;86(2):124-36.

Zhang et al., Engineered biosynthesis of a novel amidated polyketide, using the malonamylspecific initiation module from the oxytetracycline polyketide synthase. Appl Environ Microbiol. 2006 Apr;72(4):2573-80.

Zhao et al., Nucleotide Sequence Analysis of the Class G Tetracycline Resistance Determinant From *Vibrio anguillarm*. Microbiol Immunol. 1992;36:1051-1060.

| Compound | Structure | SA101 (29213) S. aureus | SA191 S. aureus | SA161 (tetM) S. aureus | SA158 (tetK) S. aureus | SE164 (12228) S. epidermidis | EF159 (tetM) E. faecalis | SP106 (49619) S. pneumoniae | SP160 (tetM) S. pneumoniae | SP312 (tetM) S. pneumoniae | HI262 (33929) H. influenzae | MC205 (8176) M. catarrhalis |
|---|---|---|---|---|---|---|---|---|---|---|---|---|
| 5a-Methyl-minocycline | | 1 | 32 | 32 | 0.25 | 1 | >32 | 0.125 | >32 | >32 | 4 | 0.5 |
| 5a-Hydroxymethyl-minocycline | | 1 | >32 | >32 | 0.5 | 4 | >32 | 0.25 | >32 | >32 | 8 | 0.5 |
| 5a-Methoxymethyl-minocycline | | 4 | >32 | >32 | 1 | 2 | >32 | 0.5 | >32 | >32 | 4 | 1 |
| 5a-Carbomethoxy-minocycline | | 2 | >32 | >32 | 0.5 | 4 | >32 | 0.125 | >32 | >32 | 1 | 1 |

All units are in µg/mL.

Fig. 2A

| Compound | Structure | EC107 (25922) E. coli | EC155 (tetA) E. coli | KP153 (tetA) K. pneumoniae | KP457 (ESBL) K. pneumoniae | PM112 (35659) P. mirabilis | PA555 (BAA-47) P. aeruginosa | PA556 P. aeruginosa | AB250 A. baumannii | SM256 S. maltophilia | BC240 B. cenocepacia |
|---|---|---|---|---|---|---|---|---|---|---|---|
| 5a-Methyl-minocycline | | 4 | >32 | >32 | >32 | >32 | >32 | 2 | 32 | 4 | >32 |
| 5a-Hydroxymethyl-minocycline | | 2 | >32 | >32 | 32 | >32 | >32 | 0.5 | >32 | 16 | >32 |
| 5a-Methoxymethyl-minocycline | | 8 | >32 | >32 | >32 | >32 | >32 | 4 | 16 | 8 | >32 |
| 5a-Carbomethoxy-minocycline | | 4 | >32 | >32 | 32 | 8 | >32 | 2 | 16 | 8 | >32 |

All units are in μg/mL.

Fig. 2B

| Viable Count | SA101 (29213) 5.00E+05 | SA161 (tetM) 7.00E+05 | SA158 (tetK) 7.00E+05 | EF327 (tetM) 1.20E+05 | EF404 (tetM) 4.00E+04 | SP160 (tetM) 1.20E+05 | SP312 (tetM) 1.00E+06 | EC107 (25922) 4.00E+05 | EC155 (tetA) 1.00E+05 | EC878 (tolC) 2.00E+05 |
|---|---|---|---|---|---|---|---|---|---|---|
| | S. aureus | S. aureus | S. aureus | E. faecalis | E. faecalis | S. pneumoniae | S. pneumoniae | E. coli | E. coli | E. coli |
| STRUCTURE | 8 | >32 | 1 | >32 | >32 | >32 | >32 | 32 | >32 | 4 |
| | 4 | >32 | 1 | >32 | >32 | >32 | >32 | 16 | >32 | 2 |
| | 2 | >32 | 0.5 | >32 | >32 | >32 | >32 | 4 | >32 | 1 |

Fig. 3A

| Viable Count | SA101 (29213) 5.00E+05 | SA161 (tetM) 7.00E+05 | SA158 (tetK) 7.00E+05 | EF327 (tetM) 1.20E+05 | EF404 (tetM) 4.00E+04 | SP160 (tetM) 1.20E+05 | SP312 (tetM) 1.00E+06 | EC107 (25922) 4.00E+05 | EC155 (tetA) 1.00E+05 | EC878 (tolC) 2.00E+05 |
|---|---|---|---|---|---|---|---|---|---|---|
| | S. aureus | S. aureus | S. aureus | E. faecalis | E. faecalis | S. pneumoniae | S. pneumoniae | E. coli | E. coli | E. coli |
| STRUCTURE 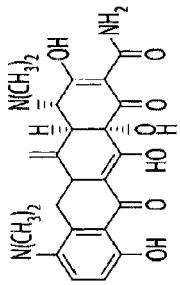 | 8 | 32 | 2 | >32 | >32 | >32 | >32 | 8 | 32 | 8 |
| 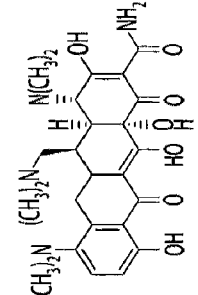 | 16 | 32 | 16 | 32 | >32 | >32 | 32 | >32 | >32 | 16 |
| 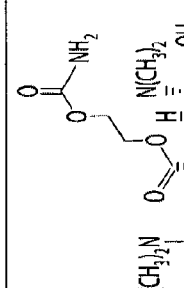 | >32 | >32 | >32 | >32 | >32 | >32 | >32 | >32 | >32 | >32 |
Fig. 3B

| | SA101 (29213) | SA161 (tetM) | SA158 (tetK) | EF327 (tetM) | EF404 (tetM) | SP160 (tetM) | SP312 (tetM) | EC107 (25922) | EC155 (tetA) | EC878 (tolC) |
|---|---|---|---|---|---|---|---|---|---|---|
| Viable Count | 5.00E+05 | 7.00E+05 | 7.00E+05 | 1.20E+05 | 4.00E+04 | 1.20E+05 | 1.00E+06 | 4.00E+05 | 1.00E+05 | 2.00E+05 |
| | S. aureus | S. aureus | S. aureus | E. faecalis | E. faecalis | S. pneumoniae | S. pneumoniae | E. coli | E. coli | E. coli |
| STRUCTURE  | >32 | >32 | 16 | >32 | >32 | >32 | >32 | >32 | >32 | 16 |
| Tetracycline | 0.5 | 8 | 32 | >32 | 32 | >32 | >32 | 2 | >32 | 1 |
| Minocycline | 0.0625 | | ≤0.0156 | | 8 | 4 | 16 | 0.5 | 16 | 0.25 |

| Viable Count | EC880 (lpxC) 4.00E+04 E.coli | EC882 (imp) 1.30E 05 E.coli | KP457 (CTX-M) 1.80E+05 K. pneumoniae | PM385 (ESBL) 3.00E+05 P. mirabilis | PA555 (BAA-47) 7.00E+05 P. aeruginosa | PA556 (KO) 7.00E+05 P. aeruginosa | PA884 (35151) 2.40E+04 P. aeruginosa | PA689 2.00E+03 P. aeruginosa | EC603 (tetA) 6.00E+05 E.coli | AB250 (tetB) 1.10E-05 A. baumannii | SM256 2.40E+05 S. maltophilia | BC240 9.00E+04 B. cenocepacia |
|---|---|---|---|---|---|---|---|---|---|---|---|---|
| STRUCTURE 1 | 2 | 2 | >32 | >32 | >32 | 8 | 8 | >32 | >32 | >32 | >32 | >32 |
| STRUCTURE 2 | 2 | 1 | >32 | >32 | >32 | 4 | 4 | >32 | >32 | >32 | 32 | >32 |
| STRUCTURE 3 | 1 | 0.5 | >32 | 32 | >32 | 1 | 1 | 32 | >32 | >32 | 16 | >32 |
| STRUCTURE 4 | 1 | 2 | >32 | >32 | >32 | 4 | 8 | >32 | >32 | 32 | 8 | >32 |

Fig. 3D

| Viable Count | EC880 (lpxC) 4.00E+04 E. coli | EC882 (imp) 1.30E+05 E. coli | KP457 (CTX-M) 1.80E+05 K. pneumoniae | PM385 (ESBL) 3.00E+05 P. mirabilis | PA555 (BAA-47) 7.00E+05 P. aeruginosa | PA556 (KO) 7.00E+05 P. aeruginosa | PA884 (35151) 2.40E+04 P. aeruginosa | PA689 2.00E+03 P. aeruginosa | EC603 (tetA) 6.00E+05 E. coli | AB250 (tetB) 1.10E+05 A. baumannii | SM256 2.40E+05 S. maltophilia | BC240 9.00E+04 B. cenocepacia |
|---|---|---|---|---|---|---|---|---|---|---|---|---|
| STRUCTURE | 8 | 8 | >32 | >32 | >32 | 32 | 32 | >32 | >32 | >32 | >32 | >32 |
| | >32 | >32 | >32 | >32 | >32 | 32 | >32 | >32 | >32 | >32 | >32 | >32 |
| | >32 | 16 | 4 | >32 | 32 | 8 | 32 | >32 | >32 | >32 | >32 | >32 |
| Tetracycline | 1 | 0.5 | 4 | 16 | 16 | 0.25 | 0.5 | 8 | >32 | >32 | 16 | 32 |
| Minocycline | ≤0.0156 | ≤0.0156 | 8 | 16 | 16 | 0.25 | 1 | 8 | >32 | 8 | 0.25 | 4 |

Fig. 3E

| STRUCTURE | SA101 (29213) S. aureus | SA191 (tetM) S. aureus | SA161 (tetM) S. aureus | SA158 (tetK) S. aureus | SE164 (tetK) S. epidermidis | EF159 (tetM) E. faecalis | SP106 (49619) S. pneumoniae | SP160 (tetM) S. pneumoniae | SP312 (tetM) S. pneumoniae | HI262 (tetB) H. influenzae | MC205 (8176) M. catarrhalis |
|---|---|---|---|---|---|---|---|---|---|---|---|
| Viable Count | 4.10E+05 | 1.70E+05 | 4.20E+05 | 1.30E+05 | 1.10E+05 | 8.00E+04 | 2.00E+04 | 2.00E+05 | 2.50E+05 | 2.00E+05 | 1.80E+05 |
| [structure] | 8 | 16 | 16 | 4 | 4 | 32 | 4 | >32 | 32 | >32 | 4 |
| [structure] | 32 | >32 | >32 | 4 | 8 | >32 | 2 | >32 | 32 | 8 | 4 |
| [structure] | 16 | 32 | >32 | 4 | 4 | >32 | 4 | >32 | >32 | >32 | 4 |
| [structure] | 32 | >32 | >32 | 8 | 16 | >32 | 8 | >32 | >32 | >32 | 8 |

Fig. 4A

| STRUCTURE | SA101 (29213) S. aureus | SA191 (tetM) S. aureus | SA161 (tetM) S. aureus | SA158 (tetK) S. aureus | SE164 (tetK) S. epidermidis | EF159 (tetM) E. faecalis | SP106 (49619) S. pneumoniae | SP160 (tetM) S. pneumoniae | SP312 (tetM) S. pneumoniae | HI262 (tetB) H. influenzae | MC205 (8176) M. catarrhalis |
|---|---|---|---|---|---|---|---|---|---|---|---|
| Viable Count | 4.10E+05 | 1.70E+05 | 4.20E+05 | 1.30E+05 | 1.10E+05 | 8.00E+04 | 2.00E+04 | 2.00E+04 | 2.50E+05 | 2.00E+05 | 1.80E+05 |
| (structure) | 16 | 32 | >32 | 8 | 8 | >32 | 4 | >32 | 32 | >32 | 4 |
| (structure) | 32 | >32 | >32 | 8 | 8 | >32 | 8 | >32 | >32 | >32 | 8 |
| (structure) | >32 | >32 | >32 | >32 | >32 | >32 | >32 | >32 | >32 | >32 | >32 |

Fig. 4A Cont.

| STRUCTURE | SA101 (29213) S. aureus | SA191 (tetM) S. aureus | SA161 (tetM) S. aureus | SA158 (tetK) S. aureus | SE164 (tetK) S. epidermidis | EF159 (tetM) E. faecalis | SP106 (49619) S. pneumoniae | SP160 (tetM) S. pneumoniae | SP312 (tetM) S. pneumoniae | HI262 (tetB) H. influenzae | MC205 (8176) M. catarrhalis |
|---|---|---|---|---|---|---|---|---|---|---|---|
| Viable Count | 4.10E+05 | 1.70E+05 | 4.20E+05 | 1.30E+05 | 1.10E+05 | 8.00E+04 | 2.00E+04 | 2.00E+04 | 2.50E+05 | 2.00E+05 | 1.80E+05 |
| 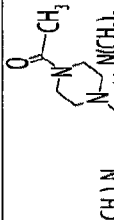 | 16 | >32 | >32 | 4 | 8 | >32 | 2 | >32 | >32 | >32 | 8 |
| Minocycline | 0.0312 | 8 | 8 | ≤0.0156 | 0.125 | 16 | ≤0.0156 | 4 | 16 | 2 | ≤0.0156 |
| 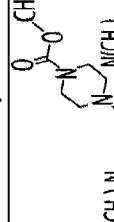 | 16 | 16 | 16 | 8 | 8 | 32 | 4 | >32 | 32 | >32 | 8 |
| 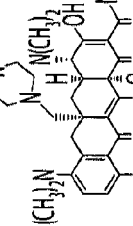 | 16 | 16 | 16 | 8 | 8 | 16 | 4 | 32 | 16 | >32 | 8 |
Fig. 4B

| STRUCTURE | SA101 (29213) S. aureus | SA191 (tetM) S. aureus | SA161 (tetM) S. aureus | SA158 (tetK) S. aureus | SE164 (tetK) S. epidermidis | EF159 (tetM) E. faecalis | SP106 (49619) S. pneumoniae | SP160 (tetM) S. pneumoniae | SP312 (tetM) S. pneumoniae | HI262 (tetB) H. influenzae | MC205 (8176) M. catarrhalis |
|---|---|---|---|---|---|---|---|---|---|---|---|
| Viable Count | 4.10E+05 | 1.70E+05 | 4.20E+05 | 1.30E+05 | 1.10E+05 | 8.00E+04 | 2.00E+04 | 2.00E+04 | 2.50E+05 | 2.00E+05 | 1.80E+05 |
| 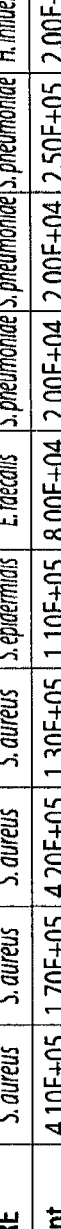 | 8 | 8 | 8 | 4 | 4 | 8 | 8 | 32 | 8 | >32 | 8 |
|  | 16 | 32 | 32 | 8 | 8 | >32 | 4 | >32 | >32 | >32 | 4 |
Fig. 4B Cont.

| STRUCTURE | SA101 (29213) S. aureus | SA191 (tetM) S. aureus | SA161 S. aureus | SA158 (tetK) S. aureus | SE164 (tetK) S. epidermidis | EF159 (tetM) E. faecalis | SP106 (49619) S. pneumoniae | SP160 (tetM) S. pneumoniae | SP312 (tetM) S. pneumoniae | HI262 (tetB) H. influenzae | MC205 (8176) M. catarrhalis |
|---|---|---|---|---|---|---|---|---|---|---|---|
| Viable Count | 4.10E+05 | 1.70E+05 | 4.20E+05 | 1.30E+05 | 1.10E+05 | 8.00E+04 | 2.00E+04 | 2.00E+05 | 2.50E+05 | 2.00E+05 | 1.80E+05 |
| (structure 1) | 16 | >32 | >32 | 4 | 4 | >32 | 2 | 32 | 32 | 32 | 2 |
| (structure 2) | 32 | >32 | >32 | 8 | 8 | >32 | 4 | >32 | >32 | >32 | 8 |
| (structure 3) | 1 | 32 | >32 | 0.25 | 0.5 | >32 | 0.25 | >32 | >32 | 8 | 0.25 |
| (structure 4) | 1 | 32 | 32 | 0.25 | 1 | >32 | 0.125 | >32 | >32 | 4 | 0.5 |

Fig. 4C

| STRUCTURE | SA101 (29213) | SA191 (tetM) | SA161 (tetM) | SA158 (tetK) | SE164 (tetK) | EF159 (tetM) | SP106 (49619) | SP160 (tetM) | SP312 (tetM) | HI262 (tetB) | MC205 (8176) |
|---|---|---|---|---|---|---|---|---|---|---|---|
| | S. aureus | S. aureus | S. aureus | S. aureus | S. epidermidis | E. faecalis | S. pneumoniae | S. pneumoniae | S. pneumoniae | H. influenzae | M. catarrhalis |
| Viable Count | 4.10E+05 | 1.70E+05 | 4.20E+05 | 1.30E+05 | 1.10E+05 | 8.00E+04 | 2.00E+04 | 2.00E+04 | 2.50E+04 | 2.00E+05 | 1.80E+05 |
| 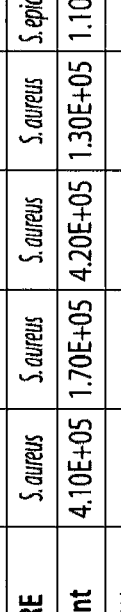 | 1 | >32 | >32 | 0.5 | 4 | >32 | 0.25 | >32 | >32 | 8 | 0.5 |
| 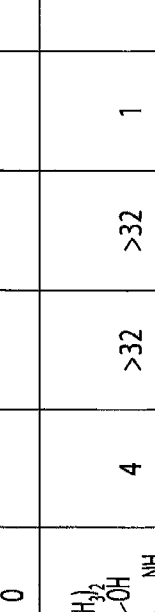 | 4 | >32 | >32 | 1 | 2 | >32 | 0.5 | >32 | >32 | 4 | 1 |
Fig. 4C Cont.

| | SA101 (29213) | SA191 (tetM) | SA161 (tetM) | SA158 (tetK) | SE164 (tetK) | EF159 (tetM) | SP106 (49619) | SP160 (tetM) | SP312 (tetM) | HI262 (tetB) | MC205 (8176) |
|---|---|---|---|---|---|---|---|---|---|---|---|
| STRUCTURE | S. aureus | S. aureus | S. aureus | S. aureus | S. epidermidis | E. faecalis | S. pneumoniae | S. pneumoniae | S. pneumoniae | H. influenzae | M. catarrhalis |
| Viable Count | 4.10E+05 | 1.70E+05 | 4.20E+05 | 1.30E+05 | 1.10E+05 | 8.00E+04 | 2.00E+04 | 2.00E+05 | 2.50E+05 | 2.00E+05 | 1.80E+05 |
| 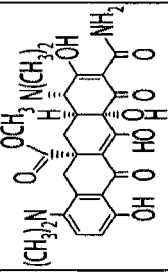 | 2 | >32 | >32 | 0.5 | 4 | >32 | 0.125 | >32 | >32 | 1 | 1 |
| 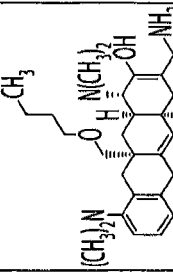 | 2 | 4 | 4 | 2 | 2 | 4 | 0.5 | 4 | 4 | 32 | 2 |
| Tetracycline | 0.5 | >32 | >32 | 32 | >32 | >32 | 0.125 | >32 | >32 | 8 | 0.25 |
| Tigecycline | 0.125 | 0.5 | 0.25 | 0.0625 | 0.125 | 0.0625 | ≤0.0156 | ≤0.0156 | ≤0.0156 | 1 | ≤0.0156 |
Fig. 4D

| | EC107 (25922) | EC155 (tetA) | KP153 (tetA) | KP457 (ESBL) | PM112 (35659) | PA555 (BAA-47) | PA556 (KO) | AB250 (tetB) | SM256 | BC240 |
|---|---|---|---|---|---|---|---|---|---|---|
| STRUCTURE | E.coli | E.coli | K.pneumoniae | K.pneumoniae | P.mirabilis | P.aeruginosa | P.aeruginosa | A.baumannii | S.maltophilia | B.cenocepacia |
| Viable Count | 1.30E+05 | 3.50E+05 | 9.00E+05 | 3.60E+05 | 9.00E+05 | 2.90E+05 | 2.70E+05 | 2.10E+05 | 7.00E+04 | 2.60E+05 |
| [structure] | 32 | >32 | >32 | >32 | >32 | >32 | 16 | 32 | 32 | >32 |
| [structure] | >32 | >32 | >32 | >32 | >32 | >32 | 2 | >32 | >32 | >32 |
| [structure] | 8 | 32 | 16 | 32 | 32 | >32 | 4 | 16 | 8 | >32 |
| [structure] | 32 | >32 | >32 | >32 | >32 | >32 | 8 | >32 | 32 | >32 |

Fig. 4E

| STRUCTURE | EC107 (25922) | EC155 (tetA) | KP153 (tetA) | KP457 (ESBL) | PM112 (35659) | PA555 (BAA-47) | PA556 (KO) | AB250 (tetB) | SM256 | BC240 |
|---|---|---|---|---|---|---|---|---|---|---|
| | E. coli | E. coli | K. pneumoniae | K. pneumoniae | P. mirabilis | P. aeruginosa | P. aeruginosa | A. baumannii | S. maltophilia | B. cenocepacia |
| Viable Count | 1.30E+05 | 3.50E+05 | 9.00E+05 | 3.60E+05 | 9.00E+05 | 2.90E+05 | 2.70E+05 | 2.10E+05 | 7.00E+04 | 2.60E+05 |
| 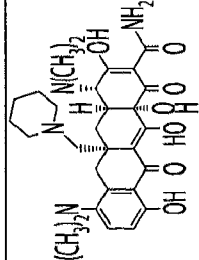 | 8 | >32 | 32 | >32 | >32 | >32 | 32 | 32 | 16 | >32 |
| 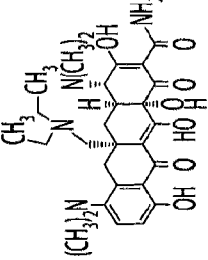 | 16 | >32 | 32 | >32 | >32 | >32 | 16 | 32 | 16 | >32 |
| 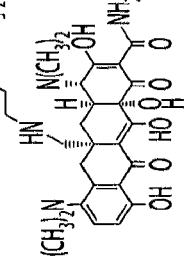 | >32 | >32 | >32 | >32 | >32 | >32 | >32 | >32 | >32 | >32 |
Fig. 4E Cont.

| STRUCTURE | EC107 (25922) E. coli | EC155 (tetA) E. coli | KP153 (tetA) K. pneumoniae | KP457 (ESBL) K. pneumoniae | PM112 (35659) P. mirabilis | PA555 (BAA-47) P. aeruginosa | PA556 (KO) P. aeruginosa | AB250 (tetB) A. baumannii | SM256 S. maltophilia | BC240 B. cenocepacia |
|---|---|---|---|---|---|---|---|---|---|---|
| Viable Count | 1.30E+05 | 3.50E+05 | 9.00E+05 | 3.60E+05 | 9.00E+05 | 2.90E+05 | 2.70E+05 | 2.10E+05 | 7.00E+04 | 2.60E+05 |
| (structure 1) | >32 | >32 | >32 | >32 | >32 | >32 | 32 | >32 | >32 | >32 |
| Minocycline | 0.25 | 8 | 8 | 4 | 8 | 32 | 0.25 | 8 | 0.5 | 4 |
| (structure 2) | >32 | >32 | >32 | >32 | >32 | >32 | >32 | >32 | >32 | >32 |
| (structure 3) | >32 | >32 | >32 | >32 | >32 | >32 | >32 | >32 | >32 | >32 |

Fig. 4F

| STRUCTURE | EC107 (25922) E. coli | EC155 (tetA) E. coli | KP153 (tetA) K. pneumoniae | KP457 (ESBL) K. pneumoniae | PM112 (35659) P. mirabilis | PA555 (BAA-47) P. aeruginosa | PA556 (KO) P. aeruginosa | AB250 (tetB) A. baumannii | SM256 S. maltophilia | BC240 B. cenocepacia |
|---|---|---|---|---|---|---|---|---|---|---|
| Viable Count | 1.30E+05 | 3.50E+05 | 9.00E+05 | 3.60E+05 | 9.00E+05 | 2.90E+05 | 2.70E+05 | 2.10E+05 | 7.00E+04 | 2.60E+05 |
| (cyclohexylcarbonyl-piperazinyl structure) | >32 | >32 | >32 | >32 | >32 | >32 | >32 | >32 | >32 | >32 |
| (methanesulfonyl-piperazinyl structure) | >32 | >32 | >32 | >32 | >32 | >32 | >32 | >32 | >32 | >32 |

Fig. 4F Cont.

| STRUCTURE | EC107 (25922) E. coli Viable Count 1.30E+05 | EC155 (tetA) E. coli 3.50E+05 | KP153 (tetA) K. pneumoniae 9.00E+05 | KP457 (ESBL) K. pneumoniae 3.60E+05 | PM112 (35659) P. mirabilis 9.00E+05 | PA555 (BAA-47) P. aeruginosa 2.90E+05 | PA556 (KO) P. aeruginosa 2.70E+05 | AB250 (tetB) A. baumannii 2.10E+05 | SM256 S. maltophilia 7.00E+04 | BC240 B. cenocepacia 2.60E+05 |
|---|---|---|---|---|---|---|---|---|---|---|
| (structure 1) | 8 | 32 | 32 | >32 | >32 | >32 | 32 | 32 | 32 | >32 |
| (structure 2) | >32 | >32 | >32 | >32 | >32 | >32 | 32 | >32 | >32 | >32 |
| (structure 3) | 4 | >32 | >32 | >32 | >32 | >32 | 2 | 16 | 8 | >32 |
| (structure 4) | 4 | >32 | >32 | >32 | >32 | >32 | 2 | 32 | 4 | >32 |

Fig. 4G

| STRUCTURE | EC107 (25922) | EC155 (tetA) | KP153 (tetA) | KP457 (ESBL) | PM112 (35659) | PA555 (BAA-47) | PA556 (KO) | AB250 (tetB) | SM256 | BC240 |
|---|---|---|---|---|---|---|---|---|---|---|
| | E. coli | E. coli | K. pneumoniae | K. pneumoniae | P. mirabilis | P. aeruginosa | P. aeruginosa | A. baumannii | S. maltophilia | B. cenocepacia |
| Viable Count | 1.30E+05 | 3.50E+05 | 9.00E+05 | 3.60E+05 | 9.00E+05 | 2.90E+05 | 2.70E+05 | 2.10E+05 | 7.00E+04 | 2.60E+05 |
| (structure 1) | 2 | >32 | >32 | 32 | >32 | >32 | 0.5 | >32 | 16 | >32 |
| (structure 2) | 8 | >32 | >32 | >32 | >32 | >32 | 4 | 16 | 8 | >32 |

Fig. 4G Cont.

| STRUCTURE | EC107 (25922) E. coli | EC155 (tetA) E. coli | KP153 (tetA) K. pneumoniae | KP457 (ESBL) K. pneumoniae | PM112 (35659) P. mirabilis | PA555 (BAA-47) P. aeruginosa | PA556 (KO) P. aeruginosa | AB250 (tetB) A. baumannii | SM256 S. maltophilia | BC240 B. cenocepacia |
|---|---|---|---|---|---|---|---|---|---|---|
| Viable Count | 1.30E+05 | 3.50E+05 | 9.00E+05 | 3.60E+05 | 9.00E+05 | 2.90E+05 | 2.70E+05 | 2.10E+05 | 7.00E+04 | 2.60E+05 |
| 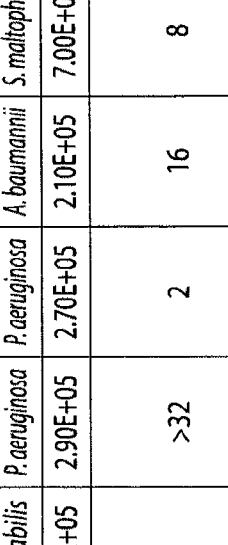 | 4 | >32 | >32 | 32 | 8 | >32 | 2 | 16 | 8 | >32 |
| 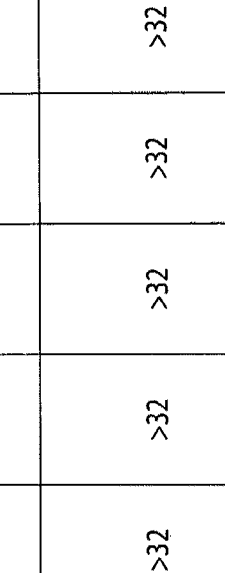 | >32 | >32 | >32 | >32 | >32 | >32 | >32 | >32 | >32 | >32 |
| Tetracycline | 2 | >32 | 1 | 1 | 2 | 32 | 0.25 | >32 | 16 | 32 |
| Tigecycline | 0.0312 | | | | 2 | 8 | 0.25 | 4 | 1 | 8 |
Fig. 4H

| COMPOUND | SA101 (29213) S. aureus | SA161 (tetM) S. aureus | SA158 (tetK) S. aureus | EF327 (tetM) E. faecalis | EF404 (tetM) E. faecalis | SP160 (tetM) S. pneumoniae | SP312 (tetM) S. pneumoniae | EC107 (25922) E. Coli | EC155 (tetA) E. Coli | EC878 (tolC) E. Coli | EC880 (lpxC) E. Coli |
|---|---|---|---|---|---|---|---|---|---|---|---|
| [structure] | 1 | 4 | 0.25 | 16 | 8 | 16 | 16 | 8 | 32 | 2 | 1 |
| [structure] | 16 | >32 | 4 | >32 | >32 | >32 | >32 | 8 | >32 | 2 | 4 |
| [structure] | 1 | 4 | 0.25 | 16 | 8 | 16 | 16 | 8 | 32 | 2 | 0.5 |
| Tetracycline | 0.5 | >32 | 32 | >32 | 32 | >32 | >32 | 1 | >32 | 1 | 1 |
| [structure] | 16 | >32 | 4 | >32 | >32 | >32 | 32 | 8 | >32 | 16 | 8 |

Fig. 5A

| COMPOUND | SA101 (29213) S. aureus | SA161 (tetM) S. aureus | SA158 (tetK) S. aureus | EF327 (tetM) E. faecalis | EF404 (tetM) E. faecalis | SP160 (tetM) S. pneumoniae | SP312 (tetM) S. pneumoniae | EC107 (25922) E. coli | EC155 (tetA) E. coli | EC878 (tolC) E. coli | EC880 (lpxC) E. coli |
|---|---|---|---|---|---|---|---|---|---|---|---|
| [structure 1] | >32 | >32 | >32 | >32 | >32 | >32 | >32 | >32 | >32 | >32 | >32 |
| [structure 2] | 8 | 32 | 2 | >32 | >32 | >32 | >32 | 32 | >32 | 4 | 8 |
| [structure 3] | 16 | >32 | 4 | 32 | 32 | 32 | 16 | >32 | >32 | >32 | 4 |

Fig. 5B

| COMPOUND | SA101 (29213) S. aureus | SA161 (tetM) S. aureus | SA158 (tetK) S. aureus | EF327 (tetM) E. faecalis | EF404 (tetM) E. faecalis | SP160 (tetM) S. pneumoniae | SP312 (tetM) S. pneumoniae | EC107 (25922) E. coli | EC155 (tetA) E. coli | EC878 (tolC) E. coli | EC880 (lpxC) E. coli |
|---|---|---|---|---|---|---|---|---|---|---|---|
| [structure with O=S(CH₃)-NH-...] | >32 | >32 | 2 | >32 | >32 | >32 | >32 | >32 | >32 | 8 | >32 |
| [structure with OCH₃-C(=O)-NH-...] | 16 | >32 | 2 | >32 | >32 | >32 | >32 | 32 | >32 | 4 | 4 |
| [structure with OCH₃-C(=O)-NH-...] | 4 | >32 | 0.5 | >32 | >32 | >32 | >32 | 8 | >32 | 2 | 1 |

Fig. 5C

| COMPOUND | SA101 (29213) S. aureus | SA161 (tetM) S. aureus | SA158 (tetK) S. aureus | EF327 (tetM) E. faecalis | EF404 (tetM) E. faecalis | SP160 (tetM) S. pneumoniae | SP312 (tetM) S. pneumoniae | EC107 (25922) E. coli | EC155 (tetA) E. coli | EC878 (tolC) E. coli | EC880 (lpxC) E. coli |
|---|---|---|---|---|---|---|---|---|---|---|---|
| [benzamide tetracycline structure] | 8 | 16 | 2 | >32 | 32 | 2 | 4 | 32 | >32 | 32 | 2 |
| [acetamide tetracycline structure] | 8 | >32 | 2 | >32 | >32 | >32 | >32 | >32 | >32 | 4 | 16 |
| [difluorobenzamide tetracycline structure] | 4 | 8 | 1 | 8 | 8 | 2 | 4 | >32 | >32 | >32 | 4 |

Fig. 5D

| COMPOUND | SA101 (29213) | SA161 (tetM) | SA158 (tetK) | EF327 (tetM) | EF404 (tetM) | SP160 (tetM) | SP312 (tetM) | EC107 (25922) | EC155 (tetA) | EC878 (tolC) | EC880 (lpxC) |
|---|---|---|---|---|---|---|---|---|---|---|---|
| | S. aureus | S. aureus | S. aureus | E. faecalis | E. faecalis | S. pneumoniae | S. pneumoniae | E. coli | E. coli | E. coli | E. coli |
| [structure] | 16 | 16 | 4 | >32 | >32 | 8 | 8 | 32 | >32 | 32 | 2 |

Fig. 5E

| COMPOUND | EC882 (imp) E.coli | KP457 (CTX-M) K. pneumoniae | PM385 (ESBL) P. mirabilis | PA555 (BAA-47) P. aeruginosa | PA556 (KO) P. aeruginosa | PA884 (35151) P. aeruginosa | PA689 P. aeruginosa | EC603 (tetA) E.coli | AB250 (tetB) A. baumannii | SM256 S. maltophilia | BC240 B. cenocepacia |
|---|---|---|---|---|---|---|---|---|---|---|---|
| [structure] | 1 | >32 | 8 | >32 | 2 | 4 | >32 | >32 | 32 | 32 | >32 |
| [structure] | 2 | 32 | >32 | >32 | 2 | 1 | 32 | >32 | >32 | >32 | >32 |
| [structure] | 1 | >32 | 8 | >32 | 2 | 4 | >32 | >32 | 32 | 32 | >32 |
| Tetracycline | 0.5 | 4 | 32 | 32 | 0.25 | 0.5 | 8 | >32 | >32 | 16 | 16 |
| [structure] | 8 | 32 | 16 | 32 | 4 | 4 | 8 | >32 | >32 | >32 | >32 |

Fig. 5F

| COMPOUND | EC882 (imp) E.coli | KP457 (CTX-M) K. pneumoniae | PM385 (ESBL) P. mirabilis | PA555 (BAA-47) P. aeruginosa | PA556 (KO) P. aeruginosa | PA884 (35151) P. aeruginosa | PA689 P. aeruginosa | EC603 (tetA) E.coli | AB250 (tetB) A. baumannii | SM256 S. maltophilia | BC240 B. cenocepacia |
|---|---|---|---|---|---|---|---|---|---|---|---|
| ![structure] | 2 | >32 | >32 | >32 | 4 | 4 | >32 | >32 | >32 | >32 | >32 |
| ![structure] | 4 | >32 | >32 | >32 | >32 | 8 | >32 | >32 | >32 | >32 | >32 |
| ![structure] | 4 | >32 | >32 | >32 | 2 | 2 | >32 | >32 | >32 | >32 | >32 |

Fig. 5G

| COMPOUND | EC882 (imp) E.coli | KP457 (CTX-M) K.pneumoniae | PM385 (ESBL) P.mirabilis | PA555 (BAA-47) P. aeruginosa | PA556 (KO) P. aeruginosa | PA884 (35151) P. aeruginosa | PA689 P. aeruginosa | EC603 (tetA) E.coli | AB250 (tetB) A.baumannii | SM256 S. maltophilia | BC240 B. cenocepacia |
|---|---|---|---|---|---|---|---|---|---|---|---|
| (structure) | 2 | >32 | >32 | >32 | 2 | 4 | >32 | >32 | >32 | >32 | >32 |

| COMPOUND | EC882 (imp) E. coli | KP457 (CTX-M) K. pneumoniae | PM385 (ESBL) P. mirabilis | PA555 (BAA-47) P. aeruginosa | PA556 (KO) P. aeruginosa | PA884 (35151) P. aeruginosa | PA689 P. aeruginosa | EC603 (tetA) E. coli | AB250 (tetB) A. baumannii | SM256 S. maltophilia | BC240 B. cenocepacia |
|---|---|---|---|---|---|---|---|---|---|---|---|
| [structure] | 4 | >32 | >32 | >32 | >32 | 16 | >32 | >32 | >32 | 16 | >32 |

Fig. 5H Cont.

| COMPOUND | EC882 (imp) E. coli | KP457 (CTX-M) K. pneumoniae | PM385 (ESBL) P. mirabilis | PA555 (BAA-47) P. aeruginosa | PA556 (KO) P. aeruginosa | PA884 (35151) P. aeruginosa | PA689 P. aeruginosa | EC603 (tetA) E. coli | AB250 (tetB) A. baumannii | SM256 S. maltophilia | BC240 B. cenocepacia |
|---|---|---|---|---|---|---|---|---|---|---|---|
| [structure] | 4 | >32 | >32 | >32 | 32 | 8 | >32 | >32 | >32 | 32 | >32 |

Fig. 51

ACTIVITY AGAINST SELECTED GRAM-POSITIVE BACTERIAL STRAINS:

| COMPOUND | SA101 (29213) S. aureus | SA191 S. aureus | SA161 (tetM) S. aureus | SA158 (tetK) S. aureus | SE164 (12228) S. epidermidis | EF159 (tetM) E. faecalis | SP106 (49619) S. pneumoniae | SP160 (tetM) S. pneumoniae | SP132 (tetM) S. pneumoniae |
|---|---|---|---|---|---|---|---|---|---|
| COMPOUND 71 | 0.5 | 1 | 1 | 0.125 | 0.5 | 0.25 | ≤0.0156 | ≤0.0156 | 0.125 |
| COMPOUND 72 | 1 | 1 | 2 | 0.125 | 0.25 | 0.25 | ≤0.0156 | ≤0.0156 | 0.25 |
| COMPOUND 73 | 0.5 | 4 | 1 | 0.25 | 1 | 0.25 | ≤0.0156 | ≤0.0156 | 0.125 |

Fig. 6A

ACTIVITY AGAINST SELECTED GRAM-POSITIVE BACTERIAL STRAINS:

| COMPOUND | SA101 (29213) S. aureus | SA191 S. aureus | SA161 (tetM) S. aureus | SA158 (tetK) S. aureus | SE164 (12228) S. epidermidis | EF159 (tetM) E. faecalis | SP106 (49619) S. pneumoniae | SP160 (tetM) S. pneumoniae | SP132 (tetM) S. pneumoniae |
|---|---|---|---|---|---|---|---|---|---|
| COMPOUND 74 | 1 | 1 | 0.5 | 0.125 | 0.25 | 0.25 | ≤0.0156 | ≤0.0156 | 0.0625 |
| COMPOUND 75 | 2 | 2 | 2 | 0.25 | 1 | 1 | ≤0.0156 | ≤0.0156 | 0.5 |
| COMPOUND 76 | 1 | 0.5 | 1 | 0.125 | 0.25 | 0.125 | ≤0.0156 | ≤0.0156 | 0.0625 |

Fig. 6B

ACTIVITY AGAINST SELECTED GRAM-POSITIVE BACTERIAL STRAINS:

| COMPOUND | SA101 (29213) S. aureus | SA191 S. aureus | SA161 (tetM) S. aureus | SA158 (tetK) S. aureus | SE164 (12228) S. epidermidis | EF159 (tetM) E. faecalis | SP106 (49619) S. pneumoniae | SP160 (tetM) S. pneumoniae | SP132 (tetM) S. pneumoniae |
|---|---|---|---|---|---|---|---|---|---|
| COMPOUND 85 | 2 | 2 | 4 | 0.5 | 0.5 | 4 | 0.0313 | 0.5 | 2 |
| COMPOUND 91 | 4 | >32 | >32 | 32 | >32 | >32 | 0.5 | >32 | >32 |

Fig. 6C

ACTIVITY AGAINST SELECTED GRAM-NEGATIVE BACTERIAL STRAINS:

| COMPOUND | HI262 (33929) *H. influenza* | MC205 (8176) *M. catarrhalis* | EC107 (25922) *E. coli* | EC155 (tetA) *E. coli* | KP153 (tetA) *K. pneumoniae* | KP457 (CTX-M-15) *K. pneumoniae* | PM112 (35659) *P. mirabilis* | PA555 (BAA-47) *P. aeruginosa* | PA556 *P. aeruginosa* | AB250 *A. baumanii* | SM256 *S. marcescens* | BC240 *B. cenocepacia* |
|---|---|---|---|---|---|---|---|---|---|---|---|---|
| COMPOUND 71 | 0.25 | 0.0625 | 0.25 | 4 | 2 | 4 | 1 | >32 | 0.25 | 4 | 2 | 16 |
| COMPOUND 72 | 0.25 | 0.125 | 0.5 | 4 | 2 | 4 | 2 | >32 | 2 | 4 | 4 | 16 |
| COMPOUND 73 | 0.5 | 0.125 | 1 | 32 | 32 | 16 | 2 | >32 | 0.5 | 8 | 8 | >32 |
| COMPOUND 74 | 0.5 | 0.125 | 0.5 | 16 | 16 | 16 | 2 | >32 | 1 | 4 | 4 | 32 |

Fig. 7A

ACTIVITY AGAINST SELECTED GRAM-NEGATIVE BACTERIAL STRAINS:

| COMPOUND | HI262 (33929) H. influenza | MC205 (8176) M. catarrhalis | EC107 (25922) E. coli | EC155 (tetA) E. coli | KP153 (tetA) K. pneumoniae | KP457 (CTX-M-15) K. pneumoniae | PM112 (35659) P. mirabilis | PA555 (BAA-47) P. aeruginosa | PA556 P. aeruginosa | AB250 A. baumanii | SM256 S. marcescens | BC240 B. cenocepacia |
|---|---|---|---|---|---|---|---|---|---|---|---|---|
| COMPOUND 75 | 0.5 | 0.25 | 0.5 | 8 | 4 | 8 | 8 | >32 | 2 | 16 | 4 | 16 |

Fig. 7A Cont.

ACTIVITY AGAINST SELECTED GRAM-NEGATIVE BACTERIAL STRAINS:

| COMPOUND | HI262 (33929) H. influenza | MC205 (8176) M. catarrhalis | EC107 (25922) E.coli | EC155 (tetA) E.coli | KP153 (tetA) K. pneumoniae | KP457 (CTX-M-15) K. pneumoniae | PM112 (35659) P. mirabilis | PA555 (BAA-47) P. aeruginosa | PA556 P. aeruginosa | AB250 A. baumanii | SM256 S. marcescens | BC240 B. cenocepacia |
|---|---|---|---|---|---|---|---|---|---|---|---|---|
| COMPOUND 76 | 0.25 | 0.125 | 0.5 | 32 | 16 | 32 | 8 | >32 | 1 | 16 | 8 | >32 |
| COMPOUND 85 | 2 | 0.5 | 4 | 16 | 8 | 32 | 16 | >32 | 16 | 16 | 8 | >32 |
| COMPOUND 91 | 8 | 0.5 | 2 | >32 | >32 | 4 | 32 | >32 | 1 | >32 | >32 | >32 |

Fig. 7B

SYNTHESIS OF TETRACYCLINES AND INTERMEDIATES THERETO

PRIORITY INFORMATION

The present application a national stage filing under 35 U.S.C. §371 of international PCT application, PCT/US2010/001284, filed Apr. 30, 2010, which claims priority under 35 U.S.C. §119(e) to U.S. provisional patent applications, U.S. Ser. No. 61/174,185, filed Apr. 30, 2009, and U.S. Ser. No. 61/322,613, filed Apr. 9, 2010, each of which is incorporated herein by reference.

GOVERNMENT SUPPORT

This invention was made with U.S. Government support under grant R01 AI048825 and predoctoral fellowship GM007598-30 awarded by the National Institutes of Health. The U.S. Government has certain rights in the invention.

BACKGROUND OF THE INVENTION

The tetracyclines are broad spectrum antimicrobial agents that are widely used in human and veterinary medicine (Schappinger et al., "Tetracyclines: Antibiotic Action, Uptake, and Resistance Mechanisms" *Arch. Microbiol.* 165: 359-69, 1996; Mitscher, Medicinal Research Series, Vol. 9, The Chemistry of the Tetracycline Antibiotics, Marcel Dekker Inc. New York, 1978). The total production of tetracyclines by fermentation or semi-synthesis is measured in the thousands of metric tons per year. The first tetracycline, chlorotetracycline (1) (AUREOMYCIN™), was isolated from the soil bacterium *Streptomyces aureofaciens* by Lederle Laboratories (Wyeth-Ayerst Research) in 1945 (Duggar, *Ann. N.Y. Acad. Sci.* 51:177-181, 1948; Duggar, Aureomycin and Preparation of Some, U.S. Pat. No. 2,482,055, 1949; incorporated herein by reference). Oxytetracycline (2) was isolated soon after from *S. rimosus* by scientists at Pfizer Laboratories (Finlay et al., *Science* 111:85, 1950). The structures of chlorotetracycline and oxytetracycline were elucidated by scientists at Pfizer in collaboration with R. B. Woodward and co-workers at Harvard University (Hochstein et al., *J. Am. Chem. Soc.* 74:3708-3709, 1952; Hochstein et al., *J. Am. Chem. Soc.* 75:5455-75, 1953; Stephens et al., *J. Am. Chem. Soc.* 74:4976-77, 1952; Stephens et al., *J. Am. Chem. Soc.* 76:3568-75, 1954). Tetracycline (3) was later prepared by the hydrogenolysis of chlorotetracycline and was found to retain the antimicrobial activity of chlorotetracycline and oxytetracycline and had increased stability (Boothe et al. *J. Am. Chem. Soc.* 75:4621, 1953; Conover et al. *J. Am. Chem. Soc.* 75:4622-23, 1953). Tetracycline was later found to be a natural product of *S. aureofaciens, S. viridofaciens,* and *S. rimosus*.

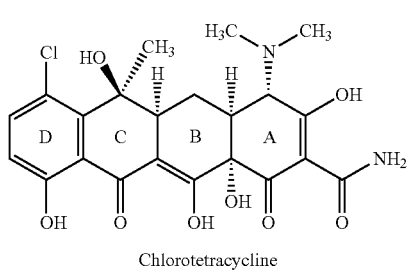

Chlorotetracycline (1)

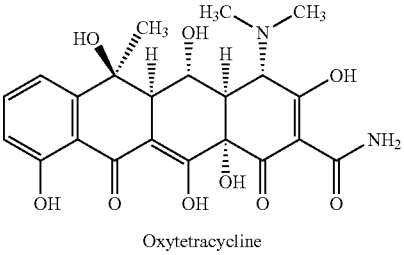

Oxytetracycline (2)

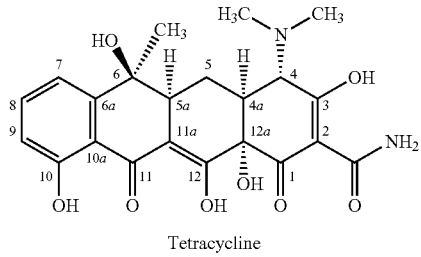

Tetracycline (3)

The primary tetracyclines of clinical importance today include tetracycline (3) (Boothe et al., *J. Am. Chem. Soc.* 75:4621, 1953), oxytetracycline (2, TERRAMYCIN™) (Finlay et al., *Science* 111:85, 1950), (−)-doxycycline (Stephens et al., *J. Am. Chem. Soc.* 85:2643, 1963), (−)-minocycline (Martell et al., *J. Med. Chem.* 10:44, 1967; Martell et al., *J. Med. Chem.* 10:359, 1967), and tigecycline. The tetracyclines exert their antimicrobial activity by inhibition of bacterial protein synthesis (Bentley and O'Hanlon, Eds., *Anti-Infectives: Recent Advances in Chemistry and Structure-Activity Relationships* The Royal Society of Chemistry: Cambridge, UK, 1997). Most tetracyclines are bacteriostatic rather than bactericidal (Rasmussen et al., *Antimicrob. Agents Chemother.* 35:2306-11, 1991; Primrose and Wardlaw, Ed. "The Bacteriostatic and Bacteriocidal Action of Antibiotics" *Sourcebook of Experiments for the Teaching of Microbiology* Society for General Microbiology, Academic Press Ltd., London, 1982). It has been proposed that after tetracycline passes through the cytoplasmic membrane of a bacterium it chelates $Mg^{+2}$, and this tetracycline-$Mg^{+2}$ complex binds the 30S subunit of the bacterial ribosome (Goldman et al., *Biochemistry* 22:359-368, 1983). Binding of the complex to the ribosome inhibits the binding of aminoacyl-tRNAs, resulting in inhibition of protein synthesis (Wissmann et al., *Forum Mikrobiol.* 292-99, 1998; Epe et al., *EMBO J.* 3:121-26, 1984). Tetracyclines have also been found to bind to the 40S subunit of eukaryotic ribosome; however, they do not achieve sufficient concentrations in eukaryotic cells to affect protein synthesis because they are not actively transported in eukaryotic cells (Epe et al., *FEBS Lett.* 213:443-47, 1987).

Structure-activity relationships for the tetracycline antibiotics have been determined empirically from 50 years of semi-synthetic modification of the parent structure (Sum et al., *Curr. Pharm. Design* 4:119-32, 1998). Permutations of the upper left-hand portion of the natural product, also known as the hydrophobic domain, have provided new therapeutically active agents, while modifications of the polar hydrophobic domain result in a loss of activity. However, semi-synthesis by its very nature has limited the number of tetracycline analogs that can be prepared and studied.

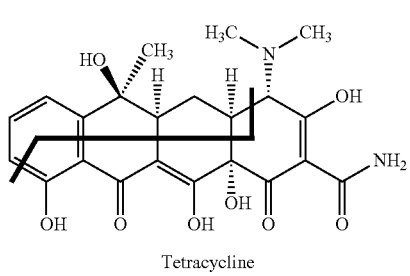

Tetracycline (3)

The tetracyclines are composed of four linearly fused six-membered rings with a high density of polar functionality and stereochemical complexity. Previous approaches to the synthesis of tetracyclines typically proceeded via a stepwise assembly of the tetracyclic ring system. In 1962, Woodward and co-workers reported the first total synthesis of racemic 6-desmethyl-6-deoxytetracycline (sancycline, 4), the simplest biologically active tetracycline (Conover et al., *J. Am. Chem. Soc.* 84:3222-24, 1962). The synthetic route was a remarkable achievement for the time and proceeded by the stepwise construction of the rings in a linear sequence of 22 steps (overall yield ~0.003%). The first enantioselective synthesis of (−)-tetracycline (3) from the A-ring precursor D-glucosamine (34 steps, 0.002% overall yield) was reported by Tatsuda and co-workers in 2000 (Tatsuta et al., *Chem. Lett.* 646-47, 2000). Other approaches to the synthesis of tetracycline antibiotics, which have also proceeded by the stepwise assembly of the ABCD ring system beginning with D or CD precursors, include the Shemyakin synthesis of (±)-12a-deoxy-5a,6-anhydrotetracycline (Gurevich et al., *Tetrahedron Lett.* 8:131, 1967; incorporated herein by reference) and the Muxfeldt synthesis of (±)-5-oxytetracycline (terramycin, 22 steps, 0.06% yield) (Muxfeldt et al., *J. Am. Chem. Soc.* 101:689, 1979; incorporated herein by reference). Due to the length and poor efficiency of the few existing routes to tetracyclines, which were never designed for synthetic variability, synthesis of tetracycline analogs is still limited.

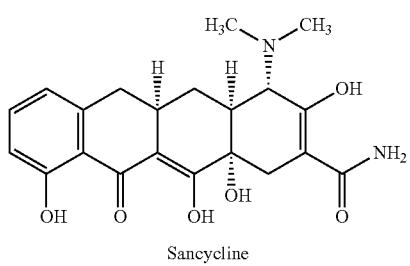

Sancycline (4)

More recently, a novel convergent synthetic route to tetracyclines and various analogs, including pentacycline and heterocycle-containing tetracyclines, has been developed by Myers and co-workers. See US 2005/0282787, published Dec. 22, 2005; incorporated herein by reference; and Charest et al., *Science,* 308:395-398, 15 Apr. 2005; Charest et al., *J. Am. Chem. Soc.* 127:8292-93, 2005. This route proceeds through the highly functionalized chiral enone intermediate (5) which is prepared starting from benzoic acid in ten steps (11% yield, >95% ee) (Charest et al., *Science* 308:395-398, Apr. 15, 2005; Charest et al., *J. Am. Chem. Soc.* 127:8292-8293, 2005; Myers et al., *Org. Lett.* 3(18):2923-26, 2001). A second generation route to the enone intermediate (5) was later developed starting from an isoxazole aldehyde. The second generation route yields the enone in eight steps in an improved yield. See US 2009/0093640, published Apr. 9, 2009; U.S. 60/850,859, filed Oct. 11, 2006; and WO2008/127361, published Oct. 23, 2008; each of which is incorporated herein by reference.

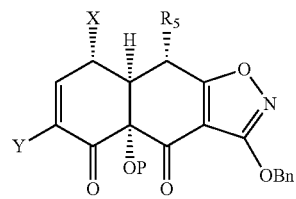

(5)

Several approaches were developed to react the enone 5 with a toluate (6), benzylic halide, or benzocyclobutenol (8) to form the tetracycline core ring system. The first approach involves the reaction of the enone with an anion formed by the deprotonation of a toluate (6) or metallation of a benzylic halide as shown below.

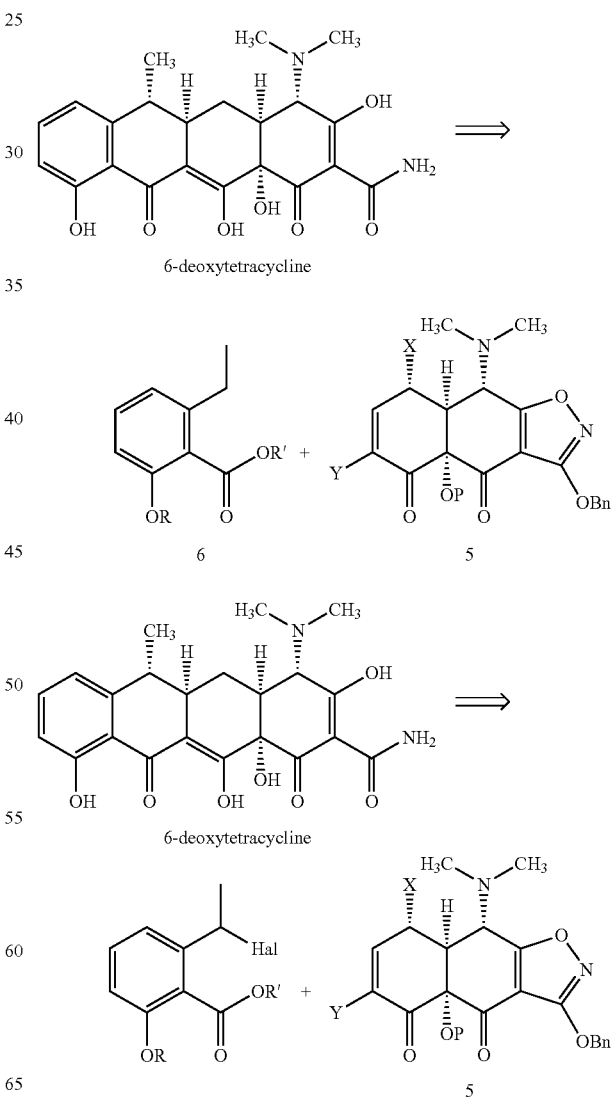

A second approach involves reacting the enone in a Diels-Alder-type reaction with a diene (7) or a benzocyclobutenol (8).

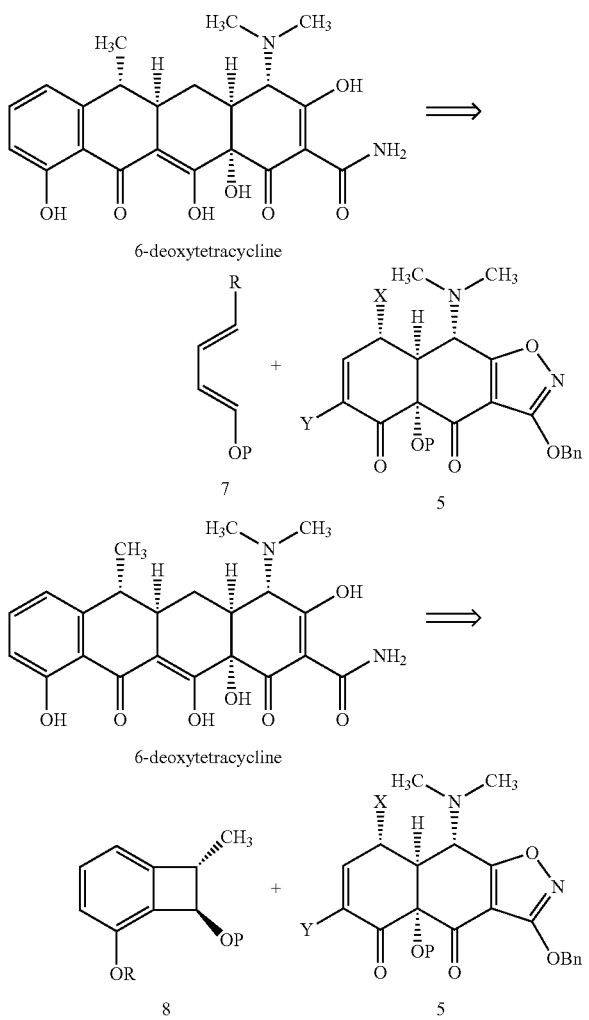

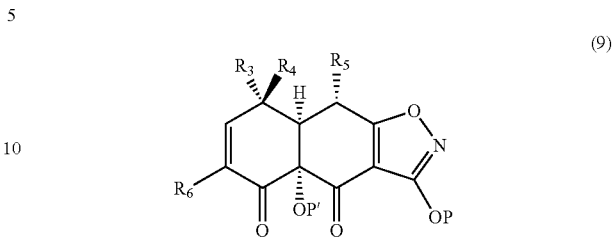

The route yields the highly functionalized chiral enone intermediate (9) in eight steps from an isoxazole aldehyde and allows for the preparation of tetracycline analogs in higher yields that previously attainable.

Although the above approaches to tetracycline analogs are much more efficient than earlier approaches and allow for synthetic variability, there remains a need for improving the efficiency and versatility of these routes to new tetracycline analogs.

SUMMARY OF THE INVENTION

The present invention provides a novel synthetic approach to the functionalized chiral enone of formula (VII) useful in the synthesis of tetracycline analogs. As described herein and in published patent applications (US patent application publication 2005/0282782, published Dec. 1, 2005; international PCT Application WO 2005/112985, published Dec. 1, 2005; international PCT application WO 2007/117639, pupblished Oct. 18, 2007; US patent application publication 2009/0093640, published Apr. 9, 2009; and WO 2008/127361, published Oct. 23, 2008; each of which is incorporated herein by reference), the enone of formula (VII) can be used in various approaches to prepare tetracyclines and analogs thereof. The new synthesis of the enone intermediate, in particular, allows for derivatives with different substituents at positions 4a, 5, 5a, and/or 12a of the tetracycline core to be prepared.

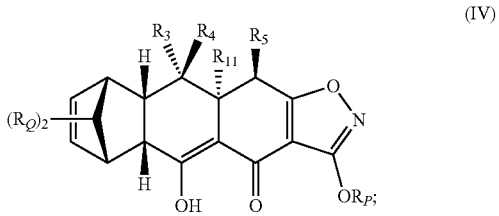

In these approaches, the chiral enone provides the functionalized A and B rings of the tetracycline core, and the D-ring is derived from the toluate (6), benzylic halide, or benzocyclobutenol (8). In bringing the two portions of the tetracycline core together the C-ring is formed, preferably in a stereoselective manner. These new synthetic approaches to tetracycline analogs not only allow for the stereoselective and efficient synthesis of a wide variety of tetracycline analogs never before prepared, but they also allow for preparation of tetracycline analogs in which the D-ring is replaced with a heterocycle, 5-membered ring, or other ring systems. The new methodologies also allow for the prepartion of various pentacyclines or higher cyclines containing aromatic and non-aromatic carbocycles and heterocycles. See U.S. patent application, US2005/0282782, published Dec. 1, 2005; PCT Application WO 05/112985, published Dec. 1, 2005; and U.S. Provisional Patent Application, U.S. Ser. No. 60/790,413, filed Apr. 7, 2006; each of which is incorporated herein by reference.

A second generation route to the functionalized chiral enone intermediate (9) useful in synthesizing tetracyclines was also recently described by Myers and coworkers (US 2009/0093640, published Apr. 9, 2009; U.S. 60/850,859, filed Oct. 11, 2006; and WO2008/127361, published Oct. 23, 2008; each of which is incorporated herein by reference).

An exemplary synthesis of an enone of formula VII is shown below. The synthesis begins with an isoxazole of formula I and a compound of formula II and in four steps yields enone VII. Isoxazole I is deprotonated and allowed to react with a compound of formula II to give an adduct of formula III, where $R_Q$ is, for example, hydrogen, an alkyl moiety, or a silyl moiety. Without work-up or purification, the compound of formula III is treated with a suitable base to induce ring closure and yield a compound of formula IV. A retro Diels-Alder reaction gives a compound of formula V, which is deprotonated and reacted with an electrophile to yield an enone of formula VI. Epimerization at C4 leads to a compound of formula VII. Advantageously, in some embodiments, the use of compounds of formulae II, III, and IV which include at least one silyl moiety at $R_Q$ may reduce the temperature at which the retro Diels-Alder reaction is performed compared to when $R_Q$ is hydrogen. Additionally or alternatively, such compounds including at least one silyl moiety at $R_Q$ may allow synthesis of compounds of formula V in higher yields and/or at reduced reaction times compared to when $R_Q$ is hydrogen, as described in more detail below.

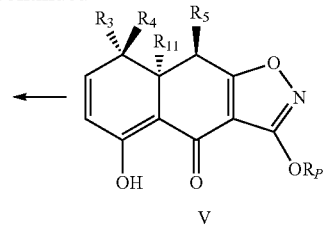

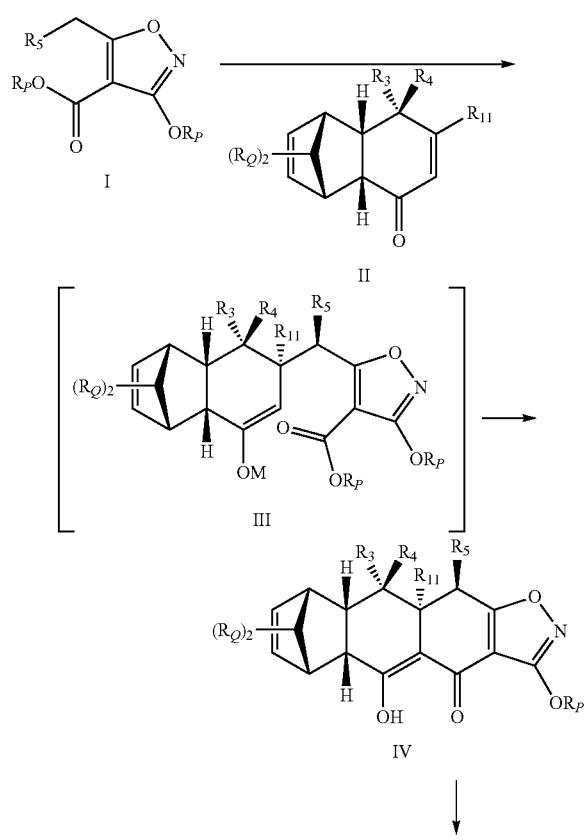

Another exemplary synthesis of an enone of formula VII is shown below, where both $R_Q$ are hydrogen. The synthesis begins with an isoxazole of formula I and a compound of formula IIA and in four steps yields enone VII. Isoxazole I is deprotonated and allowed to react with a compound of formula IIA to give an adduct of formula IIIA. Without work-up or purification, the compound of formula IIIA is treated with a suitable base to induce ring closure and yield a compound of formula IVA. A retro Diels-Alder reaction gives a compound of formula V, which is deprotonated and reacted with an electrophile to give an enone of formula VI. Epimerization leads to a compound of formula VII.

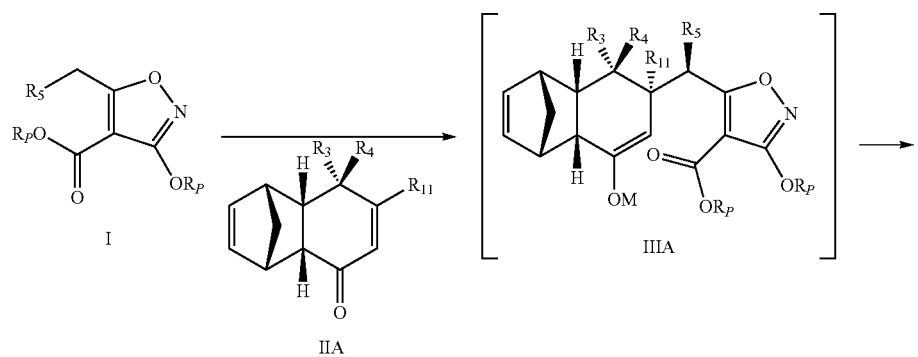

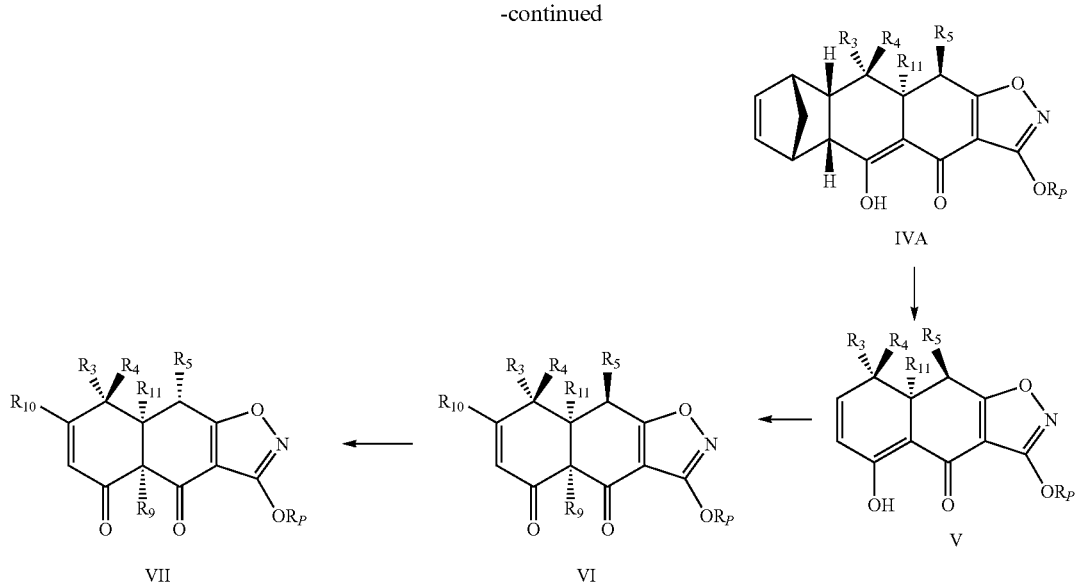

VII  VI  IVA → V

As would be appreciated by one of skill in the art, various substitutions, derivatives, and modifications of the starting materials, intermediates, reagents, and synthetic methodology may be used to prepare enone VI or VII, or derivatives thereof, without departing from the present invention.

In one aspect, the present invention provides for the synthesis of tetracycline analogs and intermediates thereto wherein either or both of $R_{10}$ (at position 5a of the tetracycline core) and $R_{11}$ (at position 4a) are not hydrogen, and also allows for analogs wherein $R_9$ (at position 12a) is not hydroxyl or a protected or modified hydroxyl. In some embodiments, when $R_9$ is not hydroxyl or a protected or modified hydroxyl, $R_{10}$ and $R_{11}$ are both simultaneously hydrogen. Substituents at positions 4a and 5a include, for example, methyl, trifluoromethyl, methoxymethyl, hydroxyl, methoxy, trifluoromethoxy, amino, alkylamino, azido, methylene, fluorine, and other substituents described herein. Substituents at position 12a include, for example, alkyl, alkoxy, methyl, methoxy, alkylamino, dialkylamino, fluoroalkyl, trifluoromethyl, difluoromethyl, fluoromethyl, and other substituents described herein. Substituents such as methyl or other alkyl groups at position C12a would eliminate the teeth- and bone-staining property of many tetracyclines, which many times prevents the use of these antibiotics in the pediatric population.

In another aspect, the invention provides various useful intermediates in the synthetic scheme leading to enones of the formula VII. Particularly useful intermediates include compounds of the formulae:

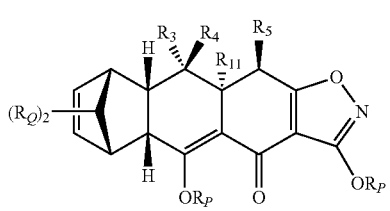

IV

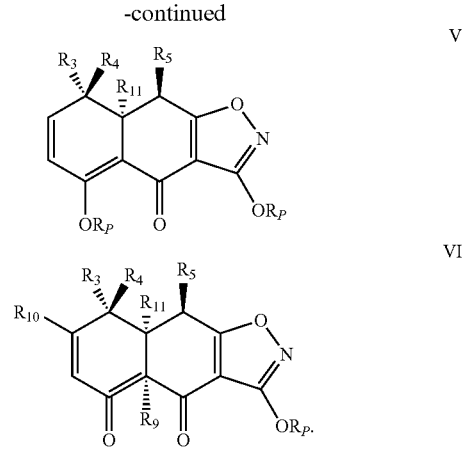

V

VI

The various intermediates with chiral centers are provided in enantiomeric or diasteroemeric pure form or are provided as a mixture of stereoisomers.

The present invention also provides the synthesis of tetracycline anlogs using the synthetic methodology for preparing the enone VII, described herein. In certain embodiments, a chiral enone VII prepared by the methodology described herein is used in combination with the methodologies described in US 2005/0292787, which is incorporated herein by reference, to prepare a tetracycline analog. In certain embodiments, the inventive methods of synthesis of the enone intermediate is used to synthesize any compound described in U.S. patent application, US 2005/0282787, published Dec. 22, 2005; international PCT application, WO 05/112945, published Dec. 1, 2005; U.S. provisional patent application, U.S. Ser. No. 60/790,413, filed Apr. 7, 2006; international PCT application, WO 07/117,639, published Oct. 18, 2007; or international PCT application, WO 08/127, 361, published Oct. 23, 2008; each of which is incorporated herein by reference. The inventive methods and intermediates may also be used to prepare tetracyclines or tetracycline analogs known in the art (e.g., doxycycline, sancycline, minocycline, tigecycline, tetracycline, etc.). The new synthetic approach to the enone intermediate is particularly useful in preparing 6-deoxytetracyclines. The new synthetic methodology and intermediates are also useful in preparing 6-hydroxytetracyclines, pentacyclines, hexacyclines, C5-substituted tetracyclines, C5-unsubstituted tetracyclines, C5a-substituted tetracyclines, C4a-substituted tetracyclines, C12a-substituted tetracyclines, tetracyclines with heterocyclic b-rings, and other tetracycline analogs. Such structures may include $R_9$, $R_{10}$, and $R_{11}$ substituents, wherein one or more of the following conditions are met: i) $R_9$ is not hydroxyl or a protected hydroxyl; ii) $R_{10}$ is not hydrogen; and iii) $R_{11}$ is not hydrogen. As would be appreciated by one of skill in this art, the new synthesis of enone VII is also useful in preparing other organic compounds which may or may not be related to tetracyclines.

Some of the broad classes of compounds available through these new approaches and considered to be a part of the present invention include tetracyclines and various analogs with substituents at positions 4a, 5, 5a, and/or 12a of the tetracycline ring system, wherein substituents at the 12a ($R_9$) position is not —$OR_C$, or substituents at the 5a ($R_{10}$) and 4a ($R_{11}$) positions are not simultaneously hydrogen. Important subclasses of tetracyclines include 6-deoxytetracyclines with or without a C5-hydroxyl group, and 6-hydroxytetracyclines with or without a C5-hydroxyl group. Many of the analogs available through these new approaches have never been synthesized before given the limitations of semi-synthetic approaches and earlier total syntheses. For example, certain substitutions about the D-ring become accessible using the present invention's novel methodologies. In certain classes of compounds of the invention, the D-ring of the tetracyclines analog, which is usually a phenyl ring, is replaced with a heterocyclic moiety, which may be bicyclic or tricyclic. In other classes, the D-ring is replaced with a non-aromatic ring. The size of the D-ring is also not limited to six-membered rings, but instead it may be three-membered, four-membered, five-membered, seven-membered, or larger. In the case of pentacyclines, the five rings may or may not be linear in arrangement. Each of the D- and E-rings may be heterocyclic or carbocyclic, may be aromatic or non-aromatic, and may contain any number of atoms ranging from three to ten atoms. In addition, higher cyclines such as hexacyclines may be prepared. In certain classes, the C-ring may not be fully formed, leading to dicyclines with the A-B fused ring system intact. The compounds of the invention include isomers, stereoisomers, enantiomers, diastereomers, tautomers, protected forms, pro-drugs, salts, and derivatives of any particular compound.

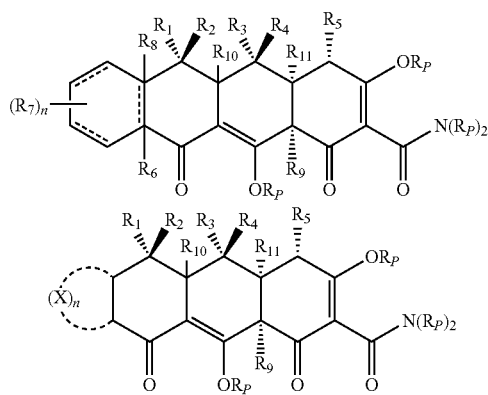

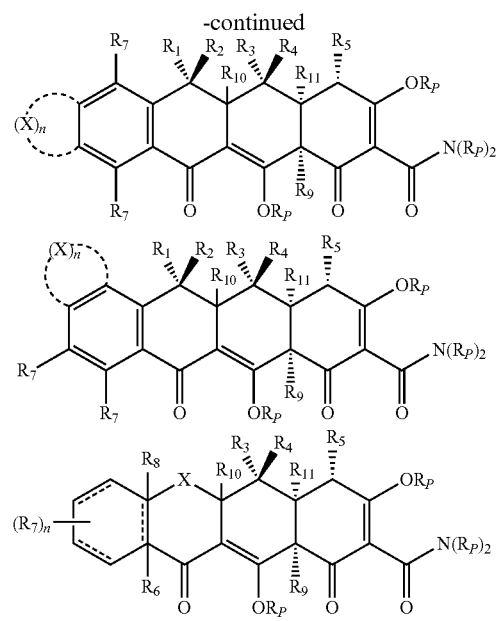

In certain embodiments, the invention provides several basic approaches to the synthesis of tetracycline analogs using the synthesis described herein for preparing the enone intermediate. The first approach to preparing tetracycline analogs involves reaction of the enone with an anion formed by the deprotonation of a toluate or metalation of a benzylic halide. The deprotonation of a toluate is particularly useful in preparing 6-deoxytetracyclines with or without a C5-substituent. The metalation (e.g., metal-halogen exchange (e.g., lithium-halogen exchange), metal-metalloid exchange (e.g., lithium-metalloid exchange) is particularly useful in preparing 6-deoxytetracyclines with or without a C5-substituent as well as pentacyclines. The second approach to preparing tetracycline analogs involves reacting the enone intermediate, as prepared by the inventive methodology, in a Diels-Alder-type reaction with a diene or a benzocyclobutenol. In both of these approaches, the chiral enone provides the functionalized A and B rings of the tetracycline core, and the D-ring is derived from the toluate, benzylic halide, or benzocyclobutenol. In bringing these two portions of the molecule together the C-ring is formed. In certain embodiments, the C-ring is formed in a stereoselective manner. These approaches not only allow for the stereoselective and efficient synthesis of a wide variety of tetracycline analogs, but they also allow for the efficient preparation of tetracycline analogs in which the D-ring is replaced with a heterocycle, 5-membered ring, or other ring system. They also allow the prepartion of various pentacyclines or higher cyclines containing aromatic and non-aromatic carbocycles and heterocycles. These approaches also allow for the preparation of various tricyclines.

In certain embodiments, the inventive intermediates (e.g., enone, derivatives of enone, dicyclines) have biological activity. For example, an intermediate may possess anti-microbial or anti-proliferative activity. In another aspect, the present invention provides methods of treatment and pharmaceutical compositions including the novel compounds of the present invention. The pharmaceutical compositions may optionally include a pharmaceutically acceptable excipient. The methods and pharmaceutical compositions may be used to treat any infection including cholera, influenza, bronchitis, acne, malaria, urinary tract infections, sexually transmitted diseases including syphilis and gonorrhea, Legionnaires' disease, Lyme disease, Rocky Mountain spotted fever, Q fever, typhus, bubonic plague, gas gangrene, hospital acquired infections, leptospirosis, whooping cough, and anthrax. In certain embodiments, the infections are caused by tetracycline-resistant organisms. In certain instances, the compounds of the invention exhibit anti-neoplastic or anti-proliferative activity, in which case the compounds may be useful in the treatment of diseases such as cancer, autoimmune diseases, inflammatory diseases, and diabetic retinopathy. The methods and compositions may be used to treat disease in humans and other animals including domesticated animals. Any mode of administration including oral and parenteral administration of a pharmaceutical composition comprising an inventive compound may be used.

In some embodiments, tetracycline analogs having non-hydrogen substituents at position C4a and/or C12a have reduced metabolism or phototransformation to B-ring quinone derivatives as compared to known tetracyclines. A reduction in this undesired chemistry may reduce photosensitivity and teeth-staining properties of tetracycline analogs.

Given the versatility and efficiency of the synthesis of tetracycline analogs using enone VII as an intermediate, the present invention represents an improvement in the overall synthetic approach to tetracycline analogs. The present invention allows for the preparation of tetracycline analogs in higher yields than previously attainable and allows for the synthesis of novel tetracycline analogs that were previously inaccessible. The new synthetic approach to the enone intermediate also makes the synthesis of tetracycline analogs more amenable to large-scale production given its improved overall yield. In some embodiments, the present invention provides new synthetic methods to enones of formula VII, new intermediates to enones of formula VII, and/or new tetracycline analogs and the synthesis of the same from enones of formula VII.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999; *Strategic Applications of Named Reactions in Organic Synthesis*, Laszlo Kurti and Barbara Czako, Academic Press, 1$^{st}$ edition: Mar. 18, 2005; *Comprehensive Organic Transformations: A Guide to Functional Group Preparations*, Richard C. Larock, Wiley-VCH, 2$^{nd}$ edition: Nov. 3, 1999; *Name Reactions of Functional Group Transformations, Comprehensive Name Reactions*, Jie Jack Li and E. J. Corey, Wiley: Jul. 16, 2007; *Greene's Protective Groups in Organic Synthesis*, Peter G. M. Wuts and Theodora W. Greene, Wiley-Interscience, 4$^{th}$ edition: Oct. 30, 2006; and *March's Advanced Organic Chemistry: Reactions, Mechanisms, and Structure*, Michael B. Smith and Jerry March, Wiley-Interscience, 6$^{th}$ edition: Jan. 16, 2007, the entire contents of which are incorporated herein by reference.

It should be understood that any atom described herein includes all isotope forms of that atom. For example, —H may be —$^1$H, —$^2$H (-D), —$^3$H, etc. Accordingly, the structures described herein include all isotopologues thereof.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

One of ordinary skill in the art will appreciate that the synthetic methods, as described herein, utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)-ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethlsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Fourth Ed. Greene, T. W. and Wuts, P. G., Eds., John Wiley & Sons, New York: 2007, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkoxy," or "thioalkyl" as used herein refers to an alkyl group, as previously defined, attached to the parent molecule through an oxygen atom or through a sulfur atom. In certain embodiments, the alkyl, alkenyl, and alkynyl groups contain 1-20 alipahtic carbon atoms. In certain other embodiments, the alkyl, alkenyl, and alkynyl groups contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms. Examples of alkoxy, include but are not limited to, methoxy, ethoxy, propoxy, isopropoxy, n-butoxy, tert-butoxy, neopentoxy, and n-hexoxy. Examples of thioalkyl include, but are not limited to, methylthio, ethylthio, propylthio, isopropylthio, n-butylthio, and the like.

The term "alkylamino" refers to a group having the structure —NHR', wherein R' is aliphatic, as defined herein. In certain embodiments, the aliphatic group contains 1-20 aliphatic carbon atoms. In certain other embodiments, the aliphatic group contains 1-10 aliphatic carbon atoms. In yet other embodiments, the aliphatic group employed in the invention contain 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "dialkylamino" refers to a group having the structure —NRR', wherein R and R' are each an aliphatic group, as defined herein. R and R' may be the same or different in an dialkyamino moiety. In certain embodiments, the aliphatic groups contains 1-20 aliphatic carbon atoms. In certain other embodiments, the aliphatic groups contains 1-10 aliphatic carbon atoms. In yet other embodiments, the aliphatic groups employed in the invention contain 1-8 aliphatic carbon atoms. In still other embodiments, the aliphatic groups contains 1-6 aliphatic carbon atoms. In yet other embodiments, the aliphatic groups contains 1-4 aliphatic carbon atoms. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —N$_3$; —NO$_2$; —CN; —CF$_3$; —CH$_2$CF$_3$; —CHCl$_2$; —CH$_2$OH; —CH$_2$OR$_x$; —CH$_2$N(R$_x$)$_2$; =C(R$_x$)$_2$; —CH$_2$R$_x$; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; -OCO$_2$R$_x$; —OC(R$_x$)$_3$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, haloaliphatic, aryl, heteroaryl, arylalkyl, or heteroarylalkyl, wherein any of the aliphatic, heteroaliphatic, haloaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl," as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —N$_3$; —NO$_2$; —CN; —CF$_3$; —CH$_2$CF$_3$; —CHCl$_2$; —CH$_2$OH; —CH$_2$OR$_x$; —CH$_2$R$_x$; —CH$_2$CH$_2$OH; —CH$_2$NH$_2$; —CH$_2$N(R$_x$)$_2$; =C(R$_x$)$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OC(R$_x$)$_3$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, haloaliphatic, aryl, heteroaryl, arylalkyl, or heteroarylalkyl, wherein any of the aliphatic, heteroaliphatic, haloaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "cycloalkyl," as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, haloaliphatic, or heterocyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —N$_3$; —NO$_2$; —CN; —CF$_3$; —CH$_2$CF$_3$; —CHCl$_2$; —CH$_2$OH; —CH$_2$OR$_x$; —CH$_2$R$_x$; —CH$_2$CH$_2$OH; —CH$_2$NH$_2$; —CH$_2$N(R$_x$)$_2$; =C(R$_x$)$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OC(R$_x$)$_3$; —OCON(R$_x$)$_2$; —N(R$_x$)$_2$; —S(O)$_2$R$_x$; —NR$_x$(CO)R$_x$, wherein each occurrence of $R_x$ independently includes, but is not limited to, aliphatic, heteroaliphatic, haloaliphatic, aryl, heteroaryl, arylalkyl, or heteroarylalkyl, wherein any of the aliphatic, heteroaliphatic, haloaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroaliphatic," as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —N$_3$; —NO$_2$; —CN; —CF$_3$; —CH$_2$CF$_3$; —CHCl$_2$; —CH$_2$OH; —CH$_2$OR$_x$; —CH$_2$R$_x$; —CH$_2$CH$_2$OH; —CH$_2$NH$_2$; —CH$_2$N(R$_x$)$_2$; =C(R$_x$)$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OC(R$_x$)$_3$; —OCON(R$_x$)$_2$; —N(R$_x$)$_2$; —S(O)$_2$R$_x$; —NR$_x$(CO)R$_x$, wherein each occurrence of $R_x$ independently includes, but is not limited to, aliphatic, heteroaliphatic, haloaliphatic, aryl, heteroaryl, arylalkyl, or heteroarylalkyl, wherein any of the aliphatic, heteroaliphatic, haloaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The terms "halo" and "halogen" as used herein refer to an atom selected from fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like. The term "haloaliphatic" denotes an aliphatic group, as defined above, having one, two, or three halogen atoms attached thereto.

The term "heterocycloalkyl" or "heterocycle," as used herein, refers to a non-aromatic 5-, 6-, or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —N$_3$; —NO$_2$; —CN; —CF$_3$; —CH$_2$CF$_3$; —CHCl$_2$; —CH$_2$OH; —CH$_2$OR$_x$; —CH$_2$R$_x$; —CH$_2$CH$_2$OH; —CH$_2$NH$_2$; —CH$_2$N(R$_x$)$_2$; =C(R$_x$)$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OC(R$_x$)$_3$; —OCON(R$_x$)$_2$; —N(R$_x$)$_2$; —S(O)$_2$R$_x$; —NR$_x$(CO)R$_x$, wherein each occurrence of $R_x$ independently includes, but is not limited to, aliphatic, heteroaliphatic, haloaliphatic, aryl, heteroaryl, arylalkyl, or heteroarylalkyl, wherein any of the aliphatic, heteroaliphatic, haloaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples which are described herein.

"Carbocycle": The term "carbocycle," as used herein, refers to an aromatic or non-aromatic ring in which each atom of the ring is a carbon atom.

"Independently selected": The term "independently selected" is used herein to indicate that the R groups can be identical or different.

"Labeled": As used herein, the term "labeled" is intended to mean that a compound has at least one element, isotope, or chemical compound attached to enable the detection of the compound. In general, labels typically fall into three classes: a) isotopic labels, which may be radioactive or heavy isotopes, including, but not limited to, $^2$H, $^3$H, $^{32}$P, $^{35}$S, $^{67}$Ga, $^{99m}$Tc (Tc-99m), $^{111}$In, $^{123}$I, $^{125}$I, $^{169}$Yb and $^{186}$Re; b) immune labels, which may be antibodies or antigens, which may be bound to enzymes (such as horseradish peroxidase) that produce detectable agents; and c) colored, luminescent, phosphorescent, or fluorescent dyes. It will be appreciated that the labels may be incorporated into the compound at any position that does not interfere with the biological activity or characteristic of the compound that is being detected. In certain embodiments, hydrogen atoms in the compound are replaced with deuterium atoms ($^2$H) to slow the degradation of compound in vivo. Due to isotope effects, enzymatic degradation of the deuterated tetracyclines may be slowed thereby increasing the half-life of the compound in vivo. The term "isotopologue" refers to a species that has the same chemical structure and formula as a specific compound of this invention, with the exception of the isotopic composition at one or more positions, e.g., H vs. D. Thus, an isotopologue differs from a specific compound of this invention in the isotopic composition thereof. In certain embodiments of the invention, photoaffinity labeling is utilized for the direct elucidation of intermolecular interactions in biological systems. A variety of known photophores can be employed, most relying on photoconversion of diazo compounds, azides, or diazirines to nitrenes or carbenes (See, Bayley, H., Photogenerated Reagents in Biochemistry and Molecular Biology (1983), Elsevier, Amsterdam.), the entire contents of which are hereby incorporated by reference. In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

"Tautomers": As used herein, the term "tautomers" are particular isomers of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, and pyridione-hydroxypyridine forms.

Definitions of non-chemical terms used throughout the specification include:

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). A non-human animal may be a transgenic animal.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

"Effective amount": In general, the "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient. For example, the effective amount of a tetracycline analog antibiotic is the amount that results in a sufficient concentration at the site of the infection to kill the microorganism causing the infection (bacteriocidal) or to inhibit the reproduction of such microorganisms (bacteriostatic). In another example, the effective amount of tetracycline analog antibiotic is the amount sufficient to reverse clinicals signs and symptoms of the infection, including fever, redness, warmth, pain, chills, cultures, and pus production.

BRIEF DESCRIPTION OF THE DRAWING

FIGS. 2-7 are tables showing $IC_{50}$ values for tetracyclines described herein tested with various Gram-positive and Gram-negative bacterial strains.

DETAILED DESCRIPTION OF CERTAIN EMBODIMENTS OF THE INVENTION

Figure 1:
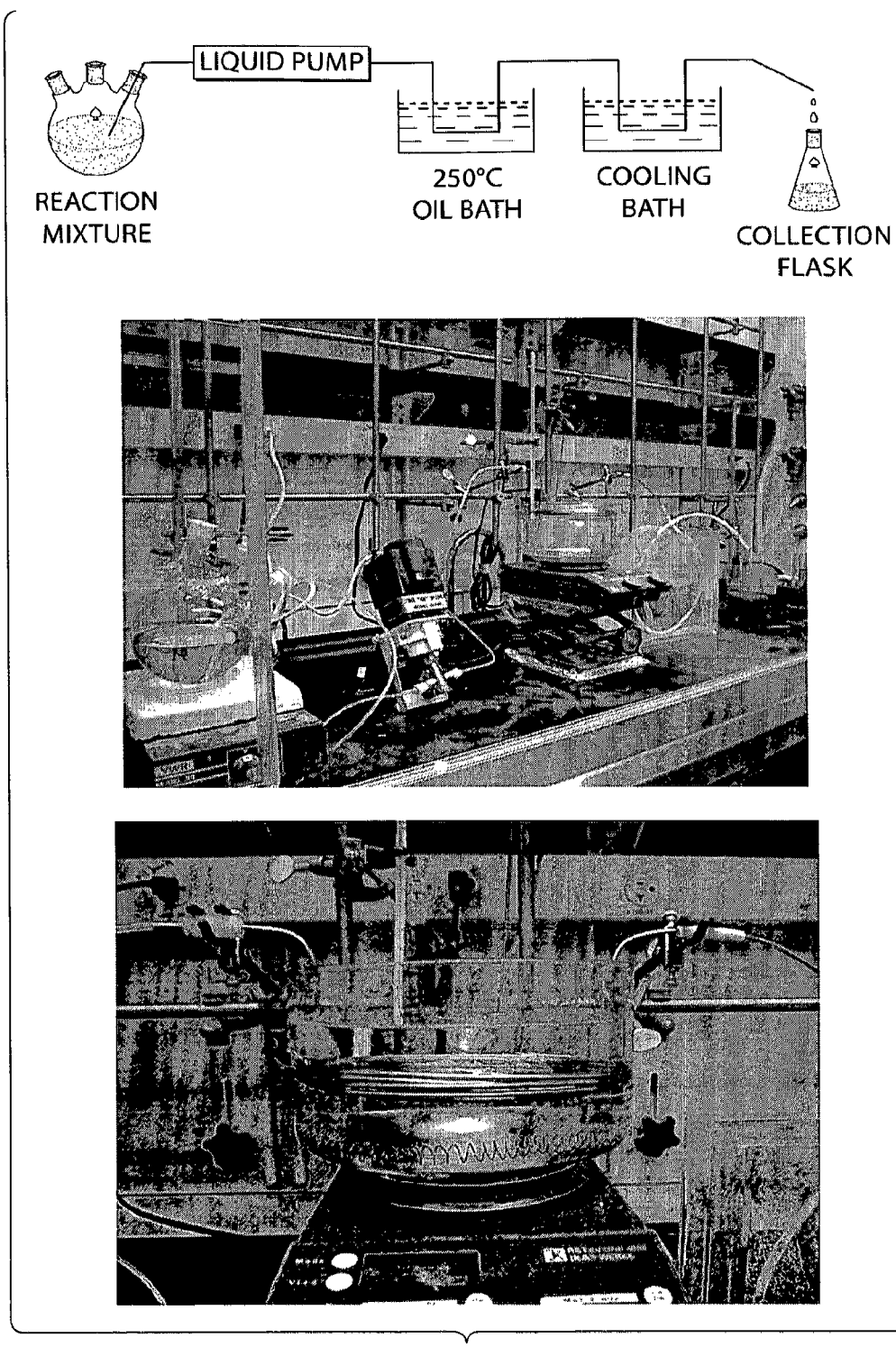
FIG. 1 shows a setup for a continuous flow reaction useful in converting a compound of formula IV or IVA into a compound of formula V.
Figure 3C:
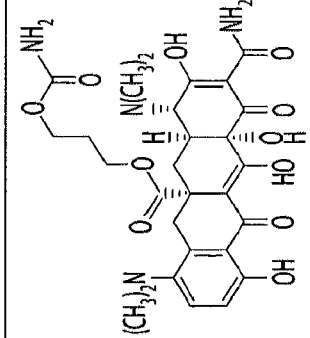
Figure 5F:
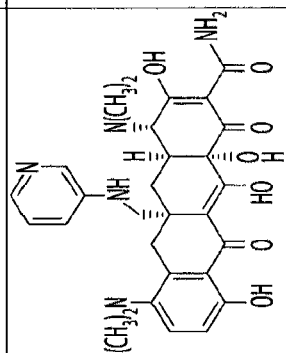
Figure 5G:
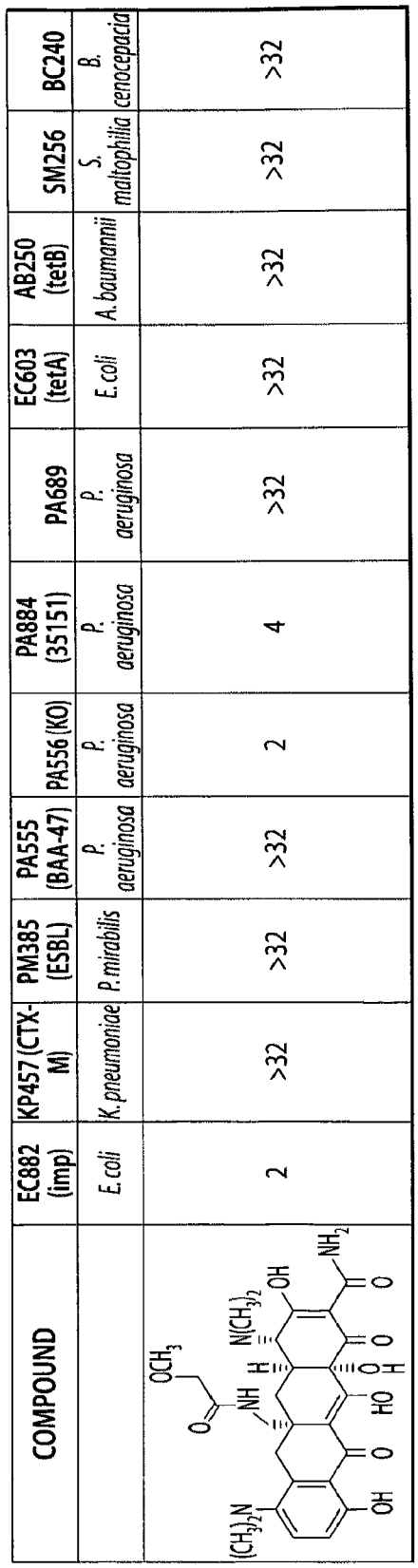
Figure 5H:
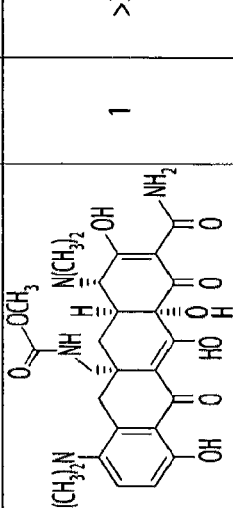

The present invention provides a strategy for the synthesis of tetracycline analogs (particularly, position 4a, 5, 5a, and 12a analogs) via a convergent synthesis using, as an intermediate, the highly functionalized chiral enone VII as shown below:

wherein $R_3$ and $R_4$ are each independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_B$; =O; —$CH_2OR_B$; —$CH_2R_B$; —$CH_2N(R_B)_2$; =$C(R_B)_2$; —$C(=O)R_B$; —$CO_2R_B$; —CN; —SCN; —$SR_B$; —$SOR_B$; —$SO_2R_B$; —$NO_2$; —$N_3$; —$N(R_B)_2$; —$NHC(O)R_B$; or —$C(R_B)_3$; wherein each occurrence of $R_B$ is independently hydrogen, halogen, azido, a protecting group, aliphatic, heteroaliphatic, haloaliphatic, acyl, aryl, heteroaryl, alkoxy, aryloxy, alkylthio, arylthio, amino, alkylamino, dialkylamino, heteroaryloxy, or heteroarylthio;

$R_5$, $R_9$, $R_{10}$, and $R_{11}$ are each independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —$CH_2OR_C$; —$CH_2R_C$; —$CH_2N(R_C)_2$; =$C(R_C)_2$; —$C(=O)R_C$; —$CO_2R_C$; —CN; —SCN; —$SR_C$; —$SOR_C$; —$SO_2R_C$; —$NO_2$; —$N_3$; —$N(R_C)_2$; —$NHC(O)R_C$; or —$C(R_C)_3$; wherein each occurrence of $R_C$ is independently hydrogen, halogen, azido, a protecting group, aliphatic, heteroaliphatic, haloaliphatic, acyl, aryl, heteroaryl, alkoxy, aryloxy, alkylthio, arylthio, amino, alkylamino, dialkylamino, heteroaryloxy, or heteroarylthio; and $R_P$ is hydrogen, substituted or unsubstituted aliphatic, substituted or unsubstituted heteroaliphatic, haloaliphatic, a protecting group, substituted or unsubstituted acyl, substituted or unsubstituted aryl, or substituted or unsubstituted heteroaryl;

provided that when $R_9$ is —$OR_C$, $R_{10}$ and $R_{11}$ are not simultaneously hydrogen.

In some embodiments, $R_{10}$ is not hydrogen. In some embodiments, $R_{11}$ is not hydrogen. In some embodiments, at least one of $R_{10}$ and $R_{11}$ is not hydrogen. In some embodiments, both $R_{10}$ and $R_{11}$ are not hydrogen.

In some embodiments, $R_9$ is not —$OR_C$. In some embodiments, $R_9$ is not —$OR_C$ when both $R_{10}$ and $R_{11}$ are hydrogen. In some embodiments, $R_9$ is not —$OR_C$, wherein $R_C$ is hydrogen or an oxygen-protecting group. In certain embodiments, $R_9$ is not —OH. In other embodiments, when $R_9$ is —$OR_C$, the substituents at $R_{10}$ and $R_{11}$ are not simultaneously hydrogen, and $R_3$ and $R_4$ are not hydrogen or —$OR_B$. In some embodiments, when $R_9$ is not hydroxyl or a protected hydroxyl, $R_{10}$ and $R_{11}$ may be simultaneously hydrogen.

In embodiments in which $R_9$ is not —$OR_C$, the enone may have the formula:

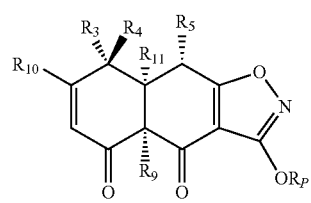

(VII)

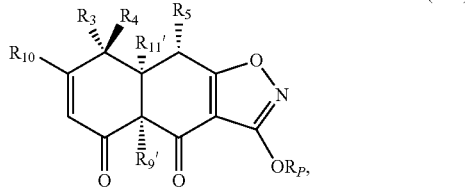

(VII')

wherein $R_9'$ is hydrogen; a halogen; cyclic or acyclic, substituted or unsubstituted, branched or unbranched aliphatic;

cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_C$; —CH$_2$R$_C$; —CH$_2$N(R$_C$)$_2$; =C(R$_C$)$_2$; —C(=O)R$_C$; —CO$_2$R$_C$; —CN; —SCN; —SR$_C$; —SOR$_C$; —SO$_2$R$_C$; —NO$_2$; —N$_3$; —N(R$_C$)$_2$; —NHC(O)R$_C$; or —C(R$_C$)$_3$; wherein each occurrence of R$_C$ is independently hydrogen, halogen, azido, a protecting group, aliphatic, heteroaliphatic, haloaliphatic, acyl, aryl, heteroaryl, alkoxy, aryloxy, alkylthio, arylthio, amino, alkylamino, dialkylamino, heteroaryloxy, or heteroarylthio; and R$_3$, R$_4$, R$_5$, R$_{10}$, R$_{11}$, and R$_P$ are as defined above and described herein.

In embodiments in which R$_{10}$ is not hydrogen, the enone may have the formula:

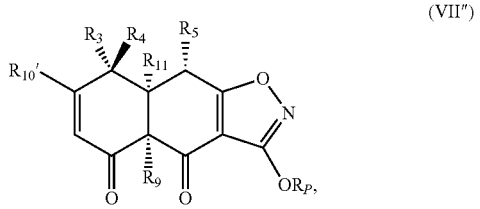

(VII″)

wherein R$_{10}$' is a halogen but not hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_C$; —CH$_2$OR$_C$; —CH$_2$R$_C$; —CH$_2$N(R$_C$)$_2$; =C(R$_C$)$_2$; —C(=O)R$_C$; —CO$_2$R$_C$; —CN; —SCN; —SR$_C$; —SOR$_C$; —SO$_2$R$_C$; —NO$_2$; —N$_3$; —N(R$_C$)$_2$; —NHC(O)R$_C$; or —C(R$_C$)$_3$; wherein each occurrence of R$_C$ is independently hydrogen, halogen, azido, a protecting group, aliphatic, heteroaliphatic, haloaliphatic, acyl, aryl, heteroaryl, alkoxy, aryloxy, alkylthio, arylthio, amino, alkylamino, dialkylamino, heteroaryloxy, or heteroarylthio; and R$_3$, R$_4$, R$_5$, R$_9$, R$_{11}$, and R$_P$ are as defined above and described herein.

In embodiments in which R$_{11}$ is not hydrogen, the enone may have the formula:

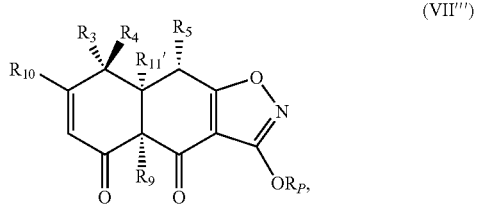

(VII‴)

wherein R$_{11}$' is a halogen but not hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_C$; —CH$_2$OR$_C$; —CH$_2$R$_C$; —CH$_2$N(R$_C$)$_2$; =C(R$_C$)$_2$; —C(=O)R$_C$; —CO$_2$R$_C$; —CN; —SCN; —SR$_C$; —SOR$_C$; —SO$_2$R$_C$; —NO$_2$; —N$_3$; —N(R$_C$)$_2$; —NHC(O)R$_C$; or —C(R$_C$)$_3$; wherein each occurrence of R$_C$ is independently hydrogen, halogen, azido, a protecting group, aliphatic, heteroaliphatic, haloaliphatic, acyl, aryl, heteroaryl, alkoxy, aryloxy, alkylthio, arylthio, amino, alkylamino, dialkylamino, heteroaryloxy, or heteroarylthio; and R$_3$, R$_4$, R$_5$, R$_9$, R$_{10}$, and R$_P$ are as defined above and described herein.

The chiral enone of formulas VII, VII', VII″, and VII‴ can be reacted with anions of phthalides, anions of toluates, benzocyclobutenole, or dienes to yield tetracycline analogs including tetracyclines, heterocyclic tetracyclines, pentacyclines, heterocyclic pentacyclines, tricyclines, polycyclines, and heterocyclic polycyclines. The new compounds are expected to have anti-microial activity and/or aniproliferative activity, and may be tested for anti-microbial activity against microbes including traditionally tetracycline-sensitive organisms as well as organisms known to be tetracycline-resistant. Compounds found to be bacteriocidal or bacteriostatic may be used in formulating pharmaceutical compositions for the treatment of infections in human and veterinary medicine. The compounds may also be tested for antiproliferative activity. Compounds described herein may be useful in the treatment of proliferative diseases including cancer, anti-inflammatory diseases, autoimmune diseases, benign neoplasms, and diabetic retinopathy, as well as other diseases and conditions. The inventive approach to the synthesis of tetracycline analogs allows for the efficient synthesis of many compounds never before prepared or available using earlier routes and semi-synthetic techniques.

In some embodiments, tetracycline analogs having non-hydrogen substituents at position C4a or C12a are precluded from metabolism or phototransformation to B-ring quinone derivatives, unlike known tetracyclines. This undesired chemistry leads to photosensitivity and teeth-staining properties, preventing the use of tetracyclines in children.

Compounds

Compounds of the present invention include tetracycline analogs, heterocyclic tetracycline analogs, dicyclines, tricyclines, pentacyclines, heterocylic pentatcyclines, bridged pentacyclines, heterocyclic polycyclines, bridged polycyclines, and other polycyclines. In certain embodiments, the compounds of the invention exhibit antimicrobial activity. For example, the compound may have a mean inhibitory concentration, with respect to a particular bacteria, of less than 50 µg/mL, preferably less than 25 µg/mL, more preferably less than 5 µg/mL, and most preferably less than 1 µg/mL. For example, infection caused by the following organisms may be treated with antimicrobial compounds of the invention: Gram-positives—*Staphylococcus aureus, Streptococcus* Group A, *Streptococcus viridans, Streptococcus pneumoniae*; Gram-negatives—*Neisseria meningitidis, Neisseria gonorrhoeae, Haemophilus influenzae, Escherichia coli, Bacteroides fragilis*, other *Bacteroides*; and Others—*Mycoplasma pneumoniae, Treponema pallidum, Rickettsia*, and *Chlamydia*. In other embodiments, the compounds of the invention exhibit antiproliferative activity.

In certain embodiments, the tetracycline analogs of the present invention are represented by the formula:

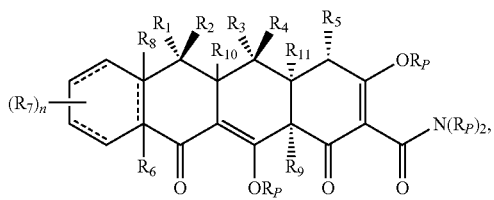

(XI)

or a pharmaceutically acceptable salt thereof;
wherein
---- represents a single or double bond;
$R_1$ and $R_2$ are each independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —$CH_2OR_A$; —$CH_2N(R_A)_2$; =$C(R_A)_2$; —$CH_2R_A$; —$C(=O)R_A$; —$CO_2R_A$; —CN; —SCN; —$SR_A$; —$SOR_A$; —$SO_2R_A$; —$N_3$; —$NO_2$; —$N(R_A)_2$; —$NHC(O)R_A$; —$NHSO_2R_A$; or —$C(R_A)_3$; wherein each occurrence of $R_A$ is independently hydrogen, halogen, azido, a protecting group, aliphatic, heteroaliphatic, haloaliphatic, acyl, aryl, heteroaryl, alkoxy, aryloxy, alkylthio, arylthio, amino, alkylamino, dialkylamino, heteroaryloxy, or heteroarylthio; or $R_1$ and $R_2$ are taken together to form =O;

$R_3$, $R_4$, $R_5$, $R_9$, $R_{10}$, and $R_{11}$ are defined herein;

$R_7$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —$CH_2OR_C$; —$CH_2R_C$; —$CH_2N(R_C)_2$; =$C(R_C)_2$; —$C(=O)R_C$; —$CO_2R_C$; —CN; —SCN; —$SR_C$; —$SOR_C$; —$SO_2R_C$; —$N_3$; —$NO_2$; —$N(R_C)_2$; —$NHC(O)R_C$; —$NHSO_2R_C$; or —$C(R_C)_3$; wherein each occurrence of $R_C$ is independently hydrogen, halogen, azido, a protecting group, aliphatic, heteroaliphatic, haloaliphatic, acyl, aryl, heteroaryl, alkoxy, aryloxy, alkylthio, arylthio, amino, alkylamino, dialkylamino, heteroaryloxy, or heteroarylthio;

$R_6$ and $R_8$ are absent if the dashed line between the carbon atoms to which $R_6$ and $R_8$ are attached represents a bond, or are each independently hydrogen, halogen, substituted or unsubstituted aliphatic, substituted or unsubstituted heteroaliphatic, haloaliphatic, substituted or unsubstituted alkoxy, —OH, —CN, —SCN, —SH, alkylthio, —$NO_2$, amino, alkylamino, or dialkylamino;

each $R_P$ is independently hydrogen, substituted or unsubstituted aliphatic, substituted or unsubstituted heteroaliphatic, haloaliphatic, a protecting group, substituted or unsubstituted acyl, substituted or unsubstituted aryl, or substituted or unsubstituted heteroaryl; and n is an integer in the range of 0 to 8, inclusive; provided that when $R_9$ is —$OR_C$, $R_{10}$ and $R_{11}$ are not simultaneously hydrogen.

In some embodiments, $R_{10}$ is not hydrogen. In some embodiments, $R_{11}$ is not hydrogen. In some embodiments, at least one of $R_{10}$ and $R_{11}$ is not hydrogen. In some embodiments, both $R_{10}$ and $R_{11}$ are not hydrogen.

In some embodiments, $R_9$ is not —$OR_C$. In some embodiments, $R_9$ is not —$OR_C$ when both $R_{10}$ and $R_{11}$ are hydrogen. In some embodiments, $R_9$ is not —$OR_C$, wherein $R_C$ is hydrogen or an oxygen-protecting group. In certain embodiments, $R_9$ is not —OH. In other embodiments, when $R_9$ is —$OR_C$, the substituents at $R_{10}$ and $R_{11}$ are not simultaneously hydrogen, and $R_3$ and $R_4$ are not hydrogen or —$OR_B$. In some embodiments, when $R_9$ is not hydroxyl or a protected hydroxyl, $R_{10}$ and $R_{11}$ may be simultaneously hydrogen.

In embodiments in which $R_9$ is not —$OR_C$, the tetracycline analog may have the formula:

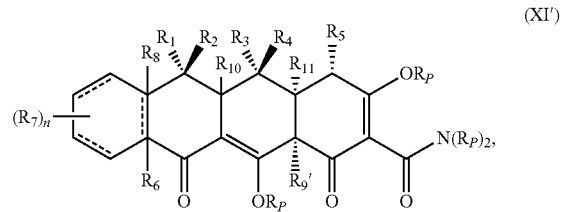

(XI')

wherein $R_1$, $R_2$, $R_3$, $R_4$, $R_5$, $R_6$, $R_7$, $R_8$, $R_9'$, $R_{10}$, $R_{11}$, and $R_P$ are as defined above and described herein, and n is an integer in the range of 0 to 8, inclusive.

In embodiments in which $R_{10}$ is not hydrogen, the enone may have the formula:

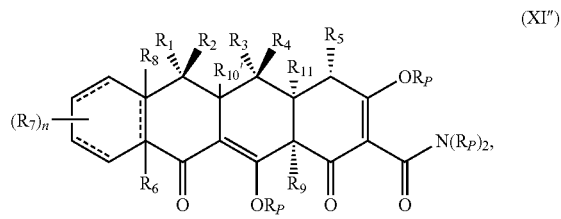

(XI'')

wherein $R_1$, $R_2$, $R_3$, $R_4$, $R_5$, $R_6$, $R_7$, $R_8$, $R_9$, $R_{10}'$, $R_{11}$, and $R_P$ are as defined above and described herein, and n is an integer in the range of 0 to 8, inclusive.

In embodiments in which $R_{11}$ is not hydrogen, the enone may have the formula:

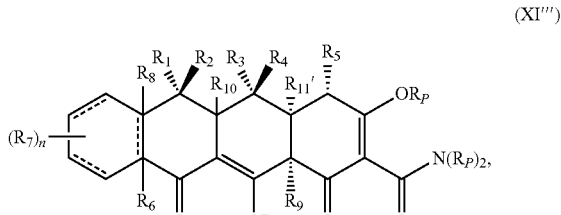

(XI''')

wherein $R_1$, $R_2$, $R_3$, $R_4$, $R_5$, $R_6$, $R_7$, $R_8$, $R_9$, $R_{10}$, $R_{11}'$, and $R_P$ are as defined above and described herein, and n is an integer in the range of 0 to 8, inclusive.

In some embodiments, the tetracycline analogs of formula XI are of one of the following formulae:

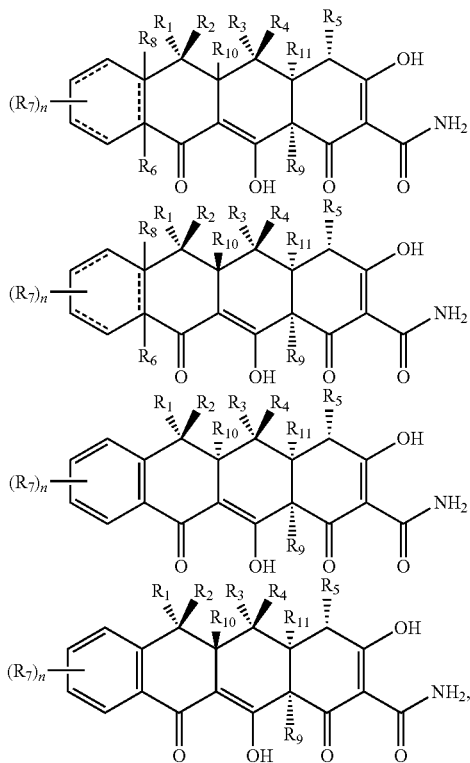

wherein $R_1$, $R_2$, $R_3$, $R_4$, $R_5$, $R_6$, $R_7$, $R_8$, $R_{10}$, and $R_{11}$ are as defined above and described herein; and n is an integer in the range of 0 to 8, inclusive; provided that when $R_9$ is —$OR_C$, and $R_{11}$ are not simultaneously hydrogen.

The D-ring of the tetracycline analogs may include one, two, or three double bonds. In certain embodiments, the D-ring is aromatic. In other embodiments, the D-ring includes only one double bond, and in yet other embodiments, the D-ring includes two double bonds which may or may not be in conjugation. The D-ring may be substituted with various groups $R_7$, $R_6$, and $R_8$ as defined above and described herein.

In certain embodiments, $R_1$ is hydrogen. In other embodiments, $R_1$ is lower alkyl, alkenyl, or alkynyl. In some embodiments, $R_1$ is $C_{1-6}$ alkyl. In yet other embodiments, $R_1$ is methyl, ethyl, n-propyl, cyclopropyl, or isopropyl. In still other embodiments $R_1$ is methyl.

In certain embodiments, $R_2$ is hydrogen. In other embodiments, $R_2$ is hydroxyl or a protected hydroxyl group. In certain embodiments, $R_2$ is alkoxy. In yet other embodiments, $R_2$ is a lower alkyl, alkenyl, or alkynyl group. In some embodiments, $R_2$ is $C_{1-6}$ alkyl. In certain embodiments, $R_1$ is methyl, and $R_2$ is hydroxyl. In other embodiments, $R_1$ is methyl, and $R_2$ is hydrogen. In other embodiments, $R_1$ and $R_2$ are both hydrogen. In certain other embodiments, $R_1$ and $R_2$ are taken together to form a carbocyclic or heterocyclic ring system spiro-linked to the C ring of the tetracycline analog.

In certain embodiments, $R_3$ is hydrogen. In some embodiments, $R_3$ is halogen. In some embodiments, $R_3$ is aliphatic. In certain embodiments, $R_3$ is $C_{1-6}$ alkyl. In certain embodiments, $R_3$ is fluorine. In some embodiments, $R_3$ is —$OR_B$. In certain embodiments, embodiments, $R_3$ is a hydroxyl group or a protected hydroxyl group. In other embodiments, $R_3$ is alkoxy. In still further embodiments, $R_3$ is lower alkyl, alkenyl, or alkynyl.

In certain embodiments, $R_4$ is hydrogen. In some embodiments, $R_4$ is halogen. In some embodiments, $R_4$ is aliphatic. In certain embodiments, $R_4$ is $C_{1-6}$ alkyl. In certain embodiments, $R_4$ is fluorine. In some embodiments, $R_4$ is —$OR_B$. In certain embodiments, embodiments, $R_4$ is a hydroxyl group or a protected hydroxyl group. In other embodiments, $R_4$ is alkoxy. In still further embodiments, $R_4$ is lower alkyl, alkenyl, or alkynyl. In certain embodiments, both $R_3$ and $R_4$ are hydrogen. In certain other embodiments, $R_3$ and $R_4$ are both fluorine. In yet other embodiments, $R_3$ and $R_4$ are taken together to form a carbocyclic or heterocyclic ring system spiro-linked to the B-ring of the tetracycline analog.

In some embodiments, $R_5$ is —$N(R_C)_2$ or —$OR_C$. In some embodiments, $R_5$ is amino, alkylamino, or dialkylamino. In certain embodiments, $R_5$ is dimethylamino, diethylamino, methyl(ethyl)amino, dipropylamino, methyl(propyl)amino, or ethyl(propyl)amino. In other embodiments, $R_5$ is (tert-butyldiphenylsilyl)amino. In some embodiments, $R_5$ is —$C(R_C)_3$, wherein $R_C$ is as defined and described herein. In some embodiments, $R_5$ is methylene. In some embodiments, $R_5$ is —$CH_2N(R_C)_2$, wherein $R_C$ is as defined and described herein. In some embodiments, $R_5$ is —$CH_2N(CH_3)_2$. In other embodiments, $R_5$ is hydroxyl, protected hydroxyl, or alkoxy. In yet other embodiments, $R_5$ is sulfhydryl, protected sulfhydryl, or alkylthioxy.

In certain embodiments, $R_7$ is hydroxyl, protected hydroxyl, alkoxy, lower alkyl, lower alkenyl, lower alkynyl, or halogen. In certain other embodiments, $R_7$ is —$OR_C$, —$SR_C$, —$N(R_C)_2$, or —$NHC(O)R_C$. In yet other embodiments, $R_7$ is —$C(R_C)_3$ or —$CH_2R_C$. In some embodiments, $R_7$ is not a substituted or unsubstituted phenyl ring.

$R_6$ and $R_8$ are absent if the dashed line between the carbon atoms to which $R_6$ and $R_8$ are attached represents a bond, or are each selected independently from the group consisting of hydrogen, halogen, substituted or unsubstitued aliphatic, substituted or unsubstituted heteroaliphatic, haloaliphatic, substituted or unsubstituted alkoxy, —OH, —CN, —SCN, —SH, alkylthio, —$N_3$; —$NO_2$, amino, alkyl amino, and dialkyl amino groups. In certain embodiments, $R_6$ and $R_8$ are absent. In other embodiments, $R_6$ or $R_8$ is absent. In some embodiments, $R_6$ and $R_8$ are each hydrogen.

The variable n is an integer in the range of 0 to 8, inclusive. As will be appreciated by one of skill in the art, when the D-ring is aromatic n is an integer between 0 and 4. In some embodiments, n is an integer between 1 and 3. In certain embodiments, n is an integer between 1 and 2. In certain embodiments, when n is 2, the substituents $R_7$ are in the ortho configuration. In other embodiments, when n is 2, the substituents $R_7$ are in the para configuration. In yet other embodiments, when n is 2, the substituents $R_7$ are in the meta configuration.

In certain embodiments, $R_9$ is hydrogen. In certain embodiments, $R_9$ is halogen. In certain embodiments, $R_9$ is fluorine. In some embodiments, $R_9$ is —$OR_C$. In some embodiments, $R_9$ is —$OR_C$ or —$CH_2OR_C$, wherein $R_C$ is an oxygen protecting group. In some embodiments, $R_9$ is —$OC(R_C)_3$ wherein at least one $R_C$ is a halogen. In certain embodiments, $R_9$ is —$OCF_3$, —$OCHF_2$, or —$OCH_2F$. In certain embodiments, $R_9$ is alkoxy. In certain embodiments, $R_9$ is $C_{1-6}$ alkoxy. In certain embodiments, $R_9$ is methoxy. In certain embodiments, $R_9$ is ethoxy. In certain embodiments, $R_9$ is propoxy. In certain embodiments, $R_9$ is butoxy. In certain embodiments, $R_9$ is hydroxyl. In other embodiments, $R_9$ is a protected hydroxyl group. In some embodiments, $R_9$ is —$SR_C$. In some embodiments, $R_9$ is —$SR_C$, wherein $R_C$ is an sulfur protecting group. In certain embodiments, $R_9$ is alkylthiol. In certain embodiments, $R_9$ is $C_{1-6}$ alkylthiol. In certain embodiments, $R_9$ is methanethiol. In certain embodiments, $R_9$ is ethanethiol. In certain embodiments, $R_9$ is propanethiol. In certain embodiments, $R_9$ is butanethiol. In certain embodiments, $R_9$ is thiol. In some embodiments, $R_9$ is cyclic or acyclic, substituted or unsubstituted, branched or unbranched aliphatic. In some embodiments, $R_9$ is acyclic, substituted or unsubstituted, branched or unbranched aliphatic. In some embodiments, $R_9$ is alkyl. In some embodiments, $R_9$ is $C_{1-6}$ alkyl. In certain embodiments, $R_9$ is methyl. In certain embodiments, $R_9$ is ethyl. In certain embodiments, $R_9$ is propyl. In certain embodiments, $R_9$ is butyl. In certain other embodiments, $R_9$ is —$CF_3$, —$CHF_2$, or —$CH_2F$. In other embodiments, $R_9$ is —$NH_2$. In other embodiments, $R_9$ is —$N(R_C)_2$ or —$NH(R_C)$. In certain embodiments, $R_9$ is alkylamino or dialkylamino.

In some embodiments, $R_{10}$ is substituted or unsubstituted alkyl. In other embodiments, $R_{10}$ is —$OR_C$. In some embodiments, $R_{10}$ is —$OR_C$ or —$CH_2OR_C$, wherein $R_C$ is an oxygen protecting group. In certain embodiments, $R_{10}$ is alkoxy. In certain embodiments, $R_{10}$ is $C_{1-6}$ alkoxy. In certain embodiments, $R_{10}$ is —$CH_2OH$. In some embodiments, $R_{10}$ is an alkoxyalkyl. In some embodiments, $R_{10}$ is an alkoxymethyl. In some embodiments, $R_{10}$ is —$CH_2OR_C$, wherein $R_C$ is as defined and described herein. For instance $R_C$ may be —$CH_2CH_3OCH_3$ in some instances. In certain embodiments, $R_{10}$ is —$CH_2OCH_3$. In some embodiments, $R_{10}$ is methoxymethyl or butoxymethyl. In some embodiments, $R_{10}$ is —$CH_2N(R_C)_2$, wherein $R_C$ is as defined and described herein. In some such embodiments, $R_C$ is cyclic or heterocyclic. In certain embodiments, $R_{10}$ is —$CH_2N_3$. In some embodiments, $R_{10}$ is morpholinomethyl. In some embodiments, $R_{10}$ is piperazinylmethyl. In other embodiments, $R_{10}$ is pyrrolidinomethyl. In some embodiments, $R_{10}$ is piperidinylmethyl. In some embodiments, $R_{10}$ is cyclopropylaminomethyl. In other embodiments, $R_{10}$ is diethylaminomethyl. In some embodiments, $R_{10}$ is alkylaminomethyl. In some embodiments, $R_{10}$ is N,N'-hydroxyethylmethylaminomethyl. In some embodiments, $R_{10}$ is (3-dimethylaminopropyl)aminomethyl. In other embodiments, $R_{10}$ is N-imidazolylmethyl. In some embodiments, $R_{10}$ is pyridin-3-aminomethyl. In some embodiments, $R_{10}$ is aminomethyl. In some embodiments, $R_{10}$ is acetylaminomethyl. In some embodiments, $R_{10}$ is N-trimethylacetylaminomethyl. In other embodiments, $R_{10}$ is N-benzoylaminomethyl. In some embodiments, $R_{10}$ is N-methoxyacetylaminomethyl. In some embodiments, $R_{10}$ is N-3,5-difluorobenzoylaminomethyl. In some embodiments, $R_{10}$ is N-methanesulfonylaminomethyl. In some embodiments, $R_{10}$ is —$C(=O)R_C$. In other embodiments, $R_{10}$ is —$COOR_C$. In some embodiments, $R_{10}$ is —$C(=O)NR_C$. In certain embodiments, $R_{10}$ is —$CH_2R_C$, where $R_C$ is a halogen. In some embodiments, $R_{10}$ is —$CH_2SH$. In other embodiments, $R_{10}$ is —$CH_2SCH_3$. In certain embodiments, $R_{10}$ is hydroxyl, methoxy, or trifluoromethoxy. In some embodiments, $R_{10}$ is —$N(R_C)_2$. In some embodiments, $R_{10}$ is —$SR_C$. In some embodiments, $R_{10}$ is —$SR_C$, wherein $R_C$ is an sulfur protecting group. In certain embodiments, $R_{10}$ is alkylthiol. In certain embodiments, $R_{10}$ is $C_{1-6}$ alkylthiol. In certain embodiments, $R_{10}$ is methanethiol. In certain embodiments, $R_{10}$ is ethanethiol. In certain embodiments, $R_{10}$ is propanethiol. In certain embodiments, $R_{10}$ is butanethiol. In certain embodiments, $R_{10}$ is thiol. In certain embodiments, $R_{10}$ is hydroxyl. In certain embodiments, $R_{10}$ is halogen. In other embodiments, $R_{10}$ is fluorine. In some embodiments, $R_{10}$ is $C_{1-6}$ alkyl. In certain embodiments, $R_{10}$ is methyl. In certain embodiments, $R_{10}$ is ethyl In certain embodiments, $R_{10}$ is propyl. In certain embodiments, $R_{10}$ is butyl. In certain other embodiments, $R_{10}$ is —$CF_3$, —$CHF_2$, or —$CH_2F$. In certain embodiments, $R_{10}$ is hydrogen. In other embodiments, $R_{10}$ is not hydrogen.

In some embodiments, $R_{11}$ is substituted or unsubstituted alkyl. In other embodiments, $R_{11}$ is —$OR_C$. In yet other embodiments, $R_{11}$ is —$N(R_C)_2$. In some embodiments, $R_{11}$ is —$OR_C$ or —$CH_2OR_C$, wherein $R_C$ is an oxygen protecting group. In certain embodiments, $R_{11}$ is alkoxy. In certain embodiments, $R_{11}$ is $C_{1-6}$ alkoxy. In certain embodiments, $R_{11}$ is hydroxyl, methoxy, or trifluoromethoxy. In some embodiments, $R_{11}$ is —$SR_C$. In some embodiments, $R_{11}$ is —$SR_C$, wherein $R_C$ is an sulfur protecting group. In certain embodiments, $R_{11}$ is alkylthiol. In certain embodiments, $R_{11}$ is $C_{1-6}$ alkylthiol. In certain embodiments, $R_{11}$ is methanethiol. In certain embodiments, $R_{11}$ is ethanethiol. In certain embodiments, $R_{11}$ is propanethiol. In certain embodiments, $R_{11}$ is butanethiol. In certain embodiments, $R_{11}$ is thiol. In certain embodiments, $R_{11}$ is hydroxyl, methoxy, or trifluoromethoxy. In certain embodiments, $R_{11}$ is hydroxyl. In certain embodiments, $R_{11}$ is halogen. In other embodiments, $R_{11}$ is fluorine. In some embodiments, $R_{11}$ is $C_{1-6}$ alkyl. In certain embodiments, $R_{11}$ is methyl. In certain embodiments, $R_{11}$ is ethyl. In certain embodiments, $R_{11}$ is propyl. In certain embodiments, $R_{11}$ is butyl. In certain other embodiments, $R_{11}$ is —$CF_3$, —$CHF_2$, or —$CH_2F$. In certain embodiments, $R_{11}$ is hydrogen. In other embodiments, $R_{11}$ is not hydrogen.

In some embodiments, $R_{10}$ is not hydrogen. In some embodiments, $R_{11}$ is not hydrogen. In some embodiments, at least one of $R_{10}$ and $R_{11}$ is not hydrogen. In some embodiments, both $R_{10}$ and $R_{11}$ are not hydrogen.

In some embodiments, $R_9$ is not —$OR_C$. In some embodiments, $R_9$ is not —$OR_C$ when both $R_{10}$ and $R_{11}$ are hydrogen. In some embodiments, $R_9$ is not —$OR_C$, wherein $R_C$ is hydrogen or an oxygen-protecting group. In certain embodiments, $R_9$ is not —OH. In other embodiments, when $R_9$ is —$OR_C$, the substituents at $R_{10}$ and $R_{11}$ are not simultaneously hydrogen, and $R_3$ and $R_4$ are not hydrogen or —$OR_B$. In some embodiments, when $R_9$ is not hydroxyl or a protected hydroxyl, $R_{10}$ and $R_{11}$ may be simultaneously hydrogen.

As will be appreciated by one of skill in this art, compounds of the invention include derivatives, labeled forms, salts, pro-drugs, isomers, and tautomers of the formulae defined and described herein. Derivatives include protected forms. Salts include any pharmaceutically acceptable salts including HCl, HBr, HI, acetate, and fatty acid (e.g., lactate, citrate, myristoleate, oleate, valerate) salts. In certain embodiments, the inventive compound exists in zwitterionic form at neutral pH with the $R_5$ being a protonated amino group and the C-3 hydroxyl group deprotonated as shown, for example, in formula XIa:

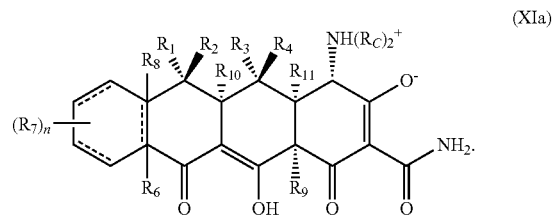

(XIa)

Isomers include geometric isomers, diastereomers, and enantiomers. Tautomers include both keto and enol forms of carbonyl moieties as well as various tautomeric forms of substituted and unsubstituted heterocycles. For example, the B-ring as shown in formula XI includes an enol moiety as drawn, but the enol may exist as the keto form in certain compounds as shown below in formula XIb and XIc:

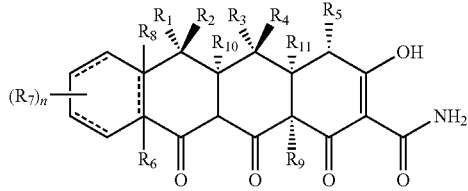
(XIb)

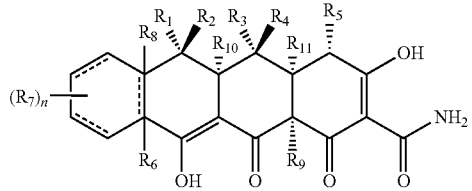
(XIc)

Other tautomeric forms will be appreciated by one of skill in the art and will depend on the substitution pattern of the core ring structure. The formulae drawn are only given as examples and do not in any way represent the full range of tautomers that may exist for a particular compound.

In certain embodiments, inventive compounds are of formula XId:

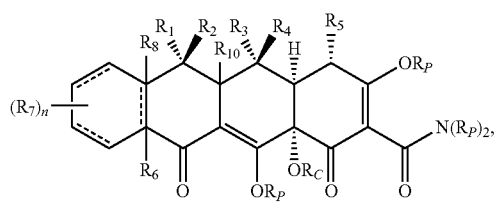
(XId)

or a pharmaceutically acceptable salt thereof;

wherein ----, $R_1$, $R_2$, $R_3$, $R_4$, $R_5$, $R_6$, $R_7$, $R_8$, $R_{10}$, $R_P$, and $R_C$ are as defined above and described herein; and n is an integer in the range of 0 to 8, inclusive; provided that $R_{10}$ and $R_{11}$ are not simultaneously hydrogen.

In certain embodiments, inventive compounds are of formula XIe:

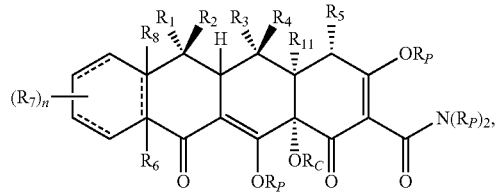
(XIe)

or a pharmaceutically acceptable salt thereof;

wherein ----, $R_1$, $R_2$, $R_3$, $R_4$, $R_5$, $R_6$, $R_7$, $R_8$, $R_{11}$, n, $R_P$, and $R_C$ are as defined above and described herein.

In certain embodiments, inventive compounds are of formula XIf:

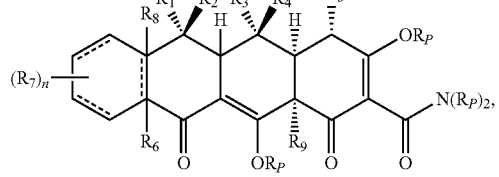

or a pharmaceutically acceptable salt thereof;

wherein ----, $R_1$, $R_2$, $R_3$, $R_4$, $R_5$, $R_6$, $R_7$, $R_8$, $R_9$, and $R_P$ are as defined above and described herein; and n is an integer in the range of 0 to 8, inclusive; provided that when $R_9$ is —$OR_C$, $R_{10}$ and $R_{11}$ are not simultaneously hydrogen.

In some embodiments, $R_{10}$ is not hydrogen. In some embodiments, $R_{11}$ is not hydrogen. In some embodiments, at least one of $R_{10}$ and $R_{11}$ is not hydrogen. In some embodiments, both $R_{10}$ and $R_{11}$ are not hydrogen.

In some embodiments, $R_9$ is not —$OR_C$. In some embodiments, $R_9$ is not —$OR_C$ when both $R_{10}$ and $R_{11}$ are hydrogen. In some embodiments, $R_9$ is not —$OR_C$, wherein $R_C$ is hydrogen or an oxygen-protecting group. In certain embodiments, $R_9$ is not —OH. In other embodiments, when $R_9$ is —$OR_C$, the substituents at $R_{10}$ and $R_{11}$ are not simultaneously hydrogen, and $R_3$ and $R_4$ are not hydrogen or —$OR_B$. In some embodiments, when $R_9$ is not hydroxyl or a protected hydroxyl, $R_{10}$ and $R_{11}$ may be simultaneously hydrogen.

Various subclasses of compounds of the formula XI which include a substituted or unsubstituted aromatic D-ring are shown below. These subclasses include unsubstituted, mono-substituted, disubstituted, and trisubstituted D-rings.

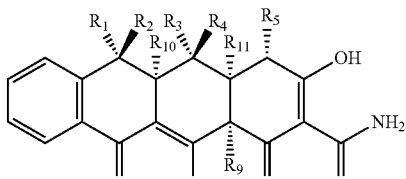

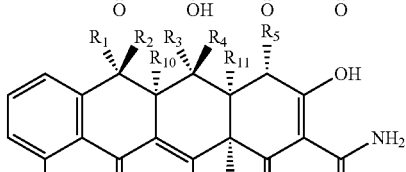

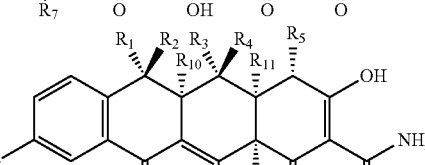

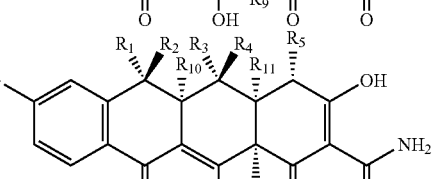

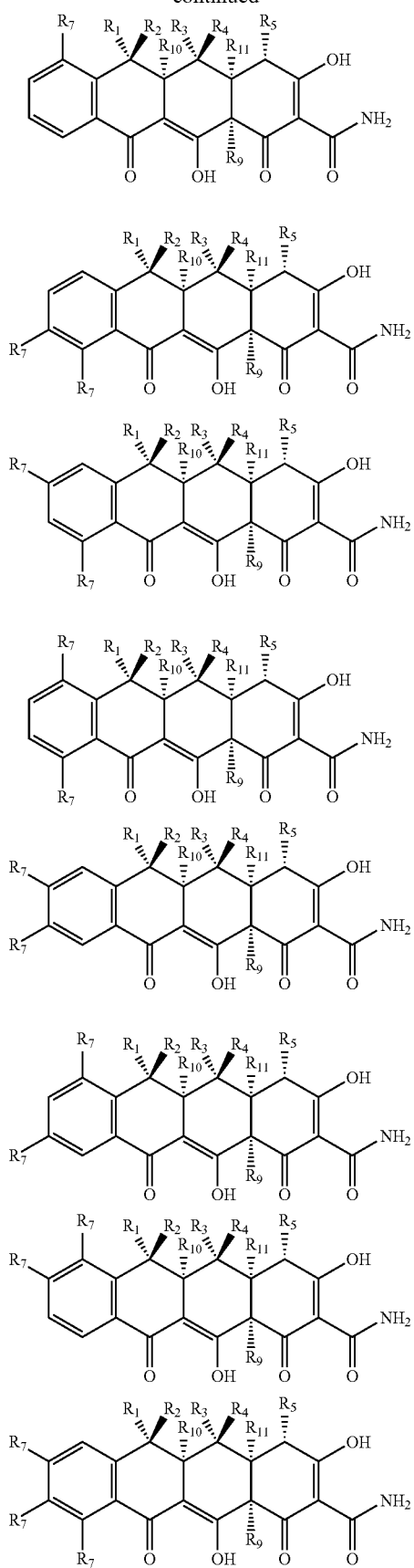

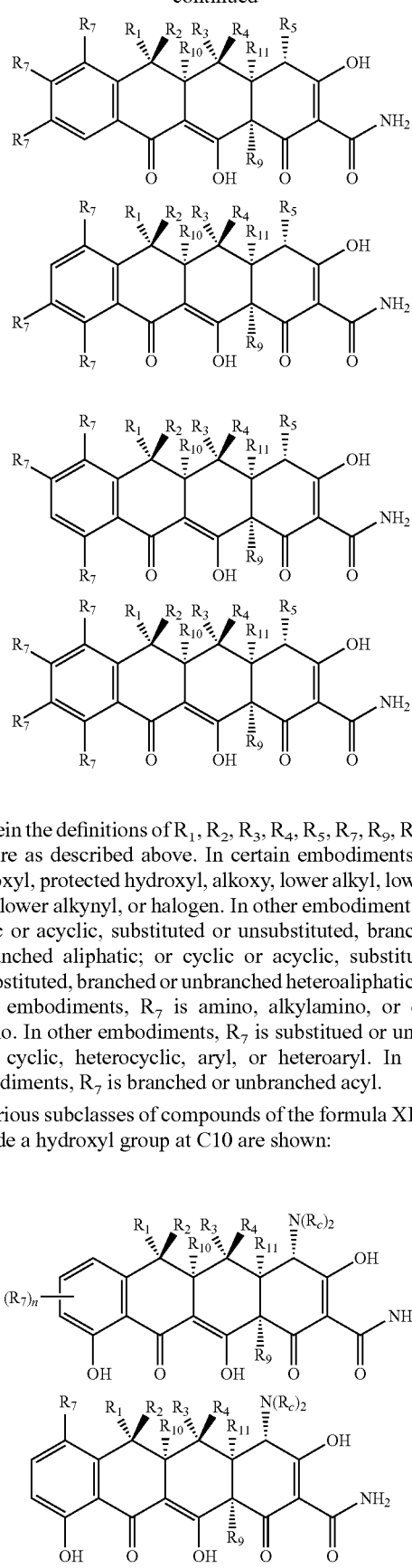

wherein the definitions of $R_1$, $R_2$, $R_3$, $R_4$, $R_5$, $R_7$, $R_9$, $R_{10}$, and $R_{11}$ are as described above. In certain embodiments, $R_7$ is hydroxyl, protected hydroxyl, alkoxy, lower alkyl, lower alkenyl, lower alkynyl, or halogen. In other embodiments, $R_7$ is cyclic or acyclic, substituted or unsubstituted, branched or unbranched aliphatic; or cyclic or acyclic, substituted or unsubstituted, branched or unbranched heteroaliphatic. In yet other embodiments, $R_7$ is amino, alkylamino, or dialkylamino. In other embodiments, $R_7$ is substitued or unsubstituted cyclic, heterocyclic, aryl, or heteroaryl. In certain embodiments, $R_7$ is branched or unbranched acyl.

Various subclasses of compounds of the formula XI which include a hydroxyl group at C10 are shown:

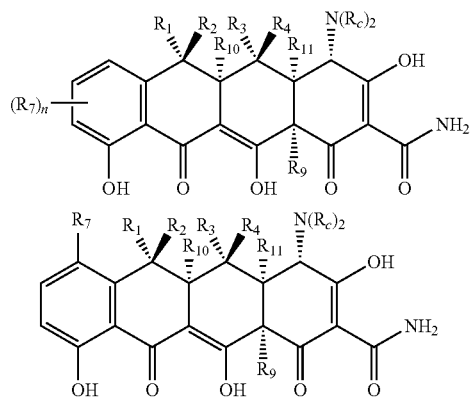

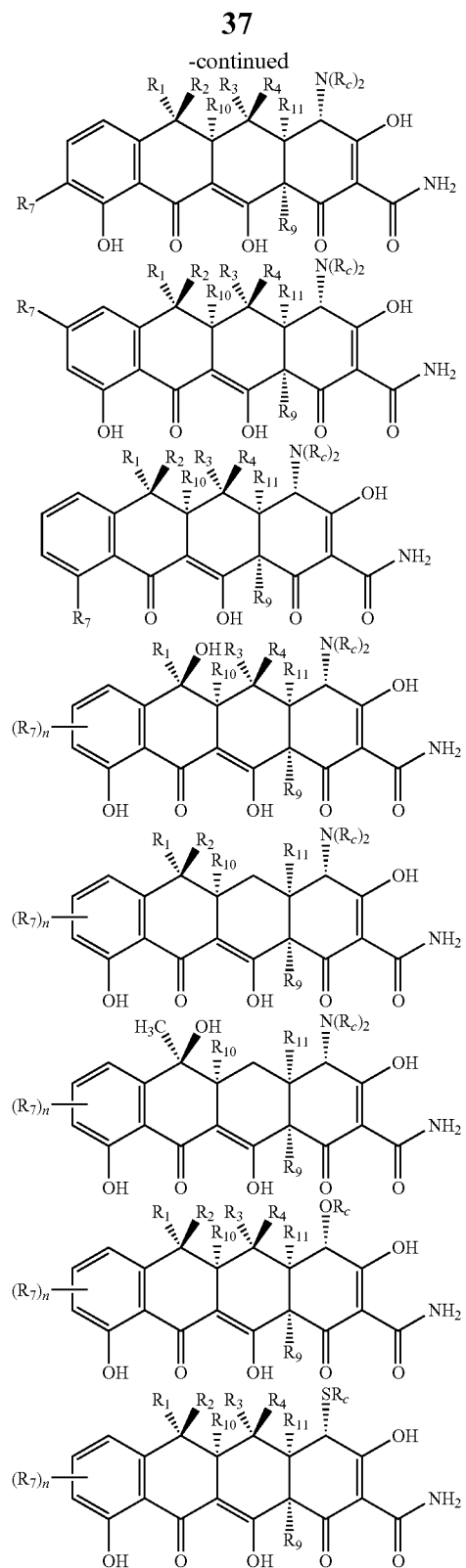
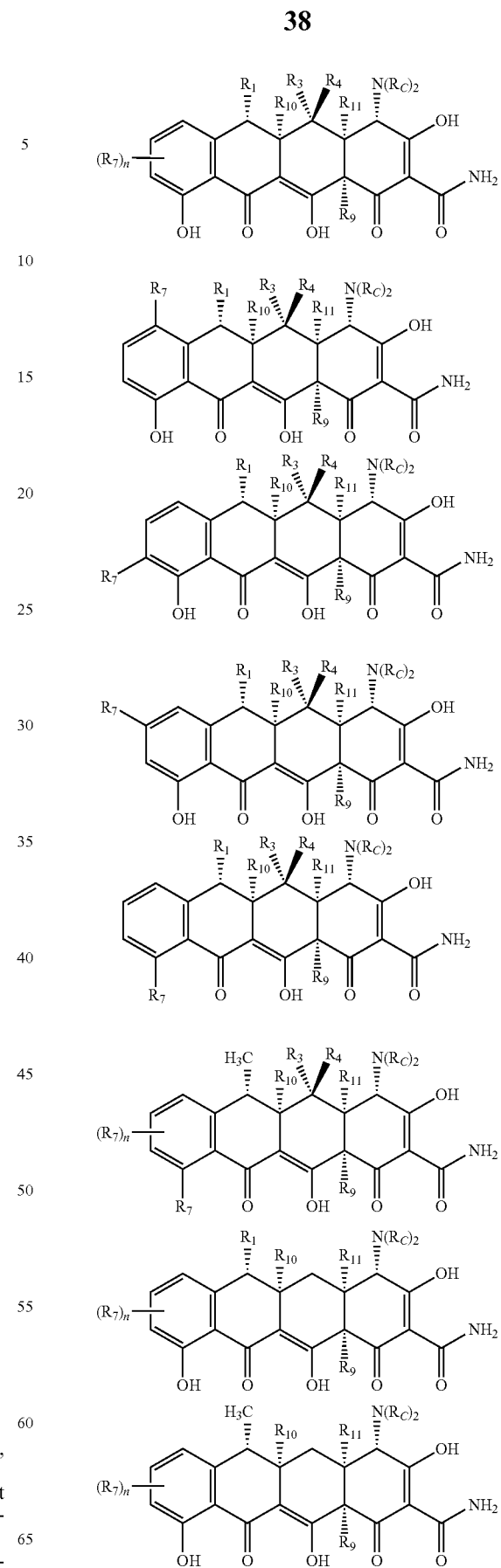
wherein the definitions of $R_1$, $R_2$, $R_3$, $R_4$, $R_7$, $R_9$, $R_{10}$, $R_{11}$, and $R_C$ are as defined above and described herein; and
n is an integer in the range of 0 to 8, inclusive; provided that when $R_9$ is —$OR_C$, $R_{10}$ and $R_{11}$ are not simultaneously hydrogen.
In certain embodiments, the compounds are 6-deoxytetracyclines as shown in the formulae below:

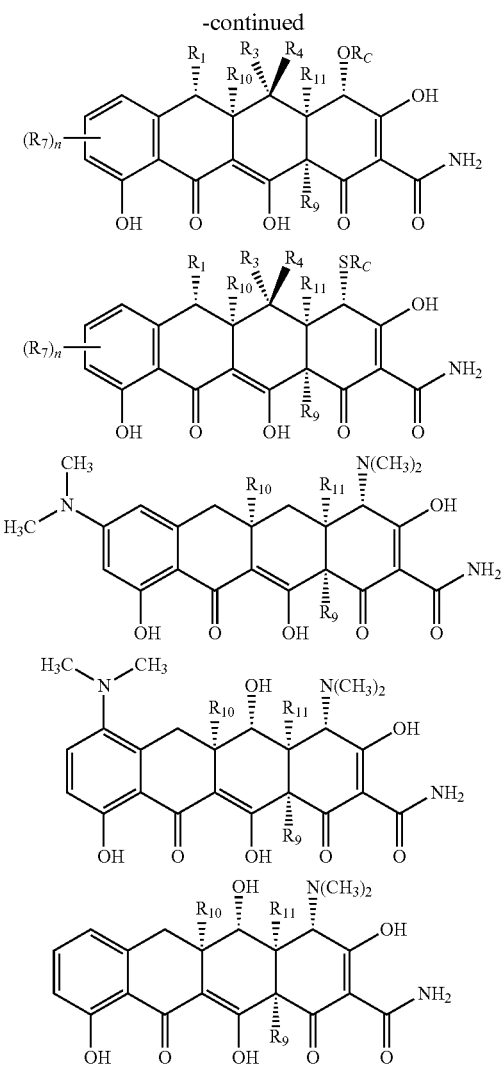
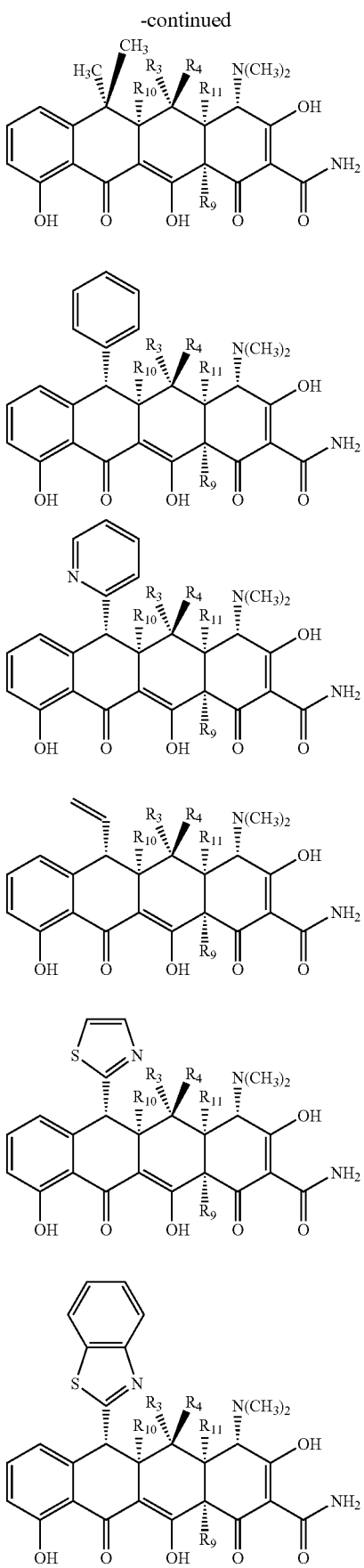
wherein the definitions of $R_1$, $R_2$, $R_3$, $R_4$, $R_7$, $R_9$, $R_{10}$, $R_{11}$, and $R_C$ are as defined above and described herein, and n is an integer in the range of 0 to 8, inclusive; provided that when $R_9$ is —$OR_C$, $R_{10}$ and $R_{11}$ are not simultaneously hydrogen.
Various subclasses of compounds of the formula XI which include a substituted C-ring are shown below:
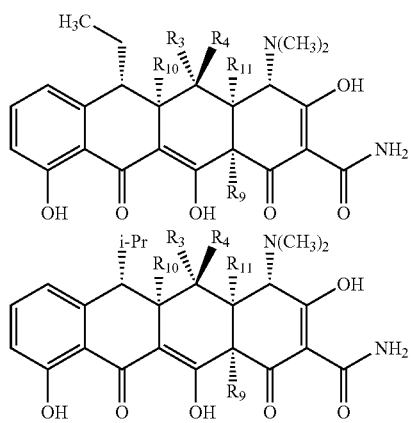

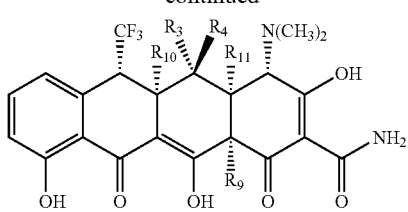
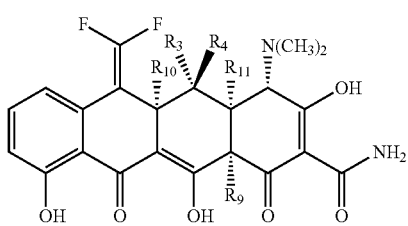
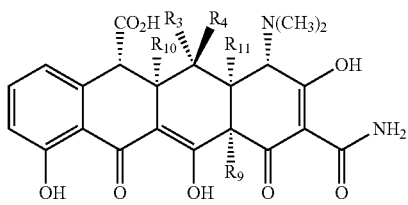
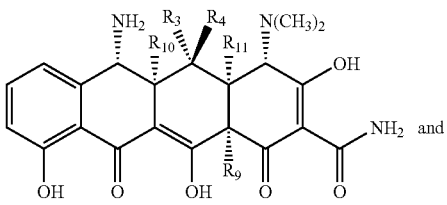
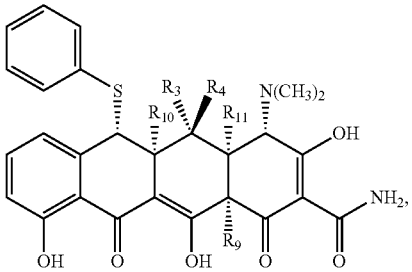

wherein $R_3$, $R_4$, $R_9$, $R_{10}$, and $R_{11}$ are as defined above and described herein; provided that when $R_9$ is —$OR_C$, $R_{10}$ and $R_{11}$ are not simultaneously hydrogen.

Various subclasses of compounds of the formula XI that include a substituent at position 5 of the tetracycline core are shown below:

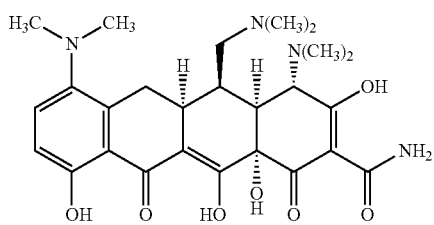

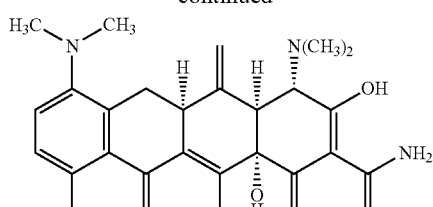
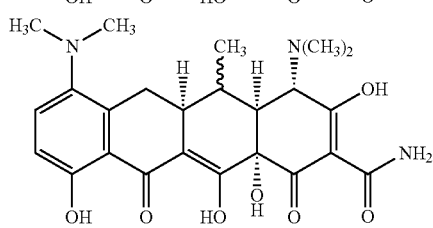

Various subclasses of compounds of the formula XI" that include a substituent at position 5a of the tetracycline core (wherein $R_{10}$ is not hydrogen) are shown below:

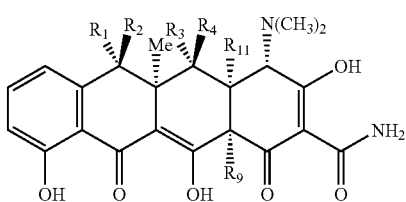
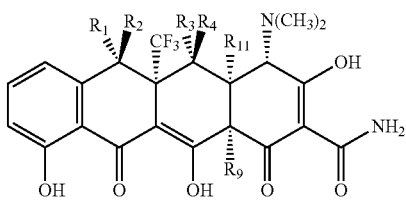
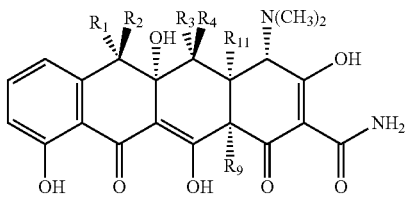
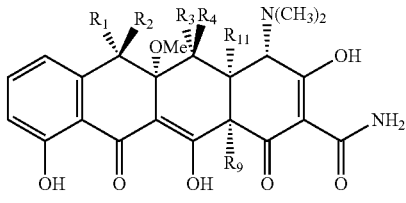
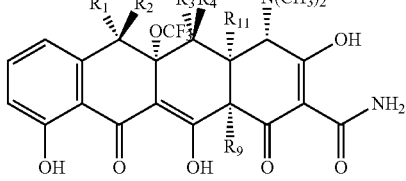

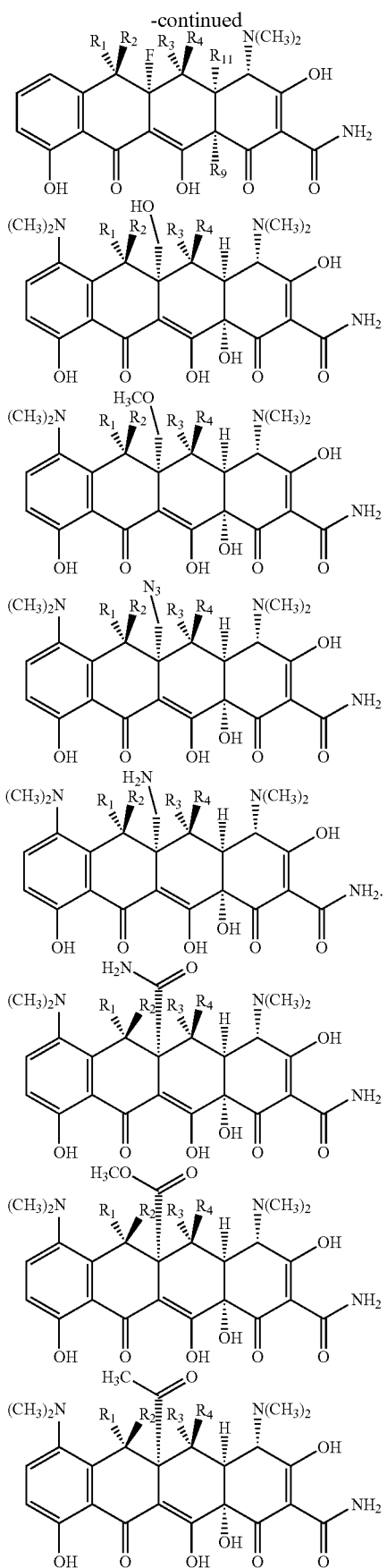
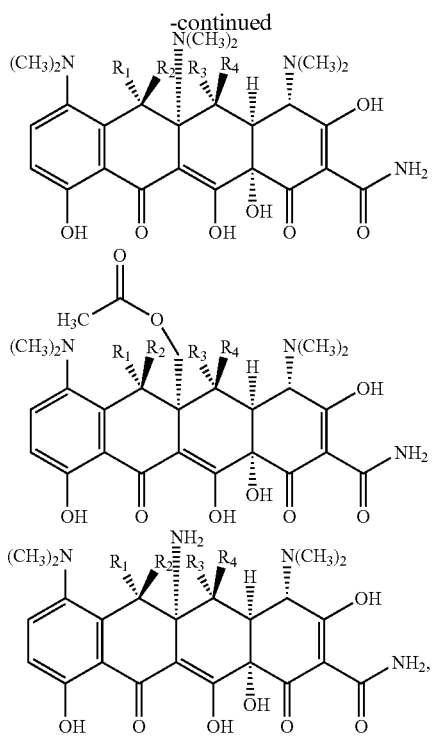
wherein $R_1$, $R_2$, $R_3$, $R_4$, $R_9$, and $R_{11}$ are as defined above and described herein.
Exemplary compounds of the formula XI that include a substituent at position 5a of the tetracycline core are shown below:
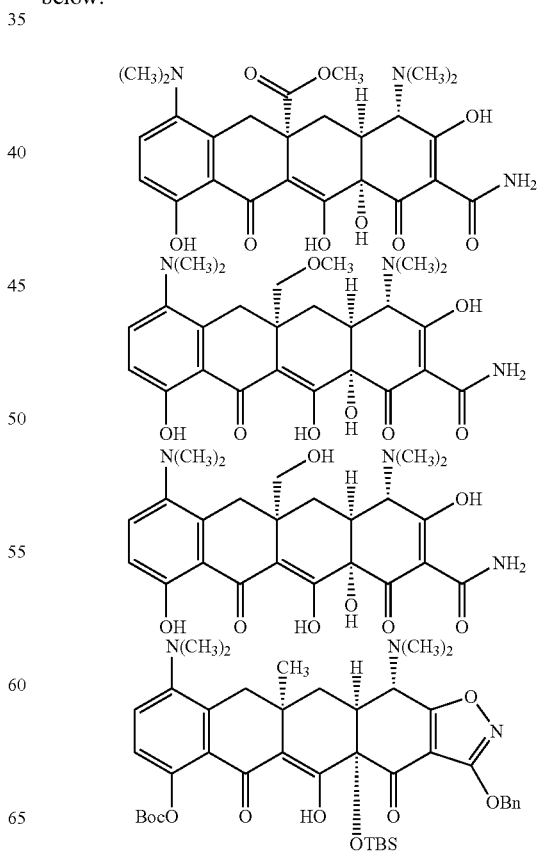

45
-continued
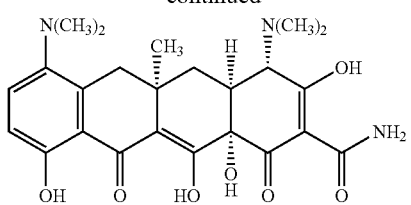
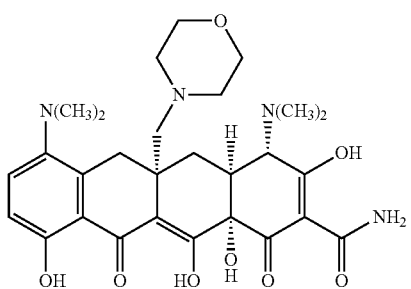
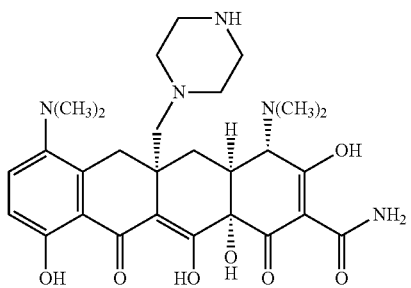
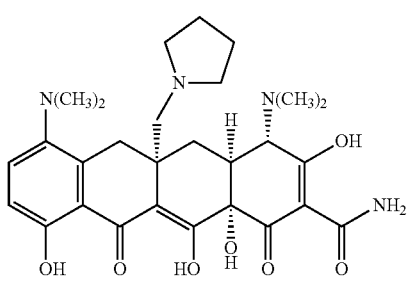
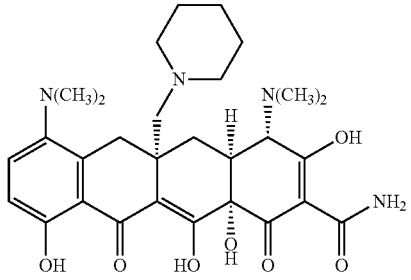
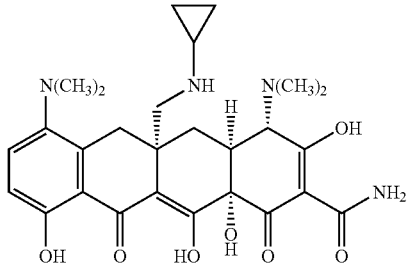
46
-continued
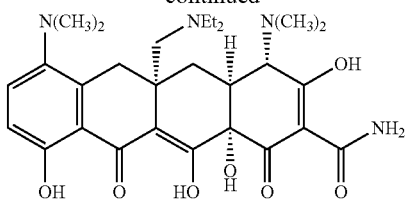
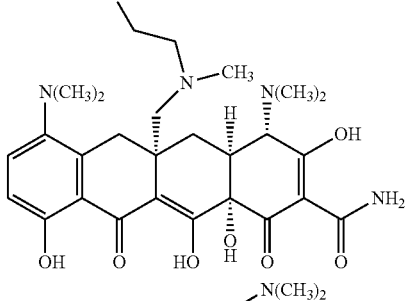
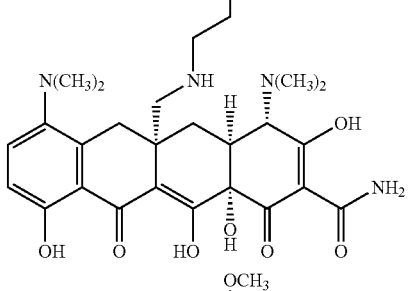
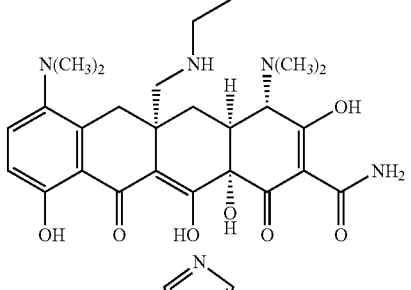
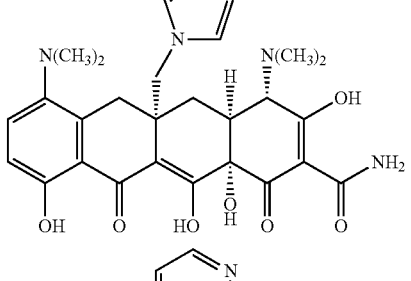
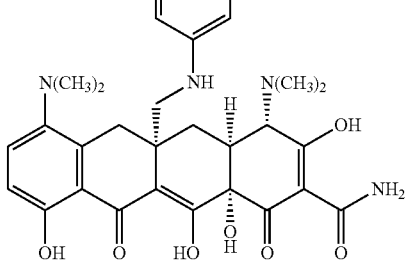

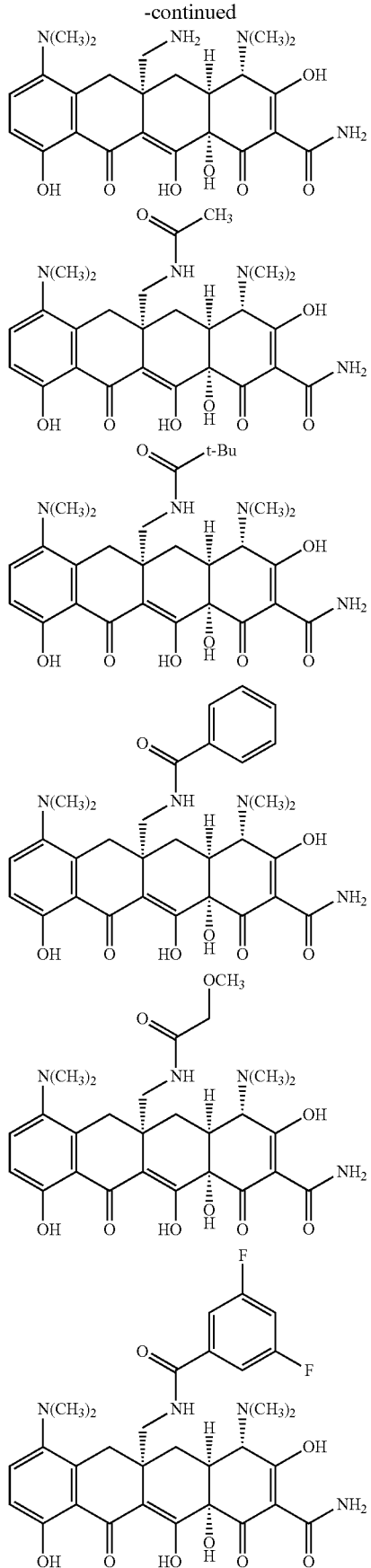
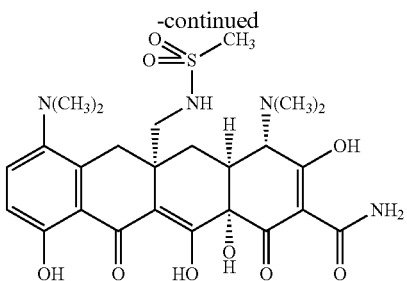
Various subclasses of compounds of the formula XI''' that include a substituent at position 4a of the tetracycline core (wherein $R_{11}$ is not hydrogen) are shown below:
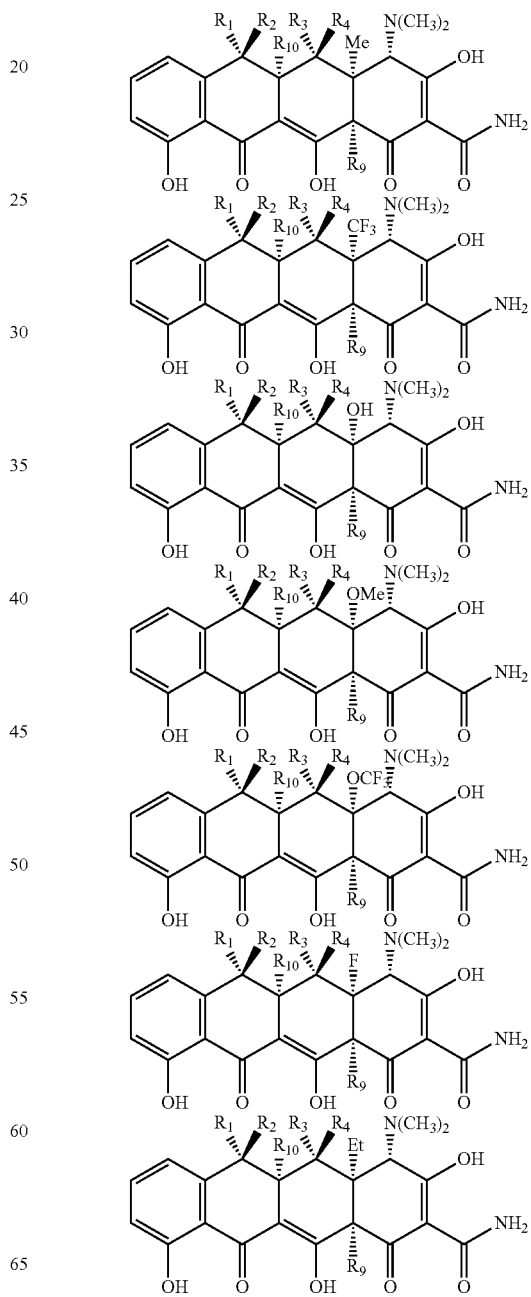

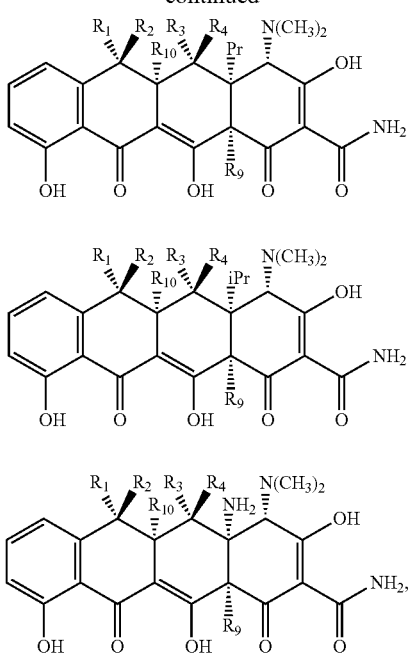
wherein $R_1$, $R_2$, $R_3$, $R_4$, $R_9$, and $R_{10}$ are as defined above and described herein.
Various subclasses of compounds of the formula XI that include a substituent at position 12a of the tetracycline core (wherein $R_9$ is not hydrogen) are shown below:
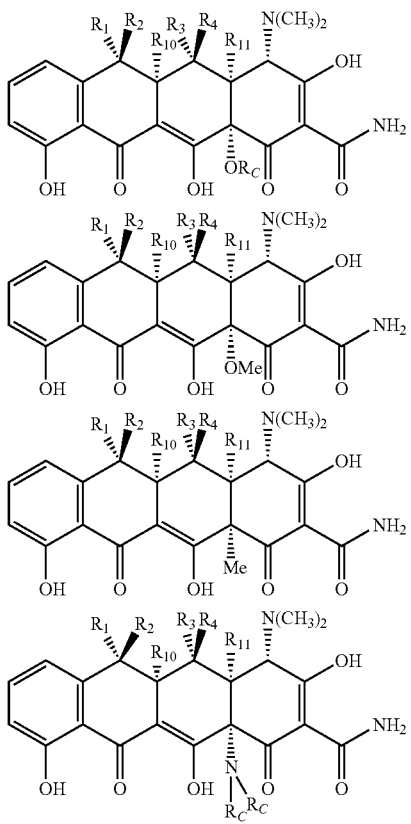
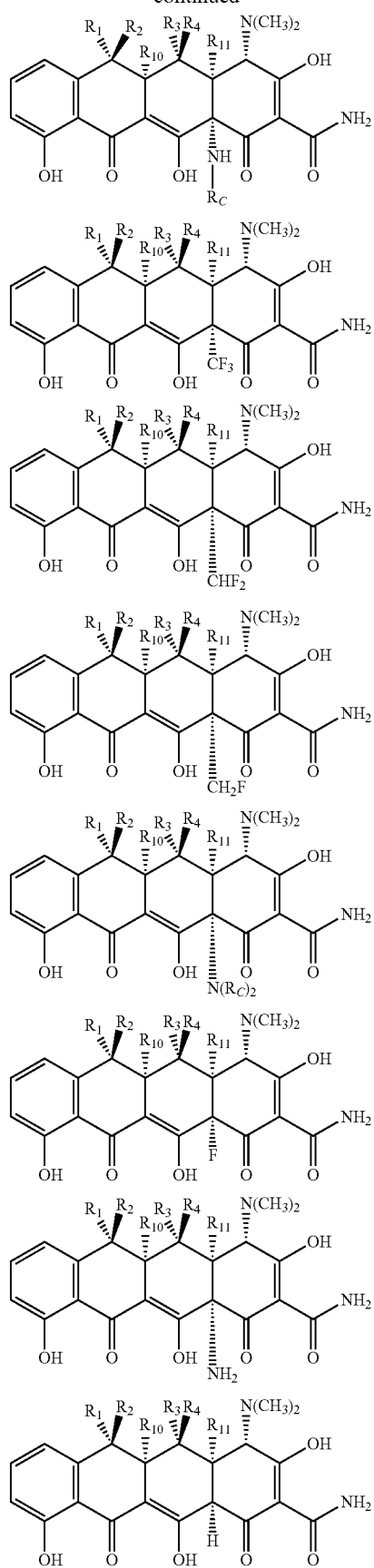

-continued

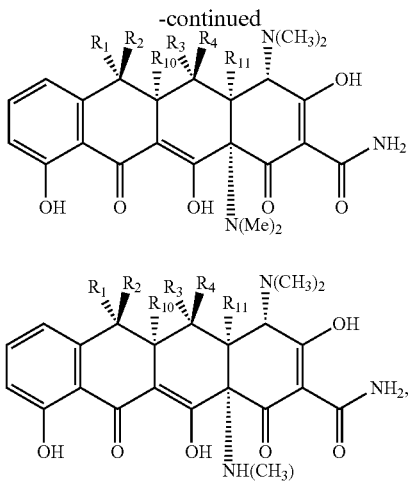

wherein $R_1$, $R_2$, $R_3$, $R_4$, $R_{10}$, and $R_{11}$ are as defined above and described herein; provided that when the substituent at $R_9$ is —$OR_C$, $R_{10}$ and $R_{11}$ are not simultaneously hydrogen.

In another aspect of the invention, the carbocyclic D-ring of tetracycline is replaced with a heterocyclic or carbocyclic moiety other than phenyl as shown in formula (XII):

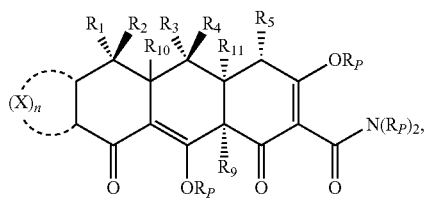

(XII)

or a pharmaceutically acceptable salt thereof;
wherein $R_1$, $R_2$, $R_3$, $R_4$, $R_5$, $R_9$, $R_{10}$, $R_{11}$, and $R_P$ are defined and described herein;

represents a substituted or unsubstituted aryl, heteroaryl, carbocyclic, or heterocyclic moiety that is not phenyl, in which each occurrence of X is independently —O—, —S—, —$NR_7$—, or —$C(R_7)_2$—; n is an integer in the range of 1 to 5, inclusive; and the bonds between adjacent X moieties are either single or double bonds; and $R_7$ is absent as valency permits; hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_C$; —$CH_2OR_C$; —$CH_2R_C$; —$CH_2N(R_C)_2$; =$C(R_C)_2$; —$C(=O)R_C$; —$CO_2R_C$; —CN; —SCN; —$SR_C$; —$SOR_C$; —$SO_2R_C$; —$N_3$; —$NO_2$; —$N(R_C)_2$; —$NHC(O)R_C$; —$NHSO_2R_C$; or —$C(R_C)_3$; wherein each occurrence of $R_C$ is independently a hydrogen, halogen, azido, a protecting group, aliphatic, heteroaliphatic, haloaliphatic, acyl, aryl, heteroaryl, alkoxy, aryloxy, alkylthio, arylthio, amino, alkylamino, dialkylamino, heteroaryloxy, or heteroarylthio;

provided that when $R_9$ is —$OR_C$, $R_{10}$ and $R_{11}$ are not simultaneously hydrogen.

In some embodiments, $R_{10}$ is not hydrogen. In some embodiments, $R_{11}$ is not hydrogen. In some embodiments, at least one of $R_{10}$ and $R_{11}$ is not hydrogen. In some embodiments, both $R_{10}$ and $R_{11}$ are not hydrogen.

In some embodiments, $R_9$ is not —$OR_C$. In some embodiments, $R_9$ is not —$OR_C$ when both $R_{10}$ and $R_{11}$ are hydrogen. In some embodiments, $R_9$ is not —$OR_C$, wherein $R_C$ is hydrogen or an oxygen-protecting group. In certain embodiments, $R_9$ is not —OH. In other embodiments, when $R_9$ is —$OR_C$, the substituents at $R_{10}$ and $R_{11}$ are not simultaneously hydrogen, and $R_3$ and $R_4$ are not hydrogen or —$OR_B$. In some embodiments, when $R_9$ is not hydroxyl or a protected hydroxyl, $R_{10}$ and $R_{11}$ may be simultaneously hydrogen.

In embodiments in which $R_9$ is not —$OR_C$, the compound of formula (XII) may have the following structure:

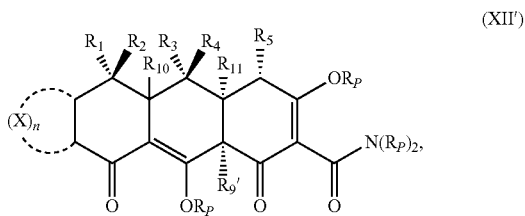

(XII')

wherein $R_1$, $R_2$, $R_3$, $R_4$, $R_5$, $R_7$, $R_9'$, $R_{10}$, $R_{11}$, $R_P$ and

are defined and described herein.

In embodiments in which $R_{10}$ is not hydrogen, the compound of formula (XII) may have the following structure:

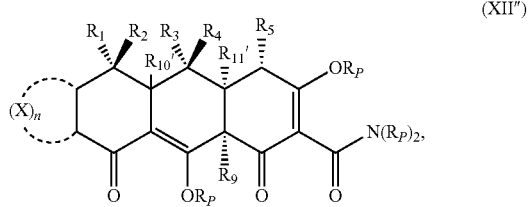

(XII")

wherein $R_1$, $R_2$, $R_3$, $R_4$, $R_5$, $R_7$, $R_9$, $R_{10}'$, $R_{11}$, $R_P$ and

are defined and described herein.

In embodiments in which $R_{11}$ is not hydrogen, the compound of formula (XII) may have the following structure:

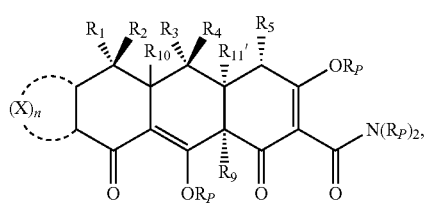

(XII''')

wherein $R_1$, $R_2$, $R_3$, $R_4$, $R_5$, $R_7$, $R_9$, $R_{10}$, $R_{11}'$, $R_P$ and

are defined and described herein.

In certain embodiments,

is a polycyclic ring system such as a bicyclic or tricyclic moiety. In other embodiments,

is a monocyclic moiety. In yet other embodiments,

is a substituted or unsubstituted heterocyclic moiety. In other embodiments,

is a pyridinyl moiety as shown:

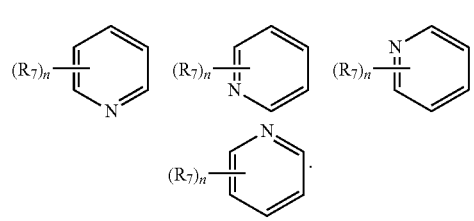

In another embodiment,

is selected from the group consisting of

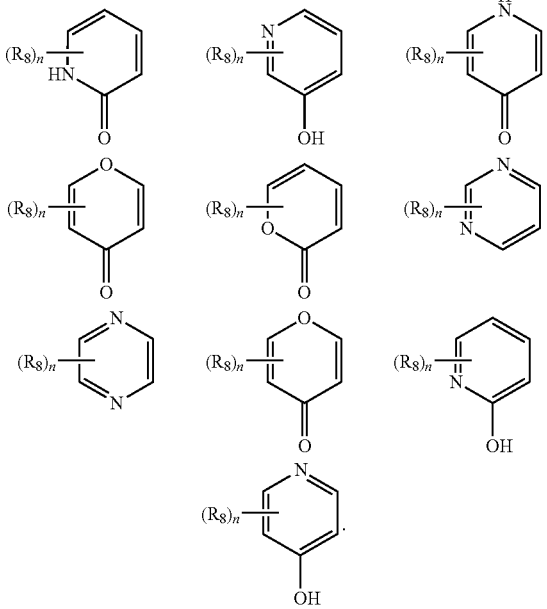

In yet another embodiment,

is a five-membered heterocyclic ring selected from the group consisting of:

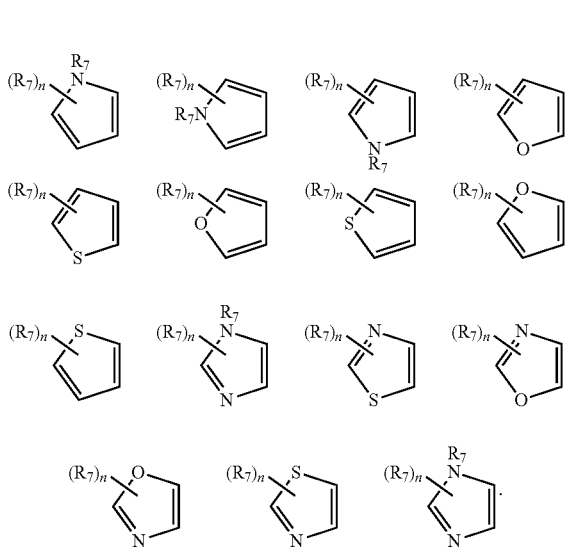

Various tetracyclines (heterocyclines) of the invention are also shown below:
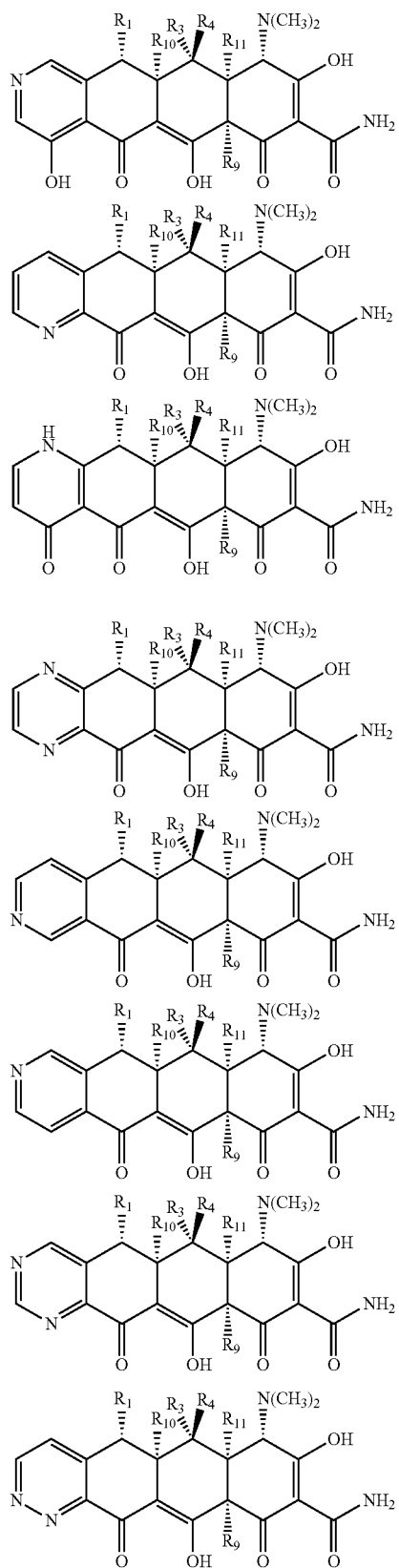
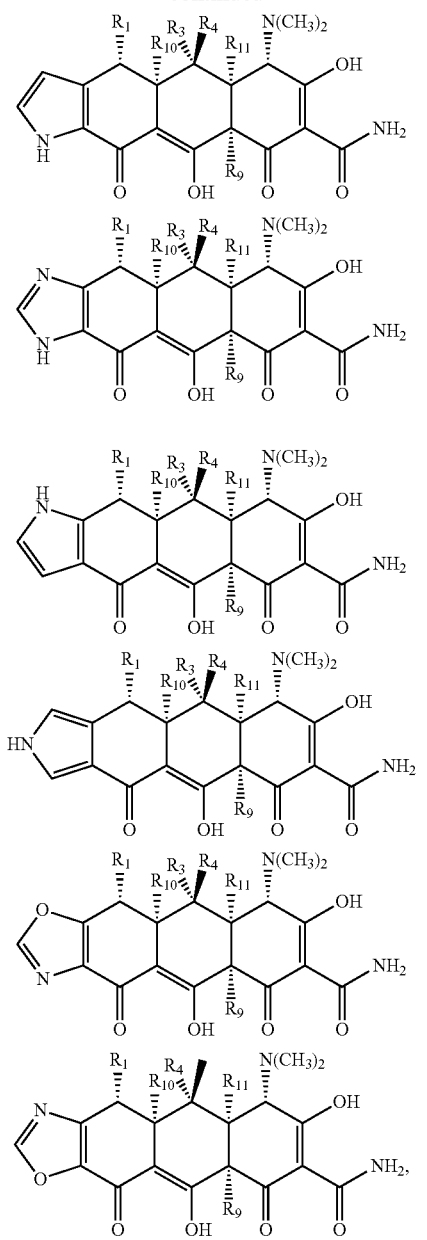
wherein $R_1$, $R_3$, $R_4$, $R_9$, $R_{10}$, and $R_{11}$ are as defined above and described herein; provided that when $R_9$ is —$OR_C$, $R_{10}$ and $R_{11}$ are not simultaneously hydrogen.
Other compounds of the invention include pentacyclines of formula XIII, XIV, or XV:
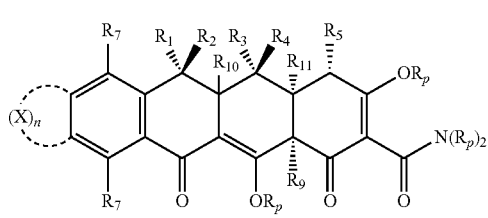
(XIII)

-continued

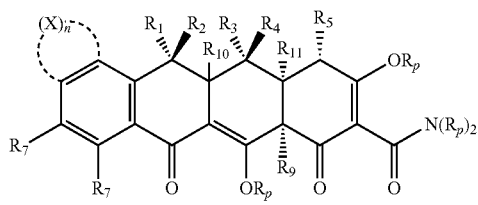
(XIV)

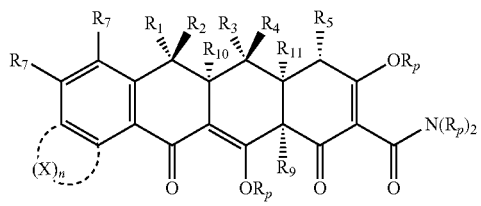
(XV)

or a pharmaceutically acceptable salt thereof;
wherein the definitions of $R_1$, $R_2$, $R_3$, $R_4$, $R_5$, $R_7$, $R_9$, $R_{10}$, $R_{11}$, $R_P$ and

are as defined above and described herein; and
$R_{12}$ is absent as valency permits; hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_D$; —$CH_2OR_D$; —$CH_2R_D$; —$CH_2N(R_D)_2$; =$C(R_D)_2$; =$O$; —$C(=O)R_D$; —$CO_2R_D$; —$CN$; —$SCN$; —$SR_D$; —$SOR_D$; —$SO_2R_D$; —$N_3$; —$NO_2$; —$N(R_D)_2$; —$NHC(O)R_D$; —$NHSO_2R_D$; or —$C(R_D)_3$; wherein each occurrence of $R_D$ is independently hydrogen, halogen, azido, a protecting group, aliphatic, heteroaliphatic, haloaliphatic, acyl, aryl, heteroaryl, alkoxy, aryloxy, alkylthio, arylthio, amino, alkylamino, dialkylamino, heteroaryloxy, or heteroarylthio;

provided that when $R_9$ is —$OR_C$, $R_{10}$ and $R_{11}$ are not simultaneously hydrogen.

In some embodiments, $R_{10}$ is not hydrogen. In some embodiments, $R_{11}$ is not hydrogen. In some embodiments, at least one of $R_{10}$ and $R_{11}$ is not hydrogen. In some embodiments, both $R_{10}$ and $R_{11}$ are not hydrogen.

In some embodiments, $R_9$ is not —$OR_C$. In some embodiments, $R_9$ is not —$OR_C$ when both $R_{10}$ and $R_{11}$ are hydrogen. In some embodiments, $R_9$ is not —$OR_C$, wherein $R_C$ is hydrogen or an oxygen-protecting group. In certain embodiments, $R_9$ is not —$OH$. In other embodiments, when $R_9$ is —$OR_C$, the substituents at $R_{10}$ and $R_{11}$ are not simultaneously hydrogen, and $R_3$ and $R_4$ are not hydrogen or —$OR_B$. In some embodiments, when $R_9$ is not hydroxyl or a protected hydroxyl, $R_{10}$ and $R_{11}$ may be simultaneously hydrogen.

In certain embodiments, one or more of the compounds of formula XIII, XIV and XV includes $R_9'$ in place of $R_9$; $R_{10}'$ in place of $R_{10}$; and/or $R_{11}'$ in place of $R_{11}$, wherein $R_9'$, $R_{10}'$, and $R_{11}'$ are as defined above and described herein.

In certain embodiments,

is a polycyclic ring system such as a bicyclic or tricyclic moiety. In other embodiments,

is a monocyclic moiety. In other embodiments,

is a substituted or unsubstituted, aromatic or nonaromatic carbocyclic moiety, for example a phenyl ring. In yet other embodiments,

is a substituted or unsubstituted heterocyclic moiety. In other embodiments,

is a pyridinyl moiety as shown:

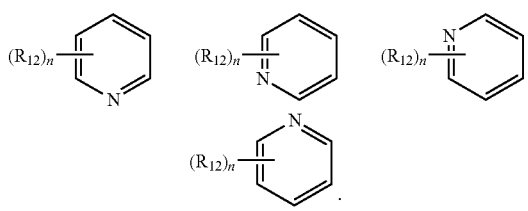

In another embodiment,

is selected from the group consisting of

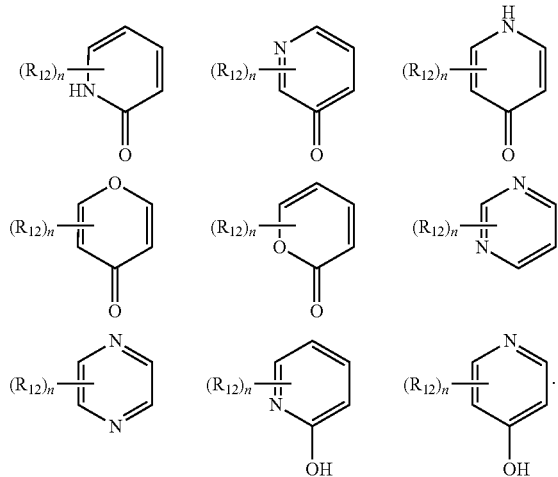

In yet another embodiment,

is a five-membered heterocyclic ring selected from the group consisting of:

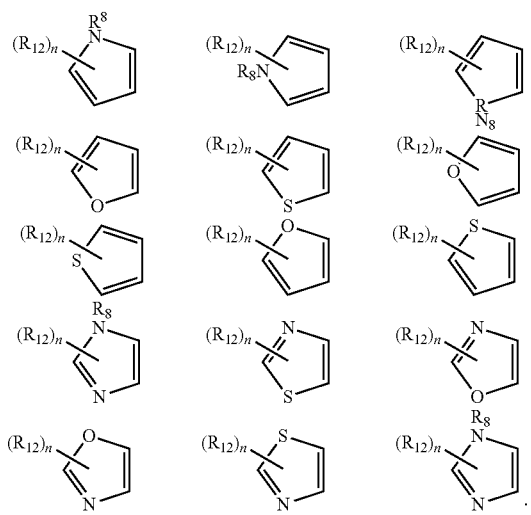

Various subclasses of the formula (XIII) include:

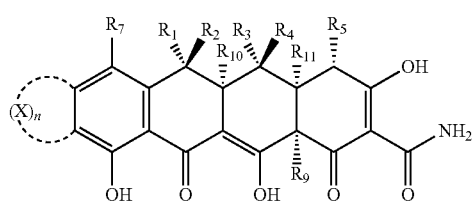

-continued

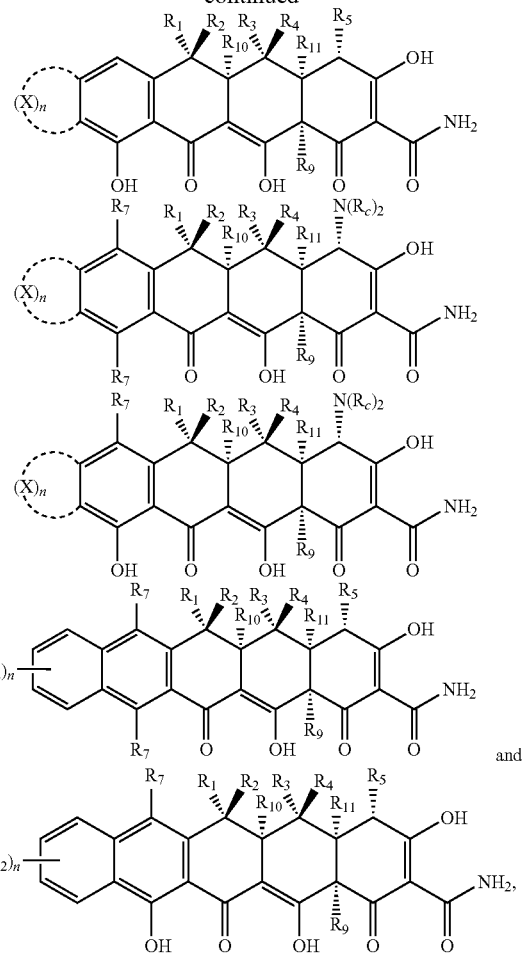

wherein $R_1$, $R_2$, $R_3$, $R_4$, $R_5$, $R_7$, $R_9$, $R_{10}$, $R_{11}$, $R_{12}$, $R_C$ and

are as defined above and described herein; provided that when $R_9$ is $-OR_C$, $R_{10}$ and $R_{11}$ are not simultaneously hydrogen.

Various subclasses of the formula (XIV) include:

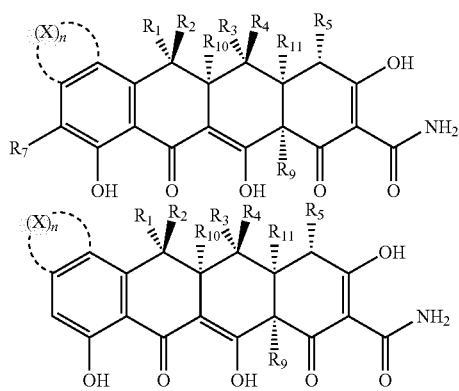

-continued

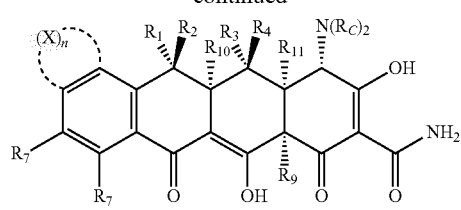

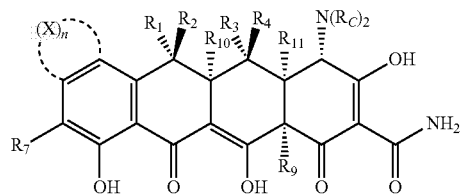

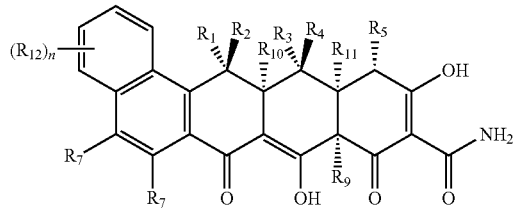

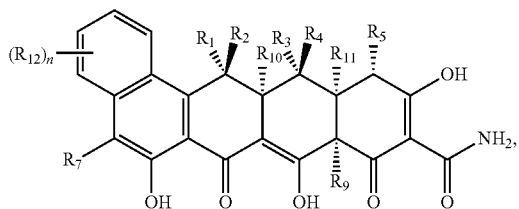

wherein $R_1$, $R_2$, $R_3$, $R_4$, $R^5$, $R_7$, $R_9$, $R_{10}$, $R_{11}$, $R_{12}$, $R_C$ and

are as defined above and described herein; provided that when $R_9$ is $-OR_C$, $R_{10}$ and $R_{11}$ are not simultaneously hydrogen.

Various subclasses of the formula (XV) include:

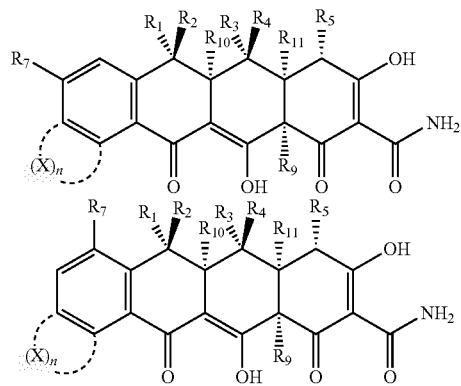

-continued

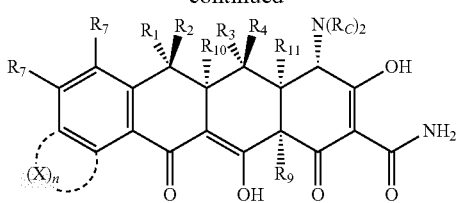

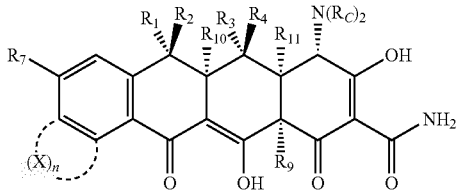

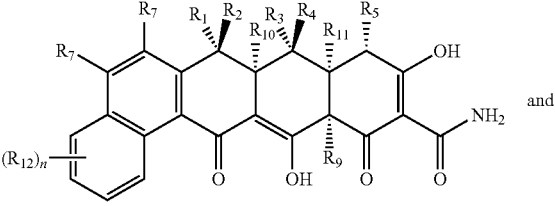

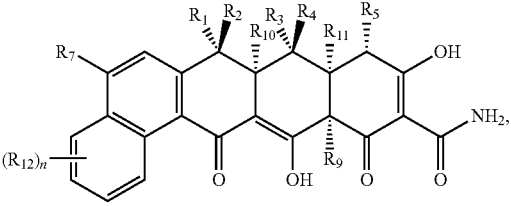

wherein $R_1$, $R_2$, $R_3$, $R_4$, $R^5$, $R_7$, $R_9$, $R_{10}$, $R_{11}$, $R_{12}$, $R_C$ and

are as defined above and described herein; provided that when $R_9$ is $-OR_C$, $R_{10}$ and $R_{11}$ are not simultaneously hydrogen.

Various pentacyclines of the invention are shown below:

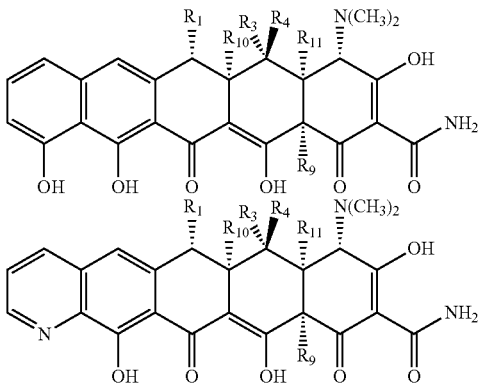

-continued

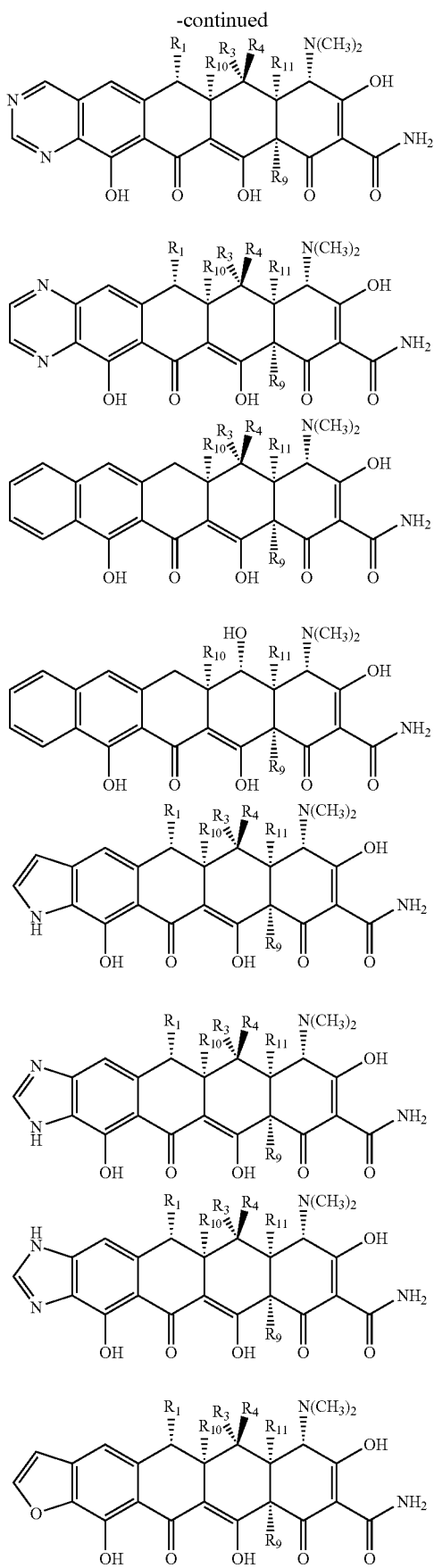

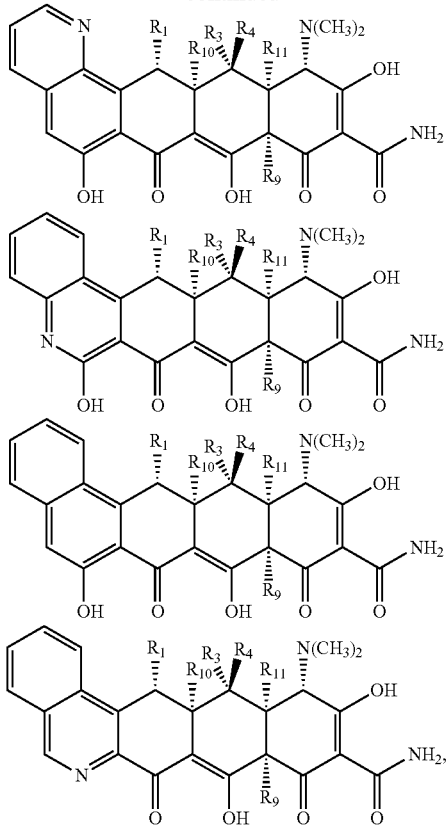

wherein $R_1$, $R_3$, $R_4$, $R_9$, $R_{10}$, and $R_{11}$ are as defined above and described herein; provided that when $R_9$ is —$OR_C$, $R_{10}$ and $R_{11}$ are not simultaneously hydrogen.

In certain embodiments, the tetracycline analogs of the present invention are represented by the formula (XVI):

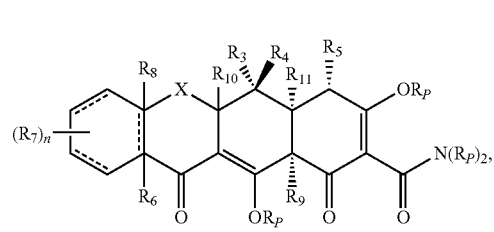

or a pharmaceutically acceptable salt thereof;
wherein
  X is —N($R_1$)—, —S—, or —O—;
  ---- represents a single or double bond;
  $R_3$, $R_4$, $R_5$, $R_6$, $R_7$, $R_8$, $R_9$, $R_{10}$, $R_{11}$, and $R_P$ are as defined above and described herein; and
  n is an integer in the range of 0 to 8, inclusive; provided that when $R_9$ is —$OR_C$, $R_{10}$ and $R_{11}$ are not simultaneously hydrogen.

In some embodiments, $R_{10}$ is not hydrogen. In some embodiments, $R_{11}$ is not hydrogen. In some embodiments, at least one of $R_{10}$ and $R_{11}$ is not hydrogen. In some embodiments, both $R_{10}$ and $R_{11}$ are not hydrogen.

In some embodiments, $R_9$ is not —$OR_C$. In some embodiments, $R_9$ is not —$OR_C$ when both $R_{10}$ and $R_{11}$ are hydrogen. In some embodiments, $R_9$ is not —$OR_C$, wherein $R_C$ is hydrogen or an oxygen-protecting group. In certain embodiments, $R_9$ is not —OH. In other embodiments, when $R_9$ is —$OR_C$, the substituents at $R_{10}$ and $R_{11}$ are not simultaneously hydrogen, and $R_3$ and $R_4$ are not hydrogen or —$OR_B$. In some embodiments, when $R_9$ is not hydroxyl or a protected hydroxyl, $R_{10}$ and $R_{11}$ may be simultaneously hydrogen.

In some embodiments, X is —N($R_1$)—. In certain embodiments, X is —NH—. In other embodiments, X is —S— or —O—.

In certain embodiments, the compound of formula XVI includes $R_9'$ in place of $R_9$; $R_{10}'$ in place of $R_{10}$; and/or $R_{11}'$ in place of $R_{11}$, wherein $R_9'$, $R_{10}'$, and $R_{11}'$ are as defined above and described herein.

Subclasses of formula XVI include:

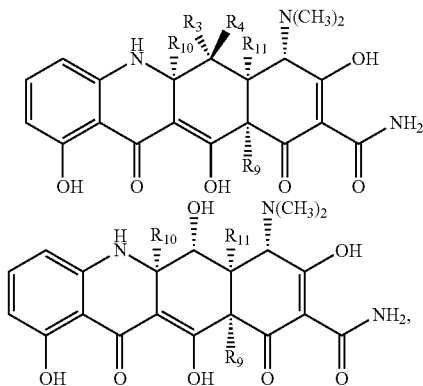

wherein $R_3$, $R_4$, $R_9$, $R_{10}$, and $R_{11}$ are as defined above and described herein; provided that when $R_9$ is —$OR_C$, $R_{10}$ and $R_{11}$ are not simultaneously hydrogen.

Synthetic Methodology

The present invention provides all steps, methodologies, intermediates, and reagents useful in preparing an enone of formula (VII):

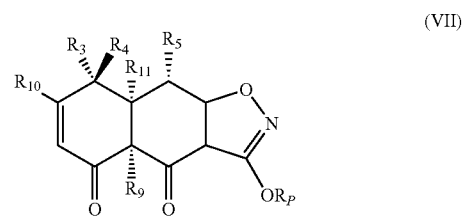

wherein $R_3$, $R_4$, $R_5$, $R_9$, $R_{10}$, $R_{11}$, and $R_P$ are as defined above and described herein, provided that when $R_9$ is —$OR_C$, $R_{10}$ and $R_{11}$ are not simultaneously hydrogen.

The present invention provides for use of this methodology in the modular synthesis of tetracycline analogs by joining the highly functionalized chiral enone, which will become the A- and B-rings of the tetracycline core, with a molecule which will become the D-ring of the tetracycline core. The joining of these two intermediates results in the formation of the C-ring, preferably in an enantioselective manner. This methodology also allows for the synthesis of pentacyclines, hexacyclines, or higher ring systems as well as the incorporation of heterocycles into the ring system. In particular, the joining of these two fragments includes various nucleophilic addition reactions and cycloaddition reactions with enone VII as described above and in published U.S. patent application US2005/0282787, published Dec. 22, 2005.

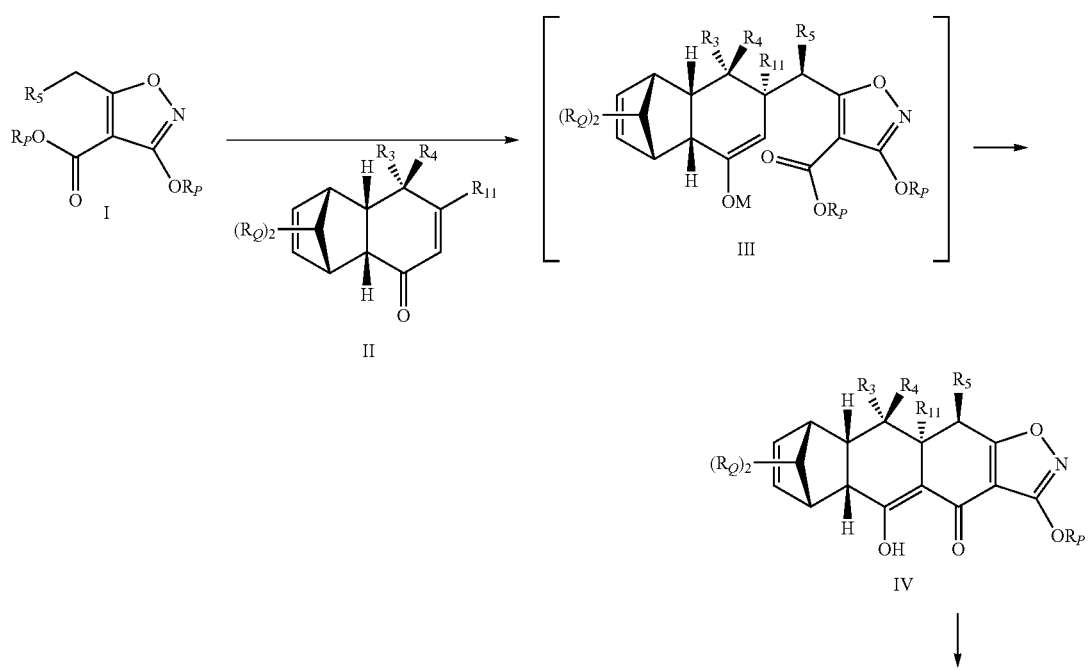

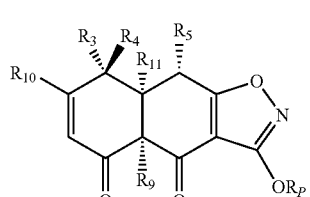 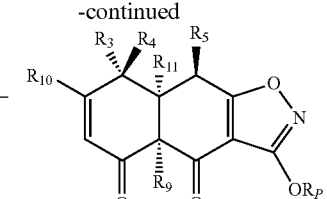 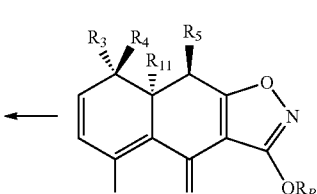

VII    VI    V

The synthesis of enone VII begins with an isoxazole of formula I. The isoxazole I is deprotonated by the addition of a suitable base and reacted with an enone of formula II to give the Michael adduct of formula III, wherein M is a counterion generated by the suitable base. The adduct of formula III is further treated, without work-up or purification, with a suitable base to effect a Claisen condensation yielding a compound of formula IV.

In some embodiments, the suitable base used to deprotonate I is a metal amide. In certain embodiments, the suitable base is a bis(trimethylsilyl)amide. In certain embodiments, the suitable base is sodium bis(trimethylsilyl)amide. In other embodiments, the base is lithium diisopropylamide or lithium diethylamide. In yet other embodiments, the base is sodium hydride or potassium hydride. In some embodiments, M is sodium, lithium, or potassium. In certain embodiments, M is sodium. In some embodiments, the reaction is performed a temperature from about −78° C. to about 0° C. In certain embodiments, the reaction is performed at −78° C. In certain other embodiments, the reaction is performed at −60° C. In yet other embodiments, the reaction is performed at −20° C. In some embodiments, the solvent used for the reaction is an aprotic solvent. In some embodiments, the solvent is a polar aprotic solvent. In certain embodiments, the solvent is an ether. In certain embodiments, the solvent is tetrahydrofuran. In some embodiments, the reaction further comprises an additive. In certain embodiments, the additive is hexamethylphosphoramide (HMPA). In certain other embodiments, the additive is 1,3-dimethyl-3,4,5,6-tetrahydro-2(1H)-pyrimidinone (DMPU). In other embodiments, the additive is a copper-containing additive.

In certain embodiments, the Michael addition is stereoselective yielding only one or substantially one diastereomer. In certain embodiments, the diastereoselective reaction results in an diastereomeric excess (de) of at least 80%, at least 90%, at least 95%, at least 98%, or at least 99%. One of ordinary skill in the art would understand that the use of a compound of formula II having a different absolute or relative stereochemistry than that shown in the above Scheme in the Michael addition may produce compounds of other absolute or relative stereochemistry than that shown explicitly in the Scheme, and all of the possible enantiomers and diastereomers are encompassed by the present invention.

In some embodiments, each occurrence of $R_Q$ is independently hydrogen, $C_{1-6}$ alkyl, $-Si(OR_Z)_3$, or $-Si(R_Z)_3$, wherein each occurrence of $R_Z$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; or a substituted or unsubstituted, branched or unbranched heteroaryl.

In some embodiments, $R_Q$ is hydrogen. In other embodiments, $R_Q$ is $-Si(Me)_3$. In other embodiments, $R_Q$ is $-Si(Me)_3$. In yet other embodiments, $R_Q$ is $-SiH(Me)_2$. In certain embodiments, $R_Q$ is $-SiH_2Me$. In certain embodiments, $R_Q$ is $-Si(CH_3)_2(Ph)$. In yet other embodiments, $R_Q$ is $-Si(Et)_3$. In certain embodiments, $R_Q$ is $-Si(iPr)_3$. In certain embodiments, $R_Q$ is $-Si(Ph_2)tBu$. In other embodiments, $R_Q$ is $-Si(tBu)(Me)_2$. In certain embodiments, $R_Q$ is $-Si(Ph)_3$. In certain embodiments, $R_Q$ is $-SiH(Ph)_2$. In certain embodiments, $R_Q$ is $-SiH_2Ph$. In other embodiments, $R_Q$ is $-SiH_3$. In certain embodiments, $R_Q$ is $-Si(TMS)_3$. In other embodiments, $R_Q$ is $-Si(OMe)_3$. In yet other embodiments, $R_Q$ is $-SiH(OMe)_2$. In certain embodiments, $R_Q$ is $-SiH_2OMe$.

In some embodiments, the suitable base used to effect the Claisen condensation is an inorganic base. In other embodiments, the suitable base is an organic base. In some embodiments, the suitable base is a metal amide. In certain embodiments, the suitable base is a bis(trimethylsilyl)amide. In certain embodiments, the suitable base is potassium bis(trimethylsilyl)amide. In other embodiments, the base is lithium diisopropylamide or lithium diethylamide. In yet other embodiments, the base is sodium hydride or potassium hydride. In some embodiments, the reaction is performed at a temperature from about −78° C. to the refluxing temperature of the solvent. In certain embodiments, the reaction is performed at −78° C. In certain other embodiments, the reaction is performed at −20° C. In yet other embodiments, the reaction is performed at room temperature. In some embodiments, the solvent used for the reaction is an aprotic solvent. In some embodiments, the solvent is a polar aprotic solvent. In certain embodiments, the solvent is an ether. In certain embodiments, the solvent is tetrahydrofuran. In some embodiments, the reaction further comprises an additive. In certain embodiments, the additive is hexamethylphosphoramide (HMPA). In certain other embodiments, the additive is 1,3-dimethyl-3,4,5,6-tetrahydro-2(1H)-pyrimidinone (DMPU). In other embodiments, the additive is a copper-containing additive.

A retro Diels-Alder reaction can be performed on the Michael-Claisen product of formula IV to give a compound of formula V. In some embodiments, the reaction is performed at an elevated temperature. In other embodiments, the reaction is performed at the reflux temperature of the solvent. In certain embodiments, the reaction is performed at about 250° C. In other embodiments, the reaction is performed at a temperature of less than about 250° C. or less than about 200° C., e.g., at a temperature of about 60° C., about 110° C., or about 170° C. In some embodiments, the solvent is a high boiling solvent. In certain embodiments, the solvent is diphenyl ether. In other embodiments, the solvent is toluent. In yet other embodiments, the solvent is hexafluoroisopropanol (HFIPA). In some embodiments, the reaction is run as a continuous-flow reaction. In certain embodiments, the continuous-flow reaction is aided by a setup as shown in FIG. 1. In some embodiments, a dienophile is present in the reaction mixture. In certain embodiments, dimethyl maleate is present in the reaction mixture. In certain other embodiments, dibutyl maleate is present in the reaction mixture. In yet other embodiments, maleic anhydride is present in the reaction mixture. In some embodiments, the continuous flow reaction can be performed using dienophile as solvent, e.g., dibutyl maleate.

In some embodiments, a retro Diels-Alder reaction yielding a compound of formula V may be followed by the reaction of this compound with a cyclopentadiene to yield an enone of formula II. The cyclopentadiene may be isolated and recycled under certain reaction conditions. An example of such a reaction includes the following:

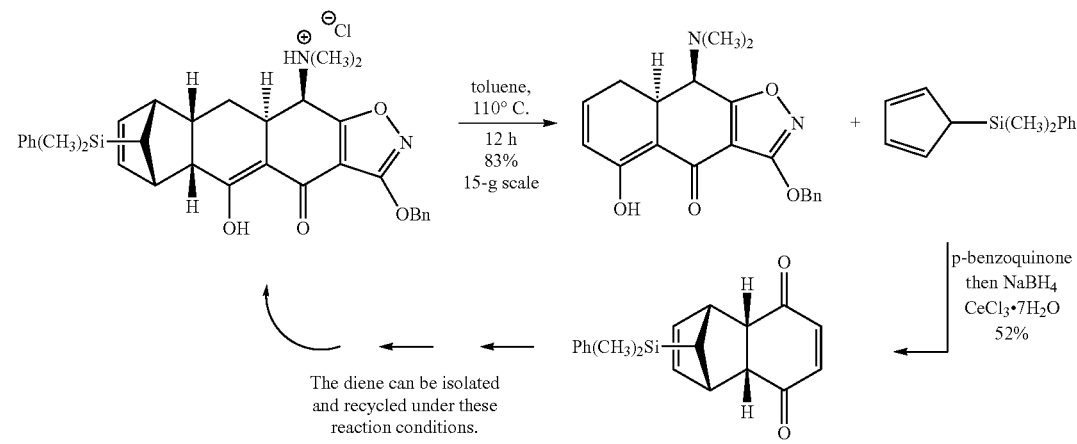

In certain embodiments, the introduction of a silyl group at $R_Q$ can make the retro Diels-Alder reaction more facile and may allow the reaction to proceed at a lower temperature and/or in higher yield. Examples include the following reactions:

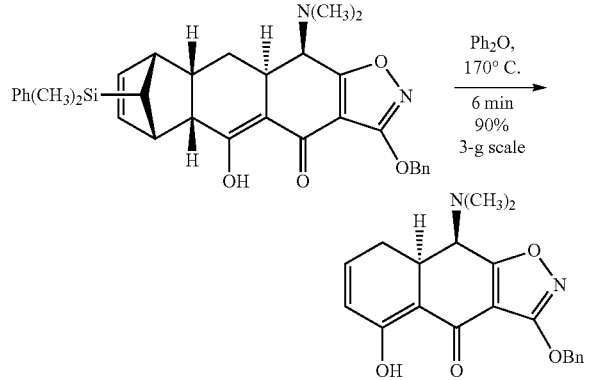

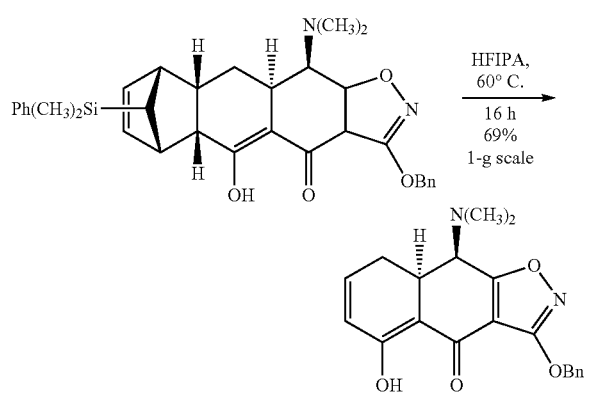

A variety of cyclopentadienes may be reacted with a compound of formula V to yield an enone of formula II. In some instances, the cyclopentadiene may have the general formula:

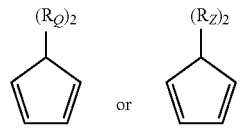

wherein each occurrence of $R_Q$ is independently hydrogen, $C_{1-6}$ alkyl, $—Si(OR_Z)_3$, or $—Si(R_Z)_3$, and wherein each occurrence of $R_Z$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; or a substituted or unsubstituted, branched or unbranched heteroaryl.

Examples of cyclopentadienes include the following:

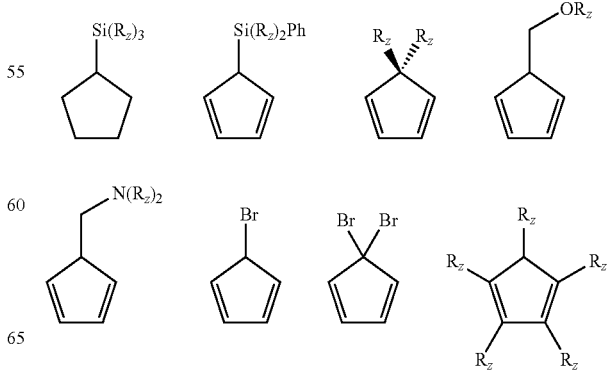

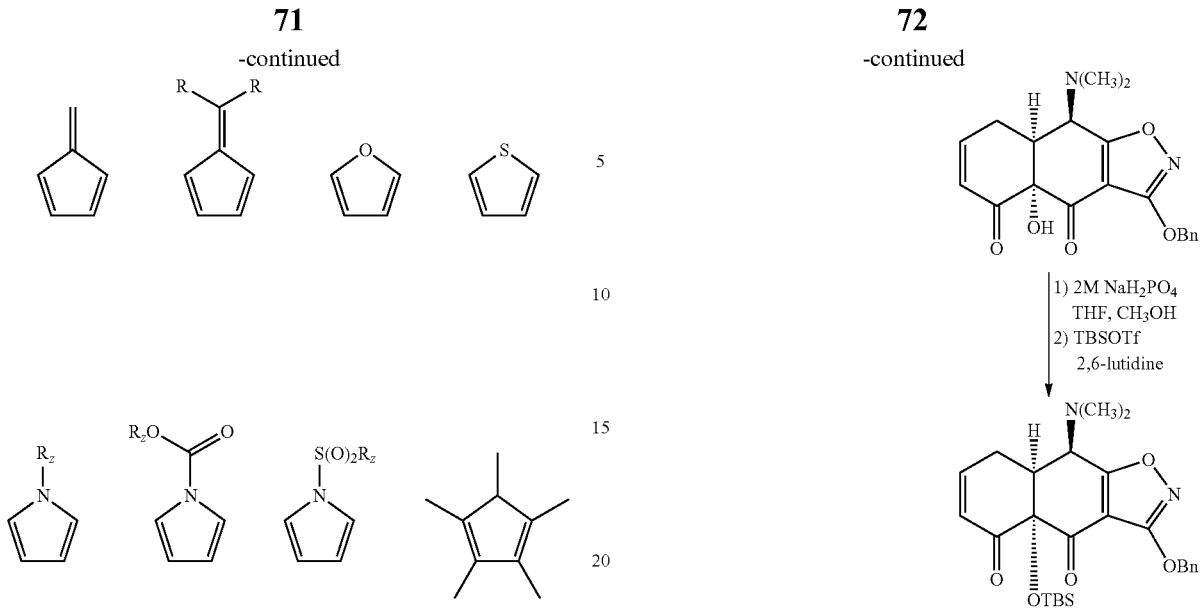

A compound of formula V can be deprotonated with a suitable base and allowed to react with an electrophile to give an enone of formula VI. In some embodiments, the suitable base is a metal amide. In certain embodiments, the suitable base is a bis(trimethylsilyl)amide. In certain embodiments, the suitable base is lithium bis(trimethylsilyl)amide. In other embodiments, the base is lithium diethylamide or lithium diisopropylamide. In other embodiments, the base is a metal alkoxide. For example, in one embodiment, the base is lithium tert-butoxide. In yet other embodiments, the base is sodium hydride or potassium hydride. In some embodiments, the reaction is performed at a temperature from about −78° C. to room temperature. In certain embodiments, the reaction is performed at −78° C. In certain other embodiments, the reaction is performed at −30° C. In other embodiments, the reaction is performed at 0° C. In yet other embodiments, the reaction is performed at room temperature. In some embodiments, the solvent used for the reaction is an aprotic solvent. In some embodiments, the solvent is a polar aprotic solvent. In certain embodiments, the solvent is an ether. In certain embodiments, the solvent is dimethoxyethane. In some embodiments, the electrophile employed in the reaction results in a hydroxyl group in the product of formula VI. In some embodiments, the electrophile is trans-2-(phenylsulfonyl)-3-phenyloxaziridine, also known as Davis oxaziridine. In certain embodiments, the electrophile is trans-2-(phenylsulfonyl)-3-p-nitrophenyloxaziridine. In some embodiments, an inorganic salt is present in the reaction mixture. In certain embodiments, the inorganic salt, lithium chloride, is present in the reaction mixture. In some embodiments, the enone of formula VI is used in the next step without purification.

An exemplary synthetic scheme is as follows:

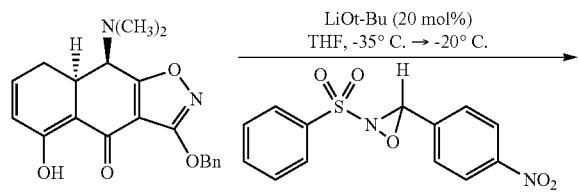

In certain embodiments, the electrophilic addition is stereoselective yielding only one or substantially one diastereomer. In certain embodiments, the diastereoselective reaction results in an diastereomeric excess (de) of at least 80%, at least 90%, at least 95%, at least 98%, or at least 99%. One of ordinary skill in the art would understand that the use of a compound of formula V with a different absolute or relative stereochemistry than that shown in the above scheme in the electrophilic addition may produce compounds of other absolute or relative stereochemistry than that shown explicitly in the scheme, and all of the possible enantiomers and diastereomers are encompassed by the present invention.

An enone of formula VI can be epimerized using a suitable acid to give an enone of formula VII. In some embodiments, the suitable acid is an inorganic acid. In certain embodiments, the suitable acid is sodium dihydrogenphosphate. In other embodiments, the suitable acid is potassium dihydrogenphosphate. In yet other embodiments, the suitable acid is sodium dihydrogenphosphate in aqueous hydrochloric acid. In some embodiments, the reaction mixture is biphasic. In some embodiments, an organic solvent is used in the reaction. In certain embodiments, the organic solvent is an ether. In certain other embodiments, the organic solvent is an alcohol. In certain embodiments, the solvent system comprises a mixture of an ether and an alcohol. In certain embodiments, the solvent system comprises methanol, tetrahydrofuran, and water. In some embodiments, the reaction takes place at a temperature between room temperature and the reflux temperature of the solvent. In certain embodiments, the reaction is performed at about 52° C.

In some embodiments, an enone of formula VI or VII can be further functionalized. In certain embodiments, when $R_9$ is —OH, the hydroxyl is optionally protected with a protecting group. In some embodiments, the protecting group is a silyl protecting group. In certain embodiments, the protecting group is a TBS group. In certain other embodiments, when $R_9$ is —OH, the hydroxyl group is optionally alkylated to form an alkoxy group. For example, the hydroxyl group can be treated with a base, e.g., lithium bis(trimethylsilyl)amide, optionally in the presence of an additive, e.g., HMPA, and reacted with an alkylating agent, e.g., methyl triflate to give a methoxy group.

In some embodiments, an enone of formula VI or VII is optionally functionalized such that $R_{10}$ is not hydrogen. For example, an enone of formula VI or VII can be treated with a suitable nucleophilic reagent in the presence of a suitable silylating reagent to effect a 1,4-conjugate addition to yield a silyl enol ether, which can then be treated with a suitable oxidant to generate the substituted enone. In some embodiments, the suitable nucleophilic reagent is an organometallic reagent. In some embodiments, the suitable nucleophilic reagent is an organocuprate. In certain embodiments, the suitable nucleophilic reagent is lithium dimethylcuprate. In some embodiments, the suitable silylating reagent is trimethylsilyl chloride. In certain embodiments, the suitable oxidant is palladium diacetate.

In some embodiments, an isoxazole of formula I' is synthesized from an isoxazole of formula IX as shown below:

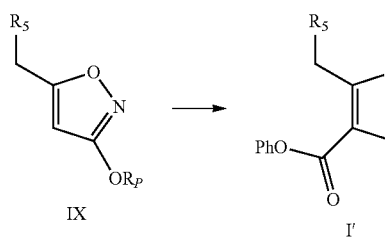

The compound of formula IX, wherein $R_5$ and $R_P$ are as defined above and described herein, can be treated with a suitable base and reacted with phenylchloroformate to yield a compound of formula I'. In some embodiments, the suitable base is an organometallic base. In certain embodiments, the suitable base is butyllithium. In certain embodiments, the suitable base is n-butyllithium.

In some embodiments, an enone of formula II, wherein $R_{11}$ is not hydrogen, is synthesized from an enone of formula II-H wherein $R_{11}$ is hydrogen as shown below:

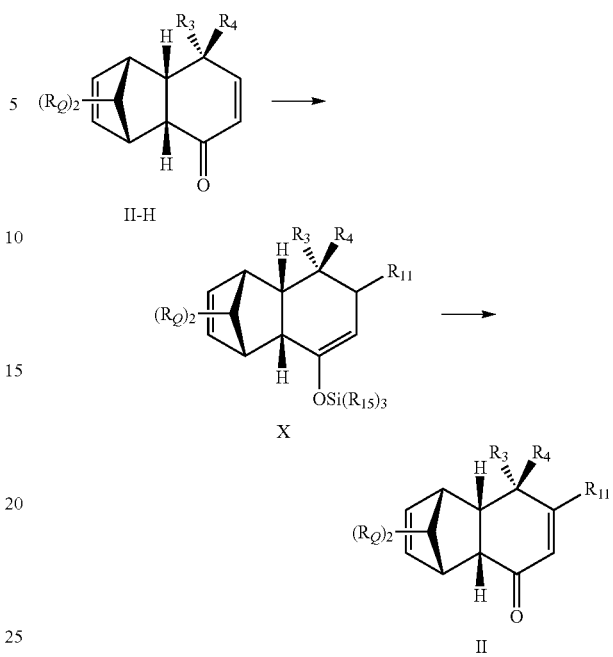

An enone of formula II-H can be treated with a suitable nucleophilic reagent in the presence of a suitable silylating reagent to effect a 1,4-conjugate addition to yield a silyl enol ether of formula X, wherein $R_{15}$ is a $C_{1-6}$ alkyl group, which can then be treated with a suitable oxidant to generate the substituted enone of formula II, wherein $R_{11}$ is not hydrogen. In some embodiments, the suitable nucleophilic reagent is an organometallic reagent. In some embodiments, the suitable nucleophilic reagent is an organocuprate. In certain embodiments, the suitable nucleophilic reagent is lithium dimethylcuprate. In some embodiments, the suitable silylating reagent is trimethylsilyl chloride. In certain embodiments, the suitable oxidant is palladium diacetate. In certain embodiments, an enone of formula II-H can be synthesized as shown below:

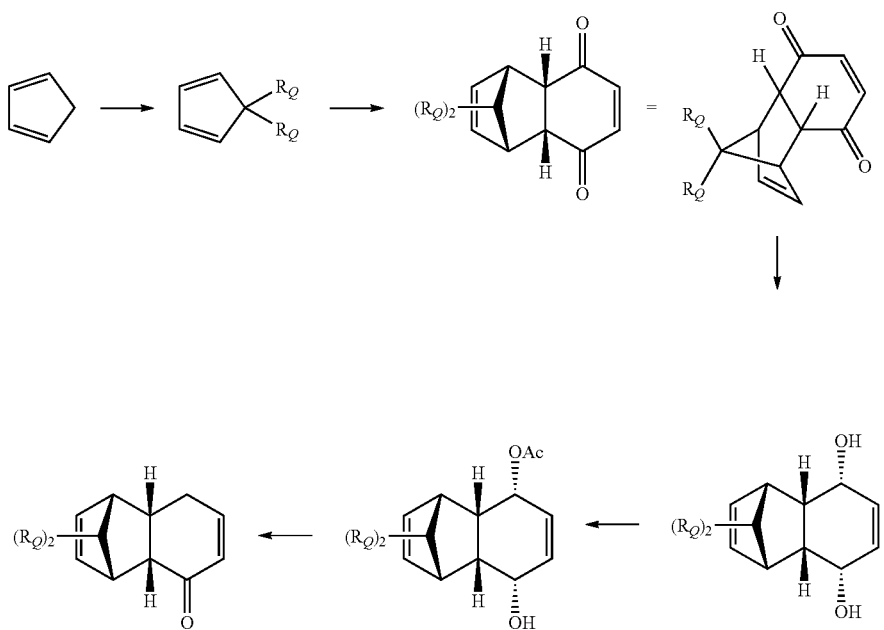

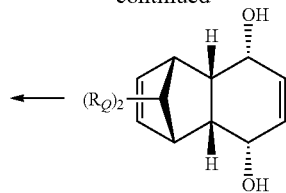

where each occurrence of $R_Q$ is independently hydrogen, $C_{1-6}$ alkyl, $-Si(OR_Z)_3$, or $-Si(R_Z)_3$, wherein each occurrence of $R_Z$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; or a substituted or unsubstituted, branched or unbranched heteroaryl.

In some embodiments, a compound of formula I' and a compound of formula II' are subjected to Michael-Claisen conditions as described herein to yield a compound of formula IV'.

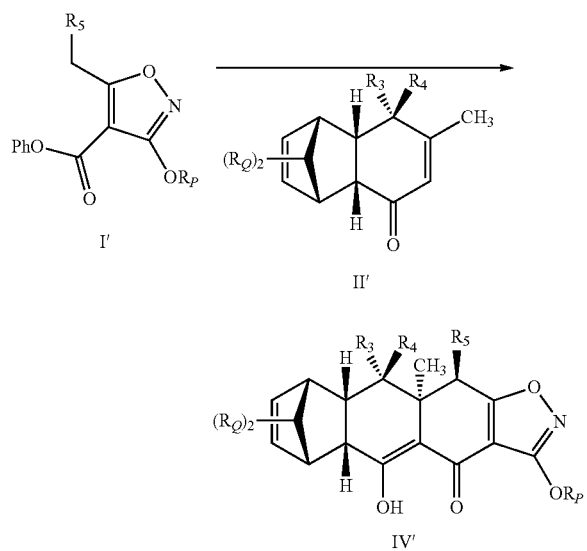

In some embodiments, the suitable base used to deprotonate I' is a metal amide. In certain embodiments, the suitable base is a bis(trimethylsilyl)amide. In certain embodiments, the suitable base is lithium bis(trimethylsilyl)amide. In other embodiments, the base is lithium diisopropylamide or lithium diethylamide. In yet other embodiments, the base is sodium hydride or potassium hydride. In some embodiments, M is sodium, lithium, or potassium. In certain embodiments, M is lithium. In some embodiments, the reaction is performed a temperature from about −78° C. to about 0° C. In certain embodiments, the reaction is performed at −78° C. In certain other embodiments, the reaction is performed at −60° C. In yet other embodiments, the reaction is performed at −20° C. In some embodiments, the solvent used for the reaction is an aprotic solvent. In some embodiments, the solvent is a polar aprotic solvent. In certain embodiments, the solvent is an ether. In certain embodiments, the solvent is tetrahydrofuran. In some embodiments, the reaction further comprises an additive. In certain embodiments, the additive is hexamethylphos- phoramide (HMPA). In certain other embodiments, the additive is 1,3-dimethyl-3,4,5,6-tetrahydro-2(1H)-pyrimidinone (DMPU). In other embodiments, the additive is a copper-containing additive.

In certain embodiments, the Michael addition is stereoselective yielding only one or substantially one diastereomer. In certain embodiments, the diastereoselective reaction results in an diastereomeric excess (de) of at least 80%, at least 90%, at least 95%, at least 98%, or at least 99%. One of ordinary skill in the art would understand that the use of a compound of formula II' with a different absolute or relative stereochemistry than that shown in the above scheme in the Michael addition may produce compounds of other absolute or relative stereochemistry than that shown explicitly in the scheme, and all of the possible enantiomers and diastereomers are contemplated by the present invention.

In some embodiments, the suitable base used to effect the Claisen condensation is an inorganic base. In other embodiments, the suitable base is an organic base. In some embodiments, the suitable base is a metal amide. In certain embodiments, the suitable base is a bis(trimethylsilyl)amide. In certain embodiments, the suitable base is potassium bis(trimethylsilyl)amide. In other embodiments, the base is lithium diisopropylamide or lithium diethylamide. In yet other embodiments, the base is sodium hydride or potassium hydride. In some embodiments, the reaction is performed at a temperature from about −78° C. to the refluxing temperature of the solvent. In certain embodiments, the reaction is performed at −78° C. In certain other embodiments, the reaction is performed at −20° C. In yet other embodiments, the reaction is performed at room temperature. In some embodiments, the solvent used for the reaction is an aprotic solvent. In some embodiments, the solvent is a polar aprotic solvent. In certain embodiments, the solvent is an ether. In certain embodiments, the solvent is tetrahydrofuran. In some embodiments, the reaction further comprises an additive. In certain embodiments, the additive is hexamethylphosphoramide (HMPA). In certain other embodiments, the additive is 1,3-dimethyl-3,4,5,6-tetrahydro-2(1H)-pyrimidinone (DMPU). In other embodiments, the additive is a copper-containing additive.

In some embodiments, when $R_9$ is alkyl, the compound of formula IIa is prepared as shown below:

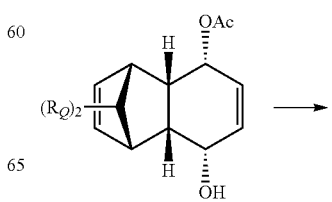

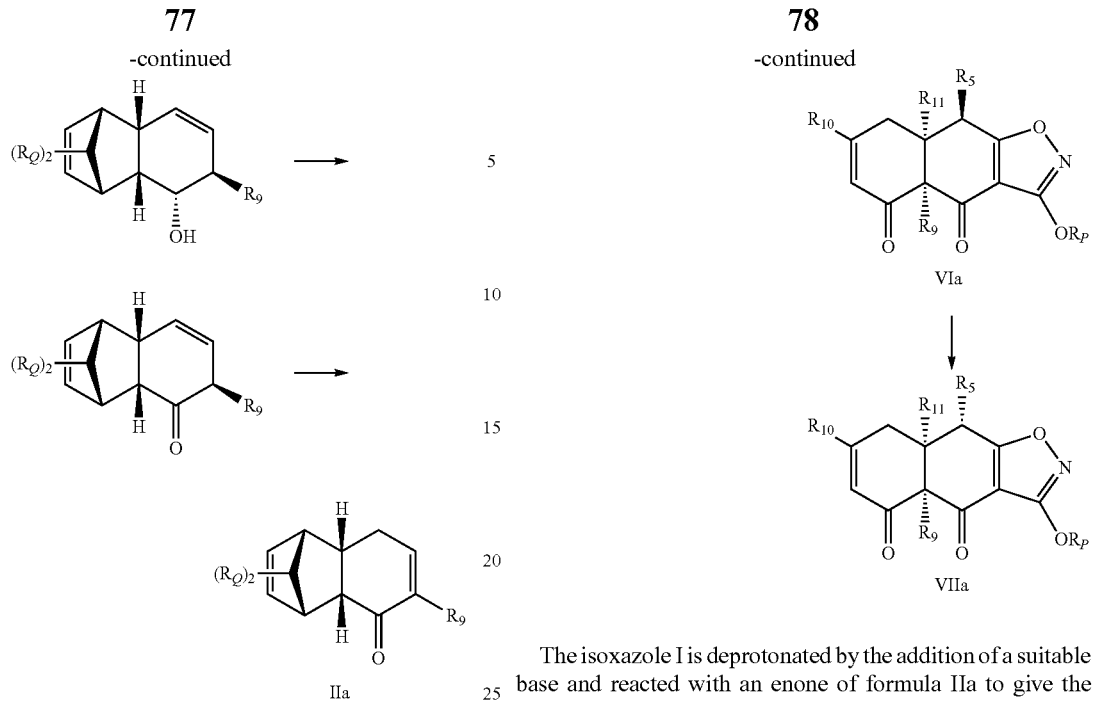

An allylic displacement reaction is performed on the allylic acetate using an organometallic reagent. In some embodiments, the organometallic reagent is an organocuprate. In certain embodiments, the organometallic reagent is an alkyllithium reagent and copper cyanide. In certain embodiments, the alkyllithium reagent is methyllithium. The resulting alcohol is oxidized to the ketone using an oxidant. In some embodiments, the oxidant is IBX. The resulting ketone is treated with a base to give the enone of formula IIa, wherein $R_9$ is alkyl. In some embodiments, the base is an alkoxide. In certain embodiments, the base is methoxide. In certain embodiments, the base is sodium methoxide in methanol.

The compound of formula IIa can then be used to synthesize a compound of formula VIIa, as shown below:

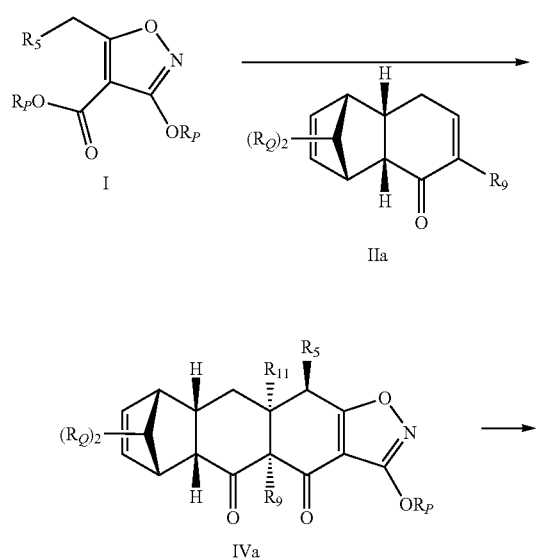

The isoxazole I is deprotonated by the addition of a suitable base and reacted with an enone of formula IIa to give the Michael-Claisen product of formula IVa. In some embodiments, the suitable base used to deprotonate I is a metal amide. In certain embodiments, the suitable base is a bis (trimethylsilyl)amide. In certain embodiments, the suitable base is sodium bis(trimethylsilyl)amide. In some embodiments, the suitable base is lithium bis(trimethylsilyl)amide. In certain embodiments, the Michael addition/Claisen condensation is stereoselective yielding only one or substantially one enantiomer. In certain embodiments, the enantioselective reaction results in an enantiomeric excess (ee) of at least 80%, at least 90%, at least 95%, at least 98%, or at least 99%. One of ordinary skill in the art would understand that the use of a compound of formula IIa having a different absolute or relative stereochemistry than that shown in the above scheme in the Michael addition may produce compounds of other absolute or relative stereochemistry than that shown explicitly in the scheme, and all of the possible enantiomers and diastereomers are encompassed by the present invention.

A retro Diels-Alder reaction can be performed on the Michael-Claisen product of formula IVa to give an enone of formula VIa. In some embodiments, the reaction is performed at an elevated temperature. In other embodiments, the reaction is performed at the reflux temperature of the solvent. In certain embodiments, the reaction is performed at about 250° C. In some embodiments, the solvent is a high boiling solvent. In certain embodiments, the solvent is diphenyl ether. In some embodiments, the reaction is run as a continuous-flow reaction. In certain embodiments, the continuous-flow reaction is aided by a setup as described in FIG. 1. In some embodiments, a dienophile is present in the reaction mixture. In certain embodiments, dimethyl maleate is present in the reaction mixture. In other embodiments, dibutyl maleate is present in the reaction mixture. In yet other embodiments, maleic anhydride is present in the reaction mixture. In some embodiments, the continuous flow reaction is performed using the dienophile as solvent, e.g., dibutyl maleate.

An enone of formula VIa can be epimerized using a suitable acid to give an enone of formula VIIa. In some embodiments, the suitable acid is an inorganic acid. In certain embodiments, the suitable acid is sodium dihydrogenphosphate. In other embodiments, the suitable acid is potassium dihydrogenphosphate. In yet other embodiments, the suitable acid is sodium dihydrogenphosphate in aqueous hydrochloric acid. In some embodiments, the reaction mixture is biphasic. In some embodiments, an organic solvent is used in the reaction. In certain embodiments, the organic solvent is an ether. In certain other embodiments, the organic solvent is an alcohol. In certain embodiments, the solvent system comprises a mixture of an ether and an alcohol. In certain embodiments, the solvent system comprises methanol, tetrahydrofuran, and water. In some embodiments, the reaction takes place at a temperature between room temperature and the reflux temperature of the solvent. In certain embodiments, the reaction is performed at a temperature ranging from about 40° C. to about 60° C. In certain embodiments, the reaction is performed at a temperature ranging from about 45° C. to about 55° C. In certain embodiments, the reaction is performed at about 52° C.

In some embodiments, an enone of formula VIIa or VIIa is optionally functionalized such that $R_{10}$ is not hydrogen. For example, an enone of formula VIIa or VIIa can be treated with a suitable nucleophilic reagent in the presence of a suitable silylating reagent to effect a 1,4-conjugate addition to yield a silyl enol ether, which can then be treated with a suitable oxidant to generate the substituted enone. In some embodiments, the suitable nucleophilic reagent is an organometallic reagent. In some embodiments, the suitable nucleophilic reagent is an organocuprate. In certain embodiments, the suitable nucleophilic reagent is lithium dimethylcuprate. In some embodiments, the suitable silylating reagent is trimethylsilyl chloride. In certain embodiments, the suitable oxidant is palladium diacetate.

In another aspect, an enone of formula VII may be functionalized at the C5 position by employing a bromination/nucleophilic displacement sequence. An exemplary scheme is shown below. The enone can be protected with a silyl protecting group, e.g., trimethylsilyl, triisopropylsilyl, tert-butyldimethylsilyl, by treating with a silylating reagent, e.g., trimethylsilyl triflate, triisopropylsilyl triflate, tert-butyldimethylsilyl triflate, then treated with a brominating agent, e.g., N-bromosuccinimide, to yield the enone having a bromine at the C5 position. The bromine can then be displaced with a variety of reagents, e.g., tetramethylguanidinium azide, to yield the desired functionality at C5, e.g., azide. Further transformations can be performed if desired to yield other functionalities, e.g., amino.

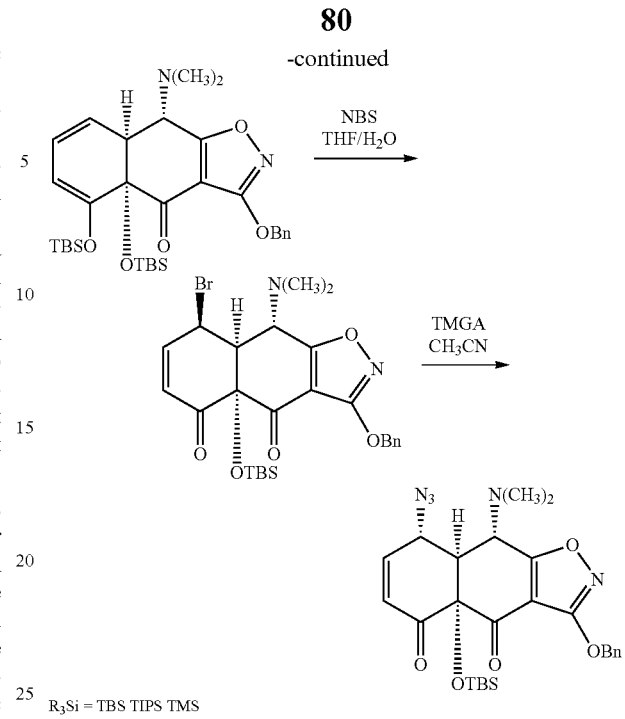

$R_3Si$ = TBS TIPS TMS

As would be appreciated by one of skill in the art, each of the steps in the synthesis of the enone may be optionally followed by the appropriate work-up and purification of the desired product. Certain steps, however, may not require purification before being used as starting material in the next reaction. The inventive synthesis of the enone may be used to prepare multi-gram quantities. In certain embodiments, at least 25 grams of the enone is prepared. In other embodiments, at least 50 grams of the enone is prepared using the inventive synthesis. In certain other embodiments, at least 100 grams of the enone is prepared. In certain embodiments, the enone is prepared on a kilogram scale or greater.

In some embodiments, an enone of formula VII may be functionalized at the C5 position by reaction with a cation. An exemplary scheme is shown below. The enone can be protected with a silyl or other protecting group, such as those described herein.

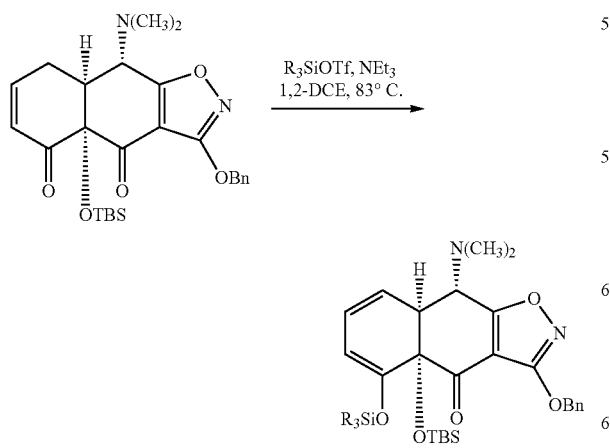

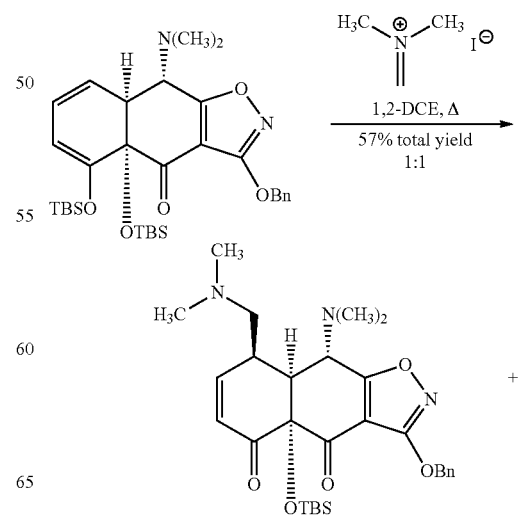

-continued

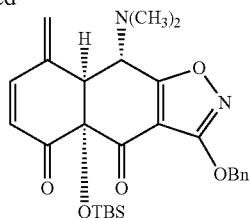

The enone VII is then optionally reacted with an anion of a phthalide, an anion of a toluate, a benzocyclobutenole, or a diene to yield a tetracycline analog. Details of these reactions and possible phthalides, toluates, benzocyclobutenoles, and dienes are described in U.S. patent application US 2005/0282787, published Dec. 22, 2005; WO 05/112945, published on Dec. 1, 2005; and U.S. provisional patent application, U.S. Ser. No. 60/790,413, filed Apr. 7, 2006. Exemplary schemes are shown below.

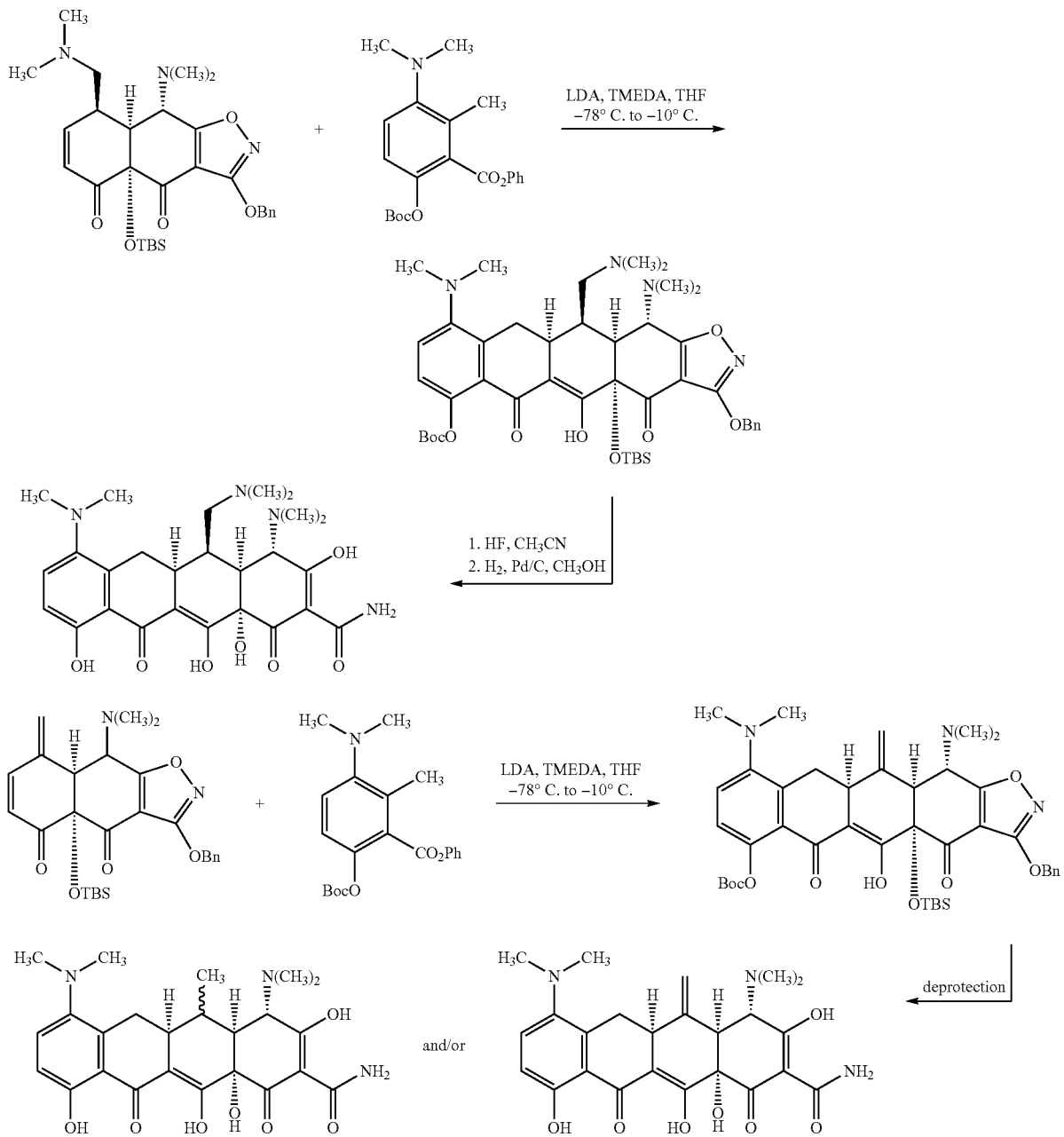

In one embodiment, an enone of formula VII is reacted with a protecting group at the C5a position, and the reaction product is reacted with a toluate to yield a tetracycline analog. An exemplary scheme is shown below:

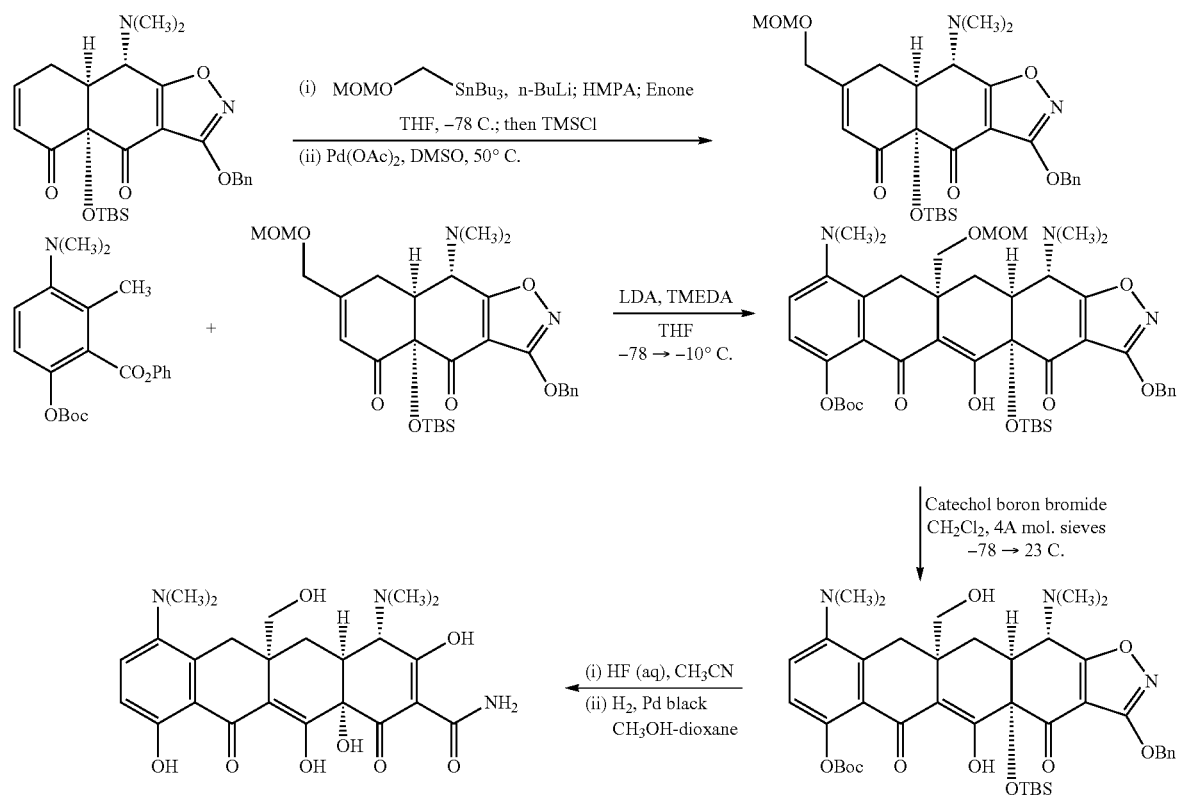
Another exemplary scheme for reacting an enone of formula VII with a protecting group at the C5a position, and then reacting the reaction product with a toluate to yield a tetracycline analog, is shown below:
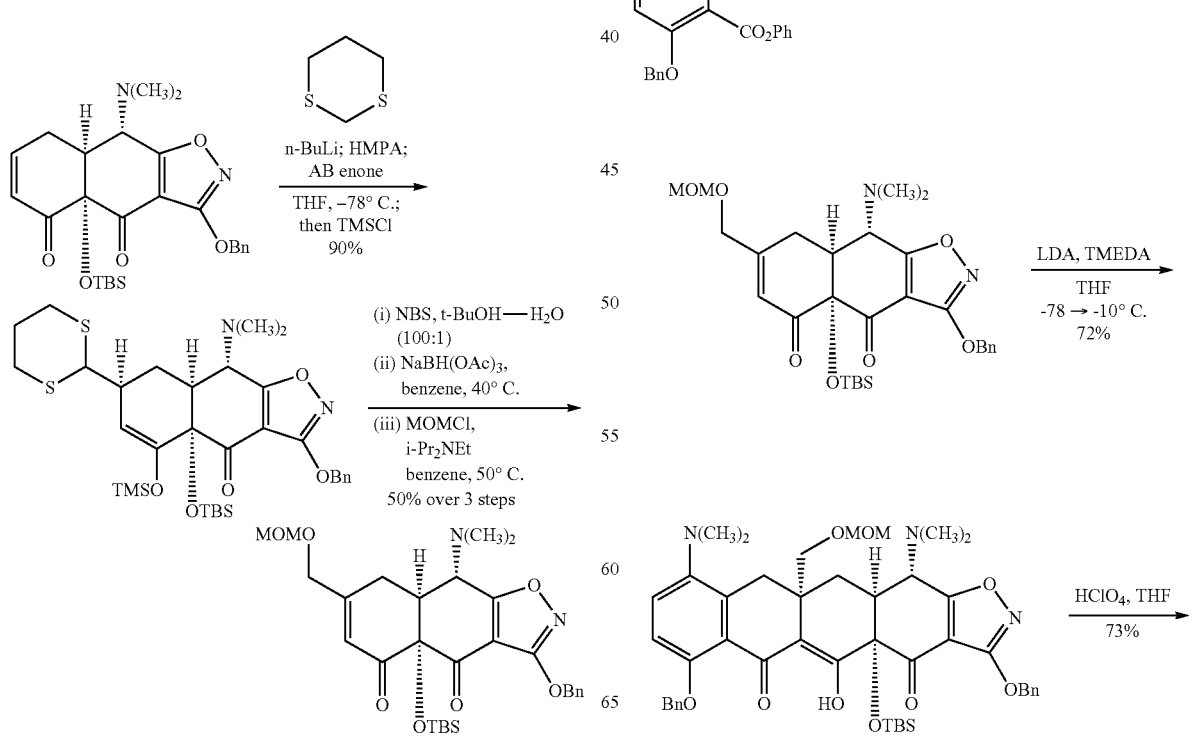

-continued

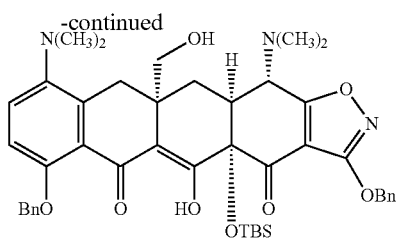

In one embodiment, an enone of formula VII is reacted with an anion resulting from the deprotonation of a toluate of formula:

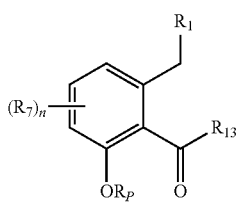

wherein $R_1$, $R_7$ and $R_P$ are as defined above and described herein;

n is an integer in the range of 0 to 3, inclusive;

$R_{13}$ is —$OR_E$, —CN, —SCN, —$SR_E$, or —$N(R_E)_2$; wherein each $R_E$ is independently hydrogen; a protecting group; a cyclic or acyclic, substituted or unsubstituted aliphatic; a cyclic or acyclic, substituted or unsubstituted heteroaliphatic; a substituted or unsubstituted aryl; or a substituted or unsubstituted heteroaryl;

is deprotonated under basic conditions (e.g., LDA, HMDS), and the resulting anion is reacted with an enone of formula:

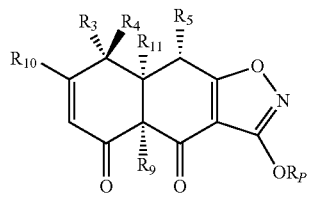

(VII)

wherein $R_3$, $R_4$, $R_5$, $R_9$, $R_{10}$, $R_{11}$, and $R_P$ are as defined above and described herein, provided that when $R_9$ is —$OR_C$, $R_{10}$ and $R_{11}$ are not simultaneously hydrogen; to form the product:

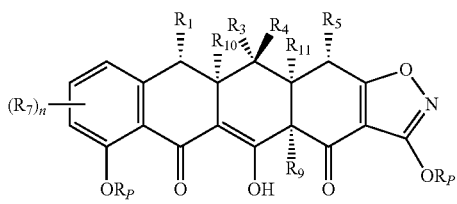

wherein $R_1$, $R_3$, $R_4$, $R_5$, $R_7$, $R_9$, $R_{10}$, $R_{11}$, $R_P$, and n are as defined above and described herein; provided that when $R_9$ is —$OR_C$, $R_{10}$ and $R_{11}$ are not simultaneously hydrogen.

As will be appreciated by one of skill in this art, the toluate may be further substituted in certain embodiments. In addition, the phenyl ring of the toluate may be substituted for an aromatic heterocyclic ring such as a pyridine ring. Other examples of carbocyclic and heterocyclic toluate analogs include:

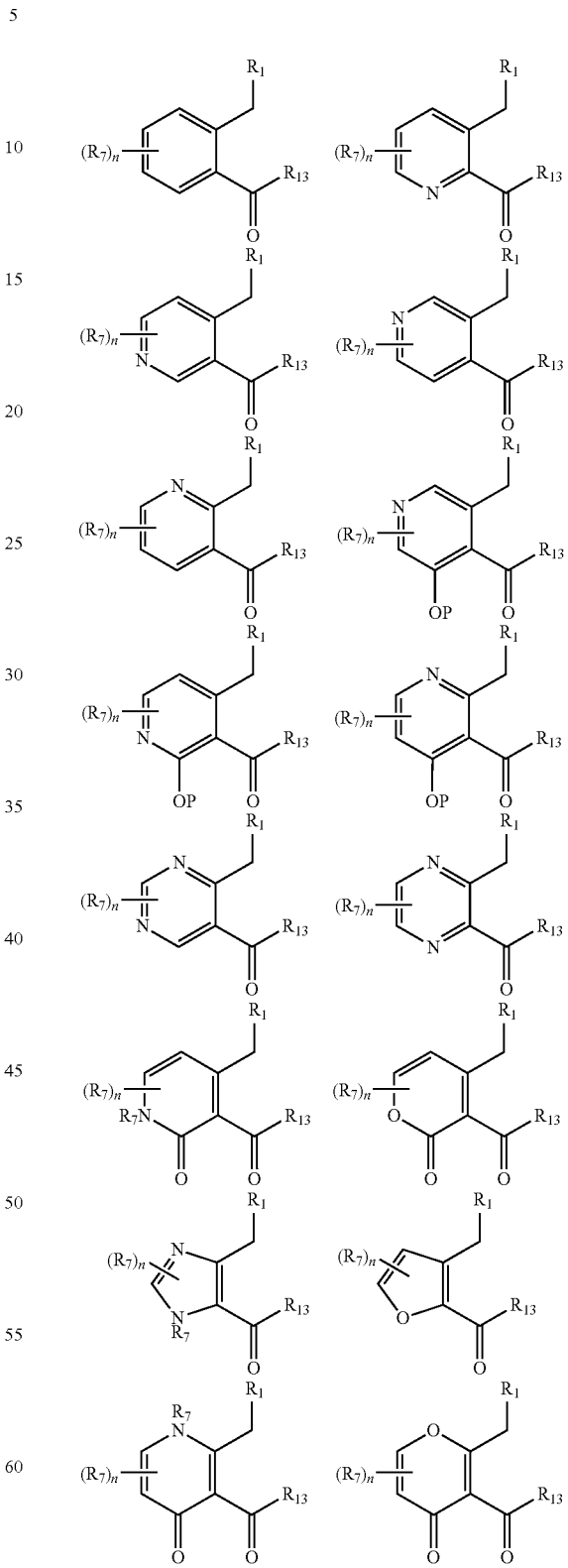

In certain embodiments, polycyclic toluates are used in the Michael-Dieckmann reaction sequence to form pentacyclines, hexacyclines, or higher cyclines. Toluates useful in preparing pentacyclines are exemplified by the formula:

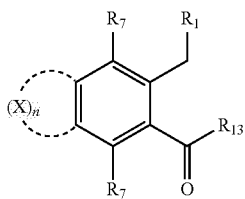

wherein $R_1$, $R_7$, $R_{13}$, $R_P$, and

are as defined above and described herein.

In another embodiment, an enone of formula VII is reacted with an anion, which is generated through metalation (e.g., metal-halogen exchange, metal-metalloid exchange, lithium-halogen exchange, lithium-tin exchange, etc. by reacting the toluate with the appropriate metal reagent) of a toluate of the following formula:

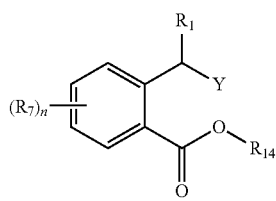

wherein $R_1$ and $R_7$ are as defined above and described herein;
n is an integer in the range of 0 to 3, inclusive;
$R_{14}$ is selected from the group consisting of substituted or unsubstituted aryl or heteroaryl groups; and
Y is hydrogen, a halogen or $Sn(R_Y)_3$, wherein $R_Y$ is alkyl. The anion generated is reacted with the enone (VII) to generate a product of formula:

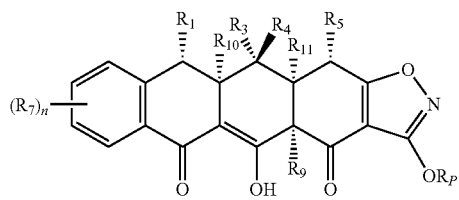

wherein $R_1$, $R_3$, $R_4$, $R_5$, $R_7$, $R_9$, $R_{10}$, $R_{11}$, $R_P$, and n are as defined above and described herein; provided that when $R_9$ is —$OR_C$, $R_{10}$ and $R_{11}$ are not simultaneously hydrogen.

Any metal may be used in the metalation reaction to generate the metal anionic reagent to be reacted with the enone. In certain embodiments, the metal is a Group I element on the periodic chart. In other embodiments, the metal is a Group II element on the periodic chart. In other embodiments, the metal is a transition metal. Exemplary metals useful in the metalation reaction include sodium, lithium, calcium, aluminium, cadmium, copper, beryllium, arsenic, antimony, tin, magnesium, titanium, zinc, manganese, iron, cobalt, nickel, zinc, platinum, palladium, mercury, and ruthenium. In certain preferred embodiments, the metal is chosen from lithium, magnesium, titanium, zinc, and copper. In yet other embodiments, the metal is magnesium, lithium, sodium, beryllium, zinc, mercury, arsenic, antimony, or tin. In certain particular embodiments, a lithium-halogen exchange is used. The lithium-halogen exchange may be performed in situ in the presence of the enone. The lithium-halogen exchange may be preformed using any lithium reagent including, for example, alkyllithium reagents, n-butyllithium, t-butyllithium, phenyl lithium, mesityl lithium, and methyllithium. In certain embodiments, other organometallics reagents are generated and reacted with the enone. Examples include Grignard reagents, zero-valent metal complexes, ate complexes, etc. In certain embodiments, the metal reagent is a magnesium reagent including, but not limited to, magnesium metal, magnesium anthracene, activated magnesium turnings, etc. In certain embodiments, the reagent is zinc-based. The reagent may be generated in situ in the presence of the enone, or the reagent may be generated separately and later contacted with the enone. In certain embodiments, milder conditions for the cyclization are used (e.g., a zinc reagent).

As will be appreciated by one of skill in this art, the toluate may be further substituted in certain embodiments. In addition, the phenyl ring of the toluate may be substituted for an aromatic heterocyclic ring or ring system such as a pyridine ring. Examples of carbocyclic and heterocyclic analogs of toluate include:

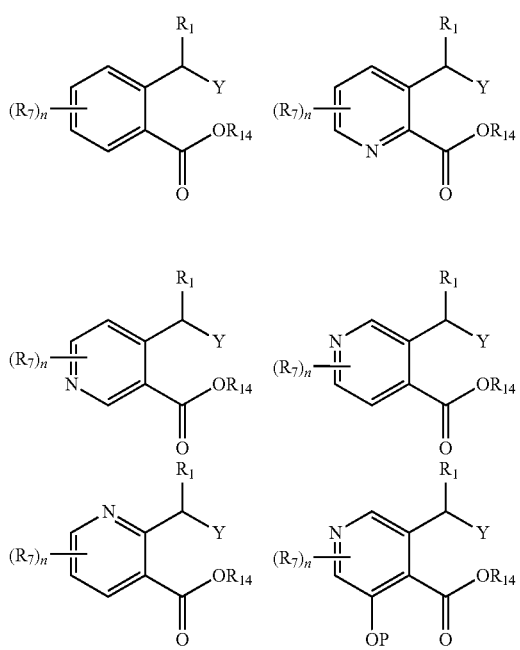

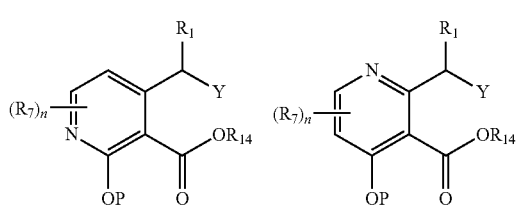

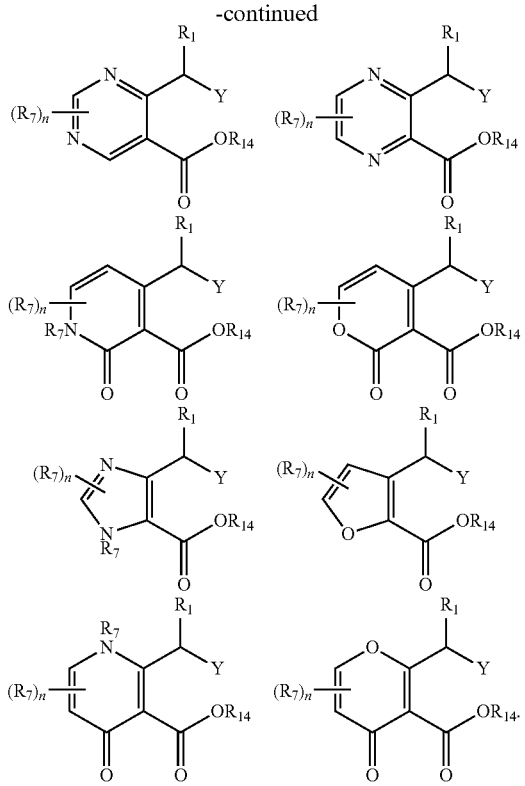

represents a substituted or unsubstituted aryl, heteroaryl, carbocyclic, or heterocyclic moiety, in which each occurrence of X is independently —O—, —S—, —NR$_{12}$—, or —C(R$_{12}$)$_2$—; n is an integer in the range of 1 to 5, inclusive; and the bonds between adjacent X moieties are either single or double bonds;

R$_{12}$ is as defined above and described herein; and

Y is hydrogen, a halogen or Sn(R$_Y$)$_3$, wherein R$_Y$ is alkyl.

In certain embodiments, the halogen Y is bromine. In certain embodiments, the halogen Y is bromine. In other embodiments, Y is iodine. In yet other embodiments, Y is chloride. In some embodiments, Y is hydrogen. In certain embodiments, Y is a metalloid (e.g., tin, selenium, tellurium, etc.). In certain embodiments, Y is —SnR$_3$, wherein each occurrence of R is independently alkyl (e.g., —Sn(CH$_3$)$_3$). After the metalation reaction, Y is a metal such as lithium, magnesium, zinc, copper, sodium, mercury, antimony, etc. In certain embodiments, R$_1$ is hydrogen or C$_{1-6}$ alkyl. In certain particular embodiments, R$_1$ is hydrogen. In certain embodiments, R$_{14}$ is phenyl or substituted phenyl. In certain embodiments, ortho-R$_7$ is alkoxy such as methoxy. In other embodiments, R$_7$ is hydrogen. Exemplary polycyclic toluates include:

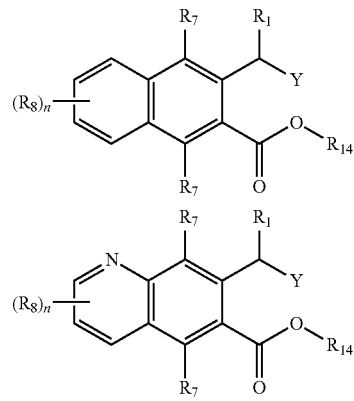

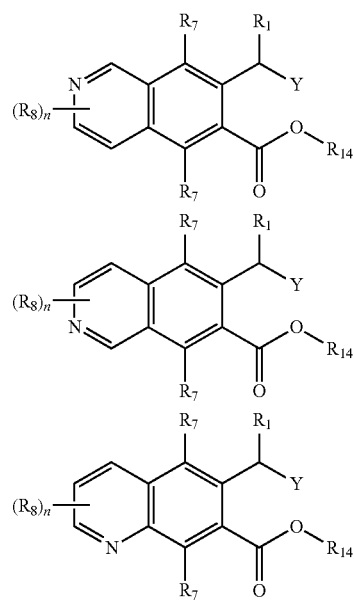

In certain embodiments, the halogen Y is bromine. In other embodiments, Y is iodine. In yet other embodiments, Y is chloride. In some embodiments, Y is hydrogen. In certain embodiments, Y is a metalloid (e.g., tin, selenium, tellurium, etc.). In certain embodiments, Y is —SnR$_3$, wherein each occurrence of R is independently alkyl (e.g., —Sn(CH$_3$)$_3$). After the metalation reaction, Y is a metal such as lithium, magnesium, zinc, copper, antimony, sodium, etc. In certain embodiments, R$_1$ is hydrogen or C$_{1-6}$ alkyl. In certain particular embodiments, R$_1$ is hydrogen.

In other embodiments, polycyclic toluates may be used to prepare pentacyclines, hexacyclines, or higher cyclines. Toluates useful in the preparation of such cyclines are of the formula:

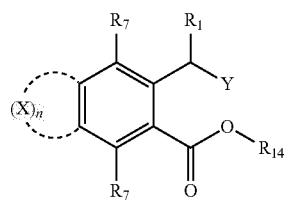

wherein R$_1$, and R$_7$ are as defined above and described herein; n is an integer in the range of 0 to 3, inclusive;

R$_{14}$ is selected from the group consisting of substituted or unsubstituted aryl or heteroaryl groups;

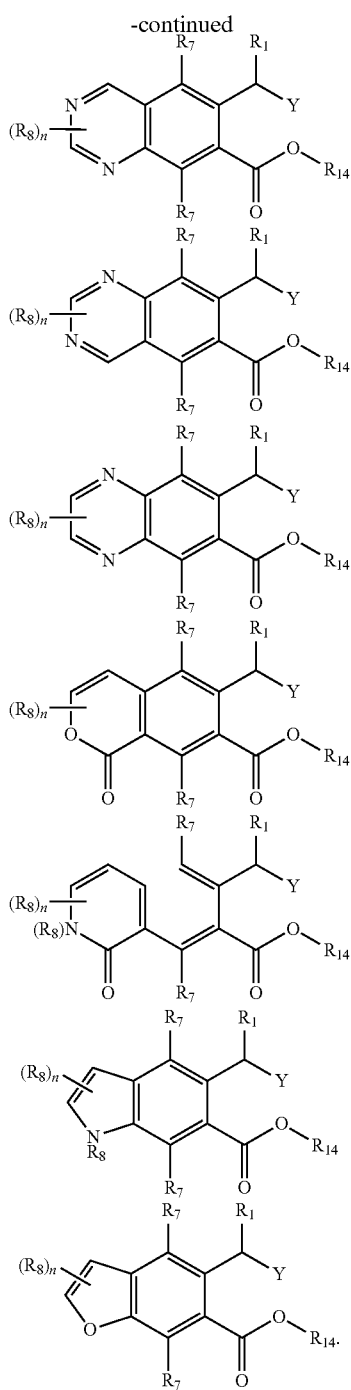

Compounds of the formula below with a heterocyclic C-ring:

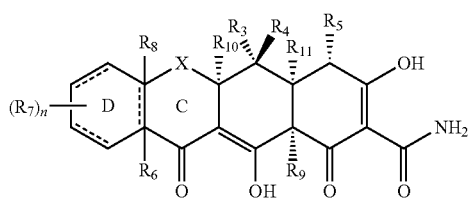

may be prepared by Michael-Dieckmann closure of a D-ring precursor derived from the corresponding anilide, phenol, or thiophenol. A representative example using anthranilic acid (i.e., anilide as the nucleophile in the Michael addition reaction) is shown below:

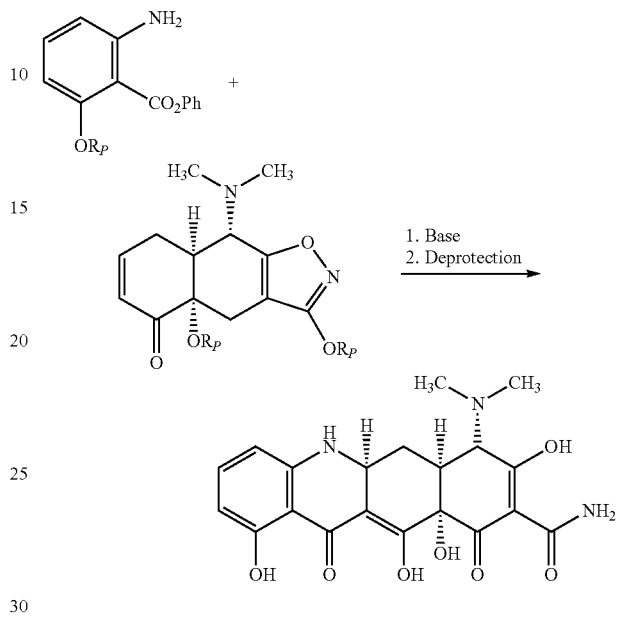

In another embodiment, the enone of formula VII is reacted with a benzocyclobutenol in an o-quinone dimethide Diels-Alder reaction. The enone VII is reacted under suitable conditions (e.g., heat) with a benzocyclobutenol of formula:

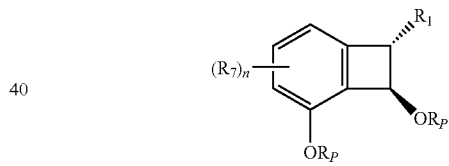

wherein $R_1$, $R_7$ and $R_P$ are as defined above and described herein;

n is an integer in the range of 0 to 3, inclusive;

to form the product of formula:

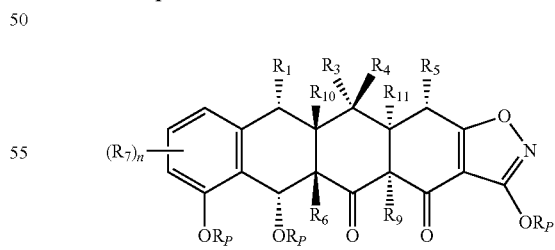

wherein $R_1$, $R_3$, $R_4$, $R_5$, $R_6$, $R_7$, $R_9$, $R_{10}$, $R_{11}$, and $R_P$ are defined as above; provided that when $R_9$ is —$OR_C$, $R_{10}$ and $R_{11}$ are not simultaneously hydrogen. As will be appreciate by one of skill in this art, the reactants may be substituted further and still fall within the claimed invention. For example, the phenyl ring of the benzocyclobutenol ring may be further substituted.

In another embodiment, the enone is reacted with a diene in a Diels-Alder reaction to yield a tricycline. The enone VII is reacted under suitable conditions (e.g., heat) with a diene of formula:

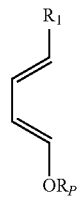

wherein $R_1$ and $R_P$ are as defined above and described herein;
to yield a protected tricycline of formula:

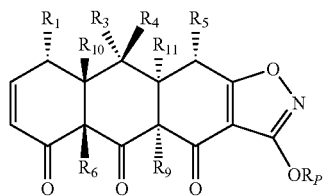

wherein $R_1$, $R_3$, $R_4$, $R_5$, $R_6$, $R_9$, $R_{10}$, $R_{11}$, and $R_P$ are as defined above and described herein; provided that when $R_9$ is $-OR_C$, $R_{10}$ and $R_{11}$ are not simultaneously hydrogen. As will be appreciated by one of skill in this art, the enone and diene may be further substituted and still be encompassed within the present invention.

In yet another embodiment, the enone is reacted with an anion of a phthalide or cyano-phthalide. The enone of formula VII is reacted under basic conditions (e.g., LDA, $Ph_3CLi$) with the anion of the phthalide of formula:

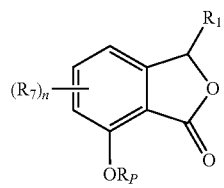

wherein $R_1$, $R_7$, and $R_P$ are as defined above and described herein; and
n is an integer in the range of 0 to 3, inclusive;
to yield a product of formula:

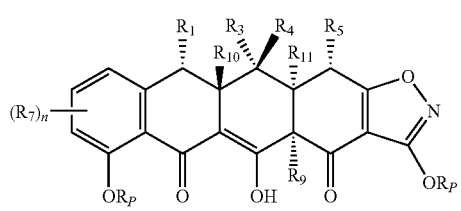

wherein $R_1$, $R_3$, $R_4$, $R_5$, $R_7$, $R_9$, $R_{10}$, $R_{11}$, $R_P$, and n are as defined above and described herein; provided that when $R_9$ is $-OR_C$, $R_{10}$ and $R_{11}$ are not simultaneously hydrogen.

The products of the above reactions are optionally further functionalized, reduced, oxidized, rearranged, protected, and deprotected to yield the final desired product. Each of the above steps may be followed with an appropriate work-up and purification of the desired product. As will be appreciated by one of skill in the art, various isolation and purification techniques including flash chromatography, crystallization, distillation, HPLC, thin layer chromatography, extraction, filtration, etc. may be used in the course of synthesizing compounds of the invention. These techniques may be used in the preparation or purification of intermediates, reagents, products, starting materials, or solvents.

As an example of a further reaction of a tetracycline, the formula:

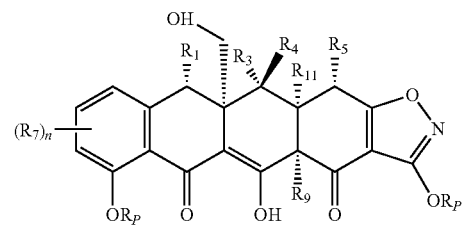

wherein $R_1$, $R_3$, $R_4$, $R_5$, $R_7$, $R_9$, $R_{11}$, and $R_P$ are as defined above and described herein and n is an integer in the range of 0 to 8, inclusive, can be reacted with carbonyl dichloride to yield a cyclopropane intermediate of formula:

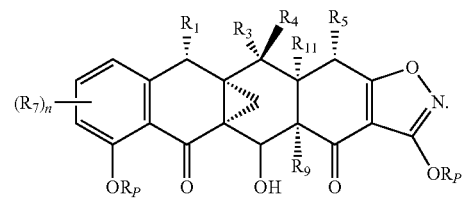

The cyclopropane intermediate can be reacted with a variety of nucleophiles (e.g., $-CN$, $-OCH_3$, $-OCHOCH_3$, morpholine, piperidine, tert-butyl 1-peperazine carboxylate, cyclopropylamine, diethylamine, 2-(methylamino)ethanol, 3-dimethylamino-1-propylamine, 2-methoxyethanol, imidazole, 3-aminopyridine) to yield a desired structure having the formula:

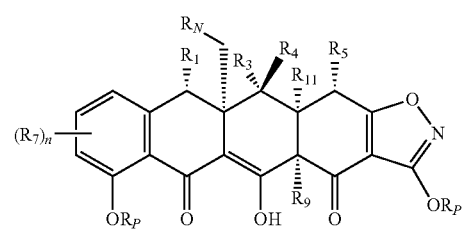

wherein $R_N$ is halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-OR_C$; $-CH_2OR_C$; $-CH_2R_C$;

—$CH_2N(R_C)_2$; =$C(R_C)_2$; —$OCHOR_C$; —$CH_2OR_C$; —$CH_2R_C$; —$OCH_2CH_2N(R_C)_2$; —$C(=O)R_C$; —$CO_2R_C$; —CN; —SCN; —$SR_C$; —$SOR_C$; —$SO_2R_C$; —$N_3$; —$NO_2$; —$N(R_C)_2$; —$NHC(O)R_C$; —$NHSO_2R_C$; or —$C(R_C)_3$; wherein each occurrence of $R_C$ is independently hydrogen, halogen, azido, a protecting group, aliphatic, heteroaliphatic, haloaliphatic, acyl, aryl, heteroaryl, alkoxy, aryloxy, alkylthio, arylthio, amino, alkylamino, dialkylamino, heteroaryloxy, or heteroarylthio.

An exemplary scheme for preparing and modifying a cyclopropane intermediate is shown below:

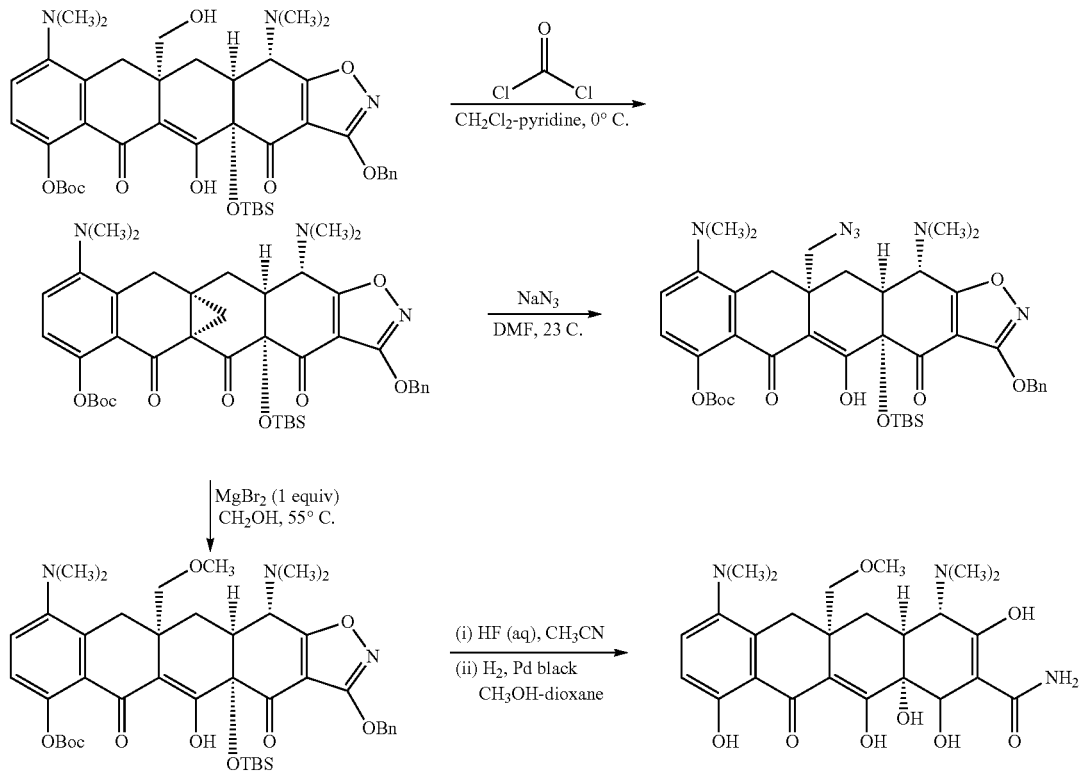

The cyclopropane chemistry may be applied to a variety of tetracycline analogs as described herein.

In certain embodiments, modification of a cyclopropane intermediate may yield a tetracycline having an aminomethyl group at the C5a position. The tetracycline analog may be further reacted, e.g., with an acyl chloride or an anhydride, to generate a variety of tetracycline analogs as described herein.

Intermediates

Along with synthetic methodology, the invention also provides useful intermediates useful in the preparation of the enone of formula VII and tetracycline analogs.

In certain embodiments, the invention provides a compound of formula (VII):

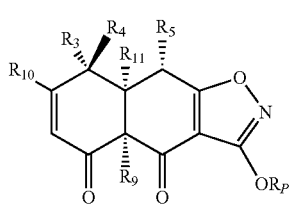

(VII)

wherein $R_3$, $R_4$, $R_5$, $R_9$, $R_{10}$, $R_{11}$, $R_P$ and n are as defined above and described herein; provided that when $R_9$ is —$OR_C$, $R_{10}$ and $R_{11}$ are not simultaneously hydrogen.

In some embodiments, $R_{10}$ is not hydrogen. In some embodiments, $R_{11}$ is not hydrogen. In some embodiments, at least one of $R_{10}$ and $R_{11}$ is not hydrogen. In some embodiments, both $R_{10}$ and $R_{11}$ are not hydrogen.

In some embodiments, $R_9$ is not —$OR_C$. In some embodiments, $R_9$ is not —$OR_C$ when both $R_{10}$ and $R_{11}$ are hydrogen. In some embodiments, $R_9$ is not —$OR_C$, wherein $R_C$ is hydrogen or an oxygen-protecting group. In certain embodiments, $R_9$ is not —OH. In other embodiments, when $R_9$ is —$OR_C$, the substituents at $R_{10}$ and $R_{11}$ are not simultaneously hydrogen, and $R_3$ and $R_4$ are not hydrogen or —$OR_B$. In some embodiments, when $R_9$ is not hydroxyl or a protected hydroxyl, $R_{10}$ and $R_{11}$ may be simultaneously hydrogen.

In some embodiments, $R_3$ is hydrogen, halogen, —$OR_B$, or $C_{1-6}$ alkyl. In other embodiments, $R_3$ is —$OR_B$. In certain embodiments, $R_3$ is hydroxyl. In certain other embodiments, $R_3$ is fluorine. In yet other embodiments, $R_3$ is hydrogen. In some embodiments, $R_4$ is hydrogen, halogen, —$OR_B$, or $C_{1-6}$ alkyl. In other embodiments, $R_4$ is —$OR_B$. In certain embodiments, $R_4$ is hydroxy. In certain other embodiments, $R_4$ is fluorine. In yet other embodiments, $R_4$ is hydrogen. In some embodiments, $R_3$ is —$N(R_B)_2$. In other embodiments, $R_4$ is —$N(R_B)_2$. In certain embodiments, $R_3$ is —$NHC(O)R_B$ or —$NHSO_2R_B$. In certain other embodiments, $R_4$ is —$NHC(O)R_B$ or —$NHSO_2R_B$. In certain embodiments, $R_3$ and $R_4$ are both hydrogen. In some embodiments, $R_3$ is —$OR_B$, and $R_4$ is hydrogen. In other embodiments, $R_3$ is hydrogen, and $R_4$ is —$OR_B$. In certain embodiments, $R_3$ is hydroxyl, and $R_4$ is hydrogen. In certain other embodiments, $R_3$ is hydrogen, and $R_4$ is hydroxyl. In some embodiments, $R_3$ is fluorine, and $R_4$ is hydrogen. In other embodiments, $R_3$ is hydrogen, and $R_4$ is fluorine. In certain embodiments, $R_3$ and $R_4$ are both fluorine.

In some embodiments, $R_5$ is $—N(R_C)_2$. In certain embodiments, $R_5$ is $—N(R_C)_2$, wherein $R_C$ is hydrogen or $C_{1-6}$ alkyl. In certain other embodiments, $R_5$ is $—N(R_E)_2$, wherein $R_E$ is methyl. In some embodiments, $R_5$ is $—OR_C$ or $—SR_C$. In other embodiments, $R_5$ is substituted or unsubstituted aliphatic. In yet other embodiments, $R_5$ is substituted or unsubstituted heteroaliphatic. In certain embodiments, $R_5$ is $C_{1-6}$ alkyl. In certain other embodiments, $R_5$ is hydrogen.

In some embodiments, $R_9$ is $—OR_C$. In certain embodiments, $R_9$ is hydroxyl. In certain other embodiments, $R_9$ is methoxy. In some embodiments, $R_9$ is $—OC(R_C)_3$, wherein at least one $R_C$ is a halogen. In certain embodiments, $R_9$ is $—OCF_3$, $OCHF_2$, or $OCH_2F$. In some embodiments, $R_9$ is $—CH_2R_C$, where $R_C$ is a halogen. In certain embodiments, $R_9$ is $—CH_2OH$, In certain embodiments, $R_9$ is $—CH_2OCH_3$. In certain embodiments, $R_9$ is $—CH_2N_3$. In some embodiments, $R_9$ is $—C(=O)R_C$. In other embodiments, $R_9$ is $—COOR_C$. In some embodiments, $R_9$ is $—C(=O)NR_C$. In some embodiments, $R_9$ is $—CH_2SH$. In other embodiments, $R_9$ is $—CH_2SCH_3$. In some embodiments, $R_9$ is alkoxy. In certain embodiments, $R_9$ is $—OR_C$. In certain embodiments, $R_9$ is ethoxy. In certain embodiments, $R_9$ is propoxy. In certain embodiments, $R_9$ is butoxy. In some embodiments, $R_9$ is $—SR_C$. In some embodiments, $R_9$ is $—SR_C$, wherein $R_C$ is an sulfur protecting group. In certain embodiments, $R_9$ is alkylthiol. In certain embodiments, $R_9$ is $C_{1-6}$ alkylthiol. In certain embodiments, $R_9$ is methanethiol. In certain embodiments, $R_9$ is ethanethiol. In certain embodiments, $R_9$ is propanethiol. In certain embodiments, $R_9$ is butanethiol. In certain embodiments, $R_9$ is thiol. In certain embodiments, $R_9$ is hydrogen. In some embodiments, $R_9$ is cyclic or acyclic, substituted or unsubstituted, branched or unbranched aliphatic. In some embodiments, $R_9$ is alkyl. In some embodiments, $R_9$ is $C_{1-6}$ alkyl. In certain embodiments, $R_9$ is methyl. In certain embodiments, $R_9$ is ethyl. In certain embodiments, $R_9$ is propyl. In certain embodiments, $R_9$ is butyl. In some embodiments, $R_9$ is halogen. In certain embodiments, $R_9$ is fluorine. In other embodiments, $R_9$ is $—N(R_C)_2$ or $—NH(R_C)$. In certain embodiments, $R_9$ is alkylamino or dialkylamino. In some embodiments, $R_9$ is a protected hydroxyl group. In certain embodiments, the $R_9$ hydroxyl group is protected with a silyl-protecting group. In certain embodiments, $R_9$ is $—OTBS$. In some embodiments, $R_9$ is a fluoroalkyl group. In certain embodiments, $R_9$ is $—CF_3$, $—CHF_2$, or $—CH_2F$.

In some embodiments, $R_{10}$ is substituted or unsubstituted alkyl. In other embodiments, $R_{10}$ is $—OR_C$. In some embodiments, $R_{10}$ is $—OR_C$ or $—CH_2OR_C$, wherein $R_C$ is an oxygen protecting group. In certain embodiments, $R_{10}$ is alkoxy. In certain embodiments, $R_{10}$ is $C_{1-6}$ alkoxy. In certain embodiments, $R_{10}$ is $—CH_2OH$, In certain embodiments, $R_{10}$ is $—CH_2OCH_3$. In certain embodiments, $R_{10}$ is $—CH_2N_3$. In certain embodiments, $R_{10}$ is hydroxyl, methoxy, or trifluoromethoxy. In some embodiments, $R_{10}$ is $—N(R_C)_2$. In some embodiments, $R_{10}$ is $—SR_C$. In some embodiments, $R_{10}$ is $—SR_C$, wherein $R_C$ is an sulfur protecting group. In certain embodiments, $R_{10}$ is alkylthiol. In certain embodiments, $R_{10}$ is $C_{1-6}$ alkylthiol. In certain embodiments, $R_{10}$ is methanethiol. In certain embodiments, $R_{10}$ is ethanethiol. In certain embodiments, $R_{10}$ is propanethiol. In certain embodiments, $R_{10}$ is butanethiol. In certain embodiments, $R_{10}$ is thiol. In certain embodiments, $R_{10}$ is hydroxyl. In certain embodiments, $R_{10}$ is halogen. In other embodiments, $R_{10}$ is fluorine. In some embodiments, $R_{10}$ is $C_{1-6}$ alkyl. In certain embodiments, $R_{10}$ is methyl. In certain embodiments, $R_{10}$ is ethyl In certain embodiments, $R_{10}$ is propyl. In certain embodiments, $R_{10}$ is butyl. In certain other embodiments, $R_{10}$ is $—CF_3$, $—CHF_2$, or $—CH_2F$. In certain embodiments, $R_{10}$ is hydrogen. In other embodiments, $R_{10}$ is not hydrogen.

In certain embodiments, $R_{11}$ is substituted or unsubstituted aliphatic. In some embodiments, $R_{11}$ is substituted or unsubstituted alkyl. In other embodiments, $R_{11}$ is $—OR_C$. In yet other embodiments, $R_{11}$ is $—N(R_C)_2$. In other embodiments, $R_{11}$ is $—OR_C$. In some embodiments, $R_{11}$ is $—OR_C$ or $—CH_2OR_C$, wherein $R_C$ is an oxygen protecting group. In certain embodiments, $R_{11}$ is alkoxy. In certain embodiments, $R_{11}$ is $C_{1-6}$ alkoxy. In certain embodiments, $R_{11}$ is hydroxyl, methoxy, or trifluoromethoxy. In some embodiments, $R_{11}$ is $—SR_C$. In some embodiments, $R_{11}$ is $—SR_C$, wherein $R_C$ is an sulfur protecting group. In certain embodiments, $R_{11}$ is alkylthiol. In certain embodiments, $R_{11}$ is $C_{1-6}$ alkylthiol. In certain embodiments, $R_{11}$ is methanethiol. In certain embodiments, $R_{11}$ is ethanethiol. In certain embodiments, $R_{11}$ is propanethiol. In certain embodiments, $R_{11}$ is butanethiol. In certain embodiments, $R_{11}$ is thiol. In certain embodiments, $R_{11}$ is hydroxyl, methoxy, or trifluoromethoxy. In certain embodiments, $R_{11}$ is hydroxyl. In certain embodiments, $R_{11}$ is halogen. In other embodiments, $R_{11}$ is fluorine. In some embodiments, $R_{11}$ is $C_{1-6}$ alkyl. In certain embodiments, $R_{11}$ is methyl. In certain embodiments, $R_{11}$ is ethyl. In certain embodiments, $R_{11}$ is propyl. In certain embodiments, $R_{11}$ is butyl. In certain other embodiments, $R_{11}$ is $—CF_3$, $—CHF_2$, or $—CH_2F$. In certain embodiments, $R_{11}$ is hydrogen. In other embodiments, $R_{11}$ is not hydrogen.

In certain embodiments, $R_P$ is benzyl. In other embodiments, $R_P$ is hydrogen. In yet other embodiments, $R_P$ is acyl. In yet other embodiments, $R_P$ is a silicon-containing protecting group.

As described above, in certain embodiments, the compounds of formula VII includes $R_9'$ in place of $R_9$; $R_{10}'$ in place of $R_{10}$; and/or $R_{11}'$ in place of $R_{11}$, wherein $R_9'$, $R_{10}'$, and $R_{11}'$ are as defined above and described herein.

In certain embodiments, a compound of formula VII has one of the following formulae:

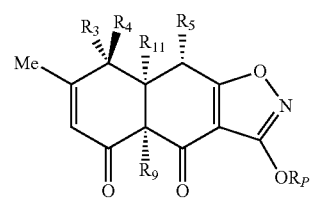

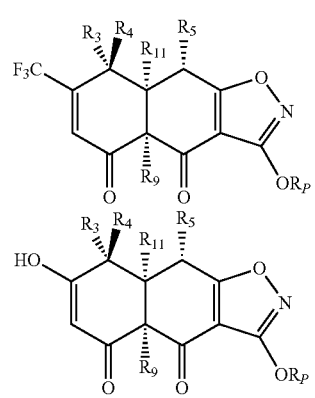

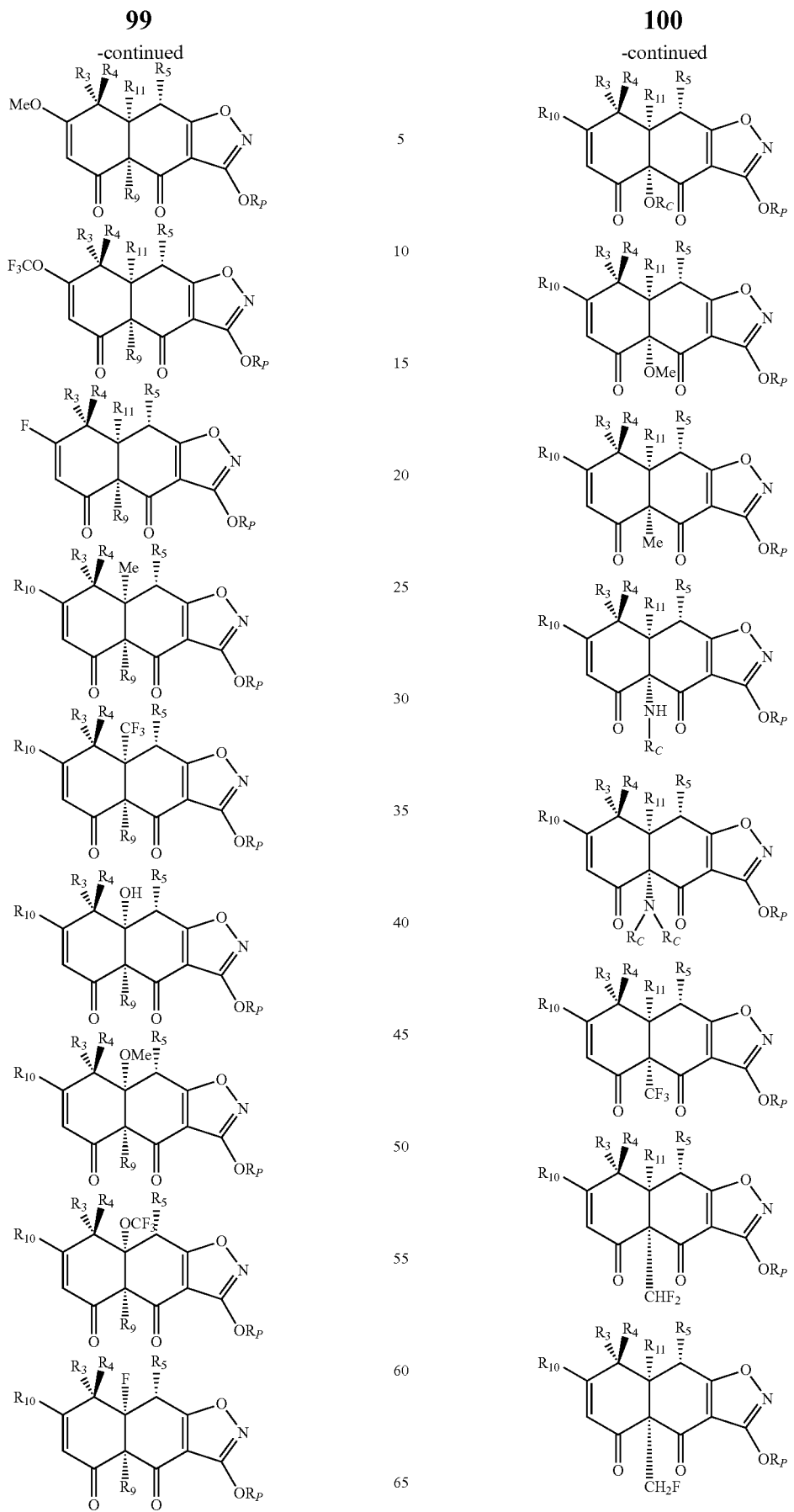

-continued

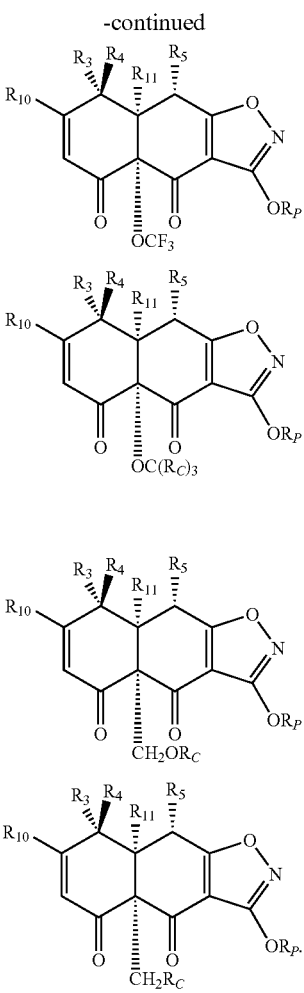

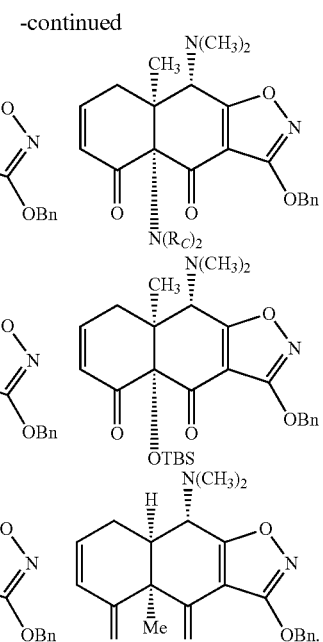

Exemplary compounds of formula VII include:

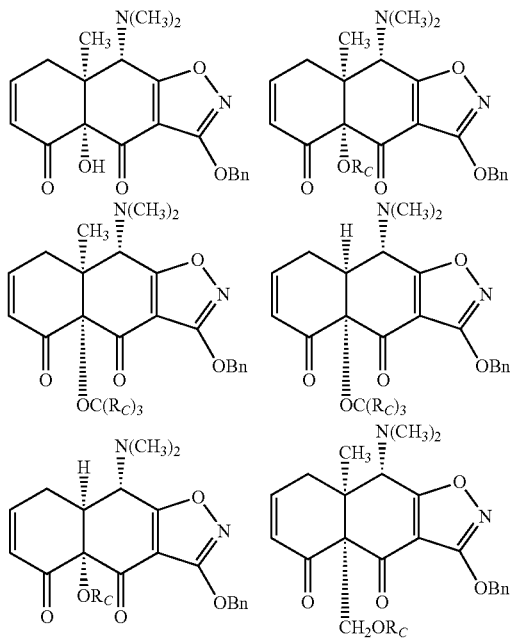

In certain embodiments, the invention provides a compound of formula (VI):

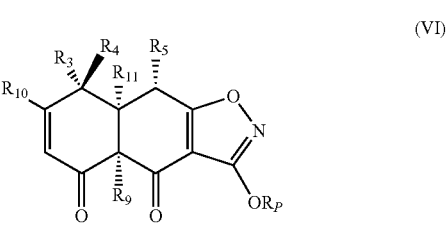

(VI)

wherein $R_3$, $R_4$, $R_5$, $R_9$, $R_{10}$, $R_{11}$, and $R_P$ are as defined above and described herein; provided that when $R_9$ is —$OR_C$, $R_{10}$ and $R_{11}$ are not simultaneously hydrogen.

In certain embodiments, the compound of formula VI includes $R_9'$ in place of $R_9$; $R_{10}'$ in place of $R_{10}$; and/or $R_{11}'$ in place of $R_{11}$, wherein $R_9'$, $R_{10}'$, and $R_{11}'$ are as defined above and described herein.

In some embodiments, $R_{10}$ is not hydrogen. In some embodiments, $R_{11}$ is not hydrogen. In some embodiments, at least one of $R_{10}$ and $R_{11}$ is not hydrogen. In some embodiments, both $R_{10}$ and $R_{11}$ are not hydrogen.

In some embodiments, $R_9$ is not —$OR_C$. In some embodiments, $R_9$ is not —$OR_C$ when both $R_{10}$ and $R_{11}$ are hydrogen. In some embodiments, $R_9$ is not —$OR_C$, wherein $R_C$ is hydrogen or an oxygen-protecting group. In certain embodiments, $R_9$ is not —OH. In other embodiments, when $R_9$ is —$OR_C$, the substituents at $R_{10}$ and $R_{11}$ are not simultaneously hydrogen, and $R_3$ and $R_4$ are not hydrogen or —$OR_B$. In some embodiments, when $R_9$ is not hydroxyl or a protected hydroxyl, $R_{10}$ and $R_{11}$ may be simultaneously hydrogen.

In some embodiments, $R_3$ is hydrogen, halogen, —$OR_B$, or $C_{1-6}$ alkyl. In other embodiments, $R_3$ is —$OR_B$. In certain embodiments, $R_3$ is hydroxyl. In certain other embodiments, $R_3$ is fluorine. In yet other embodiments, $R_3$ is hydrogen. In some embodiments, $R_4$ is hydrogen, halogen, —$OR_B$, or $C_{1-6}$ alkyl. In other embodiments, $R_4$ is —$OR_B$. In certain embodiments, $R_4$ is hydroxy. In certain other embodiments, $R_4$ is fluorine. In yet other embodiments, $R_4$ is hydrogen. In some embodiments, $R_3$ is —$N(R_B)_2$. In other embodiments, $R_4$ is —$N(R_B)_2$. In certain embodiments, $R_3$ is —NHC(O)$R_B$ or —NHSO$_2R_B$. In certain other embodiments, $R_4$ is —NHC(O)$R_B$ or —NHSO$_2R_B$. In certain embodiments, $R_3$ and $R_4$ are both hydrogen. In some embodiments, $R_3$ is —O$R_B$, and $R_4$ is hydrogen. In other embodiments, $R_3$ is hydrogen, and $R_4$ is —O$R_B$. In certain embodiments, $R_3$ is hydroxyl, and $R_4$ is hydrogen. In certain other embodiments, $R_3$ is hydrogen, and $R_4$ is hydroxyl. In some embodiments, $R_3$ is fluorine, and $R_4$ is hydrogen. In other embodiments, $R_3$ is hydrogen, and $R_4$ is fluorine. In certain embodiments, $R_3$ and $R_4$ are both fluorine.

In some embodiments, $R_5$ is —$N(R_C)_2$. In certain embodiments, $R_5$ is —$N(R_C)_2$, wherein $R_C$ is hydrogen or $C_{1-6}$ alkyl. In certain other embodiments, $R_5$ is —$N(R_E)_2$, wherein $R_E$ is methyl. In some embodiments, $R_5$ is —O$R_C$ or —S$R_C$. In other embodiments, $R_5$ is substituted or unsubstituted aliphatic. In yet other embodiments, $R_5$ is substituted or unsubstituted heteroaliphatic. In certain embodiments, $R_5$ is $C_{1-6}$ alkyl. In certain other embodiments, $R_5$ is hydrogen.

In some embodiments, $R_9$ is —O$R_C$. In certain embodiments, $R_9$ is hydroxyl. In certain other embodiments, $R_9$ is methoxy. In some embodiments, $R_9$ is alkoxy. In certain embodiments, $R_9$ is —O$R_C$. In some embodiments, $R_9$ is —OC$(R_C)_3$, wherein at least one $R_C$ is a halogen. In certain embodiments, $R_9$ is —OCF$_3$, —OCHF$_2$, or —OCH$_2$F. In certain embodiments, $R_9$ is ethoxy. In certain embodiments, $R_9$ is propoxy. In certain embodiments, $R_9$ is butoxy. In some embodiments, $R_9$ is —S$R_C$. In some embodiments, $R_9$ is —S$R_C$, wherein $R_C$ is an sulfur protecting group. In certain embodiments, $R_9$ is alkylthiol. In certain embodiments, $R_9$ is $C_{1-6}$ alkylthiol. In certain embodiments, $R_9$ is methanethiol. In certain embodiments, $R_9$ is ethanethiol. In certain embodiments, $R_9$ is propanethiol. In certain embodiments, $R_9$ is butanethiol. In certain embodiments, $R_9$ is thiol. In certain embodiments, $R_9$ is hydrogen. In some embodiments, $R_9$ is cyclic or acyclic, substituted or unsubstituted, branched or unbranched aliphatic. In some embodiments, $R_9$ is alkyl. In some embodiments, $R_9$ is $C_{1-6}$ alkyl. In certain embodiments, $R_9$ is methyl. In certain embodiments, $R_9$ is ethyl. In certain embodiments, $R_9$ is propyl. In certain embodiments, $R_9$ is butyl. In some embodiments, $R_9$ is halogen. In certain embodiments, $R_9$ is fluorine. In other embodiments, $R_9$ is —$N(R_C)_2$ or —NH$(R_C)$. In certain embodiments, $R_9$ is alkylamino or dialkylamino. In some embodiments, $R_9$ is a protected hydroxyl group. In certain embodiments, the $R_9$ hydroxyl group is protected with a silyl-protecting group. In certain embodiments, $R_9$ is —OTBS. In some embodiments, $R_9$ is a fluoroalkyl group. In certain embodiments, $R_9$ is —CF$_3$, —CHF$_2$, or —CH$_2$F.

In some embodiments, $R_{10}$ is substituted or unsubstituted alkyl. In other embodiments, $R_{10}$ is —O$R_C$. In some embodiments, $R_{10}$ is —O$R_C$ or —CH$_2$O$R_C$, wherein $R_C$ is an oxygen protecting group. In certain embodiments, $R_{10}$ is alkoxy. In certain embodiments, $R_{10}$ is $C_{1-6}$ alkoxy. In certain embodiments, $R_{10}$ is —CH$_2$OH, In certain embodiments, $R_{10}$ is —CH$_2$OCH$_3$. In certain embodiments, $R_{10}$ is —CH$_2$N$_3$. In certain embodiments, $R_{10}$ is hydroxyl, methoxy, or trifluoromethoxy. In some embodiments, $R_{10}$ is —$N(R_C)_2$. In some embodiments, $R_{10}$ is —S$R_C$. In some embodiments, $R_{10}$ is —S$R_C$, wherein $R_C$ is an sulfur protecting group. In certain embodiments, $R_{10}$ is alkylthiol. In certain embodiments, $R_{10}$ is $C_{1-6}$ alkylthiol. In certain embodiments, $R_{10}$ is methanethiol. In certain embodiments, $R_{10}$ is ethanethiol. In certain embodiments, $R_{10}$ is propanethiol. In certain embodiments, $R_{10}$ is butanethiol. In certain embodiments, $R_{10}$ is thiol. In certain embodiments, $R_{10}$ is hydroxyl. In certain embodiments, $R_{10}$ is halogen. In other embodiments, $R_{10}$ is fluorine. In some embodiments, $R_{10}$ is $C_{1-6}$ alkyl. In certain embodiments, $R_{10}$ is methyl. In certain embodiments, $R_{10}$ is ethyl In certain embodiments, $R_{10}$ is propyl. In certain embodiments, $R_{10}$ is butyl. In certain other embodiments, $R_{10}$ is —CF$_3$, —CHF$_2$, or —CH$_2$F. In certain embodiments, $R_{10}$ is hydrogen. In other embodiments, $R_{10}$ is not hydrogen.

In certain embodiments, $R_{11}$ is substituted or unsubstituted aliphatic. In some embodiments, $R_{11}$ is substituted or unsubstituted alkyl. In other embodiments, $R_{11}$ is —O$R_C$. In yet other embodiments, $R_{11}$ is —$N(R_C)_2$. In other embodiments, $R_{11}$ is —O$R_C$. In some embodiments, $R_{11}$ is —O$R_C$ or —CH$_2$O$R_C$, wherein $R_C$ is an oxygen protecting group. In certain embodiments, $R_{11}$ is alkoxy. In certain embodiments, $R_{11}$ is $C_{1-6}$ alkoxy. In certain embodiments, $R_{11}$ is hydroxyl, methoxy, or trifluoromethoxy. In some embodiments, $R_{11}$ is —S$R_C$. In some embodiments, $R_{11}$ is —S$R_C$, wherein $R_C$ is an sulfur protecting group. In certain embodiments, $R_{11}$ is alkylthiol. In certain embodiments, $R_{11}$ is $C_{1-6}$ alkylthiol. In certain embodiments, $R_{11}$ is methanethiol. In certain embodiments, $R_{11}$ is ethanethiol. In certain embodiments, $R_{11}$ is propanethiol. In certain embodiments, $R_{11}$ is butanethiol. In certain embodiments, $R_{11}$ is thiol. In certain embodiments, $R_{11}$ is hydroxyl, methoxy, or trifluoromethoxy. In certain embodiments, $R_{11}$ is hydroxyl. In certain embodiments, $R_{11}$ is halogen. In other embodiments, $R_{11}$ is fluorine. In some embodiments, $R_{11}$ is $C_{1-6}$ alkyl. In certain embodiments, $R_{11}$ is methyl. In certain embodiments, $R_{11}$ is ethyl. In certain embodiments, $R_{11}$ is propyl. In certain embodiments, $R_{11}$ is butyl. In certain other embodiments, $R_{11}$ is —CF$_3$, —CHF$_2$, or —CH$_2$F. In certain embodiments, $R_{11}$ is hydrogen. In other embodiments, $R_{11}$ is not hydrogen.

In certain embodiments, $R_P$ is benzyl. In other embodiments, $R_P$ is hydrogen. In yet other embodiments, $R_P$ is acyl. In yet other embodiments, $R_P$ is a silicon-containing protecting group.

In certain embodiments, a compound of formula VI has one of the following formulae:

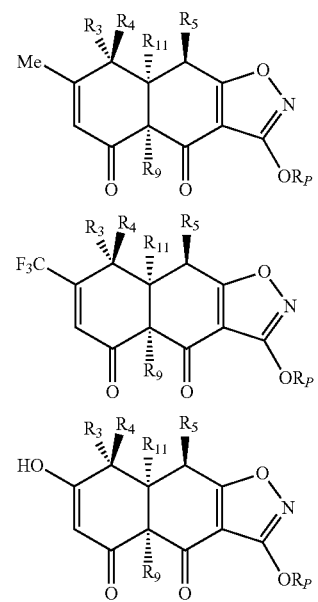

-continued
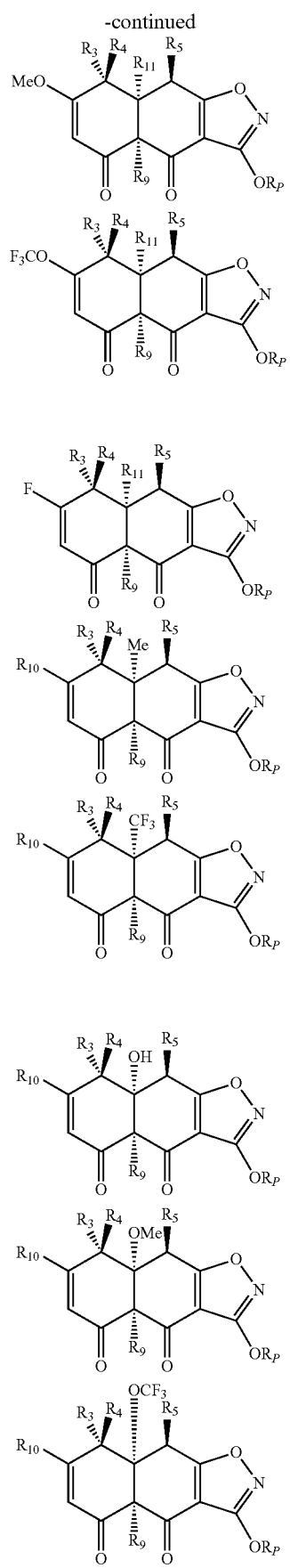
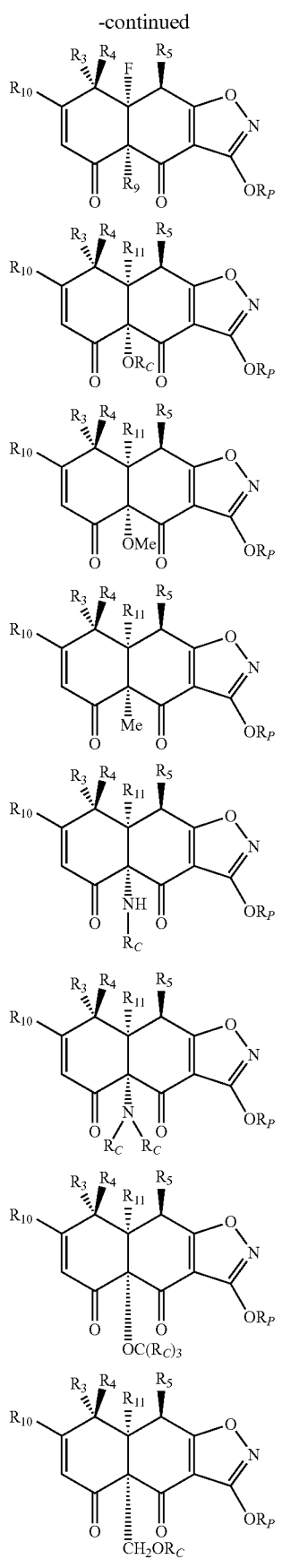

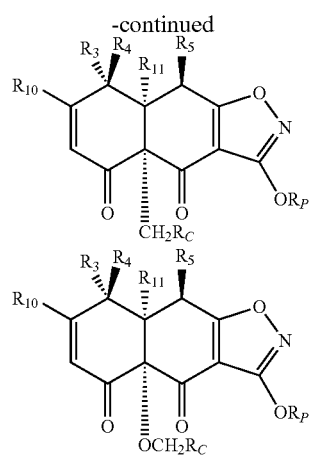

An exemplary compound of the formula VI includes:

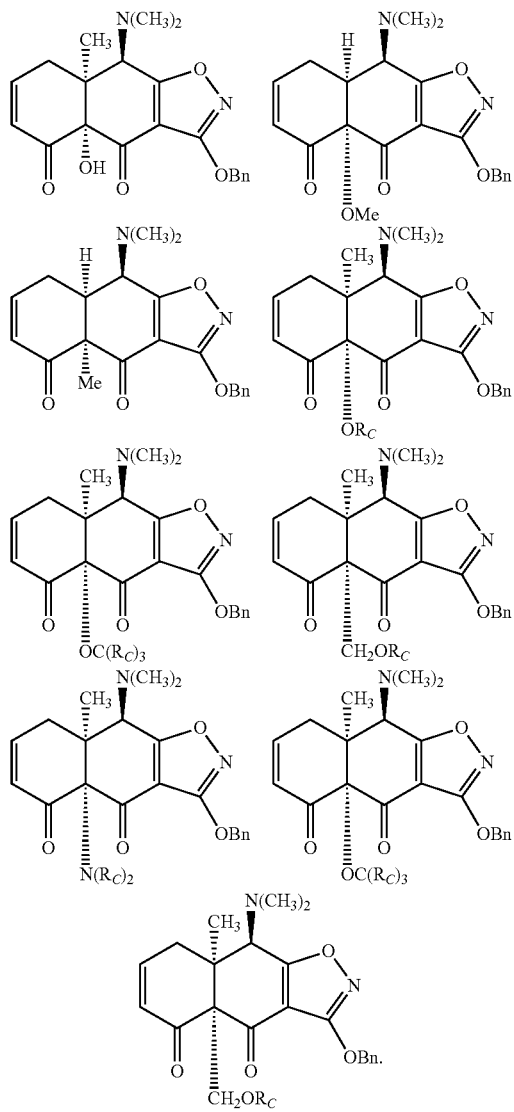

In other embodiments, the invention provides a compound of formula (V):

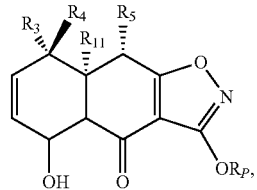

wherein $R_3$, $R_4$, $R_5$, $R_{11}$, and $R_P$ are as defined above and described herein.

Exemplary compounds of formula V include:

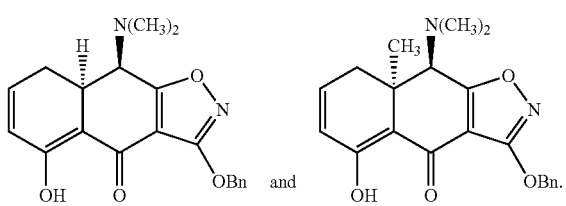 [SMILES: CN(C)[C@H]1c2onc(OCc3ccccc3)c2C(=O)C2=C(O)C=CC[C@H]21 ; "and" ; CN(C)[C@H]1c2onc(OCc3ccccc3)c2C(=O)C2=C(O)C=CC[C@]21C]

In certain embodiments, the compound is of formula (IV):

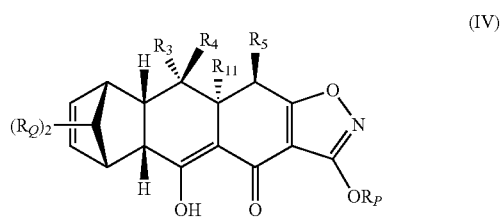

wherein $R_3$, $R_4$, $R_5$, $R_{11}$, $R_P$, $R_Q$ and $R_Z$ are as defined above and described herein.

Exemplary compounds of formula IV include:

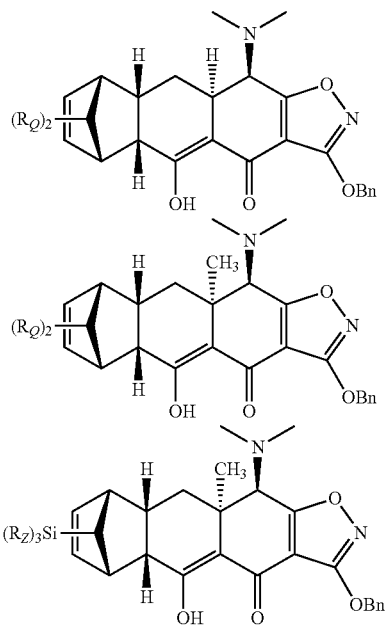

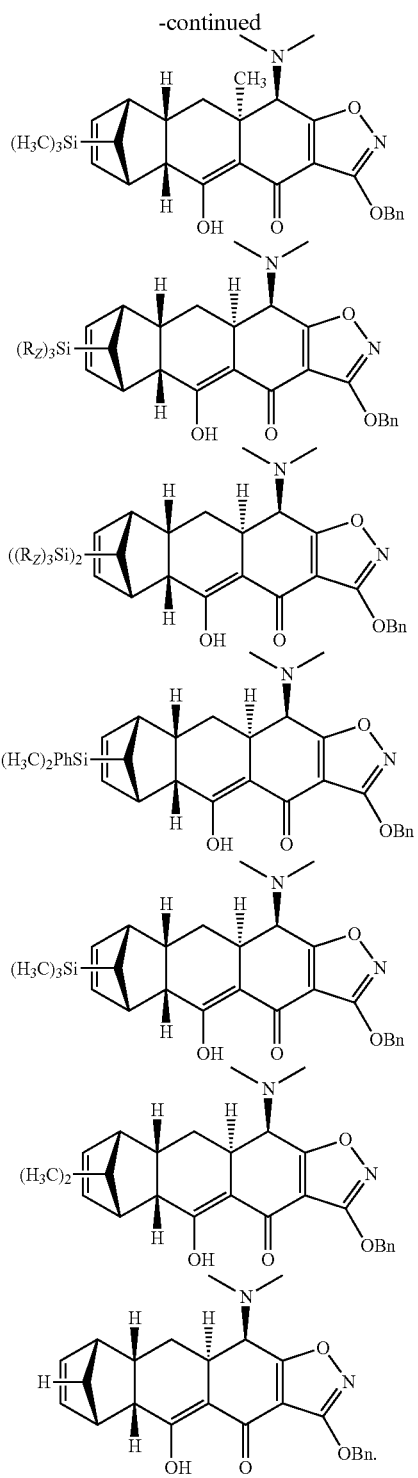

Pharmaceutical Compositions

The present invention also provides a pharmaceutical preparation comprising at least one of the compounds as described above and herein, or a pharmaceutically acceptable derivative thereof, which compounds inhibit the growth of or kill microorganisms, and, in certain embodiments, inhibit the growth of or kill tetracycline-resistant organisms including chlortetracycline-resistant organisms, oxytetracycline-resistant organisms, demeclocycline-resistant organisms, doxycycline-resistant organisms, minocycline-resistant organisms, or any organisms resistant to antibiotics of the tetracycline class used in human or veterinary medicine. In other embodiments, the compounds show cytostatic or cytotoxic activity against neoplastic cells such as cancer cells. In yet other embodiments, the compounds inhibit the growth of or kill rapidly dividing cells such as stimulated inflammatory cells.

As discussed above, the present invention provides novel compounds having antimicrobial and antiproliferative activity, and thus the inventive compounds are useful for the treatment of a variety of medical conditions including infectious diseases, cancer, autoimmune diseases, inflammatory diseases, and diabetic retinopathy. Accordingly, in another aspect of the present invention, pharmaceutical compositions are provided, wherein these compositions comprise any one of the compounds as described herein, and optionally comprise a pharmaceutically acceptable carrier. In certain embodiments, these compositions optionally further comprise one or more additional therapeutic agents, e.g., another antimicrobial agent or another antiproliferative agent. In other embodiments, these compositions further comprise an antiinflammatory agent such as aspirin, ibuprofen, acetaminophen, etc., pain reliever, or anti-pyretic.

It will also be appreciated that certain compounds of the present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof, e.g., a prodrug.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1-19, 1977; incorporated herein by reference. The salts can be prepared in situ during the final isolation and purification of the compounds of the invention, or separately by reacting the free base functionality with a suitable organic or inorganic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

Additionally, as used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates. In certain embodiments, the esters are cleaved by enzymes such as esterases.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicles, dispersion or suspension aids, surface active agents, isotonic agents, thickening or emulsifying agents, preservatives, solid binders, lubricants and the like, as suited to the particular dosage form desired. Remington's *Pharmaceutical Sciences*, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anti-cancer compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; CREMOPHOR™ (polyethoxylated castor oil); SOLUTOL® (Kolliphor); excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutical Compositions

The invention further provides a method of treating infections and inhibiting tumor growth. The method involves the administration of a therapeutically effective amount of the compound or a pharmaceutically acceptable derivative thereof to a subject (including, but not limited to a human or animal) in need of it.

The compounds and pharmaceutical compositions of the present invention may be used in treating or preventing any disease or conditions including infections (e.g., skin infections, GI infection, urinary tract infections, genito-urinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound of pharmaceutical compositions to the animal. In certain embodiments, the compound or pharmaceutical composition is administered orally. In other embodiments, the compound or pharmaceutical composition is administered parenterally.

In yet another aspect, according to the methods of treatment of the present invention, bacteria are killed, or their growth is inhibited, by contacting the bacteria with an inventive compound or composition, as described herein. Thus, in still another aspect of the invention, a method for the treatment of infection is provided comprising administering a therapeutically effective amount of an inventive compound, or a pharmaceutical composition comprising an inventive compound to a subject in need thereof, in such amounts and for such time as is necessary to achieve the desired result. In certain embodiments of the present invention, a "therapeutically effective amount" of the inventive compound or pharmaceutical composition is that amount effective for killing or inhibiting the growth of bacteria. The compounds and compositions, according to the method of the present invention, may be administered using any amount and any route of administration effective for killing or inhibiting the growth of bacteria. The exact amount required will vary from subject to subject, depending on the species, age, and general condition of the subject, the severity of the infection, the particular compound, its mode of administration, its mode of activity, and the like. The compounds of the invention are preferably formulated in dosage unit form for ease of administration and uniformity of dosage. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Liquid dosage forms for oral and parenteral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In certain embodiments for parenteral administration, the compounds of the invention are mixed with solubilizing agents such as CREMOPHOR™ (polyethoxylated castor oil), alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

In still another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

These and other aspects of the present invention will be further appreciated upon consideration of the following Examples, which are intended to illustrate certain particular embodiments of the invention but are not intended to limit its scope, as defined by the claims.

EXAMPLES

General Procedures

All reactions were performed in flame-dried round bottomed or modified Schlenk (Kjeldahl shape) flasks fitted with rubber septa under a positive pressure of argon, unless otherwise noted. Air- and moisture-sensitive liquids and solutions were transferred via syringe or stainless steel cannula. Where necessary (so noted), solutions were deoxygenated by alternative freeze (liquid nitrogen)/evacuation/thaw cycles (≥three iterations). Organic solutions were concentrated by rotary evaporation at ~25 Torr (house vacuum). Flash column chromatography was performed on silica gel (60 Å, standard grade) as described by Still et al. (Still, W. C.; Kahn, M.; Mitra, A. *J. Org. Chem.* 1978, 43, 2923-2925; incorporated herein by reference). Analytical thin-layer chromatography was performed using glass plates pre-coated with 0.25 mm 230-400 mesh silica gel impregnated with a fluorescent indicator (254 nm). Thin layer chromatography plates were visualized by exposure to ultraviolet light and/or exposure to ceric ammonium molybdate or an acidic solution of p-anisaldehyde followed by heating on a hot plate.

Materials.

Commercial reagents and solvents were used as received with the following exceptions. Chlorotrimethylsilane, triethylamine, diisopropylamine, 2,2,6,6-tetramethylpiperidine, N,N,N',N'-tetramethylethylenediamine, DMPU, HMPA, and N,N-diisopropylethylamine were distilled from calcium hydride under dinitrogen atmosphere. Benzene, dichloromethane, ethyl ether, methanol, pyridine, tetrahydrofuran, hexane, acetonitrile, N,N-dimethylformamide, and toluene were purified by the method of Pangborn et al. (Pangborn, A. B.; Giardello, M. A.; Grubbs, R. H.; Rosen, R. K.; Timmers, F. J. *Organometallics* 1996, 15, 1518-1520; incorporated herein by reference). The molarity of n-butyllithium, s-butyllithium, and t-butyllithium were determined by titration with a tetrahydrofuran solution of 2-butanol using triphenylmethane as an indicator (Duhamel, L.; Palquevent, J.-C. *J. Org. Chem.* 1979, 44, 3404-3405; incorporated herein by reference).

Instrumentation.

Proton nuclear magnetic resonance ($^1$H NMR) spectra and carbon nuclear magnetic resonance ($^{13}$C NMR) were recorded with Varian Unity/Inova 600 (600 MHz), Varian Unity/Inova 500 (500 MHz/125 MHz), or Varian Mercury 400 (400 MHz/100 MHz) NMR spectrometers. Chemical shifts for protons are reported in parts per million scale (δ scale) downfield from tetramethylsilane and are referenced to residual protium in the NMR solvents (CHCl$_3$: δ 7.26, C$_6$D$_5$H: δ 7.15, D$_2$HCOD: δ 3.31, CDHCl$_2$: δ 5.32, (CD$_2$H)CD$_3$SO: δ 2.49). Chemical shifts for carbon are reported in parts per million (δ scale) downfield from tetramethylsilane and are referenced to the carbon resonances of the solvent (CDCl$_3$: δ 77.0, C$_6$D$_6$: δ 128.0, D$_3$COD: δ 44.9, CD$_2$Cl$_2$: δ 53.8, (CD$_3$)$_2$SO: δ 39.5). Data are represented as follows: chemical shift, multiplicity (s=singlet, d=doublet, t=triplet, q=quartet, m=multiplet, br=broad), integration, coupling constant in Hz, and assignment. Infrared (IR) spectra were obtained using a Perkin-Elmer 1600 FT-IR spectrophotometer referenced to a polystyrene standard. Data are represented as follows: frequency of the absorption (cm$^{-1}$), intensity of absorption (s=strong, sb=strong broad, m=medium, w=weak, br=broad), and assignment (where appropriate). Optical rotations were determined on a JASCO DIP-370 digital polarimeter equipped with a sodium lamp source using a 200-μL or 2-mL solution cell. High resolution mass spectra were obtained at the Harvard University Mass Spectrometry Facilities.

Example 1

Preparation of Enone 4

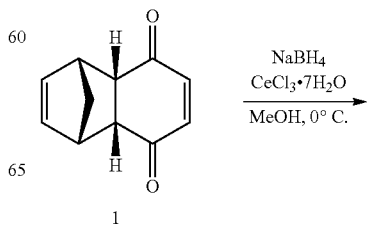

1

Wilson, et al., *J. Chem. Soc., Chem. Commun.* (1970) 213-214 and Marchand, et al., *J. Org. Chem.* (1986) 51: 1622-1625.

Step 2

Synthesis of Alcohol 3

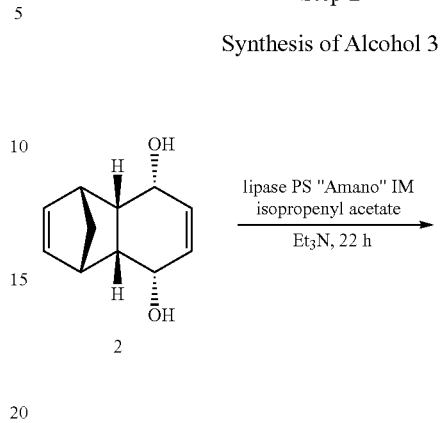

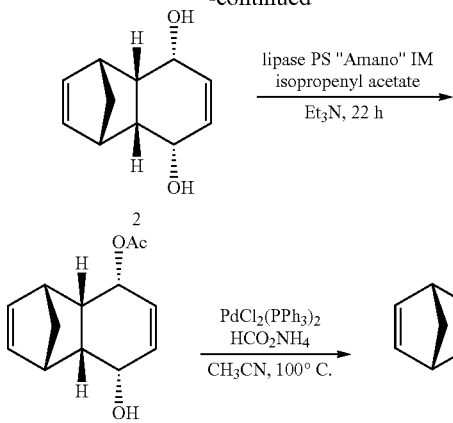

Step 1

Synthesis of Meso-Diol 2

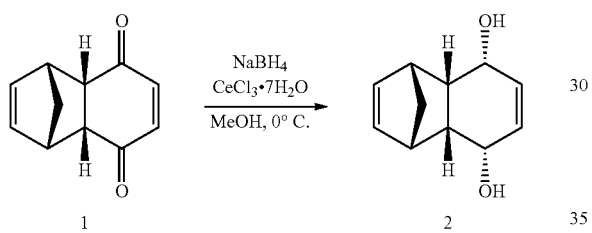

A 3-L, two-necked, round-bottomed flask equipped with a TEFLON® (polytetrafluoroethylene)-coated magnetic stirring bar and a thermometer was charged with enedione 1 (50 g, 287 mmol, 1 equiv) and methanol (960 mL). Enedione 1 was prepared in >100 g batches according to the procedure in Oda, et al., *Organic Syntheses* (1996) 73: 253-261. The reaction mixture was stirred at 23° C. until enedione 1 completely dissolved, whereupon cerium trichloride heptahydrate (214 g, 574 mmol, 2 equiv) was added and the resulting slurry was stirred for 1 h at 23° C. (resulting in an orange homogeneous reaction mixture). The reaction flask was placed in an ice-water bath until an internal temperature of 5° C. was reached. Sodium borohydride (13.6 g, 359 mmol, 1.23 equiv) was added to the cold reaction solution at a rate such that the internal temperature remained below 8° C. (addition over ~1.5 h, CAUTION—EVOLUTION OF HYDROGEN GAS). The resulting slurry was stirred for 30 min at 5-8° C., then saturated aqueous ammonium chloride solution (1 L) was added over the course of 30 min. The reaction flask was removed from the cooling bath and allowed to warm to 23° C. The homogeneous product mixture was partitioned between half-saturated aqueous ammonium chloride solution (1 L) and ethyl acetate (1 L). The layers were separated. The aqueous layer was extracted with two 1-L portions of ethyl acetate. The organic layers were combined and the combined solution was dried over sodium sulfate. The dried solution was filtered and the filtrate was concentrated to provide meso-diol 2 (49.5 g, 97%) as an off-white solid that was used directly in the next step. Meso-diol 2 is a known compound; see, for example, A 2-L, one-necked, round-bottomed flask equipped with a TEFLON®-coated magnetic stirring bar was charged with meso-diol 2 (47 g, 264 mmol, 1 equiv), immobilized lipase PS from Amano (47 g), isopropenyl acetate (87.2 mL, 792 mmol, 3 equiv) and triethylamine (754 mL). The resulting slurry was stirred for 22 h at 23° C., then filtered through a 350-mL sintered glass funnel of medium porosity. The filter cake was rinsed with ethyl acetate (800 mL), then the filtrate was concentrated. The yellow concentrate was dissolved with ethyl acetate (800 mL), then was washed sequentially with 0.2 N aqueous hydrochloric acid solution (500 mL), water (500 mL), and saturated aqueous sodium chloride solution (500 mL). The washed organic solution was dried over sodium sulfate. The dried solution was filtered and the filtrate was concentrated to provide alcohol 3 (55.4 g, 95%) as a yellow oil that was used directly in the next step. Alcohol 3 is a known compound; see, for example, Takano, et al., *Synthesis* 1993, 948-950; Nakashima, et al., *Synlett* 1999, 1405-1406; and Konno, et al., A Practical Preparation of Versatile Cyclohexenoid Chiral Building Blocks. *Synthesis* 1999, 1135-1140.

Step 3

Synthesis of Enone 4

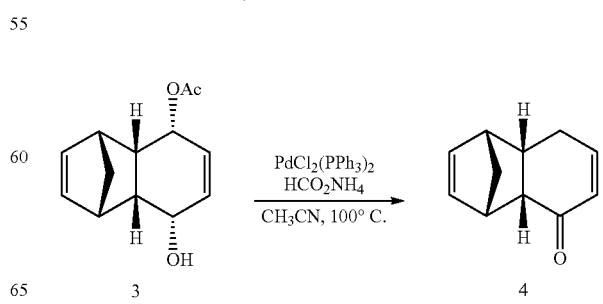

A 3-L, three-necked, round-bottomed flask was equipped with a TEFLON® (polytetrafluoroethylene)-coated magnetic stirring bar, a thermometer, a reflux condenser, and a glass stopcock. The reaction flask was flushed with argon, then was charged with a solution of alcohol 3 (55.4 g, 252 mmol, 1 equiv) in acetonitrile (840 mL). To the stirring solution was added sequentially ammonium formate (19.9 g, 315 mmol, 1.25 equiv) and dichlorobis(triphenylphosphine)palladium (II) (1.8 g, 2.52 mmol, 0.01 equiv) (resulting in a yellow slurry). The reaction solution was heated to reflux (internal temperature of 100-105° C.) and stirring was continued for 20 min. The resulting dark-orange, near-homogeneous solution was removed from the hot oil bath and allowed to cool to 23° C. The product mixture was transferred to a 3-L, one-necked, round-bottomed flask with a minimal amount of ethyl acetate and the resulting organic solution was concentrated. The dark-red concentrate was suspended in ethyl acetate (500 mL), then was filtered through a pad of CELITE® (diatomaceous earth) rinsing with ethyl acetate (500 mL). The combined organics were washed sequentially with half-saturated aqueous sodium bicarbonate solution (1 L) and half-saturated aqueous sodium chloride solution (1 L). The washed organic solution was dried over sodium sulfate. The dried solution was filtered and the filtrate was concentrated. The residue was purified by flash column chromatography (7:1 hexanes-ethyl acetate grading to 4:1 hexanes-ethyl acetate) to provide enone 4 (31.9 g, 79%) as a yellow oil which solidified at −20° C. The enantiomeric excess of the purified product was determined to be >99% by chiral GC analysis (RESTEK Rt®-βDEXsm column (fused silica), 30 m, 0.25 mmID, oven T=40° C. for 5 min then increase 2° C./min, $t_R$(major, enone enantiomer 4)=55.202 min, $t_R$(minor, enone enantiomer 4)=56.453 min. Enone 4 is a known compound; see, for example, Takano, et al., *Synthesis* (1993) 948-950.

Example 2

Preparation of Isoxazole 7

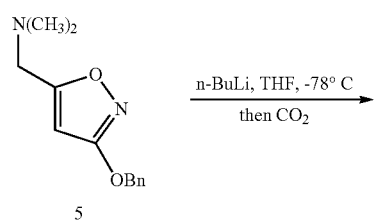

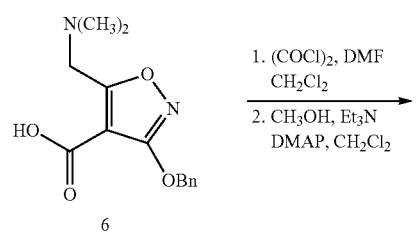

Step 1

Synthesis of Carboxylic Acid 6

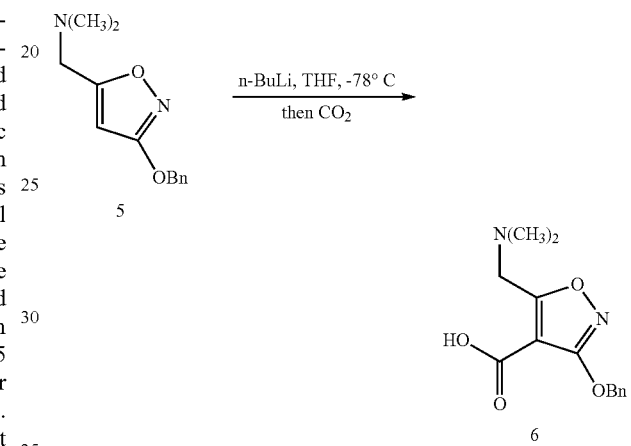

A 5-L, three-necked, oven dried round-bottomed flask equipped with a mechanical stirrer, a 500-mL pressure-equalizing addition funnel, and a thermometer was flushed with argon. The flask was charged with a solution of isoxazole 5 (155 g, 668 mmol, 1 equiv) in THF (3 L). Isoxazole 5 is a known compound; see, for example, Charest, et al. A Convergent Enantioselective Route to Structurally Diverse 6-Deoxytetracycline Antibiotics. *Science* 2005, 308, 395-398 and Myers, et al. Synthesis of Tetracyclines and Analogues Thereof. US 2005/0282787, published Dec. 22, 2005. The reaction flask was placed in a dry ice-acetone bath and the solution allowed to cool to −78° C., whereupon a solution of n-butyllithium in hexanes (2.5 M, 280 mL, 701 mmol, 1.05 equiv) was added dropwise through the addition funnel at a rate such that the internal reaction temperature was <−68° C. (addition time ~40 min). The resulting slurry was stirred for 1 h at −78° C., whereupon carbon dioxide was bubbled into the reaction mixture through a dry 8-gauge stainless-steel needle for 2 h at which point the reaction solution became near homogeneous. The reaction flask was removed from the cooling bath and placed into a 23° C. water bath and the reaction mixture was allowed to warm to 23° C. Argon was bubbled through the 23° C. reaction mixture for 15 min, then 1 N aqueous sodium hydroxide solution (1.4 L) and hexanes (200 mL) was added. The resulting biphasic mixture was stirred for 25 min, then was transferred to a 6-L separation funnel. Hexanes (800 mL) and ethyl acetate (200 mL) was added and the biphasic mixture was shaken vigorously, then the layers were separated. The organic layer was extracted with two 200-mL portions of 0.5 N aqueous sodium hydroxide solution. The combined aqueous layers were washed with hexanes-ethyl acetate (2:1, 500 mL). The aqueous alkali layer was transferred to a 3-L round-bottomed flask equipped with a TEFLON®-coated magnetic stirring bar, then the flask was placed into a 23° C. water bath. The stirring aqueous solution was made acidic with 12 N hydrochloric acid (pH ~6-6.5 by litmus paper test, CAUTION—GAS EVOLUTION). The acidic aqueous solution was stirred for 15 minutes at 23° C., then sodium chloride (475 g) was added. The aqueous solution was transferred to a 6-L separation funnel, then extracted with one 4-L portion of dichloromethane and four 700-mL portions of dichloromethane. The combined organic layers were dried over sodium sulfate. The dried solution was filtered and the filtrate was concentrated to provide carboxylic acid 6 (146 g) as a pale yellow solid that was used directly in the next step.

Step 2

Synthesis of Methyl Ester 7

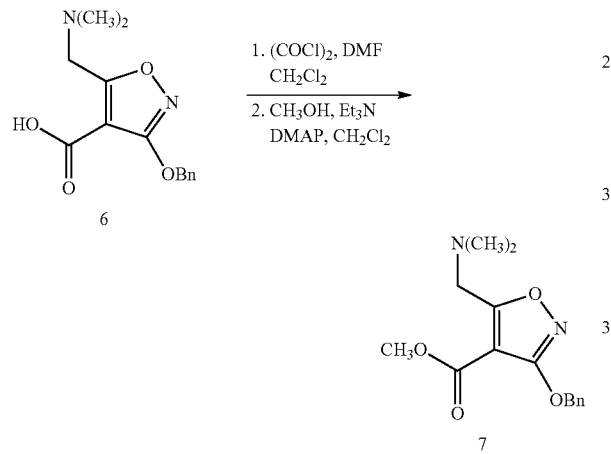

A 5-L, three-necked, oven dried round-bottomed flask equipped with a mechanical stirrer, a 500-mL pressure-equalizing addition funnel, and a thermometer was flushed with argon. The reaction flask was charged with a solution of the carboxylic acid 6 (146 g, 668 mmol, 1 equiv) in dichloromethane (3.5 L) and N,N-dimethylformamide (1.98 mL, 26.3 mmol, 0.05 equiv). The resulting white slurry was cooled to ~8° C., then a solution of oxalyl chloride in dichloromethane (2 M, 342 mL, 685 mmol, 1.3 equiv) was added dropwise through the funnel over the course of 2 h. The flask was removed from the cooling bath, then the reaction mixture was stirred for 3 h at 23° C. The reaction flask was placed into an ice-water bath and the reaction mixture was allowed to cool to 5° C. A separate 5-L, two-necked, oven dried round-bottomed flask equipped with a TEFLON® (polytetrafluoroethylene)-coated magnetic stirring bar was charged with 4-dimethylaminopyridine (1.92 g, 15.8 mmol, 0.03 equiv), dichloromethane (400 mL), methanol (107 mL, 2.63 mol, 5 equiv) and triethylamine (221 mL, 1.58 mol, 3 equiv), then the resulting solution was cooled to 0° C. To this cold solution was added dropwise by cannula the above cold carboxylic acid chloride solution. The resulting homogeneous brown solution was removed from the cooling bath and stirred for 3 h at 23° C., then saturated aqueous sodium bicarbonate solution (1 L) was added. The resulting biphasic mixture was stirred for 20 min, then transferred to a separation funnel and the layers separated. The organic layer was washed sequentially with two 800-mL portions of water and one 800-mL portion of saturated aqueous sodium chloride solution. The washed organic solution was dried over sodium sulfate. The dried solution was filtered and the filtrate was concentrated. The concentrate was dissolved in dichloromethane-ethyl acetate (1:1, 400 mL), then hexanes (800 mL) was added. The product mixture was shaken by hand for 2 min, then filtered through silica gel rinsing with hexanes-acetone (1:1, 1.5 L). The filtrate was concentrated by high vacuum for 4 h at 50° C. to provide the methyl ester 7 (134 g, 87%). The methyl ester 7 is a known compound; see Stork, et al. Stereocontrolled Synthesis of (±)-12a-Deoxytetracycline. *J. Am. Chem. Soc.* 1996, 118, 5304-5305. TLC (50% acetone-hexanes): $R_f$=0.55 (UV, CAM). $^1$H NMR (600 MHz, CDCl$_3$), δ: 7.49-7.48 (m, 2H), 7.41-7.34 (m, 3H), 5.36 (s, 2H), 3.90 (s, 2H), 3.85 (s, 3H), 2.36 (s, 6H). $^{13}$C NMR (125 MHz, CDCl$_3$), δ: 176.2, 168.9, 161.5, 135.6, 128.5, 128.3, 127.8, 102.1, 71.7, 53.6, 51.8, 45.2.

Example 3

Synthesis of Michael-Claisen product 9

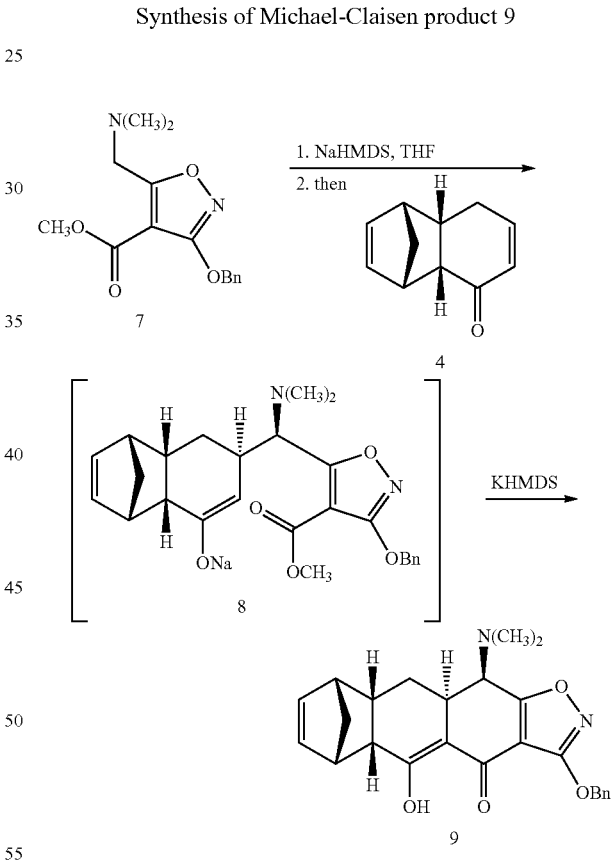

A solution of sodium bis(trimethylsilyl)amide in tetrahydrofuran (1 M, 27.6 mL, 27.6 mmol, 1.2 equiv) was added dropwise to a solution of methyl ester 7 (8.02 g, 27.5 mmol, 1.2 equiv) in tetrahydrofuran (137 mL) at −78° C. over the course of seven min resulting in a dark brown solution. The reaction flask was placed in a −20° C. cooling bath and the solution was stirred for 30 min at this temperature. The resulting dark brown slurry was cooled to −78° C., then a solution of enone 4 (3.67 g, 22.9 mmol, 1 equiv) in tetrahydrofuran (22 mL) was added dropwise over the course of four min. The reaction mixture was stirred for 40 minutes was at −60° C.

then cooled to −78° C., whereupon a solution of potassium bis(trimethylsilyl)amide in toluene (0.5 M, 48 mL, 24 mmol, 1.05 equiv) was added dropwise over the course of 20 minutes. The resulting reaction mixture was warmed to −20° C. over 40 min and stirring continued at this temperature for 6 h, then saturated aqueous ammonium chloride solution (80 mL) was added. The reaction flask was removed from the cooling bath and the biphasic product solution was allowed to warm to 23° C., then saturated aqueous sodium chloride solution (50 mL) and ethyl acetate (200 mL) was added and stirring was continued for 10 min. The phases were separated and the aqueous phase was extracted with two 100-mL portions of ethyl acetate. The organic layers were combined and the combined solution was dried over sodium sulfate. The dried solution was filtered and the filtrate was concentrated. The residue was purified by flash-column chromatography on silica gel (10% ethyl acetate-hexanes, grading to 20% ethyl acetate-hexanes) to provide the Michael-Claisen product 9 as a pale yellow solid (7.4 g, 77%). TLC (33% ethyl acetate-hexanes): $R_f$=0.38 (UV, CAM). $[\alpha]^{23}_D$-7.28 (c 0.70, CHCl$_3$). $^1$H NMR (600 MHz, CDCl$_3$), δ: 15.16 (s, 1H), 7.50-7.49 (m, 2H), 7.38-7.32 (m, 3H), 6.04-6.00 (m, 2H), 5.39-5.34 (m, 2H), 3.61 (d, J=6.5 Hz, 1H), 3.20 (s, 1H), 2.91 (s, 1H), 2.87 (dd, 1H, J=4.0, 9.0 Hz), 2.75-2.71 (m, 2H), 2.17-2.10 (m, 1H), 2.13 (s, 6H), 1.80 (dd, 1H, J=5.0, 15.0 Hz), 1.46 (d, 1H, J=8.5 Hz), 1.42 (d, 1H, J=8.5 Hz). $^{13}$C NMR (125 MHz, CDCl$_3$), δ: 183.8, 180.9, 176.6, 167.6, 135.6, 135.4, 135.1, 128.4, 128.3, 128.2, 107.9, 105.4, 72.2, 58.2, 50.9, 49.5, 46.8, 42.7, 41.9, 37.5, 34.1, 26.0. IR (neat), cm$^{-1}$: 2964 (s), 2937 (s), 1627 (s), 1610 (s), 1573 (s), 1506 (s), 1330 (s). HRMS (ESI): Calcd for $(C_{25}H_{26}N_2O_4+Na)^+$: 441.1785. Found: 441.1793.

Example 4

Synthesis of Retro-Diels-Alder Product 10

~14 mL per min into a 1-L round-bottomed flask. The flask containing the product mixture was placed into a 20° C. water bath and hexanes (400 mL) was added, then a solution of hydrogen chloride in ether (2.0 N, 9.9 mL, 19.8 mmol, 1.7 equiv) was added dropwise. The resulting mixture was rigorously stirred for 45 min during which time a solid formed. The slurry was filtered. The filter cake was washed with three 30-mL portions of hexanes and the washed filter cake was air-dried for 1 h. The dried filter cake was dissolved with aqueous dipotassium hydrogenphosphate solution (1 N, 60 mL) and ethyl acetate (150 mL). The resulting biphasic mixture was stirred for 30 min at 23° C. The layers were separated. The aqueous layer was extracted with ethyl acetate (100 mL). The organic phases were combined and the combined solution was dried over sodium sulfate. The dried solution was filtered and the filtrate was concentrated. The residue obtained was purified by flash-column chromatography on silica gel (10% ethyl acetate-hexanes grading to 20% ethyl acetate-hexanes) to provide the retro-Diels-Alder product 10 (2.67 g, 65%) as a pale yellow solid. TLC (33% ethyl acetate-hexanes): $R_f$=0.24 (UV, CAM). $[\alpha]^{23}_D$ 373 (c 0.65, CHCl$_3$). $^1$H NMR (600 MHz, CDCl$_3$), δ: 15.06 (s, 1H), 7.52-7.51 (m, 2H), 7.40-7.33 (m, 3H), 6.60 (ddd, 1H, J=2.4, 6.0, 9.0 Hz), 6.04 (dd, 1H, J=3.0, 9.0 Hz), 5.40 (s, 2H), 3.84 (d, 1H, J=7.2 Hz), 3.40 (dt, 1H, J=7.2, 15.6 Hz), 2.96-2.89 (m, 1H), 2.37-2.32 (m, 1H), 2.27 (s, 6H). $^{13}$C NMR (125 MHz, CDCl$_3$), δ: 181.2, 175.6, 172.6, 167.6, 142.3, 135.2, 128.5, 128.4, 128.3, 124.2, 107.7, 102.1, 73.3, 57.6, 41.9, 34.9, 25.6. IR (neat), cm$^{-1}$: 2978 (s), 2939 (s), 2831 (s), 2360 (s), 1627 (s), 1566 (s), 1504 (s). HRMS (ESI): Calcd for $(C_{20}H_{20}N_2O_4+H)^+$: 353.1496. Found: 353.1508.

Example 5

Synthesis of Alcohol 11

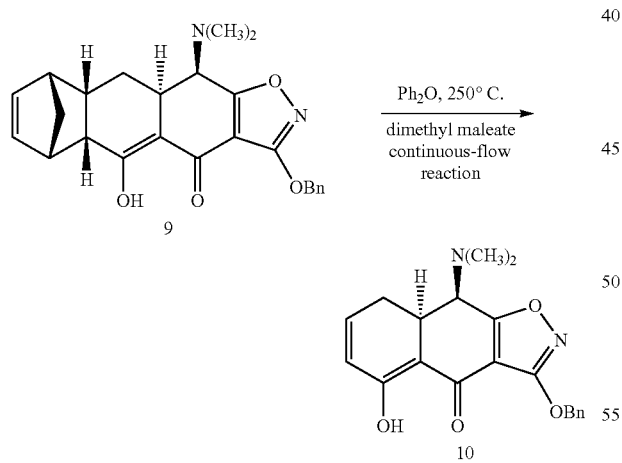

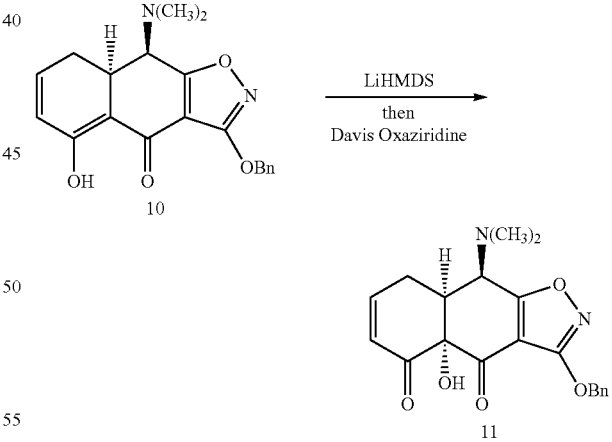

A special setup was constructed for this transformation (see FIG. 1). A 1-L, 3-necked, round-bottomed flask was charged with 9 (4.9 g, 11.7 mmol, 1 equiv), diphenyl ether (490 mL) and dimethyl maleate (7.3 mL, 58.3 mmol, 5 equiv). The homogeneous solution was degassed by bubbling with argon for 30 min. The degassed solution was passed through a stainless steel loop (304 ss, ⅛ in ×0.147 in ×10 ft, VWR) preheated to 250° C. then a 23° C. water cooling bath using a liquid pump (CERAMPUMP® FMI Q PUMP) at a rate of A 100-mL, single-necked, round-bottomed flask was equipped with a TEFLON® (polytetrafluoroethylene)-coated magnetic stirring bar and charged with lithium chloride (189 mg, 4.52 mmol, 1.1 equiv). The flask was flame dried under vacuum with stirring. The flask was flushed with argon three times, then allowed to cool to 23° C. under argon. The flask was charged with a solution of 10 (1.45 g, 4.11 mmol, 1 equiv) in 1,2-dimethoxyethane (12 mL). The resulting slurry was cooled to −30° C., then a solution of lithium bis(trimethylsilyl)amide in 1,2-dimethoxyethane [prepared by adding a solution of n-butyllithium in hexanes (2.5 M, 1.81 mL, 4.52 mmol, 1.1 equiv) dropwise to a solution of hexamethyldisilazane (0.988 mL, 4.73 mmol, 1.15 equiv) in anhydrous 1,2-dimethoxyethane (8 mL) at −78° C., followed by stirring at 0° C. for 30 min] was added dropwise over the course of 3 min. The resulting yellow slurry was stirred for 10 min at −30° C., then a solution of trans-2-(phenylsulfonyl)-3-phenyloxaziridine (1.37 g, 4.93 mmol, 1.2 equiv) (Vishwakarma, et al., (±)-trans-2-(phenylsulfonyl)-3-Phenyloxaziridine. *Organic Syntheses* 1988, 66, 203-207) in 1,2-dimethoxyethane (6 mL) was added to the reaction mixture dropwise by syringe over the course of 5 min. The transfer was quantitated with additional 1,2-dimethoxyethane (2 mL). The resulting reaction mixture was stirred for 15 h at −30° C. during which time a dark blue solution formed, then 1 N aqueous hydrochloric acid solution (20 mL) and water (20 mL) was added. The reaction flask was removed from the cooling bath and the biphasic product mixture was and allowed to warm to 23° C., then poured into a separation funnel. The layers were separated. The organic layer was extracted with a 0.5 N aqueous hydrochloric acid solution (4 mL). The combined acid aqueous layers were washed with two 20-mL portions of hexane-ethyl acetate (2:1). These new organic layers were combined and the combined solution was extracted with water (20 mL). The water layer was combined with the aqueous acid layers and the combined solution was neutralized with potassium phosphate dibasic (7.65 g). Dichloromethane (100 mL) was added and the resulting biphasic mixture was stirred for 15 min. The layers were separated. The aqueous layer was extracted with two 30-mL portions of dichloromethane. The organic layers were combined and the combined solution was dried over sodium sulfate. The dried solution was filtered and the filtrate was concentrated to provide alcohol 11 (1.46 g) as a purple solid that was used directly in the next step. An analytical sample was prepared by radial chromatography (1:1 hexanes-ethyl acetate grading to 1:1 hexanes-acetone). White foam. TLC (50% acetone-hexanes): $R_f$=0.42 (UV, CAM). $[\alpha]^{23}_D$ 373 (c 0.65, CHCl$_3$). $^1$H NMR (500 MHz, CDCl$_3$), δ: 7.49-7.47 (m, 2H), 7.40-7.34 (m, 3H), 7.00-6.97 (m, 1H), 6.24 (dd, 1H, J=2.5, 10.5 Hz), 5.36 (s, 2H), 4.65 (br s, 1H), 4.48 (d, 1H, J=5.0 Hz), 3.10 (dt, 1H, J=5.0, 10.5 Hz), 2.80 (dt, 1H, J=5.5, 20.0 Hz), 2.62 (s, 6H), 2.49-2.41 (m, 1H). $^{13}$C NMR (125 MHz, CDCl$_3$), δ: 195.0, 185.7, 180.4, 167.9, 149.8, 134.9, 128.6, 128.5, 128.2, 126.9, 106.1, 80.4, 72.4, 59.9, 47.1, 44.5, 26.5. $[\alpha]^{23}_D$-183 (c 0.55, CHCl$_3$). IR (neat), cm$^{-1}$: 3435 (s), 2926 (m), 1703 (s), 1683 (s), 1595 (s), 1473 (s), 1369 (s). HRMS (ESI): Calcd for (C$_{20}$H$_{20}$N$_2$O$_5$+H)$^+$: 391.1264. Found: 391.1266.

Example 6

Synthesis of Enone Intermediate 12A

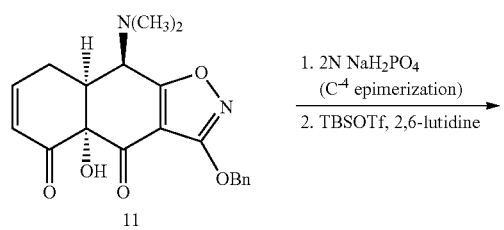

1. 2N NaH$_2$PO$_4$ (C$^{-4}$ epimerization)
2. TBSOTf, 2,6-lutidine

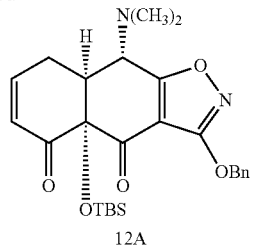

12A

Epimerization.

A 100-mL, single-necked, round-bottomed flask equipped with a TEFLON® (polytetrafluoroethylene)-coated magnetic stirring bar was flushed with argon. The flask was charged with a solution of alcohol 11 (1.46 g, 3.96 mmol, 1 equiv) in tetrahydrofuran (10 mL), methanol (10 mL), and a 2 M aqueous sodium dihydrogen phosphate solution (6 mL). The resulting biphasic mixture was degassed by bubbling with argon for 30 min. The mixture was stirred at 52° C. for 15 h. The flask was removed from the heating bath and the product mixture allowed to cool to 23° C., then water (15 mL), dipotassium hydrogenphosphate (7.83 g), and dichloromethane (40 mL) was added and the resulting biphasic mixture was stirred for 10 min. The layers were separated. The aqueous layer was extracted with two 40-mL portions of dichloromethane. The organic layers were combined and the combined layers were dried over sodium sulfate. The dried solution was filtered and the filtrate was concentrated to provide a purple residue that was used directly in the next step.

Silylation.

A 100-mL, single-necked, round-bottomed flask equipped with a TEFLON® (polytetrafluoroethylene)-coated magnetic stirring bar was flame-dried, then allowed to cool to 23° C. under argon. The flask was charged with a solution of the product obtained above in dichloromethane (20 mL). The solution was cooled to 0° C., whereupon 2,6-Lutidine (0.813 mL, 7.14 mmol, 1.8 equiv) and tert-butyldimethylsilyl trifluoromethanesulfonate (1.28 mL, 5.56 mmol, 1.4 equiv) were added sequentially dropwise by syringe. The reaction mixture was stirred for 15 min at 0° C., then the cooling bath was removed. The reaction solution was stirred for 20 min at 23° C., then was partitioned between aqueous potassium phosphate buffer solution (pH 7, 0.05 M, 40 mL) and dichloromethane (35 mL). The layers were separated. The aqueous layer was extracted with one 40-mL portion of dichloromethane. The organic layers were combined and the combined layers were dried over sodium sulfate. The dried solution was filtered and the filtrate was concentrated. The residue was purified by flash-column chromatography on silica gel (100% dichloromethane, grading to 2% ethyl acetate-dichloromethane) to provide the enone 12A (990 mg, 50% yield over 3 steps) as a light-yellow foam. TLC (20% ethyl acetate-hexanes): $R_f$=0.34 (UV, CAM). $^1$H NMR (600 MHz, CDCl$_3$), δ: 7.51 (d, 2H, J=1.5 Hz, Aril), 7.50-7.34 (m, 3H, Aril), 6.94 (m, 1H, =CHCH$_2$), 6.10 (ddd, 1H, J=10.3, 1.5, 1.5 Hz, =CHC(O)), 5.36 (m, 2H, OCH$_2$Ph), 3.79 (d, 1H, J=10.7 Hz, CHN(CH$_3$)$_2$), 2.83 (m, 2H, =CHCH$_2$), 2.78 (m, 1H, CHCHN(CH$_3$)$_2$), 2.46 (s, 6H, N(CH$_3$)$_2$), 0.84 (s, 9H, SiC(CH$_3$)$_3$), 0.27 (s, 3H, SiCH$_3$), 0.06 (s, 3H, SiCH$_3$).

127

Synthesis of C12a-methoxy AB Enone 12B

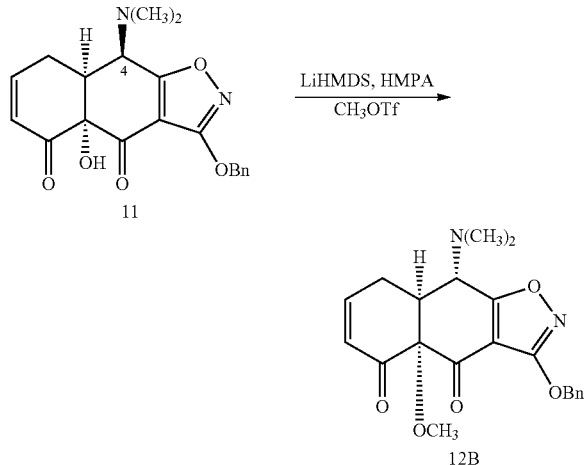

A solution of alcohol 11 (70 mg, 0.190 mmol, 1 equiv) in tetrahydrofuran (2 mL) at 23° C. was added dropwise by cannula to a stirring solution of lithium bis(trimethylsilyl) amide (1 M in THF, 230 µL, 0.228 mmol, 1.2 equiv) and hexamethylphosphoramide (66 µL, 0.380 mmol, 2 equiv) in tetrahydrofuran (2 mL) at −78° C. The resulting solution was stirred for 5 min at −78° C. whereupon methyl trifluoromethanesulfonate (43 µL, 0.380 mmol, 2 equiv) was added. The mixture was stirred at −78° C. for 30 min then the cooling bath was removed and stirring continued for 5 min with warming, whereupon water (2 mL) was added. The biphasic product mixture was poured into a separation funnel containing saturated aqueous ammonium chloride solution (10 mL) and ethyl acetate (10 mL). The layers were separated. The aqueous layer was extracted with ethyl acetate (10 mL). The organic layers were combined and the combined solution dried over sodium sulfate. The dried solution was filtered and the filtrate concentrated. The residue was purified by flash-column chromatography on silica gel (100% dichloromethane initially, grading to 8% ethyl acetate-dichloromethane) to provide the product 12B as a light yellow foam (53 mg, 73%). $^1$H NMR (600 MHz, CDCl$_3$) δ: 7.50-7.48 (m, 2H), 7.40-7.34 (m, 3H), 7.02-6.99 (m, 1H), 6.11 (m, 1H), 5.33 (AB q, 2H), 3.82 (d, 1H, J=10.5 Hz), 3.60 (s, 3H), 2.91-2.80 (m, 3H), 2.46 (s, 6H).

Example 7

Synthesis of Phenyl Ester 13

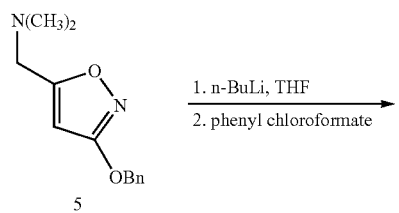

128

-continued

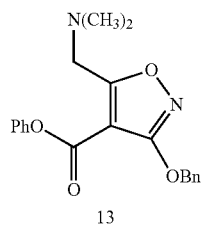

A solution of n-butyllithium in hexanes (2.5 M, 6.9 mL, 17.2 mmol, 1 equiv) was added dropwise by syringe to a stirring solution of isoxazole 5 (4 g, 17.2 mmol, 1 equiv) in tetrahydrofuran (170 mL) at −78° C. The resulting red slurry was stirred for 45 min at −78° C., then added dropwise by cannula to a stirring solution of phenyl chloroformate (2.3 mL, 18.1 mmol, 1.05 equiv) in tetrahydrofuran (50 mL) at −78° C. over the course of 20 min. The resulting yellow slurry was stirred for 2.5 h at −78° C., then the flask was removed from the cooling bath and reaction mixture allowed to warm to 23° C. Saturated aqueous ammonium chloride solution (500 mL) and ethyl acetate (200 mL) was added, then the resulting biphasic mixture poured into a separation funnel. The layers were separated. The aqueous layer was extracted with two 200-mL portions of ethyl acetate. The organic layers were combined and the combined layers were dried over sodium sulfate. The dried solution was filtered and the filtrate was concentrated. The residue was purified by flash-column chromatography on silica gel (25% ethyl acetate-hexanes grading to 50% ethyl acetate-hexanes) to provide the phenyl ester 13 (3.6 g, 59%) as a yellow oil which slowly solidified. TLC (50% Et$_2$O-hexanes): R$_f$=0.17 (UV, KMnO$_4$). $^1$H NMR (600 MHz, CDCl$_3$), δ: 7.50-7.48 (m, 2H), 7.43-7.25 (m, 6H), 7.19-7.17 (m, 2H), 5.41 (s, 2H), 3.98 (s, 2H), 2.39 (s, 6H). $^{13}$C NMR (125 MHz, CDCl$_3$), δ: 177.2, 169.0, 159.5, 150.1, 135.5, 129.5, 128.5, 128.3, 127.6, 126.1, 121.6, 101.8, 71.8, 53.8, 45.3. IR (neat), cm$^{-1}$: 2943 (m), 2785 (m), 1707 (s), 1508 (s). HRMS (ESI): Calcd for (C$_{20}$H$_{20}$N$_2$O$_4$+H)$^+$: 353.1496. Found: 353.1501.

Example 8

Synthesis of Enone 14

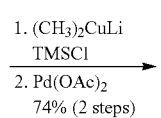

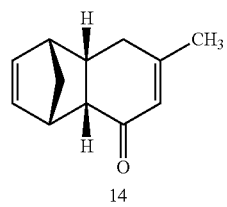

129

Conjugate Addition.

An oven-dried 200-mL, single-necked, round-bottomed flask equipped with a magnetic stirring bar was charged with copper iodide (3 g, 15.6 mmol, 2.5 equiv) and tetrahydrofuran (60 mL). The resulting slurry was cooled to 0° C., whereupon a solution of methyllithium in diethoxymethane (3 M, 10.3 mL, 30.9 mmol, 4.95 equiv) was added dropwise by syringe. The resulting orange slurry was stirred for 20 min at 0° C. resulting in a light-brown, homogeneous reaction mixture, then cooled to −78° C. resulting in a heterogeneous solution. A separate dry round-bottomed flask was charged with enone 4 (1 g, 6.24 mmol, 1 equiv), hexamethylphosphoramide (3.3 mL, 18.7 mmol, 3 equiv), trimethylsilylchloride (2.4 mL, 18.7 mmol, 3 equiv), and tetrahydrofuran (30 mL). This solution was added dropwise by cannula to the above −78° C. organo-copper solution. Additional tetrahydrofuran (5 mL) was used to quantitate the transfer. The resulting homogeneous solution was stirred for 20 min at −78° C., then diluted with ethyl acetate-hexanes (1:1, 60 mL). The reaction flask was removed from the cooling bath, then saturated aqueous ammonium chloride solution-14.8 N aqueous ammonium hydroxide solution (15:1, pH ~9.5, 60 mL) was added. The resulting slurry was stirred for 5 min at 23° C., then partitioned between saturated aqueous ammonium chloride solution-14.8 N aqueous ammonium hydroxide solution (15:1, pH ~9.5, 250 mL) and ethyl acetate-hexanes (60 mL). The layers were separated. The organic layer was washed with two 50-mL portions of saturated aqueous ammonium chloride solution and one portion 50-mL portion of saturated aqueous sodium chloride solution. The washed organic solution was dried over sodium sulfate. The dried solution was filtered and the filtrate was concentrated to provide the intermediate (trimethylsilyl)enol ether contaminated with hexamethylphosphoramide that was used directly in the next step.

Enone Formation.

The above product (trimethylsilyl)enol ether was dissolved in dimethyl sulfoxide (50 mL). Palladium diacetate (1.5 g, 6.55 mmol, 1.05 equiv) was added in one portion and the resulting black slurry stirred for 20 h at 23° C., then filtered through a pad of silica gel rinsing with ethyl acetate (100 mL). The filtrate was partitioned between hexanes (100 mL) and water (200 mL). The layers were separated. The organic layer was washed with two 100-mL portions of water and one 100-mL portion of saturated aqueous sodium chloride solution. The washed organic solution was dried over sodium sulfate. The dried solution of filtered and the filtrate was concentrated. The residue was purified by flash-column chromatography on silica gel (30% ethyl acetate-hexanes) to provide enone 14 (808 mg, 74% over 2 steps) as a yellow oil which solidifies at −20° C. TLC (25% ethyl acetate-hexanes): $R_f$=0.24 (UV, KMnO$_4$). $^1$H NMR (600 MHz, CDCl$_3$), δ: 6.10-6.06 (m, 2H), 5.74-5.73 (m, 1H), 3.36 (d, 1H, J=1.2 Hz), 3.01 (s, 1H), 2.81 (dd, 1H, J=4.0, 10.1 Hz), 2.77-2.73 (m, 1H), 2.49 (dd, 1H, J=10.4, 20 Hz), 1.92 (d, 1H, J=20 Hz), 1.82 (s, 3H), 1.42-1.40 (m, 1H), 1.35-1.33 (m, 1H). $^{13}$C NMR (125 MHz, CDCl$_3$), δ: 200.8, 160.8, 137.8, 134.1, 126.4, 49.1, 48.5, 48.3, 47.7, 34.3, 32.4, 24.4. IR (neat), cm$^{-1}$: 2965, 2936, 1651 (s). HRMS (ESI): Calcd for (C$_{12}$H$_{14}$O+Na)$^+$: 197.0937. Found: 197.0962.

130

Example 9

Synthesis of Michael-Claisen Product 15

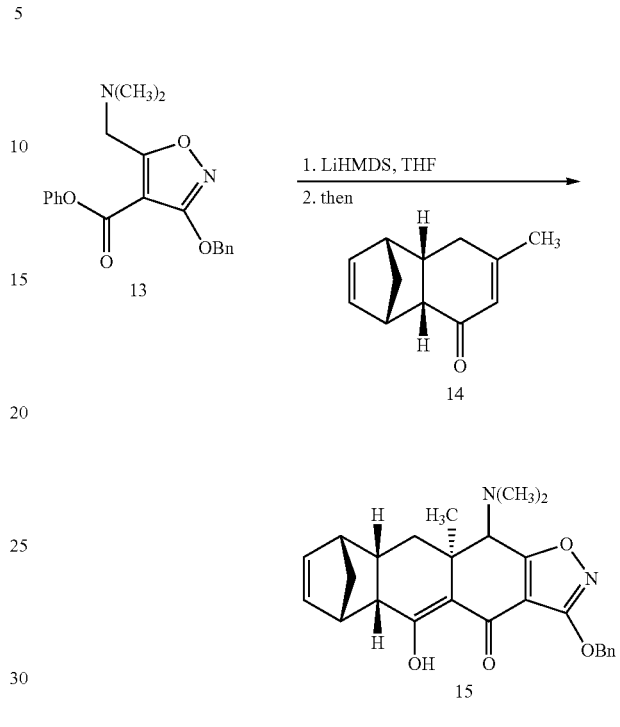

A solution of lithium bis(trimethylsilyl)amide in tetrahydrofuran (1 M, 1.15 mL, 1.15 mmol, 2 equiv) was added dropwise by syringe to a stirring solution of phenyl ester 13 (405 mg, 1.15 mmol, 2 equiv) in tetrahydrofuran (12 mL) at −78° C. The resulting brown heterogeneous mixture was stirred for 30 min at −20° C. and then cooled to −78° C., whereupon a solution of enone 14 (100 mg, 0.574 mmol, 1 equiv) in tetrahydrofuran (5 mL) was added dropwise by syringe. Additional tetrahydrofuran (1 mL) was used to quantitate the transfer. The resulting slurry was stirred for 5 min at −78° C., then the flask was removed from the cooling bath and the reaction mixture was allowed to warm to 23° C. and stirring was continued for 24 h during which time the reaction became homogeneous. Water (1 mL) was added and the resulting biphasic mixture was concentrated. Ethyl acetate (15 mL) was added to the residue and the resulting organic solution was washed with two 10-mL portions of a 1 N aqueous sodium hydroxide solution. The washed organic solution was dried over sodium sulfate. The dried solution was filtered and the filtrate was concentrated. The residue was purified by flash-column chromatography on silica gel (10% acetone-hexanes) to provide the Michael-Claisen product 15 (116 mg, 47%) as an oil which slowly solidified. TLC (10% acetone-hexanes): $R_f$=0.20 (UV, KMnO$_4$). $^1$H NMR (600 MHz, CDCl$_3$), δ: 14.55 (s, 1H), 7.51-7.52 (m, 2H), 7.40-7.33 (m, 3H), 6.20 (dd, 1H, J=3.2, 5.5 Hz), 6.12 (dd, 1H, J=3.2, 5.7 Hz), 5.40-5.35 (m, 2H), 3.35 (s, 1H), 3.22 (s, 1H), 2.93-2.91 (m, 2H), 2.85-2.81 (m, 1H), 2.79-2.74 (m, 2H), 2.18 (s, 6H), 1.56-1.54 (m, 1H), 1.43 (d, 1H, J=8.2 Hz), 1.28 (d, 1H, J=3.4 Hz), 1.07 (s, 3H). $^{13}$C NMR (125 MHz, CDCl$_3$), δ: 184.4, 178.5, 177.1, 167.9, 137.4, 135.2, 135.2, 128.6, 128.5, 128.3, 110.5, 107.1, 72.3, 66.5, 51.1, 48.6, 47.1, 42.5, 42.1, 39.0, 36.3, 33.8, 31.9. IR (neat), cm$^{-1}$: 2961, 2926, 1630 (s), 1611, 1574, 1506 (s), 1476, 1454. HRMS (ESI): Calcd for $(C_{26}H_{28}N_2O_4+H)^+$: 433.2122. Found: 433.2110.

Example 10

Synthesis of Michael Addition Product 17

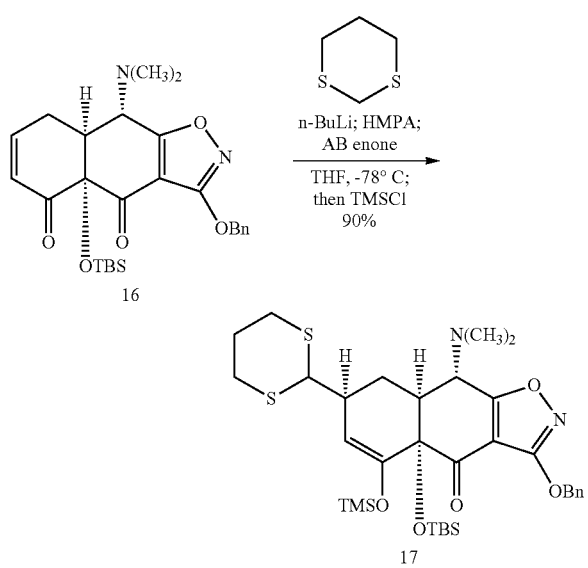

A solution of n-butyllithium in hexanes (2.5 M, 2.91 mL, 7.27 mmol, 1.15 equiv) was added to a solution of 1,3-dithiane (862 mg, 6.95 mmol, 1.1 equiv) in tetrahydrofuran (60 mL) at −78° C. The resulting solution was stirred at this temperature for 30 min, at which point hexamethylphosphoramide (2.44 mL, 13.9 mmol, 2.2 equiv) was added. After stirring at −78° C. for a further 2 min, a solution of the AB enone 16 (3.05 g, 6.32 mmol, 1 equiv) in tetrahydrofuran (25 mL) was added dropwise via syringe to the reaction solution. The brownish-yellow reaction mixture was stirred at −78° C. for 40 min whereupon trimethylsilyl chloride (1.20 mL, 9.48 mmol, 1.5 equiv) was added. After stirring at −78° C. for 40 min, aqueous potassium phosphate buffer solution (pH 7.0, 0.2 M, 100 mL) was added to the reaction solution. The resulting mixture was allowed to warm to 23° C., then was extracted with dichloromethane (3×100 mL). The organic extracts were combined and the combined solution was dried over anhydrous sodium sulfate. The dried solution was filtered and the filtrate was concentrated. The product was purified by flash-column chromatography (8% ethyl acetate-hexanes), affording the Michael addition product 17 as a foamy white solid (3.85 g, 90%). $R_f$=0.53 (30% ethyl acetate-hexanes); $^1$H NMR (500 MHz, CDCl$_3$) δ 7.48 (d, 2H, J=7.0 Hz), 7.38-7.31 (m, 3H), 5.36 (AB quartet, 2H, J=12.0 Hz, Δν=34.0 Hz), 4.98 (d, 1H, J=3.0 Hz), 4.12 (d, 1H, J=5.0 Hz), 3.89 (d, 1H, J=9.5 Hz), 2.96-2.82 (m, 5H), 2.46 (s, 6H), 2.34-2.29 (m, 1H), 2.28-2.23 (m, 2H), 2.15-2.09 (m, 1H), 1.90-1.80 (m, 1H), 0.86 (s, 9H), 0.21 (s, 3H), 0.10 (s, 3H), −0.01 (s, 9H); $^{13}$C NMR (125 MHz, CDCl$_3$) δ 189.4, 181.5, 167.3, 149.5, 135.1, 128.7, 128.5, 128.4, 108.5, 104.8, 81.0, 72.3, 61.3, 54.9, 46.1, 41.9, 37.1, 31.1, 30.8, 26.1, 25.7, 21.8, 18.9, −0.4, −2.7, −3.6; FTIR (neat film), cm$^{-1}$ 2953 (w), 1721 (s), 1653 (w), 1614 (w), 1510 (s), 1472 (w), 1454 (w), 1254 (s), 1204 (w), 1150 (w), 1024 (w), 934 (s), 901 (s), 835 (s); HRMS-ESI (m/z): [M+H]$^+$ calcd for $C_{33}H_{51}N_2O_5S_2Si_2$, 675.2772. found, 675.2783.

Example 11

Synthesis of β-Methoxymethoxymethylenone 18

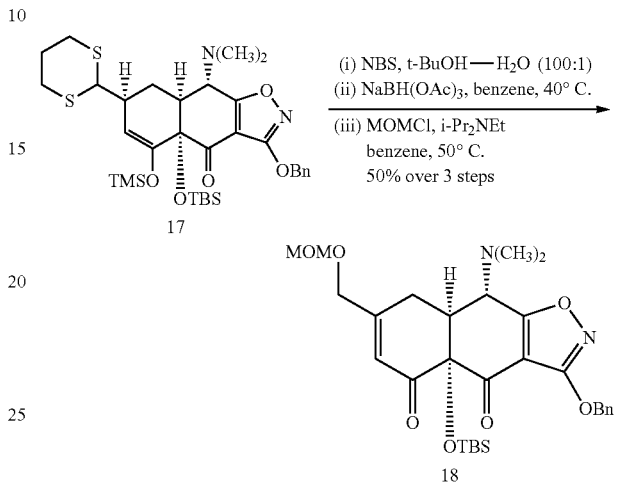

N-Bromosuccinimide (3.39 g, 19.0 mmol, 6.0 equiv) was added in one portion to a solution of the Michael addition product 17 (2.14 g, 3.17 mmol, 1 equiv) in tert-butanol (85 mL) and water (0.85 mL) at 23° C. The reaction mixture was stirred at this temperature for 100 min, then was partitioned between dichloromethane (300 mL) and saturated aqueous sodium bicarbonate solution (200 mL). The phases were separated and the aqueous phase was further extracted with dichloromethane (150 mL). The organic extracts were combined and the combined solution was dried over anhydrous sodium sulfate. The dried solution was filtered and the filtrate was concentrated, affording a yellow solid. The crude product was dissolved in diethyl ether (250 mL) and the resulting solution was washed with aqueous sodium hydroxide solution (0.5 M, 4×150 mL). The organic phase was dried over anhydrous sodium sulfate. The dried solution was filtered and the filtrate was concentrated. Sodium triacetoxyborohydride (2.62 g, 11.7 mmol, 3.7 equiv) was added to a solution of the crude product in benzene (20 mL) at 23° C. The resulting solution was heated to 40° C. After stirring at 40° C. for 4½ h, the reaction mixture was allowed to cool to 23° C. and the cooled solution was diluted with dichloromethane (100 mL). The resulting solution was added carefully to saturated aqueous sodium bicarbonate solution (100 mL). The phases were separated and the aqueous phase was further extracted with dichloromethane (100 mL). The organic extracts were combined and the combined solution was dried over anhydrous sodium sulfate. The dried solution was filtered and the filtrate was concentrated. Chloromethyl methyl ether (446 μL, 5.87 mmol, 1.85 equiv) was added to a solution of the crude reduction product and N,N-diisopropylethylamine (2.04 mL, 11.7 mmol, 3.7 equiv) in benzene (10 mL) at 23° C. The reaction flask was sealed and the solution was heated to 50° C. After stirring at 50° C. for 6 h, the reaction mixture was allowed to cool to 23° C., and the cooled solution was partitioned between dichloromethane (100 mL) and saturated aqueous sodium bicarbonate solution (100 mL). The layers were separated and the aqueous phase was further extracted with dichloromethane (100 mL). The organic extracts were combined and the combined solution was dried over anhydrous sodium sulfate. The dried solution was filtered and the filtrate was concentrated. The product was purified by flash-column chromatography (15% ethyl acetate-hexanes, grading to 20% ethyl acetate-hexanes), affording the desired β-methoxymethoxymethylenone 18 as a yellow solid (875 mg, 50% yield, three steps). $R_f$=0.40 (30% ethyl acetate-hexanes); $^1$H NMR (500 MHz, CDCl$_3$) δ 7.50 (d, 2H, J=7.0 Hz), 7.40-7.32 (m, 3H), 6.21 (s, 1H), 5.35 (AB quartet, 2H, J=12.0 Hz, Δv=2.0 Hz), 4.67 (AB quartet, 2H, J=7.0 Hz, Δv=4.5 Hz), 4.16 (m, 2H), 3.74 (d, 1H, J=10.0 Hz), 3.38 (s, 3H), 2.80-2.74 (m, 3H), 2.45 (s, 6H), 0.82 (s, 9H), 0.26 (s, 3H), 0.05 (s, 3H); $^{13}$C NMR (125 MHz, CDCl$_3$) δ 193.1, 187.7, 181.1, 167.5, 159.7, 135.0, 128.5, 128.5, 128.5, 122.4, 108.4, 96.0, 83.0, 72.6, 68.4, 59.6, 55.5, 47.5, 41.9, 25.9, 25.8, 19.0, −2.5, −4.1; FTIR (neat film), cm$^{-1}$ 2951 (w), 2930 (w), 1719 (s), 1674 (m), 1510 (s), 1175 (m), 1152 (m), 1038 (s), 934 (s), 829 (s), 735 (s); HRMS-ESI (m/z): [M+H]$^+$ calcd for C$_{29}$H$_2$O$_7$Si, 557.2678. found, 557.2690.

Example 12

Synthesis of Michael-Claisen Cyclization Product 20

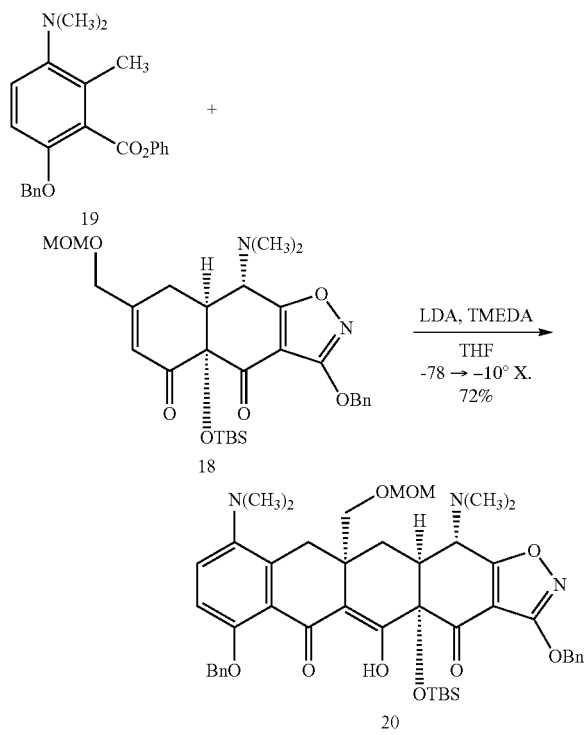

to −10° C. over 80 min, then was partitioned between aqueous potassium phosphate buffer solution (pH 7.0, 0.2 M, 100 mL) and dichloromethane (100 mL). The phases were separated and the aqueous phase was further extracted with dichloromethane (2×75 mL). The organic extracts were combined and the combined solution was dried over anhydrous sodium sulfate. The dried solution was filtered and the filtrate was concentrated, affording an orange-yellow oil. The product was purified by flash-column chromatography (3.5% ethyl acetate-dichloromethane), providing the Michael-Claisen cyclization product 20 as a yellow solid (1.29 g, 72%). $R_f$=0.31 (30% ethyl acetate-hexanes); $^1$H NMR (500 MHz, CDCl$_3$) δ 16.77 (s, 1H), 7.51 (brd, 4H, J=8.0 Hz), 7.41-7.28 (m, 6H), 7.21 (d, 1H, J=9.0 Hz), 6.90 (d, 1H, J=9.0 Hz), 5.38 (s, 2H), 5.17 (AB quartet, 2H, J=12.5 Hz, Δv=29.5 Hz), 4.47 (d, 1H, J=6.5 Hz), 4.34 (d, 1H, J=6.5 Hz), 4.15 (d, 1H, J=9.5 Hz), 3.78 (d, 1H, J=16.5 Hz), 3.38 (d, 1H, J=9.0 Hz), 3.27 (d, 1H, J=9.5 Hz), 3.12 (s, 3H), 2.63 (s, 6H), 2.65-2.58 (m, 1H), 2.51 (s, 6H), 2.51-2.41 (m, 2H), 2.32 (dd, 1H, J=14.5, 2.0 Hz), 0.93 (s, 9H), 0.29 (s, 3H), 0.20 (s, 3H); $^{13}$C NMR (125 MHz, CDCl$_3$) δ 186.9, 184.6, 183.0, 181.6, 167.7, 154.7, 145.7, 136.8, 136.1, 135.1, 128.5, 128.4, 128.4, 128.3, 127.7, 127.0, 125.0, 120.7, 113.7, 108.1, 107.2, 96.1, 82.3, 72.9, 72.4, 71.4, 61.1, 54.6, 46.4, 44.4, 41.9, 35.8, 34.7, 28.4, 26.5, 19.3, −2.0, −2.1; FTIR (neat film), 2932 (w), 1721 (s), 1611 (w), 1510 (m), 1472 (m), 1452 (m), 1269 (w), 1148 (w), 1107 (w), 1040 (s), 1020 (s), 922 (w), 831 (s), 733 (s) cm$^{-1}$; HRMS-ESI (m/z): [M+H]$^+$ calcd for C$_{46}$H$_{58}$N$_3$O$_9$Si, 824.3937. found, 824.3885.

Example 13

Synthesis of Alcohol 21

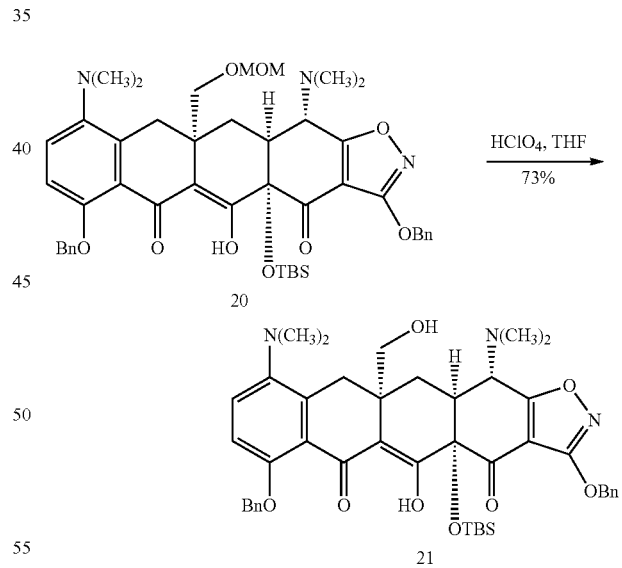

Cyclyzation Step:

A freshly solution of lithium diisopropylamide (1.0 M, 7.86 mL, 7.86 mmol, 3.6 equiv) was added dropwise via syringe to a solution of the phenyl ester D-ring precursor 19 (2.84 g, 7.86 mmol, 3.6 equiv) and N,N'-tetramethylethylenediamine (2.27 mL, 15.1 mmol, 7 equiv) in tetrahydrofuran (60 mL) at −78° C., forming a bright red solution. After stirring at −78° C. for 40 min, a solution of the β-methoxymethoxymethylenone 18 (1.20 g, 2.16 mmol, 1 equiv) in tetrahydrofuran (15 mL) was added dropwise via syringe to the reaction solution. The resulting mixture was allowed to warm slowly Deprotection Step:

Perchloric acid (13.0 mL, 70% solution) was added dropwise over 5 min to a solution of the Michael-Claisen cyclization product (1.04 g, 1.26 mmol, 1 equiv) in tetrahydrofuran (130 mL) at 23° C. After stirring at this temperature for 10 min, the reaction solution was slowly and carefully poured into ice-cold saturated aqueous sodium bicarbonate solution (300 mL). The resulting mixture was extracted with dichloromethane (2×250 mL, then 50 mL). The organic extracts were combined and the combined solution was dried over anhydrous sodium sulfate. The dried solution was filtered and the filtrate was concentrated, providing an orange-yellow oil. The product was purified by flash-column chromatography (55% ethyl acetate-hexanes, grading to 75% ethyl acetate-hexanes), affording the desired alcohol 21 as a yellow solid (720 mg, 73%). $R_f$=0.26 (65% ethyl acetate-hexanes); $^1$H NMR (500 MHz, CDCl$_3$) δ 16.76 (s, 1H), 7.53-7.49 (m, 4H), 7.41-7.28 (m, 6H), 7.22 (d, 1H, J=9.0 Hz), 6.90 (d, 1H, J=9.0 Hz), 5.38 (s, 2H), 5.17 (AB quartet, 2H, J=12.5 Hz, Δv=35 Hz), 4.11 (d, 1H, J=9.5 Hz), 3.66 (d, 1H, J=16.0 Hz), 3.48 (d, 1H, J=11.0 Hz), 3.32 (d, 1H, J=11.0 Hz), 2.64 (s, 6H), 2.68-2.59 (m, 1H), 2.56-2.48 (m, 1H), 2.51 (s, 6H), 2.38 (dd, 1H, J=14.5, 4.5 Hz), 2.23 (brd, 1H, J=14.0 Hz), 0.92 (s, 9H), 0.25 (s, 3H), 0.18 (s, 3H); $^{13}$C NMR (125 MHz, CDCl$_3$) δ 186.7, 184.7, 182.7, 181.4, 167.7, 154.9, 145.7, 136.8, 135.9, 135.1, 128.5, 128.5, 128.5, 128.3, 127.8, 126.9, 125.3, 120.7, 113.7, 108.2, 107.3, 82.3, 72.4, 71.4, 68.2, 61.3, 46.2, 44.7, 42.0, 36.8, 34.5, 28.2, 26.5, 19.3, −1.8, −2.0; FTIR (neat film), 2938 (w), 1719 (m), 1609 (w), 1510 (s), 1452 (s), 1265 (m), 1020 (m), 829 (s), 733 (s) cm$^{-1}$; HRMS-ESI (m/z): [M+H]$^+$ calcd for C$_{44}$H$_{54}$N$_3$O$_8$Si, 780.3675. found, 780.3654.

Example 14

Synthesis of Cyclopropane Intermediate 22

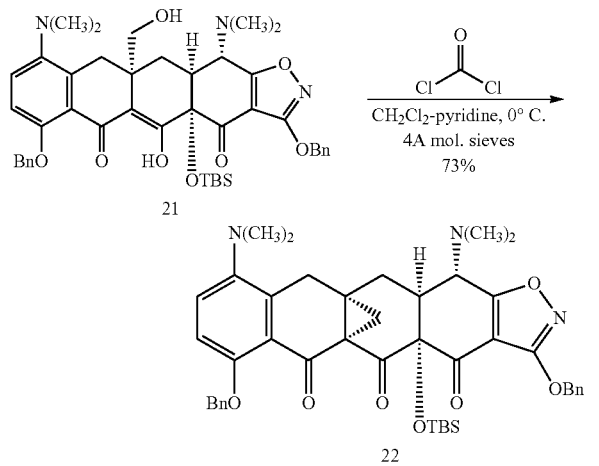

Cyclopropane Ring-Forming Step:

4 Å molecular sieves (2.4 g, small chunks) were added to a solution of the alcohol product 21 from the deprotection step above (720 mg, 0.923 mmol, 1 equiv) in dichloromethane (72 mL) and pyridine (7.2 mL) at 23° C. The resulting mixture was stirred at 23° C. for 1 h, then was cooled to 0° C. A solution of phosgene in toluene (20 wt %, 537 μL, 1.02 mmol, 1.1 equiv) was added to the cooled reaction mixture. After stirring at 0° C. for 1 h, aqueous potassium phosphate buffer solution (pH 7.0, 0.2 M, 20 mL) was added to the reaction solution. The resulting mixture was allowed to warm to 23° C., then was filtered to remove 4 Å molecular sieves. Dichloromethane (60 mL) and aqueous potassium phosphate buffer solution (pH 7.0, 0.2M, 60 mL) were added and the phases were separated. The aqueous phase was further extracted with dichloromethane (2×60 mL). The organic extracts were combined and the combined solution was dried over anhydrous sodium sulfate. The dried solution was filtered and the filtrate was concentrated, providing an orange-yellow oil. The product was purified by flash-column chromatography (20% ethyl acetate-hexanes, grading to 30% ethyl acetate-hexanes), affording the cyclopropane 22 as a yellow solid (572 mg, 81%). $R_f$=0.25 (30% ethyl acetate-hexanes); $^1$H NMR (500 MHz, CDCl$_3$) δ 7.53-7.24 (m, 10H), 7.13 (d, 1H, J=9.0 Hz), 6.86 (d, 1H, J=9.0 Hz), 5.35 (s, 2H), 5.05 (AB quartet, 2H, J=12.0 Hz, Δv=61.5 Hz), 4.01 (d, 1H, J=10.5 Hz), 3.85 (d, 1H, J=17.0 Hz), 2.77 (d, 1H, J=17.5 Hz), 2.68-2.57 (m, 3H), 2.62 (s, 6H), 2.49 (s, 6H), 2.25 (d, 1H, J=5.0 Hz), 1.71 (d, 1H, J=5.5 Hz), 0.89 (s, 9H), 0.28, (s, 3H), 0.12 (s, 3H); $^{13}$C NMR (125 MHz, CDCl$_3$) δ 194.4, 191.8, 185.3, 180.9, 167.6, 152.6, 144.8, 136.7, 135.0, 132.2, 128.6, 128.5, 128.5, 128.4, 127.6, 127.1, 123.3, 123.2, 113.5, 107.9, 84.0, 72.6, 71.2, 58.8, 49.0, 44.8, 43.1, 41.8, 32.1, 31.1, 30.9, 26.6, 26.3, 19.5, −2.0, −2.6; FTIR (neat film), 2938 (w), 1728 (s), 1711 (m), 1670 (w), 1510 (m), 1474 (m), 1452 (m), 1362 (w), 1258 (m), 916 (m), 827 (s), 733 (s) cm$^{-1}$; HRMS-ESI (m/z): [M+H]$^+$ calcd for C$_{44}$H$_{52}$N$_3$O$_7$Si, 762.3569. found, 762.3569.

Example 15

Synthesis of Azide 22

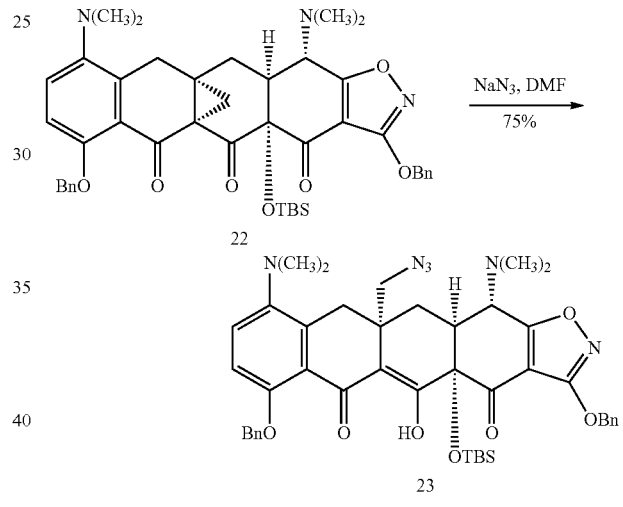

Sodium azide (12.8 mg, 0.197 mmol, 3.0 equiv) was added to a solution of the cyclopropane 22 (50 mg, 0.066 mmol, 1 equiv) in dimethylformamide (2.0 mL) at 23° C. The resulting solution was stirred for 12 h, then was partitioned between a saturated aqueous sodium chloride solution (20 mL) and diethyl ether (20 mL). The phases were separated and the aqueous phase was further extracted with diethyl ether (20 mL). The organic extracts were combined and the combined solution was dried over anhydrous sodium sulfate. The dried solution was filtered and the filtrate was concentrated. The product was purified by flash-column chromatography (12% ethyl acetate-hexanes), providing the alkyl azide 23 as a yellow solid (40 mg, 75%). $R_f$=0.41 (30% ethyl acetate-hexanes); $^1$H NMR (500 MHz, CDCl$_3$) δ 16.72 (s, 1H), 7.51 (brd, 4H, J=8.0 Hz), 7.41-7.26 (m, 7H), 6.95 (d, 1H, 8.5 Hz), 5.38 (s, 2H), 5.18 (AB quartet, 2H, J=12.5 Hz, Δv=36.5 Hz), 4.11 (d, 1H, J=10.5 Hz), 3.72 (d, 1H, J=16.5 Hz), 3.30 (d, 1H, J=11.5 Hz), 3.13 (d, 1H, J=11.5 Hz), 2.65 (s, 6H), 2.65-2.45 (m, 2H), 2.51 (s, 6H), 2.35-2.25 (m, 2H), 0.92 (s, 9H), 0.27 (s, 3H), 0.19 (s, 3H); $^{13}$C NMR (125 MHz, CDCl$_3$) δ 186.5, 184.0, 183.6, 181.5, 167.7, 154.9, 145.9, 136.7, 135.3, 135.0, 128.5, 128.5, 128.5, 128.4, 127.9, 127.0, 125.8, 120.2, 114.0, 108.3, 107.3, 82.3, 72.5, 71.5, 61.1, 59.1, 46.6, 44.6, 41.9, 36.4, 35.2, 28.3, 26.5, 19.3, −1.9, −2.1; HRMS-ESI (m/z): [M+H]+ calcd for $C_{44}H_{53}N_6O_7Si$, 805.3740. found, 805.3846.

Example 16

Synthesis of C5a-n-Butoxymethylminocycline 24

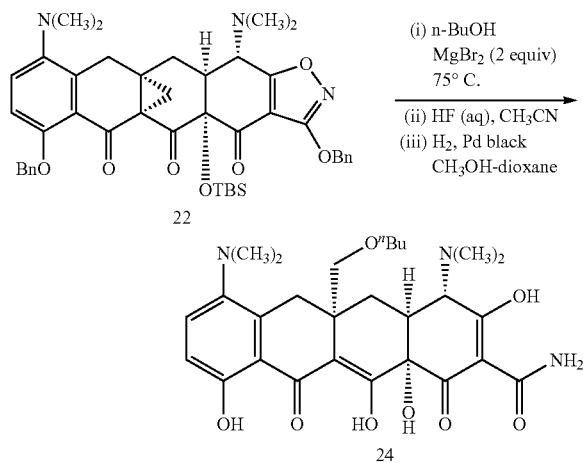

Anhydrous magnesium bromide (7.2 mg, 0.039 mmol, 2.0 equiv) was added to a solution of the cyclopropane 22 (15.0 mg, 0.020 mmol, 1 equiv) in n-butanol (1.0 mL) at 23° C. The resulting mixture was heated to 75° C. After stirring at 75° C. for 14 h, the reaction solution was allowed to cool to 23° C. The cooled solution was partitioned between aqueous potassium phosphate buffer solution (pH 7.0, 0.2 M, 10 mL) and dichloromethane (10 mL). The phases were separated and the aqueous phase was further extracted with dichloromethane (10 mL). The organic extracts were combined and the combined solution was dried over anhydrous sodium sulfate. The dried solution was filtered and the filtrate was concentrated. The residue, the crude product of cyclopropane ring-opening, was dissolved in acetonitrile (1.2 mL). The resulting solution was transferred to a polypropylene reaction vessel and concentrated aqueous hydrofluoric acid solution (48 wt %, 0.8 mL) was added. The reaction mixture was stirred vigorously at 23° C. for 13½ h, then was poured into water (30 mL) containing dipotassium hydrogenphosphate (8.0 g). The resulting mixture was extracted with ethyl acetate (3×40 mL). The organic extracts were combined and the combined solution was dried over anhydrous sodium sulfate. The dried solution was filtered and the filtrate was concentrated. Palladium black (5.0 mg, 0.047 mmol, 2.8 equiv) was added in one portion to a solution of the crude product in methanol (1.0 mL) and dioxane (1.0 mL) at 23° C. An atmosphere of hydrogen was introduced by briefly evacuating the flask, then flushing with pure hydrogen (1 atm). The reaction mixture was stirred at 23° C. for 3¾ h, then was filtered through a plug of CELITE® (diatomaceous earth). The filtrate was concentrated. The product was purified by preparatory HPLC on an AGILENT TECHNOLOGIES® Prep C18 column [10 μm, 250×21.2 mm, UV detection at 350 nm, Solvent A: 0.1% trifluoroacetic acid in water, Solvent B: acetonitrile, injection volume: 5.0 mL (4.0 mL 0.1% trifluoroacetic acid in water, 1.0 mL acetonitrile), gradient elution with 5→40% B over 50 min, flow rate: 7.5 mL/min]. Fractions eluting at 41-44 min were collected and concentrated, affording C5a-n-butoxymethylminocycline trifluoroacetate 24 as a yellow solid (7.3 mg, 56%, three steps). 1H NMR (600 MHz, CD3OD, trifluoroacetate) δ 7.81 (d, 1H, J=9.0 Hz), 7.04 (d, 1H, J=9.6 Hz), 4.16 (s, 1H), 3.50 (d, 1H, J=10.2 Hz), 3.38-3.30 (m, 3H), 3.21 (d, 1H, J=9.6 Hz), 3.13 (s, 6H), 3.11-3.06 (m, 1H), 2.98 (s, 6H), 2.58 (d, 1H, J=15.6 Hz), 2.42 (dd, 1H, J=13.8, 3.0 Hz), 1.71 (t, 1H, J=13.8 Hz), 1.50-1.39 (m, 2H), 1.34-1.24 (m, 2H), 0.87 (t, 3H, J=7.2 Hz); HRMS-ESI (m/z): [M+H]+ calcd for $C_{28}H_{38}N_3O_8$, 544.2653. found, 544.2655.

Example 17

Synthesis of C5a-Hydroxymethylminocycline 25

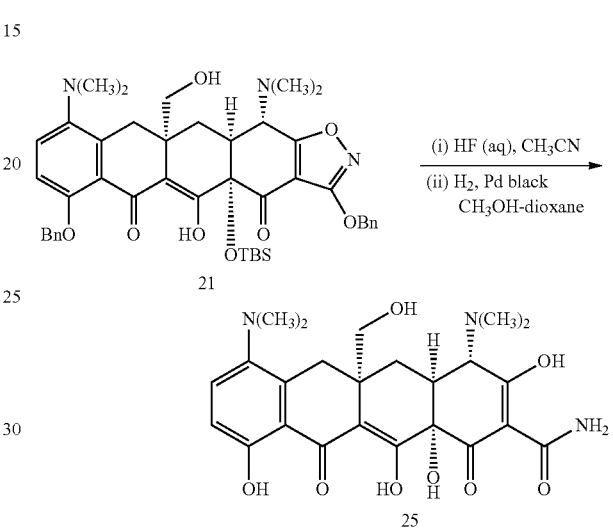

Concentrated aqueous hydrofluoric acid solution (48 wt %, 0.8 mL) was added to a solution of the alcohol 21 formed from Example 13 (10.0 mg, 0.013 mmol, 1 equiv) in acetonitrile (0.8 mL) in a polypropylene reaction vessel at 23° C. The reaction solution was stirred vigorously at 23° C. for 25 h, then was poured into water (30 mL) containing dipotassium hydrogenphosphate (8.0 g). The resulting mixture was extracted with ethyl acetate (3×40 mL). The organic extracts were combined and the combined solution was dried over anhydrous sodium sulfate. The dried solution was filtered and the filtrate was concentrated, affording an orange-yellow oil. Methanol (1.5 mL) and dioxane (1.5 mL) were added to the crude product, forming an orange-yellow solution. Palladium black (3.2 mg, 0.030 mmol, 2.3 equiv) was added in one portion at 23° C. An atmosphere of hydrogen was introduced by briefly evacuating the flask, then flushing with pure hydrogen (1 atm). The reaction mixture was stirred at 23° C. for 1½h, then was filtered through a plug of CELITE® (diatomaceous earth). The filtrate was concentrated, affording a yellow solid. The product was purified by preparatory HPLC on a PHENOMENEX POLYMERX™ DVB column [7 μm, 150×21.2 mm, UV detection at 350 nm, Solvent A: 0.05 N aq. HCl, Solvent B: acetonitrile, crude product co-injected with 10 mg oxalic acid and 500 μL methanol, gradient elution with 5→30% B over 50 min, flow rate: 6 mL/min]. Fractions eluting at 16-22 min were collected and concentrated, affording 5a-hydroxymethylminocycline hydrochloride 25 as a yellow solid (3.1 mg, 46%, two steps). 1H NMR (600 MHz, CD3OD, hydrochloride) δ 7.93 (d, 1H, J=9.6 Hz), 7.09 (d, 1H, J=9.0 Hz), 4.18 (s, 1H), 3.67 (d, 1H, J=12.0 Hz), 3.41 (d, 1H, J=15.6 Hz), 3.40-3.27 (m, 6H), 3.23 (d, 1H, J=11.4 Hz), 3.13-3.02 (m, 7H), 2.62 (d, 1H, J=15.6 Hz), 2.48 (dd, 1H, J=13.8, 2.4 Hz), 1.68 (brt, 1H, J=13.8 Hz); HRMS-ESI (m/z): [M+H]+ calcd for $C_{24}H_{30}N_3O_8$, 488.2027. found, 488.2029.

Example 18

Synthesis of C5a-Methoxymethylminocycline 27

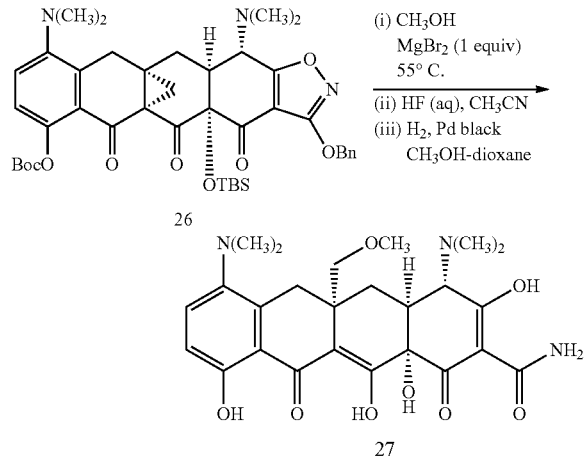

Anhydrous magnesium bromide (1.7 mg, 0.009 mmol, 1 equiv) was added to a solution of the cyclopropane 26 (7.0 mg, 0.009 mmol, 1 equiv) in methanol (1.0 mL) at 23° C. The resulting mixture was heated to 55° C. After stirring at 55° C. for 24 h, the reaction solution was allowed to cool to 23° C. The cooled solution was partitioned between aqueous potassium phosphate buffer solution (pH 7.0, 0.2 M, 10 mL) and dichloromethane (10 mL). The phases were separated and the aqueous phase was further extracted with dichloromethane (10 mL). The organic extracts were combined and the combined solution was dried over anhydrous sodium sulfate. The dried solution was filtered and the filtrate was concentrated. The residue, the crude product of cyclopropane ring-opening, was dissolved in acetonitrile (0.7 mL). The resulting solution was transferred to a polypropylene reaction vessel and concentrated aqueous hydrofluoric acid solution (48 wt %, 1.0 mL) was added. The reaction mixture was stirred vigorously at 23° C. for 22 h, then was poured into water (30 mL) containing dipotassium hydrogenphosphate (7.0 g). The resulting mixture was extracted with ethyl acetate (3×40 mL). The organic extracts were combined and the combined solution was dried over anhydrous sodium sulfate. The dried solution was filtered and the filtrate was concentrated. Palladium black (2.7 mg, 0.025 mmol, 2.8 equiv) was added in one portion to a solution of the crude product in methanol (1.0 mL) and dioxane (1.0 mL) at 23° C. An atmosphere of hydrogen was introduced by briefly evacuating the flask, then flushing with pure hydrogen (1 atm). The reaction mixture was stirred at 23° C. for 10 min, then was filtered through a plug of CELITE® (diatomaceous earth). The filtrate was concentrated, providing a yellow-brown oil. The product was purified by preparatory HPLC on a a PHENOMENEX POLYMERX™ DVB column [7 μm, 150×21.2 mm, UV detection at 350 nm, Solvent A: 0.05 N aq. HCl, Solvent B: acetonitrile, crude product co-injected with 10 mg oxalic acid and 500 μL methanol, gradient elution with 5→30% B over 50 min, flow rate: 6 mL/min]. Fractions eluting at 21-25 min were collected and concentrated, affording C5a-methoxymethylminocycline hydrochloride 27 as a yellow solid (2.5 mg, 52%, three steps). $^1$H NMR (600 MHz, CD$_3$OD, hydrochloride) δ 7.90 (d, 1H, J=9.0 Hz), 7.09 (d, 1H, J=9.6 Hz), 4.18 (s, 1H), 3.51 (d, 1H, J=10.2 Hz), 3.36-3.21 (m, 7H), 3.26 (s, 3H), 3.13 (d, 1H, J=9.6 Hz), 3.06 (brd, 1H, J=13.2 Hz), 3.02 (brs, 3H), 2.98 (brs, 3H), 2.63 (brd, 1H, J=17.4 Hz), 2.44 (dd, 1H, J=14.4, 3.0 Hz), 1.71 (t, 1H, J=14.4 Hz).

Example 19

Synthesis of 5-Dimethylphenylcyclopentadiene

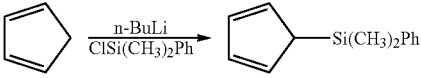

The following experimental procedure was based on literature precedent (Landais, Y.; Rapadp, P. *Eur. J. Org. Chem.* 2000, 401-418). n-Butyllithium (2.5 M solution in hexane, 230 mL, 576 mmol, 1 equiv) was added dropwise by cannula over 20 min to a dry ice-acetone cooled solution of freshly cracked cyclopentadiene (38.1 g, 576 mmol, 1 equiv) in tetrahydrofuran (576 mL). The resulting white slurry was stirred for 45 min, whereupon dimethylphenylchlorosilane (98.3 g, 576 mmol, 1 equiv) was added dropwise by cannula over 20 min. After 1.5 h, saturated aqueous ammonium chloride solution (100 mL) and water (100 mL) were added sequentially. The dry ice-acetone cooling bath was replaced with a 23° C. water bath and the mixture was stirred for 20 min. The product solution was transferred to a four liter separation funnel containing water (400 mL) and diethyl ether (400 mL). The layers were separated. The aqueous layer was extracted with diethyl ether (200 mL). The organic layers were combined and the combined solution was washed with saturated aqueous sodium chloride solution (200 mL). The washed solution was dried over sodium sulfate. The dried solution was filtered and the filtrate was concentrated first by rotary evaporation (23° C., 40 mmHg) for 45 min then on a high vacuum manifold (23° C., 0.1 mmHg) for 2 h to provide 5-dimethylphenylcyclopentadiene as a pale-yellow liquid (116 g, 101%) which was stored as a off-white solid in a −80° C. fridge. No further purification was conducted.

Example 20

Synthesis of Meso-Diol 28

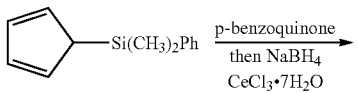

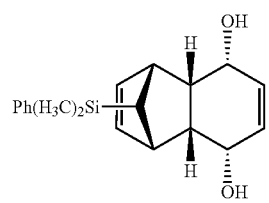

5-Diemthylphenylcyclopentadiene was removed from an −80° C. fridge and allowed to warm to 23° C. (see Example 19). An ice-water cooled solution of 5-dimethylphenylcyclopentadiene (~124 g, 586 mmol, 1 equiv) in methanol-dichloromethane (2:1, 200 mL) was added dropwise by cannula over 30 min to an ice-water cooled solution of p-benzoquinone (recrystallized from hot ethanol, 63.3 g, 586 mmol, 1 equiv) in methanol-dichloromethane (2:1, 1200 mL). The resulting dark amber solution was stirred for 12 h while maintaining the internal temperature of the reaction <5° C., whereupon cerium trichloride heptahydrate (109 g, 293 mmol, 0.5 equiv) was added in 25 g portions over 10 min. The resulting slurry was stirred for 15 min. Sodium borohydride (22.2 g, 586 mmol, 1 equiv) was added in 1 g portions over 45 min. After 10 min the product mixture was concentrated to half-volume by rotary evaporation (27° C., 40 mmHg). Ethyl acetate (500 mL) was added and the solution filtered through a 1 inch pad of silica gel rinsing with ethyl acetate (1 L). Aqueous citric acid solution (1M, 250 mL) was added to the filtrate with stirring. After 15 min the biphasic mixture was transferred to a 6-L separation funnel containing aqueous citric acid solution (750 mL) and ethyl acetate (1 L). The layers were separated. The organic layer was washed sequentially with water (2×500 mL), 1 M aqueous sodium carbonate solution containing 10% by volume 1 M aqueous sodium sulfite solution (3×500 mL), then saturated aqueous sodium chloride solution (500 mL). The washed solution was dried over sodium sulfate. The dried solution was filtered and the filtrate was concentrated to provide a light yellow solid (158 g). The crude solid was dissolved in boiling dichloromethane (350 mL) then hot (60° C.) hexanes (900 mL) was added slowly over 10 min with stirring. The solution was allowed to slowly cool to 23° C. during which time a white crystalline solid formed. The mixture was further cooled in a ice-water bath for 1 h. The mixture was filtered and the filter cake washed with ice-water cooled hexanes to provide the meso-diol 28 as a white crystalline solid (129 g, 70%). $^1$H NMR (600 MHz, CDCl$_3$) δ: 7.45-7.43 (m, 2H), 7.33-7.31 (m, 3H), 5.82 (s, 2H), 5.55 (s, 2H), 4.41-4.39 (m, 2H), 3.11 (s, 2H), 2.79-2.78 (m, 2H), 1.63 (d, 2H, J=5.6 Hz), 1.23 (s, 1H), 0.21 (s, 6H); $^{13}$C NMR (125 MHz, CDCl$_3$) δ: 140.2, 135.0, 133.5, 131.9, 128.5, 127.6, 66.7, 51.7, 47.8, 45.2, −1.3; FTIR (neat), cm$^{-1}$: 3383 (br), 2967 (w), 2911 (w).

Example 21

Synthesis of Mono-Acetate 29

A 5-liter, 3-neck round bottom flask equipped with an overhead mechanical stirrer, a nitrogen-inlet, and a rubber septum was charged with meso-diol 28 (150 g, 480 mmol, 1 equiv) and triethylamine (1.6 L). The mixture was stirred resulting in a light-brown homogeneous solution. Isopropenyl acetate (168 g, 1680 mmol, 3.5 equiv) was added, then the lipase (Amano "PS" IM, 150 g). The resulting slurry was stirred for 20 h at 23° C. and then filtered through a sintered-glass funnel, rinsing with ethyl acetate (1 L). The filtrate was concentrated to afford a dark brown liquid which was dissolved in ethyl acetate (1.5 L) and transferred to a 4 L separation funnel. The organic product solution was wash sequentially with saturated aqueous ammonium chloride solution (800 mL), saturated aqueous sodium bicarbonate solution (800 mL), and saturated aqueous sodium chloride solution (800 mL). The washed solution was dried over sodium sulfate. The dried solution was filtered and the filtrate was concentrated to provide an off-white solid (161 g, 95%). The product was dissolved with ethyl acetate (1.2 L) and charcoal (32 g, DARCO® G-60) was added. The resulting black heterogeneous mixture was stirred at 50° C. for 60 min and then cooled to 23° C. The mixture was filtered through a 2 in pad of CELITE® (diatomaceous earth) rinsing with ethyl acetate. The filtrate was concentrated to a white soild (159 g, 94%) to yield mono-Acetate 29. $^1$H NMR (600 MHz, CDCl$_3$) δ: 7.44-7.42 (m, 2H), 7.33-7.31 (m, 3H), 5.76 (dd, 1H, J=2.8, 5.4 Hz), 5.69 (dd, 1H, J=2.8, 5.4 Hz), 5.43-5.40 (m, 1H), 5.38-5.35 (m, 1H), 5.27-5.24 (m, 1H), 4.78-4.44 (m, 1H), 3.14 (s, 1H), 3.03-2.99 (m, 1H), 2.91 (s, 1H), 2.87-2.84 (m, 1H), 2.11 (s, 3H), 1.52 (d, 1H, J=6.1 Hz), 1.17 (s, 1H), 0.19 (s, 3H), 0.18 (s, 3H); $^{13}$C NMR (125 MHz, CDCl$_3$) δ: 170.7, 140.1, 135.3, 135.1, 133.5, 131.8, 128.5, 127.6, 126.7, 70.1, 66.7, 50.4, 48.5, 47.8, 44.0, 40.8, 21.1, −1.3, −1.4; FTIR (neat), cm$^{-1}$: 3455 (br), 3067 (w), 2967 (w), 1738 (s), 1371 (s), 1246 (s); HRMS (ESI): Calcd for $(C_{21}H_{26}O_3Si+Na)^+$ 377.1543. found 377.1544.

Example 22

Synthesis of Enone 30

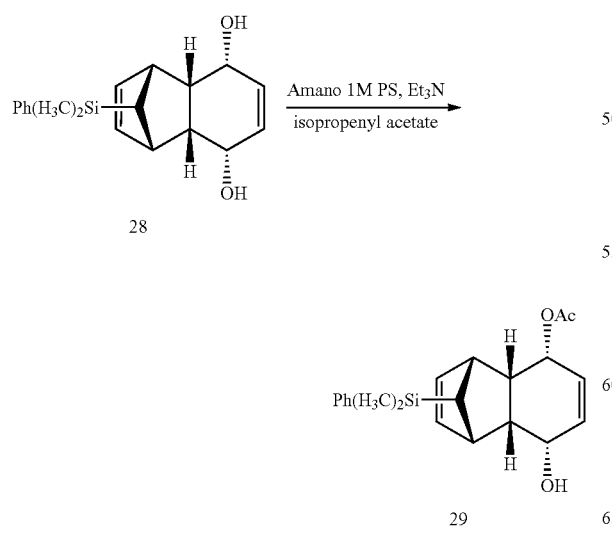

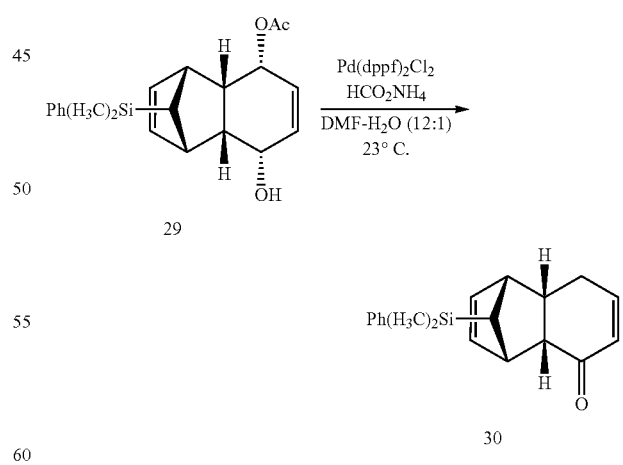

Ammonium formate (48 g, 0.760 mmol, 1.5 equiv) was added in one portion to a stirring solution of mono-acetate 29 (180 g, 0.510 mmol, 1 equiv) in dimethylformamide (1.3 L) and water (100 mL) at 23° C. The resulting solution was degassed by bubbling argon gas for 40 min, whereupon Pd(dppf)$_2$Cl$_2$ (16.9 g, 0.020 mmol, 0.04 equiv) was added in one portion. The resulting reaction mixture was stirred at 23° C. for 16 h. The reaction was cooled to −20° C., then methyl tert-butyl ether (500 mL), water (250 mL), and charcoal (36 g, DARCO® G-60) was added. The resulting slurry was stirred at −10° C. for 1 h. The product mixture was filtered through a 2-L sintered glass funnel containing CELITE® (diatomaceous earth), rinsing with methyl tert-butyl ether. Water (500 mL) was added to the filtrate and the layers were separated. The organic layer was washed with saturated aqueous sodium chloride solution (4×300 mL), saturated aqueous sodium bicarbonate solution (2×300 mL), and water (300 mL). The washed solution was dried over magnesium sulfate and the dried solution was filtered. The filtered solution was concentrated to provide a brown solid (135 g). The solid was dissolved in methyl tert-butyl ether (1 L) then MP-TMT resin (73 g, BIOTAGE®) was added. The resulting slurry was stirred at 23° C. for 16 h then filtered through a sintered glass funnel rinsing with methyl tert-butyl ether. The filtrate was concentrated to provide enone 30 as an orange solid (124 g, 82%) which was used in the next step (Example 23) without any further purification. $^1$H NMR (500 MHz, CDCl$_3$) δ: 7.44-7.42 (m, 2H), 7.34-7.32 (m, 3H), 6.63 (ddd, 1H, J=4.1, 4.1, 10.3 Hz), 6.03 (dd, 1H, J=2.8, 5.6 Hz), 5.98 (dd, 1H, J=2.9, 5.7 Hz), 5.84 (ddd, 1H, J=2.3, 2.3, 10.3 Hz), 3.50-3.48 (m, 1H), 3.09-3.07 (m, 1H), 2.92 (dd, 1H, J=4.0, 9.8 Hz), 2.74 (dddd, 1H, J=3.5, 3.5, 10.3, 10.3), 2.55 (dddd, 1H, J=2.6, 3.8, 10.5, 20.9 Hz), 2.01-1.96 (m, 1H), 1.21 (s, 1H), 0.21 (s, 3H), 0.20 (s, 3H); $^{13}$C NMR (125 MHz, CDCl$_3$) δ: 200.8, 149.6, 139.9, 137.5, 134.5, 133.8, 129.4, 129.0, 128.0, 52.3, 51.9, 51.4, 50.8, 36.5, 27.7, −1.22, −1.23.

Example 23

Synthesis of Michael-Claisen Cyclization Product 33

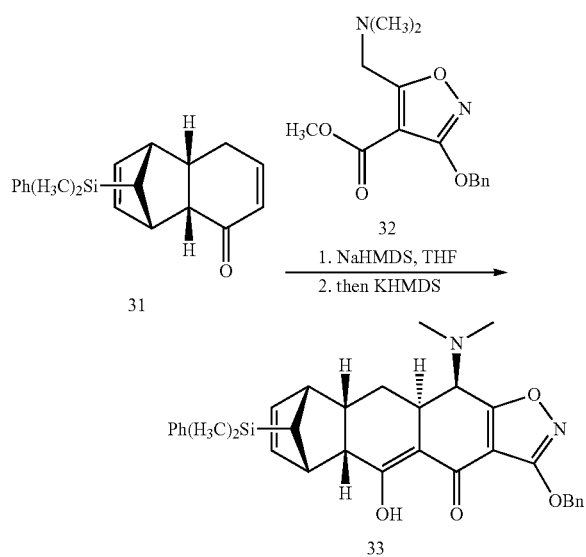

A 5-liter, 3-neck, round-bottom flask equipped with an overhead mechanical stirrer, an argon inlet, and a rubber septum was charged with a solution of methyl ester 32 (134 g, 462 mmol, 1.1 equiv) in tetrahydrofuran (1.2 L). The resulting yellow solution was cooled to −50° C. in a dry ice-acetone bath, whereupon a solution of NaHMDS (93.2 g, 483 mmol, 1.15 equiv) in tetrahydrofuran (500 mL) was added dropwise by cannula over 30 min. The resulting mixture was stirred at −50° C. for 1 h during which time a fine off-white suspension was observed. A solution of enone 31 (124 g, 421 mmol, 1 equiv) in tetrahydrofuran (200 mL) was added dropwise by cannula over 40 min and the resulting mixture stirred for 1 h at −50° C., whereupon a solution of KHMDS (88 g, 421 mmol, 1 equiv) in tetrahydrofuran (420 mL) was added dropwise by cannula over 30 min. The resulting solution was warmed to −20° C. over the course of 1 h then held at this temperature for 2 h. The reaction mixture was warmed to −10° C. over 20 min and held at this temperature for 2 h, and then water (300 mL) was added and the cooling bath was removed. The tetrahydrofuran was removed by rotary evaporation then ethyl acetate (1 L) and water (500 mL) was added. The biphasic mixture was separated and the aqueous layer was extracted with ethyl acetate (2×500 mL). The organic layers were combined and the combined solution was dried over magnesium sulfate. The dried solution was filtered and the filtrate was concentrated to afford a brown foam. The residue was dissolved with methyl tert-butyl ether (1.2 L) and transferred to a 3-liter, 3-neck, round-bottom flask equipped with an overhead mechanical stirrer. The solution was cooled in an ice-water bath then a solution of hydrochloric acid in ether (2 N, 260 mL, 520 mmol, 1.24 equiv) was added dropwise by syringe over 30 min. The resulting slurry was stirred for 1 h then filtered. The filter cake was washed with methyl tert-butyl ether (2×500 mL) and ethyl ether (500 mL) then dried on a high vacuum manifold (0.1 mmHg) at 23° C. to provide the hydrochloride salt of 33 (250 g) as an orange solid. This solid was separated into two equal portions (~125 g each) and each portion was dissolved in dichloromethane (700 mL). Ethyl acetate (400 mL) was added to each portion. An off-white solid began to crash out of each solution. The slurry was concentrated to a volume of 800 mL on a rotary evaporator then filtered through a sintered glass funnel. The filter cake was rinsed with ethyl acetate (2×400 mL) and the two filter cakes were combined and dried on a high vacuum manifold (0.1 mmHg, 23° C.) to afford the hydrochloride salt of 33 as an off-white solid (155 g).

The mother liquor from above was concentrated and then dissolved with dichloromethane (800 mL). This solution was washed with a 1 M aqueous dipotassium hydrogen phosphate solution (2×400 mL) and then a saturated aqueous sodium chloride solution (400 mL). The washed solution was dried over magnesium sulfate. The dried solution was filtered and the filtrate was concentrated to provide a brown oil (85 g). This oil was dissolved with dichloromethane (75 mL) then filtered through a pad of neutral alumina rinsing with 20% ethyl acetate-hexanes. The filtrate was concentrated to afford an orange oil (25 g) which was dissolved in ethyl ether (226 mL) then cooled in an ice-water bath. A 2 N solution of hydrochloric acid in ethyl ether (23 mL) was added. The resulting slurry was stirred for 30 min then filtered through a sintered glass funnel. The filter cake was rinsed with ethyl ether then dried on a high vacuum manifold to afford an off-white solid. This solid was dissolved in dichloromethane (200 mL) and ethyl acetate (150 mL), and this solution was concentrated to a volume of 150 mL at which point an off-white solid began to crash out. This slurry was filtered through a sintered glass funnel and the filter cake was rinsed with ethyl acetate, and then dried on a high vacuum manifold to provide the hydrochloride salt of 33 as an off-white solid (10 g). Total weight=155 g+10 g=165 g. This solid was recrystallized from dichloromethane-ethyl acetate and washed with 1 M aqueous dipotassium hydrogen phosphate solution to provide 33 (146 g, 62%) as a white foam. $^1$H NMR (500 MHz, CDCl$_3$) δ: 15.1 (s, 1H), 7.52-7.50 (m, 2H), 7.47-7.28 (m, 8H), 5.92 (t, 2H, J=1.4 Hz), 5.37 (s, 2H), 3.59 (d, 1H, J=6.8 Hz), 3.32 (s, 1H), 2.98 (s, 1H), 2.91-2.88 (m, 1H), 2.76-2.69 (m, 2H), 2.17-2.08 (m, 1H), 2.13 (s, 6H), 1.78 (dd, 1H, J=4.8, 15.1 Hz), 1.35 (s, 1H), 0.20 (s, 3H), 0.19 (s, 3H); $^{13}$C NMR (125 MHz, CDCl$_3$) δ: 184.2, 181.0, 168.0, 139.9, 135.6, 135.5, 133.8, 129.0, 128.8, 128.7, 127.9, 108.3, 105.7, 72.6, 58.6, 53.8, 52.8, 50.1, 45.4, 40.4, 34.6, 26.7, −1.24.

Example 24

Synthesis of C5a-Methylminocycline 37

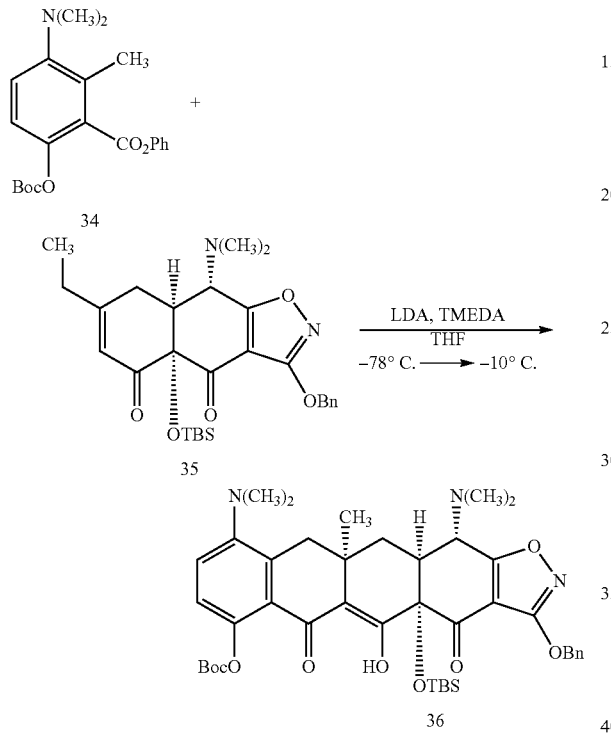

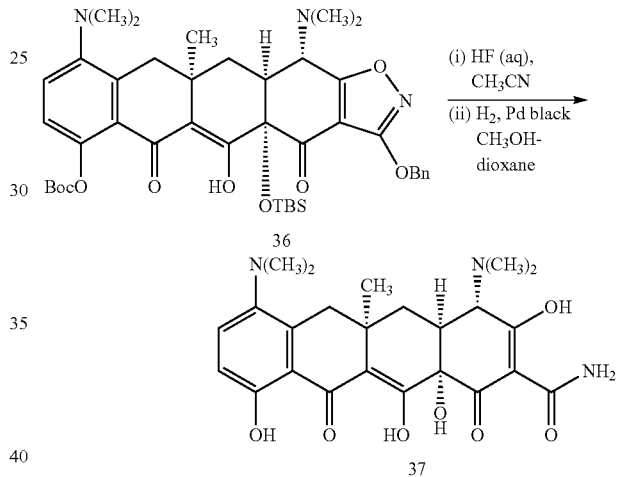

Cyclization Step.

A freshly prepared solution of lithium diisopropylamide in tetrahydrofuran (1.0 M, 121 μL, 0.121 mmol, 3.0 equiv) was added dropwise via syringe to a solution of phenyl ester 34 (45 mg, 0.121 mmol, 3.0 equiv) and TMEDA (36 μL, 0.240 mmol, 6.0 equiv) in tetrahydrofuran (2.0 mL) at −78° C., forming a bright red solution. After stirring at −78° C. for 40 min, a solution of the AB enone 35 (20.0 mg, 0.040 mmol, 1 equiv) in tetrahydrofuran (1.5 ml) was added dropwise via syringe to the reaction solution. The resulting mixture was allowed to warm slowly to −10° C. over 80 min, then was partitioned between aqueous potassium phosphate buffer solution (pH 7.0, 0.2 M, 5 mL) and dichloromethane (10 mL). The phases were separated and the aqueous phase was further extracted with dichloromethane (2×10 mL). The organic extracts were combined and the combined solution was dried over anhydrous sodium sulfate. The dried solution was filtered and the filtrate was concentrated, affording a yellow oil. The product was purified by preparatory HPLC on a Coulter Ultrasphere ODS column [5 μM, 10 mm×25 cm, UV detection at 350 nm, Solvent A: water, Solvent B: methanol, injection volume: 500 μL (methanol), gradient elution 85→100% B over 60 min, flow rate 3.5 mL/min]. Fractions eluting at 40-48 min were collected and concentrated, affording the Michael-Claisen cyclization product 36 as a yellow oil (21.5 mg, 69%).

R$_f$=0.28 (20% ethyl acetate-hexanes); $^1$H NMR (600 MHz, CDCl$_3$) δ 15.96 (s, 1H, enol-OH), 7.49 (d, 2H, J=7.8 Hz, OCH$_2$ArH), 7.39-7.33 (m, 3H, OCH$_2$ArH), 7.26-7.24 (m, 1H, ArH), 7.04 (d, 1H, J=8.5 Hz, ArH), 5.36 (s, 2H, OCH$_2$Ph), 4.16 (d, 1H, J=10.0 Hz, CHN(CH$_3$)$_2$), 3.20 (d, 1H, J=16.1 Hz, CHH'C=CN(CH$_3$)$_2$), 2.75 (d, 1H, J=16.1 Hz, CHH'C=CN (CH$_3$)$_2$), 2.66 (s, 6H, ArC-N(CH$_3$)$_2$), 2.54-2.50 (m, 7H, CHN (CH$_3$)$_2$, CHCHN(CH$_3$)$_2$), 2.37 (d, 1H, J=14.4 Hz, CHH'CHCHN(CH$_3$)$_2$), 2.16 (d, 1H, J=14.8, 4.5 Hz, CHH'CHCHN(CH$_3$)$_2$), 1.56 (s, 9H, O—C(CH$_3$)$_3$), 1.12 (s, 3H, CH$_3$), 0.90 (s, 9H, Si—C(CH$_3$)$_3$), 0.25 (s, 3H, Si—CH$_3$), 0.21 (s, 3H, Si—CH$_3$); $^{13}$C NMR (125 MHz, CDCl$_3$) δ 186.8, 185.6, 181.7, 178.3, 167.6, 152.3, 150.4, 145.4, 136.4, 135.1, 128.5, 128.4, 128.3, 124.2, 123.9, 122.3, 112.0, 108.1, 83.8, 81.7, 72.4, 60.7, 47.0, 44.2, 41.9, 40.6, 32.4, 32.1, 29.8, 27.7, 26.4, 19.2, −1.9, −2.3; FTIR (neat film), cm$^{-1}$ 2959, 2936, 1759, 1721, 1613, 1510, 1474, 1456, 1370, 1310, 1285, 1265, 1236, 1152, 831, 737, 704; UV max (0.01 M methanolic HCl), nm 245, 275, 315; HRMS-ESI (P/z): [M+H]$^+$ calcd for C$_{42}$H$_{55}$N$_3$O$_9$Si, 774.3780. found, 774.3796.

Deprotection Steps.

Concentrated aqueous hydrofluoric acid solution (48 wt %, 0.8 mL) was added to a solution of the HPLC-purified product 36 from the cyclization step above (10.0 mg, 0.013 mmol, 1 equiv) in acetonitrile (0.8 mL) in a polypropylene reaction vessel at 23° C. The reaction solution was stirred vigorously at 23° C. for 23 h, then was poured into water (30 mL) containing dipotassium hydrogenphosphate (8.0 g). The resulting mixture was extracted with ethyl acetate (3×40 mL). The organic extracts were combined and the combined solution was dried over anhydrous sodium sulfate. The dried solution was filtered and the filtrate was concentrated, affording an orange-yellow oil. Methanol (1.5 mL) and dioxane (1.5 mL) were added to the crude product, forming an orange-yellow solution. Palladium black (3.2 mg, 0.030 mmol, 2.3 equiv) was added in one portion at 23° C. An atmosphere of hydrogen was introduced by briefly evacuating the flask, then flushing with pure hydrogen (1 atm). The reaction mixture was stirred at 23° C. for 5 min, then was filtered through a plug of CELITE® (diatomaceous earth). The filtrate was concentrated, affording a yellow solid. The product was purified by preparatory HPLC on a PHENOMENEX POLYMERX™ DVB column [7 μm, 150×21.2 mm, UV detection at 350 nm, Solvent A: 0.05 N aq. HCl, Solvent B: acetonitrile, crude product co-injected with 10 mg oxalic acid and 500 μL methanol, gradient elution with 5→30% B over 50 min, flow rate: 6 mL/min]. Fractions eluting at 19-26 min were collected and concentrated, affording 5a-methylminocycline 37 as a yellow solid (3.1 mg, 51%, two steps). $^1$H NMR (600 MHz, CD$_3$OD, hydrochloride) δ 7.94 (d, 1H, J=9.6 Hz), 7.10 (d, 1H, J=9.6 Hz), 4.18 (s, 1H), 3.35-3.22 (m, 6H), 3.09-3.00 (m, 2H), 3.06 (s, 3H), 3.01 (s, 3H), 2.83 (d, 1H, J=15.0 Hz), 2.13 (dd, 1H, J=13.8, 3.0 Hz), 1.95 (brt, 1H, J=13.8 Hz), 1.31 (s, 3H); HRMS-ESI (m/z): [M+H]$^+$ calcd for C$_{24}$H$_{29}$N$_3$O$_7$, 472.2078. found, 472.2087.

Example 25

Synthesis of C5a-Morpholinomethylminocycline 38

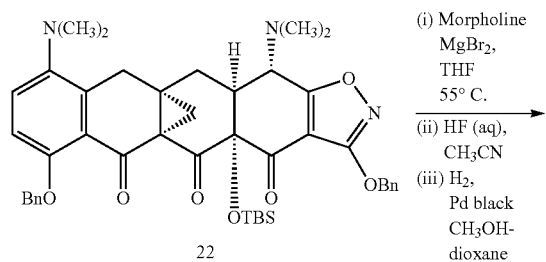

Anhydrous magnesium bromide (6.3 mg, 0.034 mmol, 2.0 equiv) was added to a solution of cyclopropane 22 (13.0 mg, 0.017 mmol, 1 equiv) and morpholine (15 μL, 0.17 mmol, 10 equiv) in tetrahydrofuran (0.5 mL) at 23° C. The reaction flask was sealed and the mixture was heated to 55° C. After stirring at 55° C. for 14 h, the reaction mixture was allowed to cool to 23° C. The cooled solution was diluted with dichloromethane (10 mL) and saturated aqueous sodium bicarbonate solution (10 mL) was added. The phases were separated and the aqueous phase was further extracted with dichloromethane (10 mL). The organic extracts were combined and the combined solution was dried over anhydrous sodium sulfate. The dried solution was filtered and the filtrate was concentrated. The residue, the crude product of cyclopropane ring-opening, was dissolved in acetonitrile (1.2 mL). The resulting solution was transferred to a polypropylene reaction vessel and concentrated aqueous hydrofluoric acid solution (48 wt %, 0.8 mL) was added. The reaction mixture was stirred vigorously at 23° C. for 16½ h, then was poured into water (30 mL) containing dipotassium hydrogenphosphate (8.0 g). The resulting mixture was extracted with ethyl acetate (3×40 mL). The organic extracts were combined and the combined solution was dried over anhydrous sodium sulfate. The dried solution was filtered and the filtrate was concentrated. Palladium black (5.0 mg, 0.047 mmol, 2.8 equiv) was added in one portion to a solution of the crude product in methanol (1.0 mL) and dioxane (1.0 mL) at 23° C. An atmosphere of hydrogen was introduced by briefly evacuating the flask, then flushing with pure hydrogen (1 atm). The reaction mixture was stirred at 23° C. for 1¾ h, then was filtered through a plug of CELITE® (diatomaceous earth). The filtrate was concentrated. The product was purified by preparatory HPLC on an AGILENT TECHNOLOGIES® Prep C18 column [10 μm, 250×21.2 mm, UV detection at 350 nm, Solvent A: 0.1% trifluoroacetic acid in water, Solvent B: acetonitrile, injection volume: 5.0 mL (4.0 mL 0.1% trifluoroacetic acid in water, 1.0 mL acetonitrile), gradient elution with 5→25% B over 50 min, then 25→100% B over 20 min, flow rate: 7.5 mL/min]. Fractions eluting at 49-52 min were collected and concentrated, affording C5a-morpholinomethylminocycline trifluoroacetate 38 as an orange-yellow solid (7.5 mg, 66%, three steps). $^1$H NMR (600 MHz, CD$_3$OD, trifluoroacetate) δ 7.56 (d, 1H, J=9.0 Hz), 6.95 (d, 1H, J=9.0 Hz), 4.04 (s, 1H), 3.77-3.69 (m, 4H), 3.53 (d, 1H, J=16.8 Hz), 3.24 (brd, 1H, J=13.2 Hz), 3.18-3.14 (m, 1H), 3.08 (s, 6H), 2.99-2.94 (m, 2H), 2.88 (brd, 1H, J=15.0 Hz), 2.81-2.72 (m, 2H), 2.74 (s, 6H), 2.62 (d, 1H, J=16.8 Hz), 2.53 (brd, 1H, J=14.4 Hz), 1.92 (t, 1H, J=14.4 Hz); HRMS-ESI (m/z): [M+H]$^+$ calcd for C$_{28}$H$_{37}$N$_4$O$_8$, 557.2606. found, 557.2611.

Example 26

Synthesis of C5a-piperazinylmethylminocycline 39

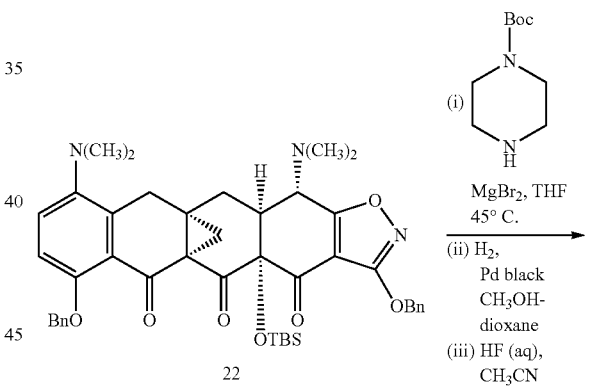

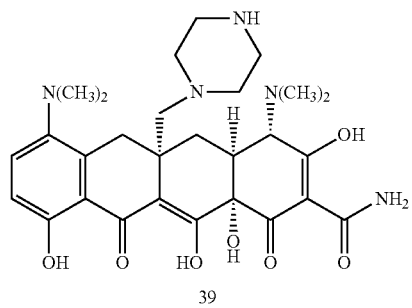

Anhydrous magnesium bromide (51.0 mg, 0.276 mmol, 2.0 equiv) was added to a solution of cyclopropane 22 (105 mg, 0.138 mmol, 1 equiv) and tert-butyl 1-piperazine carboxylate (186 mg, 1.00 mmol, 7.2 equiv) in tetrahydrofuran (2.0 mL) at 23° C. The reaction flask was sealed and the mixture was heated to 45° C. After stirring at 45° C. for 36 h, the reaction mixture was allowed to cool to 23° C. The cooled solution was diluted with dichloromethane (25 mL) and saturated aqueous sodium bicarbonate solution (25 mL) was added. The phases were separated and the aqueous phase was further extracted with dichloromethane (25 mL). The organic extracts were combined and the combined solution was dried over anhydrous sodium sulfate. The dried solution was filtered and the filtrate was concentrated. The product mixture was filtered through a short pad of silica gel (eluting with 40% ethyl acetate-hexanes) and the filtrate was concentrated, affording an orange-yellow oil. Methanol (2.5 mL) and dioxane (2.5 mL) were added to the crude product of cyclopropane ring-opening, forming an orange-yellow solution. Palladium black (25 mg, 0.235 mmol, 1.7 equiv) was added in one portion at 23° C. An atmosphere of hydrogen was introduced by briefly evacuating the flask, then flushing with pure hydrogen (1 atm). The reaction mixture was stirred at 23° C. for 2 h, then was filtered through a plug of CELITE® (diatomaceous earth). The filtrate was concentrated, providing an orange solid. Concentrated aqueous hydrofluoric acid (48 wt %, 1.5 mL) was added to a solution of the crude product in acetonitrile (2.0 mL) in a polypropylene reaction vessel at 23° C. The reaction mixture was stirred vigorously at 23° C. for 14 h. Excess hydrofluoric acid was quenched by the careful addition of methoxytrimethylsilane (10.0 mL). The resulting mixture was concentrated. The product was purified by preparatory HPLC on an AGILENT TECHNOLOGIES® Prep C18 column [10 μm, 250×21.2 mm, UV detection at 350 nm, Solvent A: 0.1% trifluoroacetic acid in water, Solvent B: acetonitrile, 2 batches, injection volume (for each batch): 5.0 mL (4.0 mL 0.1% trifluoroacetic acid in water, 1.0 mL acetonitrile), gradient elution with 5→35% B over 50 min, flow rate: 7.5 mL/min]. Fractions eluting at 22-29 min were collected and concentrated, affording C5a-piperazinylmethylminocycline trifluoroacetate 39 as a yellow solid (63 mg, 68%, three steps).

$^{1}$H NMR (600 MHz, CD$_3$OD, trifluoroacetate) δ 7.58 (d, 1H, J=9.6 Hz), 6.93 (d, 1H, J=9.0 Hz), 4.06 (s, 1H), 3.44 (d, 1H, J=16.2 Hz), 3.11 (brd, 1H, J=12.6 Hz), 3.08-3.02 (m, 2H), 3.05 (s, 6H), 3.01-2.95 (m, 2H), 2.82 (s, 6H), 2.61-2.56 (m, 3H), 2.50 (d, 1H, J=16.2 Hz), 2.48-2.42 (m, 3H), 2.20 (dd, 1H, J=13.8, 3.0 Hz), 1.74 (t, 1H, J=13.8 Hz); HRMS-ESI (m/z): [M+H]$^{+}$ calcd for C$_{28}$H$_{38}$N$_{5}$O$_{7}$, 556.2766. found, 556.2771.

Example 27

Synthesis of C5a-Pyrrolidinomethylminocycline 40

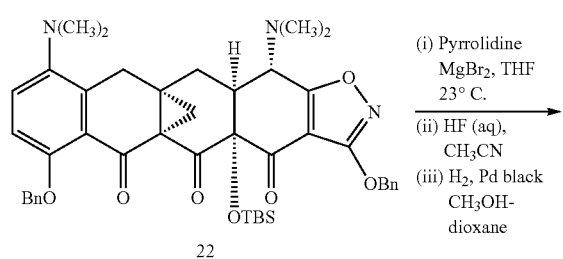

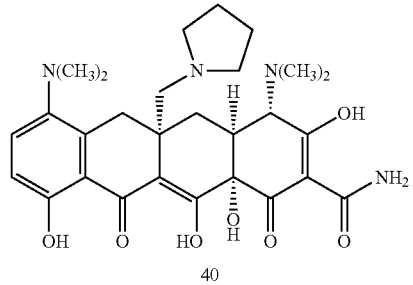

Anhydrous magnesium bromide (8.2 mg, 0.045 mmol, 2.0 equiv) was added to a solution of cyclopropane 22 (17.0 mg, 0.022 mmol, 1 equiv) and pyrrolidine (18 μL, 0.223 mmol, 10 equiv) in tetrahydrofuran (0.5 mL) at 23° C. The reaction solution was stirred at 23° C. for 16 h, then was partitioned between dichloromethane (10 mL) and saturated aqueous sodium bicarbonate solution (10 mL). The phases were separated and the aqueous phase was further extracted with dichloromethane (10 mL). The organic extracts were combined and the combined solution was dried over anhydrous sodium sulfate. The dried solution was filtered and the filtrate was concentrated. The residue, the crude product of cyclopropane ring-opening, was dissolved in acetonitrile (1.2 mL). The resulting solution was transferred to a polypropylene reaction vessel and concentrated aqueous hydrofluoric acid solution (48 wt %, 0.8 mL) was added. The reaction mixture was stirred vigorously at 23° C. for 20 h, then was poured into water (30 mL) containing dipotassium hydrogenphosphate (8.0 g). The resulting mixture was extracted with ethyl acetate (3×40 mL). The organic extracts were combined and the combined solution was dried over anhydrous sodium sulfate. The dried solution was filtered and the filtrate was concentrated. Palladium black (5.0 mg, 0.047 mmol, 2.1 equiv) was added in one portion to a solution of the crude product in methanol (1.0 mL) and dioxane (1.0 mL) at 23° C. An atmosphere of hydrogen was introduced by briefly evacuating the flask, then flushing with pure hydrogen (1 atm). The reaction mixture was stirred at 23° C. for 1¼ h, then was filtered through a plug of CELITE® (diatomaceous earth). The filtrate was concentrated. The product was purified by preparatory HPLC on an AGILENT TECHNOLOGIES® Prep C18 column [10 μm, 250×21.2 mm, UV detection at 350 nm, Solvent A: 0.1% trifluoroacetic acid in water, Solvent B: acetonitrile, injection volume: 5.0 mL (4.0 mL 0.1% trifluoroacetic acid in water, 1.0 mL acetonitrile), gradient elution with 5→35% B over 50 min, then 25→100% B over 20 min, flow rate: 7.5 mL/min]. Fractions eluting at 39-43 min were collected and concentrated, affording C5a-pyrrolidinomethylminocycline trifluoroacetate 40 as a yellow solid (12.5 mg, 86%, three steps). $^{1}$H NMR (600 MHz, CD$_3$OD, trifluoroacetate) δ 7.55 (d, 1H, J=9.0 Hz), 6.95 (d, 1H, J=9.0 Hz), 4.05 (s, 1H), 3.84 (brs, 1H), 3.73 (d, 2H, J=14.4 Hz), 3.62 (d, 1H, J=16.8 Hz), 3.20 (d, 1H, J=13.2 Hz), 3.14 (d, 1H, J=15.0 Hz), 3.13-3.03 (m, 1H), 3.10 (s, 6H), 2.70 (s, 6H), 2.67 (d, 1H, J=16.8 Hz), 2.59 (dd, 1H, J=15.0, 3.0 Hz), 2.50 (brs, 1H), 2.02-1.90 (m, 5H); HRMS-ESI (m/z): [M+H]$^{+}$ calcd for C$_{28}$H$_{37}$N$_{4}$O$_{7}$, 541.2657. found, 541.2684.

Example 28

Synthesis of C5a-Piperidinylmethylminocycline 41

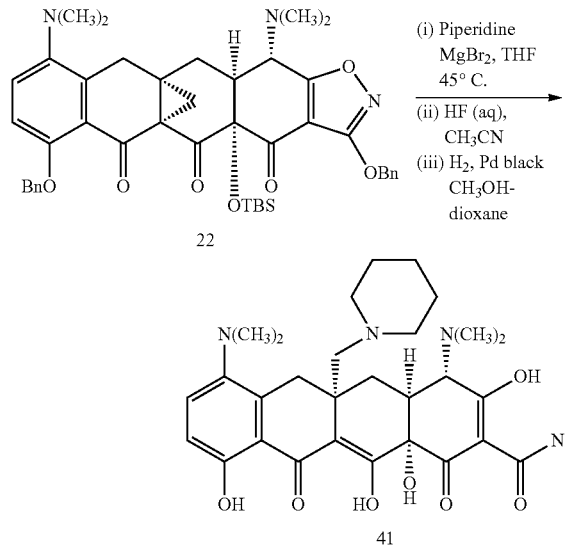

Anhydrous magnesium bromide (8.2 mg, 0.045 mmol, 2.0 equiv) was added to a solution of cyclopropane 22 (17.0 mg, 0.022 mmol, 1 equiv) and piperidine (22 µL, 0.223 mmol, 10 equiv) in tetrahydrofuran (0.5 mL) at 23° C. The reaction solution was stirred at 23° C. for 21 h, then was heated to 45° C. After stirring at this temperature for 14 h, the reaction mixture was allowed to cool to 23° C. The cooled solution was partitioned between dichloromethane (15 mL) and saturated aqueous sodium bicarbonate solution (10 mL). The phases were separated and the aqueous phase was further extracted with dichloromethane (10 mL). The organic extracts were combined and the combined solution was dried over anhydrous sodium sulfate. The dried solution was filtered and the filtrate was concentrated. The residue, the crude product of cyclopropane ring-opening, was dissolved in acetonitrile (1.2 mL). The resulting solution was transferred to a polypropylene reaction vessel and concentrated aqueous hydrofluoric acid solution (48 wt %, 0.8 mL) was added. The reaction mixture was stirred vigorously at 23° C. for 13 h, then was poured into water (30 mL) containing dipotassium hydrogenphosphate (8.0 g). The resulting mixture was extracted with ethyl acetate (3×40 mL). The organic extracts were combined and the combined solution was dried over anhydrous sodium sulfate. The dried solution was filtered and the filtrate was concentrated. Palladium black (5.0 mg, 0.047 mmol, 2.1 equiv) was added in one portion to a solution of the crude product in methanol (1.0 mL) and dioxane (1.0 mL) at 23° C. An atmosphere of hydrogen was introduced by briefly evacuating the flask, then flushing with pure hydrogen (1 atm). The reaction mixture was stirred at 23° C. for 1½ h, then was filtered through a plug of CELITE® (diatomaceous earth). The filtrate was concentrated. The product was purified by preparatory HPLC on an AGILENT TECHNOLOGIES® Prep C18 column [10 µm, 250×21.2 mm, UV detection at 350 nm, Solvent A: 0.1% trifluoroacetic acid in water, Solvent B: acetonitrile, injection volume: 5.0 mL (4.0 mL 0.1% trifluoroacetic acid in water, 1.0 mL acetonitrile), gradient elution with 5→35% B over 50 min, flow rate: 7.5 mL/min]. Fractions eluting at 40-44 min were collected and concentrated, affording C5a-piperidinylmethylminocycline trifluoroacetate 41 as a yellow solid (12.0 mg, 81%, three steps). $^1$H NMR (600 MHz, CD$_3$OD, trifluoroacetate) δ 7.56 (d, 1H, J=9.0 Hz), 6.96 (d, 1H, J=9.0 Hz), 4.10 (d, 1H, J=2.4 Hz), 3.66 (d, 1H, J=16.8 Hz), 3.46 (d, 1H, J=14.4 Hz), 3.40-3.35 (brm, 1H), 3.27-3.23 (m, 1H), 3.23-3.18 (m, 1H), 3.10 (s, 6H), 3.10-3.00 (m, 2H), 2.71 (s, 6H), 2.71-2.62 (m, 2H), 2.59 (dd, 1H, J=15.0, 3.0 Hz), 2.02 (t, 1H, J=15.0 Hz), 1.95-1.88 (brm, 1H), 1.85-1.78 (brm, 2H), 1.72-1.61 (brm, 2H), 1.43-1.36 (brm, 1H); HRMS-ESI (m/z): [M+H]$^+$ calcd for C$_{29}$H$_{39}$N$_4$O$_7$, 555.2813. found, 555.2788.

Example 29

Synthesis of C5a-Cyclopropylaminomethylminocycline 42

Anhydrous magnesium bromide (8.2 mg, 0.045 mmol, 2.0 equiv) was added to a solution of cyclopropane 22 (17.0 mg, 0.022 mmol, 1 equiv) and cyclopropylamine (15 µL, 0.223 mmol, 10 equiv) in tetrahydrofuran (0.5 mL) at 23° C. The reaction flask was sealed and the mixture was stirred at 23° C. for 16 h, then was heated to 40° C. After stirring at this temperature for 22 h, more cyclopropylamine (15 µL, 0.223 mmol, 10 equiv) was added to the reaction mixture. The flask was re-sealed and the reaction solution was stirred at 40° C. for a further 13 h, then was allowed to cool to 23° C. The cooled solution was partitioned between dichloromethane (15 mL) and saturated aqueous sodium bicarbonate solution (10 mL). The phases were separated and the aqueous phase was further extracted with dichloromethane (10 mL). The organic extracts were combined and the combined solution was dried over anhydrous sodium sulfate. The dried solution was filtered and the filtrate was concentrated. The residue, the crude product of cyclopropane ring-opening, was dissolved in acetonitrile (1.2 mL). The resulting solution was transferred to a polypropylene reaction vessel and concentrated aqueous hydrofluoric acid solution (48 wt %, 0.8 mL) was added. The reaction mixture was stirred vigorously at 23° C. for 12 h, then was poured into water (30 mL) containing dipotassium hydrogenphosphate (8.0 g). The resulting mixture was extracted with ethyl acetate (3×40 mL). The organic extracts were combined and the combined solution was dried over anhydrous sodium sulfate. The dried solution was filtered and the filtrate was concentrated. Palladium black (5.0 mg, 0.047 mmol, 2.1 equiv) was added in one portion to a solution of the crude product in methanol (1.0 mL) and dioxane (1.0 mL) at 23° C. An atmosphere of hydrogen was introduced by briefly evacuating the flask, then flushing with pure hydrogen (1 atm). The reaction mixture was stirred at 23° C. for 3½ h, then was filtered through a plug of CELITE® (diatomaceous earth). The filtrate was concentrated. The product was purified by preparatory HPLC on an AGILENT TECHNOLOGIES® Prep C18 column [10 μm, 250×21.2 mm, UV detection at 350 nm, Solvent A: 0.1% trifluoroacetic acid in water, Solvent B: acetonitrile, injection volume: 5.0 mL (4.0 mL 0.1% trifluoroacetic acid in water, 1.0 mL acetonitrile), gradient elution with 5→35% B over 50 min, flow rate: 7.5 mL/min]. Fractions eluting at 35-36 min were collected and concentrated, affording C5a-cyclopropylaminomethylminocycline trifluoroacetate 42 as a yellow solid (3.0 mg, 21%, three steps). $^1$H NMR (600 MHz, CD$_3$OD, trifluoroacetate) δ 7.58 (d, 1H, J=9.0 Hz), 6.96 (d, 1H, J=9.0 Hz), 4.00 (d, 1H, J=2.4 Hz), 3.60 (d, 1H, J=14.4 Hz), 3.55 (d, 1H, J=16.8 Hz), 3.19-3.10 (m, 1H), 3.13 (s, 6H), 3.03 (d, 1H, J=14.4 Hz), 2.76 (s, 6H), 2.76-2.70 (m, 1H), 2.62-2.58 (m, 1H), 2.25 (dd, 1H, J=15.0, 3.0 Hz), 1.98 (t, 1H, J=13.8 Hz), 0.89-0.82 (m, 1H), 0.77-0.69 (m, 3H); HRMS-ESI (m/z): [M+H]$^+$ calcd for C$_{27}$H$_{35}$N$_4$O$_7$, 527.2500. found, 527.2502.

Example 30

Synthesis of C5a-Diethylaminomethylminocycline 43

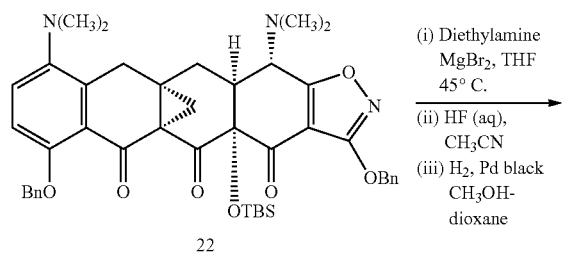

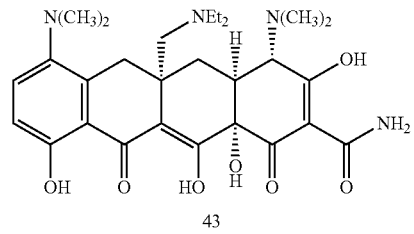

Anhydrous magnesium bromide (7.2 mg, 0.039 mmol, 2.0 equiv) was added to a solution of cyclopropane 22 (15.0 mg, 0.020 mmol, 1 equiv) and diethylamine (102 μL, 0.987 mmol, 50 equiv) in tetrahydrofuran (0.5 mL) at 23° C. The reaction flask was sealed and the mixture was heated to 45° C. After stirring at this temperature for 20 h, more diethylamine (204 μL, 1.97 mmol, 100 equiv) was added to the reaction mixture. The flask was re-sealed and the reaction solution was stirred at 45° C. for a further 55 h, then was allowed to cool to 23° C. The cooled solution was partitioned between dichloromethane (10 mL) and saturated aqueous sodium bicarbonate solution (10 mL). The phases were separated and the aqueous phase was further extracted with dichloromethane (10 mL). The organic extracts were combined and the combined solution was dried over anhydrous sodium sulfate. The dried solution was filtered and the filtrate was concentrated. The residue, the crude product of cyclopropane ring-opening, was dissolved in acetonitrile (1.2 mL). The resulting solution was transferred to a polypropylene reaction vessel and concentrated aqueous hydrofluoric acid solution (48 wt %, 0.8 mL) was added. The reaction mixture was stirred vigorously at 23° C. for 10½ h, then was poured into water (30 mL) containing dipotassium hydrogenphosphate (8.0 g). The resulting mixture was extracted with ethyl acetate (3×40 mL). The organic extracts were combined and the combined solution was dried over anhydrous sodium sulfate. The dried solution was filtered and the filtrate was concentrated. Palladium black (5.0 mg, 0.047 mmol, 2.4 equiv) was added in one portion to a solution of the crude product in methanol (1.0 mL) and dioxane (1.0 mL) at 23° C. An atmosphere of hydrogen was introduced by briefly evacuating the flask, then flushing with pure hydrogen (1 atm). The reaction mixture was stirred at 23° C. for 1¾ h, then was filtered through a plug of CELITE® (diatomaceous earth). The filtrate was concentrated. The product was purified by preparatory HPLC on an AGILENT TECHNOLOGIES® Prep C18 column [10 μm, 250×21.2 mm, UV detection at 350 nm, Solvent A: 0.1% trifluoroacetic acid in water, Solvent B: acetonitrile, injection volume: 5.0 mL (4.0 mL 0.1% trifluoroacetic acid in water, 1.0 mL acetonitrile), gradient elution with 5→40% B over 50 min, flow rate: 7.5 mL/min]. Fractions eluting at 36-39 min were collected and concentrated, affording C5a-diethylaminomethylminocycline trifluoroacetate 43 as a yellow solid (12.0 mg, 93%, three steps). $^1$H NMR (600 MHz, CD$_3$OD, trifluoroacetate) δ 7.54 (d, 1H, J=9.0 Hz), 6.95 (d, 1H, J=9.0 Hz), 4.10 (d, 1H, J=3.0 Hz), 3.61 (d, 1H, J=16.8 Hz), 3.42 (d, 1H, J=15.0 Hz), 3.25-3.20 (m, 2H), 3.16-3.02 (brm, 3H), 3.10 (s, 6H), 2.93 (brs, 1H), 2.73-2.69 (m, 1H), 2.70 (s, 6H), 2.52 (dd, 1H, J=15.0, 3.0 Hz), 2.07 (t, 1H, J=13.8 Hz), 1.28 (brs, 3H), 1.04 (brs, 3H); HRMS-ESI (m/z): [M+H]$^+$ calcd for C$_{28}$H$_{39}$N$_4$O$_7$, 543.2813. found, 543.2821.

Example 31

Synthesis of C5a-N,N'-Hydroxyethylmethylaminomethylminocycline 44

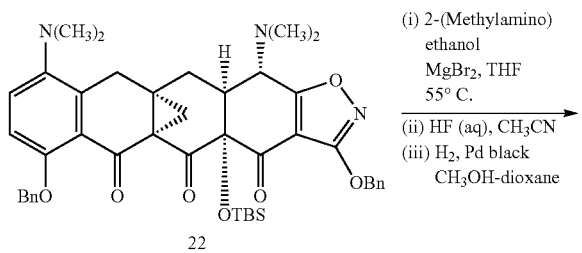

-continued

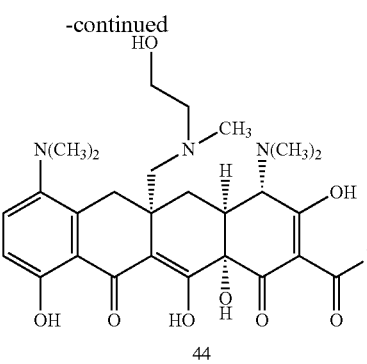

44

Anhydrous magnesium bromide (7.2 mg, 0.039 mmol, 2.0 equiv) was added to a solution of cyclopropane 22 (15.0 mg, 0.020 mmol, 1 equiv) and 2-(methylamino)ethanol (16 µL, 0.197 mmol, 10 equiv) in tetrahydrofuran (0.5 mL) at 23° C. The reaction flask was sealed and the mixture was heated to 55° C. After stirring at this temperature for 39 h, the reaction mixture was allowed to cool to 23° C. The cooled solution was partitioned between dichloromethane (10 mL) and saturated aqueous sodium bicarbonate solution (10 mL). The phases were separated and the aqueous phase was further extracted with dichloromethane (10 mL). The organic extracts were combined and the combined solution was dried over anhydrous sodium sulfate. The dried solution was filtered and the filtrate was concentrated. The product was purified by flash-column chromatography (50% ethyl acetate-hexanes, grading to 100% ethyl acetate). The product of cyclopropane ring-opening was dissolved in acetonitrile (1.2 mL). The resulting solution was transferred to a polypropylene reaction vessel and concentrated aqueous hydrofluoric acid solution (48 wt %, 0.8 mL) was added. The reaction mixture was stirred vigorously at 23° C. for 10½ h, then was poured into water (30 mL) containing dipotassium hydrogenphosphate (8.0 g). The resulting mixture was extracted with ethyl acetate (3×40 mL). The organic extracts were combined and the combined solution was dried over anhydrous sodium sulfate. The dried solution was filtered and the filtrate was concentrated. Palladium black (5.0 mg, 0.047 mmol, 2.4 equiv) was added in one portion to a solution of the crude product in methanol (1.0 mL) and dioxane (1.0 mL) at 23° C. An atmosphere of hydrogen was introduced by briefly evacuating the flask, then flushing with pure hydrogen (1 atm). The reaction mixture was stirred at 23° C. for 1½ h, then was filtered through a plug of CELITE® (diatomaceous earth). The filtrate was concentrated. The product was purified by preparatory HPLC on an AGILENT TECHNOLOGIES® Prep C18 column [10 µm, 250×21.2 mm, UV detection at 350 nm, Solvent A: 0.1% trifluoroacetic acid in water, Solvent B: acetonitrile, injection volume: 5.0 mL (4.0 mL 0.1% trifluoroacetic acid in water, 1.0 mL acetonitrile), gradient elution with 5→40% B over 50 min, flow rate: 7.5 mL/min]. Fractions eluting at 32-34 min were collected and concentrated, affording C5a-N,N'-hydroxyethylmethylaminomethylminocycline trifluoroacetate 44 as a yellow solid (3.7 mg, 29%, three steps). $^1$H NMR (600 MHz, CD$_3$OD, trifluoroacetate) δ 7.52 (d, 1H, J=8.4 Hz), 6.94 (d, 1H, J=9.0 Hz), 3.85 (brs, 2H), 3.64 (d, 1H, J=16.8 Hz), 3.34-3.23 (m, 3H), 3.19-3.10 (m, 2H), 3.12 (s, 6H), 2.76 (brs, 3H), 2.65 (brs, 7H), 2.52 (dd, 1H, J=15.0, 2.4 Hz), 2.02-1.94 (m, 1H); HRMS-ESI (m/z): [M+H]$^+$ calcd for C$_{27}$H$_{37}$N$_4$O$_8$, 545.2606. found, 545.2609.

Example 32

Synthesis of C5a-(3-Dimethylaminopropyl)aminomethylminocycline 45

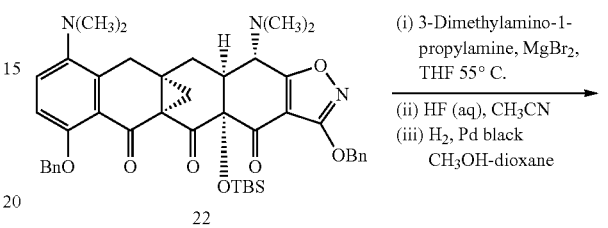

22

(i) 3-Dimethylamino-1-propylamine, MgBr$_2$, THF 55° C.
(ii) HF (aq), CH$_3$CN
(iii) H$_2$, Pd black CH$_3$OH-dioxane

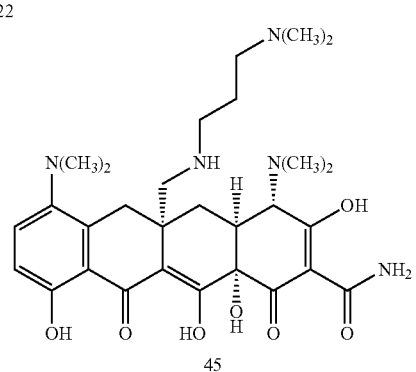

45

Anhydrous magnesium bromide (7.2 mg, 0.039 mmol, 2.0 equiv) was added to a solution of cyclopropane 22 (15.0 mg, 0.020 mmol, 1 equiv) and 3-dimethylamino-1-propylamine (25 µL, 0.197 mmol, 10 equiv) in tetrahydrofuran (0.5 mL) at 23° C. The reaction flask was sealed and the mixture was heated to 55° C. After stirring at this temperature for 17 h, the reaction mixture was allowed to cool to 23° C. The cooled solution was partitioned between dichloromethane (10 mL) and saturated aqueous sodium bicarbonate solution (10 mL). The phases were separated and the aqueous phase was further extracted with dichloromethane (10 mL). The organic extracts were combined and the combined solution was dried over anhydrous sodium sulfate. The dried solution was filtered and the filtrate was concentrated. The residue, the product of cyclopropane ring-opening was dissolved in acetonitrile (1.2 mL). The resulting solution was transferred to a polypropylene reaction vessel and concentrated aqueous hydrofluoric acid solution (48 wt %, 0.8 mL) was added. The reaction mixture was stirred vigorously at 23° C. for 17 h, then was poured into water (30 mL) containing dipotassium hydrogenphosphate trihydrate (10.0 g). The resulting mixture was extracted with ethyl acetate (3×40 mL). The organic extracts were combined and the combined solution was dried over anhydrous sodium sulfate. The dried solution was filtered and the filtrate was concentrated. Palladium black (5.0 mg, 0.047 mmol, 2.4 equiv) was added in one portion to a solution of the crude product in methanol (1.0 mL) and dioxane (1.0 mL) at 23° C. An atmosphere of hydrogen was introduced by briefly evacuating the flask, then flushing with pure hydrogen (1 atm). The reaction mixture was stirred at 23° C. for 2¼ h, then was filtered through a plug of CELITE®

(diatomaceous earth). The filtrate was concentrated. The product was purified by preparatory HPLC on an AGILENT TECHNOLOGIES® Prep C18 column [10 μm, 250×21.2 mm, UV detection at 350 nm, Solvent A: 0.1% trifluoroacetic acid in water, Solvent B: acetonitrile, injection volume: 5.0 mL (4.0 mL 0.1% trifluoroacetic acid in water, 1.0 mL acetonitrile), gradient elution with 5→35% B over 50 min, flow rate: 7.5 mL/min]. Fractions eluting at 29-31 min were collected and concentrated, affording C5a-(3-dimethylaminopropyl)aminomethylminocycline trifluoroacetate 45 as a yellow solid (1.8 mg, 13%, three steps). $^1$H NMR (600 MHz, CD$_3$OD, trifluoroacetate) δ 7.63 (d, 1H, J=9.0 Hz), 6.97 (d, 1H, J=9.6 Hz), 4.02 (d, 1H, J=2.4 Hz), 3.55 (d, 1H, J=16.8 Hz), 3.49 (d, 1H, J=14.4 Hz), 3.21-3.09 (m, 3H), 3.13 (s, 6H), 3.02-2.85 (m, 3H), 2.84 (s, 6H), 2.83 (s, 6H), 2.79 (d, 1H, J=16.8 Hz), 2.41 (dd, 1H, J=15.0, 3.0 Hz), 2.14-2.02 (m, 2H), 2.00 (t, 1H, J=13.8 Hz); HRMS-ESI (m/z): [M+H]$^+$ calcd for C$_{29}$H$_{42}$N$_5$O$_7$, 572.3079. found, 572.3081.

Example 33

Synthesis of C5a-Methoxyethoxymethylminocycline 46

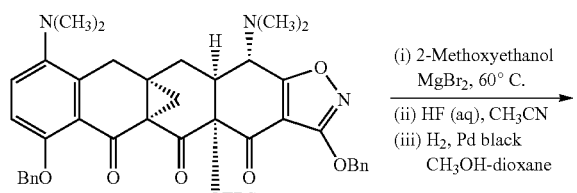

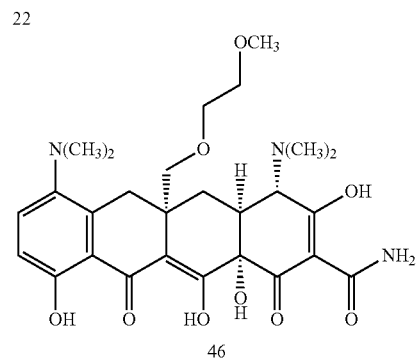

Anhydrous magnesium bromide (6.2 mg, 0.034 mmol, 2.0 equiv) was added to a solution of cyclopropane 22 (13.0 mg, 0.017 mmol, 1 equiv) in 2-methoxyethanol (0.5 mL) at 23° C. The resulting solution was heated to 60° C. After stirring at 60° C. for 26 h, the reaction mixture was allowed to cool to 23° C. The cooled solution was partitioned between aqueous potassium phosphate buffer solution (pH 7.0, 0.2 M, 10 mL) and dichloromethane (10 mL). The phases were separated and the aqueous phase was further extracted with dichloromethane (10 mL). The organic extracts were combined and the combined solution was dried over anhydrous sodium sulfate. The dried solution was filtered and the filtrate was concentrated. The residue, the crude product of cyclopropane ring-opening, was dissolved in acetonitrile (1.2 mL). The resulting solution was transferred to a polypropylene reaction vessel and concentrated aqueous hydrofluoric acid solution (48 wt %, 0.8 mL) was added. The reaction mixture was stirred vigorously at 23° C. for 10½ h, then was poured into water (30 mL) containing dipotassium hydrogenphosphate (8.0 g). The resulting mixture was extracted with ethyl acetate (3×40 mL). The organic extracts were combined and the combined solution was dried over anhydrous sodium sulfate. The dried solution was filtered and the filtrate was concentrated. Palladium black (5.0 mg, 0.047 mmol, 2.8 equiv) was added in one portion to a solution of the crude product in methanol (1.0 mL) and dioxane (1.0 mL) at 23° C. An atmosphere of hydrogen was introduced by briefly evacuating the flask, then flushing with pure hydrogen (1 atm). The reaction mixture was stirred at 23° C. for 1¾ h, then was filtered through a plug of CELITE® (diatomaceous earth). The filtrate was concentrated. The product was purified by preparatory HPLC on an AGILENT TECHNOLOGIES® Prep C18 column [10 μm, 250×21.2 mm, UV detection at 350 nm, Solvent A: 0.1% trifluoroacetic acid in water, Solvent B: acetonitrile, injection volume: 5.0 mL (4.0 mL 0.1% trifluoroacetic acid in water, 1.0 mL acetonitrile), gradient elution with 5→40% B over 50 min, flow rate: 7.5 mL/min]. Fractions eluting at 32-34 min were collected and concentrated, affording C5a-methoxyethoxymethylminocycline trifluoroacetate 46 as a yellow solid (5.8 mg, 52%, three steps). $^1$H NMR (600 MHz, CD$_3$OD, trifluoroacetate) δ 7.83 (d, 1 h, J=9.0 Hz), 7.05 (d, 1H, J=9.0 Hz), 4.13 (s, 1H), 3.54-3.45 (m, 4H), 3.44-3.40 (m, 1H), 3.34 (d, 1H, J=15.6 Hz), 3.27-3.25 (m, 1H), 3.26 (s, 3H), 3.18 (s, 6H), 3.11 (brd, 1H, J=14.4. Hz), 2.99 (s, 6H), 2.61 (d, 1H, J=16.2 Hz), 2.45 (dd, 1H, J=14.4, 3.0 Hz), 1.71 (t, 1H, J=14.4 Hz); HRMS-ESI (m/z): [M+H]$^+$ calcd for C$_{27}$H$_{36}$N$_3$O$_9$, 546.2446. found, 546.2459.

Example 34

Synthesis of C5a-N-Imidazolylmethylminocycline 47

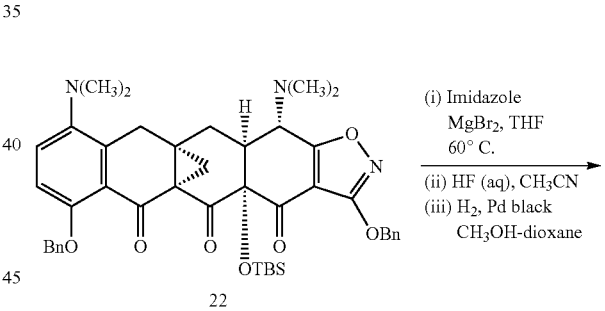

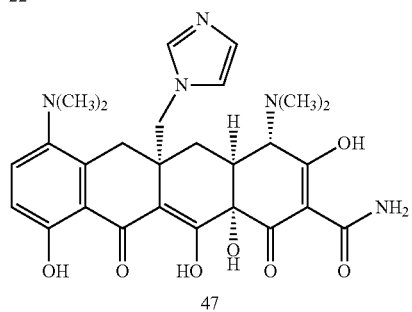

Anhydrous magnesium bromide (7.2 mg, 0.039 mmol, 3.0 equiv) was added to a solution of cyclopropane 22 (10.0 mg, 0.013 mmol, 1 equiv) and imidazole (6.2 mg, 0.091 mmol, 7.0 equiv) in tetrahydrofuran (0.5 mL) at 23° C. The reaction flask was sealed and the mixture was heated to 60° C. After stirring at this temperature for 60 h, the reaction mixture was allowed to cool to 23° C. The cooled solution was partitioned between dichloromethane (15 mL) and saturated aqueous sodium bicarbonate solution (15 mL). The phases were separated and the aqueous phase was further extracted with dichloromethane (15 mL). The organic extracts were combined and the combined solution was dried over anhydrous sodium sulfate. The dried solution was filtered and the filtrate was concentrated. The residue, the crude product of cyclopropane ring-opening, was dissolved in acetonitrile (1.2 mL). The resulting solution was transferred to a polypropylene reaction vessel and concentrated aqueous hydrofluoric acid solution (48 wt %, 0.8 mL) was added. The reaction mixture was stirred vigorously at 23° C. for 18 h, then was poured into water (30 mL) containing dipotassium hydrogenphosphate (8.0 g). The resulting mixture was extracted with ethyl acetate (3×40 mL). The organic extracts were combined and the combined solution was dried over anhydrous sodium sulfate. The dried solution was filtered and the filtrate was concentrated. Palladium black (5.0 mg, 0.047 mmol, 3.6 equiv) was added in one portion to a solution of the crude product in methanol (1.0 mL) and dioxane (1.0 mL) at 23° C. An atmosphere of hydrogen was introduced by briefly evacuating the flask, then flushing with pure hydrogen (1 atm). The reaction mixture was stirred at 23° C. for 1¼ h, then was filtered through a plug of CELITE® (diatomaceous earth). The filtrate was concentrated. The product was purified by preparatory HPLC on an AGILENT TECHNOLOGIES® Prep C18 column [10 μm, 250×21.2 mm, UV detection at 350 nm, Solvent A: 0.1% trifluoroacetic acid in water, Solvent B: acetonitrile, injection volume: 5.0 mL (4.0 mL 0.1% trifluoroacetic acid in water, 1.0 mL acetonitrile), gradient elution with 5→40% B over 50 min, flow rate: 7.5 mL/min]. Fractions eluting at 25-27 min were collected and concentrated, affording C5a-imidazolylmethylminocycline trifluoroacetate 47 as a yellow solid (7.3 mg, 86%, three steps). $^1$H NMR (600 MHz, CD$_3$OD, trifluoroacetate) δ 8.42 (t, 1H, J=1.2 Hz), 7.51 (d, 1H, J=9.0 Hz), 7.40 (t, 1H, J=1.8 Hz), 7.23 (t, 1H, J=1.8 Hz), 6.86 (d, 1H, J=9.0 Hz), 4.48 (AB quartet, 2H, J=14.4 Hz, Δv=44.4 Hz), 4.13 (s, 1H), 3.42 (d, 1H, J=16.8 Hz), 3.25 (dd, 1H, J=13.8, 1.2 Hz), 3.11 (s, 6H), 2.73 (s, 6H), 2.69 (d, 1H, J=16.2 Hz), 2.14 (dd, 1H, J=15.0, 3.0 Hz), 1.98 (t, 1H, J=14.4 Hz); HRMS-ESI (m/z): [M+H]$^+$ calcd for C$_{27}$H$_{32}$N$_5$O$_7$, 538.2296. found, 538.2285.

Example 35

Synthesis of
C5a-Pyridin-3-aminomethylminocycline 48

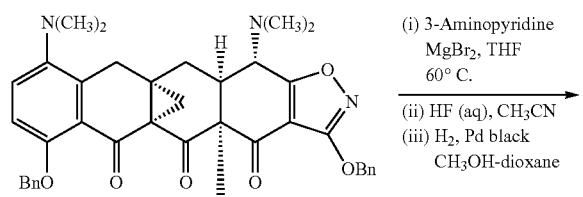

(i) 3-Aminopyridine
MgBr$_2$, THF
60° C.

(ii) HF (aq), CH$_3$CN
(iii) H$_2$, Pd black
CH$_3$OH-dioxane

22

-continued

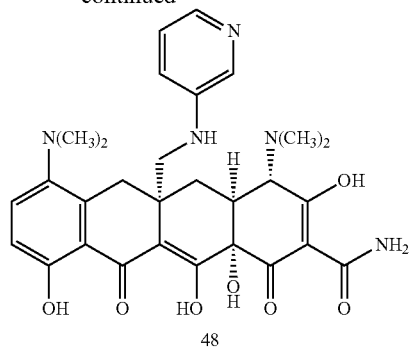

48

Anhydrous magnesium bromide (9.7 mg, 0.057 mmol, 2.0 equiv) was added to a solution of cyclopropane 22 (20.0 mg, 0.026 mmol, 1 equiv) and 3-aminopyridine (12.3 mg, 0.131 mmol, 5.0 equiv) in tetrahydrofuran (0.5 mL) at 23° C. The reaction flask was sealed and the mixture was heated to 60° C. After stirring at this temperature for 34 h, the reaction mixture was allowed to cool to 23° C. The cooled solution was partitioned between dichloromethane (15 mL) and saturated aqueous sodium bicarbonate solution (15 mL). The phases were separated and the aqueous phase was further extracted with dichloromethane (15 mL). The organic extracts were combined and the combined solution was dried over anhydrous sodium sulfate. The dried solution was filtered and the filtrate was concentrated. The product was purified by preparatory HPLC on an AGILENT TECHNOLOGIES® Prep C18 column [10 μm, 250×21.2 mm, UV detection at 350 nm, Solvent A: water, Solvent B: methanol, injection volume: 1.0 mL (methanol), gradient elution with 70100% B over 50 min, flow rate: 15 mL/min]. Fractions eluting at 8-16 min were collected and concentrated. The orange residue, the product of cyclopropane ring-opening, was dissolved in acetonitrile (1.2 mL). The resulting solution was transferred to a polypropylene reaction vessel and concentrated aqueous hydrofluoric acid solution (48 wt %, 0.8 mL) was added. The reaction mixture was stirred vigorously at 23° C. for 24 h, then was poured into water (30 mL) containing dipotassium hydrogenphosphate (8.0 g). The resulting mixture was extracted with ethyl acetate-methanol (10:1, 3×40 mL). The organic extracts were combined and the combined solution was dried over anhydrous sodium sulfate. The dried solution was filtered and the filtrate was concentrated. Palladium black (5.0 mg, 0.047 mmol, 1.8 equiv) was added in one portion to a solution of the crude product in methanol (1.0 mL) and dioxane (1.0 mL) at 23° C. An atmosphere of hydrogen was introduced by briefly evacuating the flask, then flushing with pure hydrogen (1 atm). The reaction mixture was stirred at 23° C. for 2 h, whereupon more palladium black (5.0 mg) was added. The resulting mixture was stirred at 23° C. for a further 2 h, then was filtered through a plug of CELITE® (diatomaceous earth). The filtrate was concentrated. The product was purified by preparatory HPLC on an AGILENT TECHNOLOGIES® Prep C18 column [10 μm, 250×21.2 mm, UV detection at 350 nm, Solvent A: 0.1% trifluoroacetic acid in water, Solvent B: acetonitrile, injection volume: 5.0 mL (4.0 mL 0.1% trifluoroacetic acid in water, 1.0 mL acetonitrile), gradient elution with 5→40% B over 50 min, flow rate: 7.5 mL/min]. Fractions eluting at 26-28 min were collected and concentrated, affording C5a-pyridin-3-aminomethylminocycline trifluoroacetate 48 as a yellow solid (4.0 mg, 23%, three steps). $^1$H NMR (600 MHz, CD$_3$OD, trifluoroacetate) δ 7.58 (d, 1H, J=1.8 Hz), 7.56 (d, 1H, J=5.4 Hz), 7.42 (d, 1H, J=9.0

Hz), 7.34-7.28 (m, 2H), 6.67 (d, 1H, J=8.4 Hz), 4.82 (d, 1H, J=13.2 Hz), 4.61 (d, 1H, J=13.2 Hz), 4.15 (s, 1H), 3.71 (d, 1H, J=16.8 Hz), 3.24 (d, 1H, J=13.8 Hz), 3.08 (s, 6H), 2.80 (d, 1H, J=16.8 Hz), 2.75 (s, 6H), 2.24 (dd, 1H, J=14.4, 3.0 Hz), 2.09 (t, 1H, J=14.4 Hz); HRMS-ESI (m/z): [M+H]$^+$ calcd for $C_{29}H_{34}N_5O_7$, 564.2453. found 564.2457.

Example 36

Synthesis of C5a-Aminomethylminocycline 49

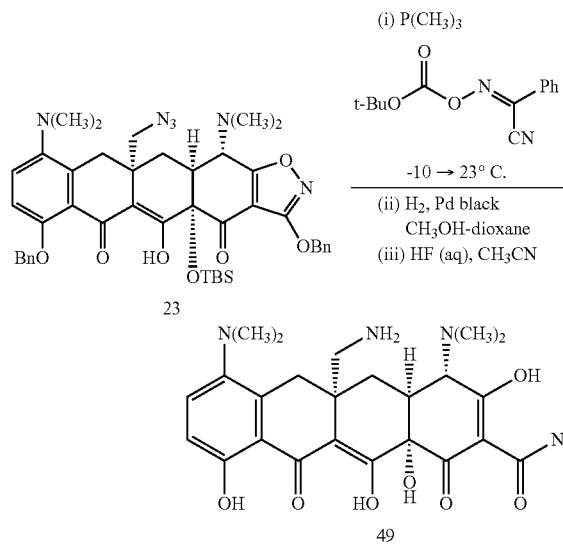

A solution of trimethylphospine in tetrahydrofuran (1.0 M, 398 μL, 0.398 mmol, 2.0 equiv) was added dropwise via syringe to a solution of alkyl azide 23 (160 mg, 0.199 mmol, 1 equiv) and 2-(tert-butoxycarbonyloxyimino)-2-phenylacetonitrile (98.0 mg, 0.398 mmol, 2.0 equiv) in tetrahydrofuran at −10° C. The reaction mixture was allowed to warm to 23° C. over 15 min, then was stirred at this temperature for a further 15 h. The resulting solution was partitioned between dichloromethane (60 mL) and water (60 mL). The phases were separated and the organic phase was washed sequentially with water (60 mL) and saturated aqueous sodium chloride solution (2×60 mL). The organic solution was then dried over anhydrous sodium sulfate. The dried solution was filtered and the filtrate was concentrated. The product was purified by flash-column chromatography (25% ethyl acetate-hexanes), providing the corresponding tert-butoxycarbamate as a yellow solid (90 mg, 51%).

Methanol (2.5 mL) and dioxane (2.5 mL) were added to this product, forming a yellow solution. Palladium black (25 mg, 0.235 mmol, 2.3 equiv) was added in one portion at 23° C. An atmosphere of hydrogen was introduced by briefly evacuating the flask, then flushing with pure hydrogen (1 atm). The reaction mixture was stirred at 23° C. for 1 h, whereupon more palladium black (25 mg) was added. The resulting mixture was stirred at 23° C. for a further 2 h, then was filtered through a plug of CELITE® (diatomaceous earth). The filtrate was concentrated, providing an orange solid. Concentrated aqueous hydrofluoric acid (48 wt %, 1.4 mL) was added to a solution of the crude product in acetonitrile (2.0 mL) in a polypropylene reaction vessel at 23° C. The reaction mixture was stirred vigorously at 23° C. for 15 h. Excess hydrofluoric acid was quenched by the careful addition of methoxytrimethylsilane (9.0 mL). The resulting mixture was concentrated. The product was purified by preparatory HPLC on an AGILENT TECHNOLOGIES® Prep C18 column [10 μm, 250×21.2 mm, UV detection at 350 nm, Solvent A: 0.1% trifluoroacetic acid in water, Solvent B: acetonitrile, injection volume: 5.0 mL (4.0 mL 0.1% trifluoroacetic acid in water, 1.0 mL acetonitrile), gradient elution with 5→40% B over 50 min, flow rate: 7.5 mL/min]. Fractions eluting at 22-27 min were collected and concentrated, affording C5α-aminomethylminocycline trifluoroacetate 49 as a yellow solid (50 mg, 42%, three steps). $^1$H NMR (500 MHz, CD$_3$OD, trifluoroacetate) δ 7.88 (d, 1H, J=9.0 Hz), 7.10 (d, 1H, J=9.0 Hz), 4.09 (d, 1H, J=2.5 Hz), 3.60 (d, 1H, J=17.0 Hz), 3.34 (d, 1H, J=14.5 Hz), 3.18 (s, 6H), 3.16 (s, 6H), 3.20-3.14 (m, 1H), 3.02 (d, 1H, J=14.5 Hz), 2.95 (d, 1H, J=17.0 Hz), 2.33 (dd, 1H, J=15.0, 3.0 Hz), 1.96 (t, 1H, J=14.5 Hz); HRMS-ESI (m/z): [M+H]$^+$ calcd for $C_{24}H_{31}N_4O_7$, 487.2187. found 487.2181.

Example 37

Synthesis of C5a-N-Acetylaminomethylminocycline 50

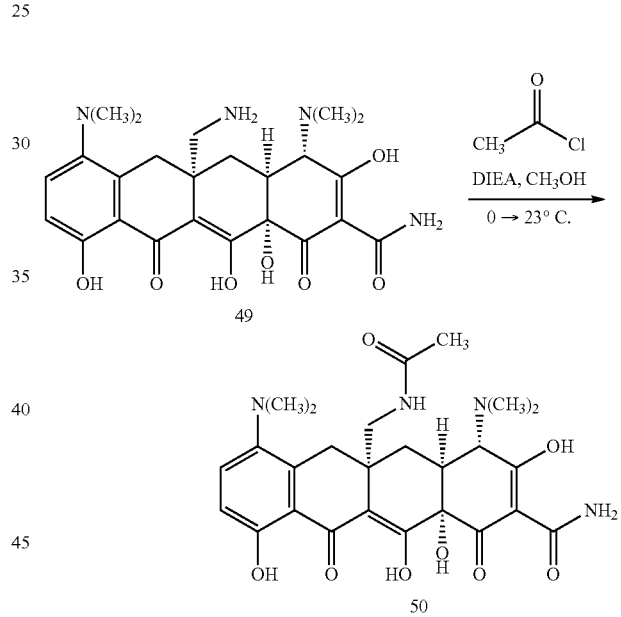

Acetyl chloride (0.9 μL, 0.013 mmol, 2.0 equiv) was added to a solution of C5a-aminomethylminocycline trifluoroacetate 49 (4.0 mg, 0.0067 mmol, 1 equiv) and N,N-diisopropylethylamine (4.6 μL, 0.027 mmol, 4.0 equiv) in methanol (200 μL) at 0° C. The resulting solution was allowed to warm to 23° C. over 5 min. The reaction mixture was stirred at this temperature for 1 h, then was concentrated. The product was purified by preparatory HPLC on an AGILENT TECHNOLOGIES® Prep C18 column [10 μm, 250×21.2 mm, UV detection at 350 nm, Solvent A: 0.1% trifluoroacetic acid in water, Solvent B: acetonitrile, injection volume: 5.0 mL (4.0 mL 0.1% trifluoroacetic acid in water, 1.0 mL acetonitrile), gradient elution with 5→40% B over 50 min, flow rate: 7.5 mL/min]. Fractions eluting at 25-28 min were collected and concentrated, affording C5a-N-acetylaminomethylminocycline trifluoroacetate 50 as a yellow solid (3.2 mg, 75%). $^1$H NMR (600 MHz, CD$_3$OD, trifluoroacetate) δ 7.80 (d, 1H, J=9.0 Hz), 7.03 (d, 1H, J=9.0 Hz), 3.89 (s, 1H), 3.46 (d, 1H, J=14.4 Hz), 3.27 (d, 1H, J=13.8 Hz), 3.23 (d, 1H, J=16.8 Hz), 3.15-3.08 (m, 13H), 2.63 (d, 1H, J=16.2 Hz), 2.11 (dd, 1H, J=14.4, 2.4 Hz), 1.91 (s, 3H), 1.69 (t, 1H, J=14.4 Hz); HRMS-ESI (m/z): [M+H]+ calcd for $C_{26}H_{33}N_4O_8$, 529.2293. found 529.2299.

Example 38

Synthesis of
C5a-N-Trimethylacetylaminomethylminocycline 51

Example 39

Synthesis of
C5a-N-Benzoylaminomethylminocycline 52

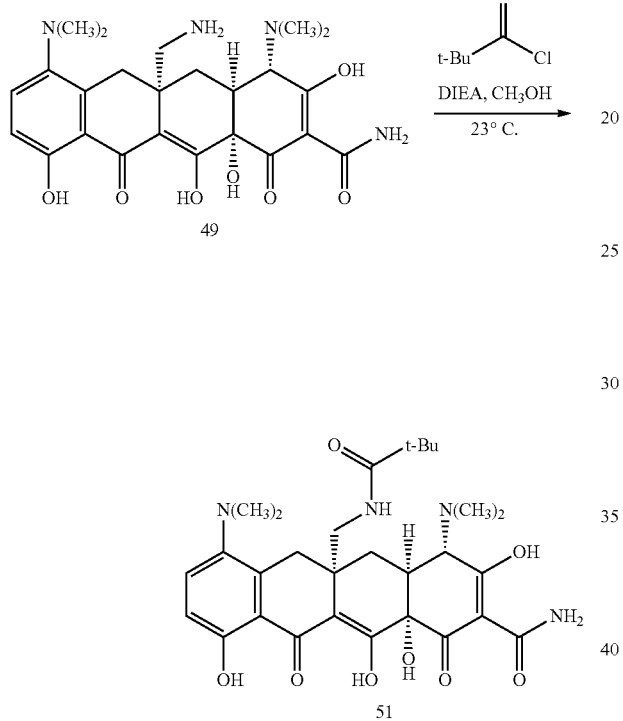

Trimethylacetyl chloride (1.6 μL, 0.013 mmol, 2.0 equiv) was added to a solution of C5α-aminomethylminocycline trifluoroacetate 49 (4.0 mg, 0.0067 mmol, 1 equiv) and N,N-diisopropylethylamine (4.6 μL, 0.027 mmol, 4.0 equiv) in methanol (200 μL) at 23° C. The reaction mixture was stirred at this temperature for 1½ h, then was concentrated. The product was purified by preparatory HPLC on an AGILENT TECHNOLOGIES® Prep C18 column [10 μm, 250×21.2 mm, UV detection at 350 nm, Solvent A: 0.1% trifluoroacetic acid in water, Solvent B: acetonitrile, injection volume: 5.0 mL (4.0 mL 0.1% trifluoroacetic acid in water, 1.0 mL acetonitrile), gradient elution with 5→40% B over 50 min, flow rate: 7.5 mL/min]. Fractions eluting at 38-40 min were collected and concentrated, affording C5a-N-trimethylacetylaminomethylminocycline trifluoroacetate 51 as a yellow solid (3.0 mg, 66%). 1H NMR (600 MHz, CD3OD, trifluoroacetate) δ 7.73 (d, 1H, J=9.0 Hz), 6.99 (d, 1H, J=9.6 Hz), 3.92 (s, 1H), 3.54 (d, 1H, J=14.4 Hz), 3.30-3.25 (m, 2H), 3.11 (s, 6H), 3.06-3.00 (m, 1H), 3.03 (s, 6H), 2.59 (d, 1H, J=16.2 Hz), 2.03 (dd, 1H, J=14.4, 3.0 Hz), 1.71 (t, 1H, J=14.4 Hz), 1.11 (s, 9H); HRMS-ESI (m/z): [M+H]+ calcd for $C_{29}H_{39}N_4O_8$, 571.2762. found 571.2771.

Benzoyl chloride (1.5 μL, 0.013 mmol, 2.0 equiv) was added to a solution of C5α-aminomethylminocycline trifluoroacetate 49 (4.0 mg, 0.0067 mmol, 1 equiv) and N,N-diisopropylethylamine (4.6 μL, 0.027 mmol, 4.0 equiv) in methanol (200 μL) at 23° C. The reaction mixture was stirred at this temperature for 1½ h, then was concentrated. The product was purified by preparatory HPLC on an AGILENT TECHNOLOGIES® Prep C18 column [10 μm, 250×21.2 mm, UV detection at 350 nm, Solvent A: 0.1% trifluoroacetic acid in water, Solvent B: acetonitrile, injection volume: 5.0 mL (4.0 mL 0.1% trifluoroacetic acid in water, 1.0 mL acetonitrile), gradient elution with 5→40% B over 50 min, flow rate: 7.5 mL/min]. Fractions eluting at 38-40 min were collected and concentrated, affording C5a-N-benzoylaminomethylminocycline trifluoroacetate 52 as a yellow solid (1.6 mg, 34%). 1H NMR (600 MHz, CD3OD, trifluoroacetate) δ 7.75 (d, 2H, J=7.2 Hz), 7.70 (d, 1H, J=9.6 Hz), 7.54 (t, 1H, J=7.8 Hz), 7.45 (t, 2H, J=7.8 Hz), 6.95 (d, 1H, J=9.0 Hz), 3.94 (s, 1H), 3.74 (d, 1H, J=14.4 Hz), 3.37 (d, 1H, J=15.6 Hz), 3.36-3.27 (m, 2H), 3.13 (s, 6H), 3.02 (s, 6H), 2.63 (d, 1H, J=16.2 Hz), 2.21 (dd, 1H, J=14.4, 2.4 Hz), 1.76 (t, 1H, J=14.4 Hz); HRMS-ESI (m/z): [M+H]+ calcd for $C_{31}H_{35}N_4O_8$, 591.2449. found 591.2459.

Example 40

Synthesis of C5a-N-Methoxyacetylaminomethylminocycline 53

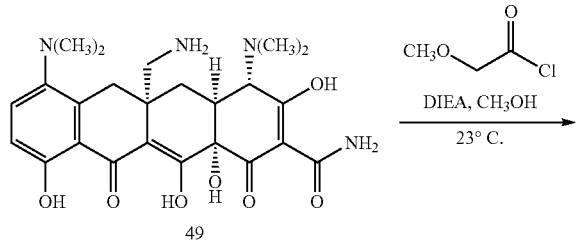

Methoxyacetyl chloride (1.2 μL, 0.013 mmol, 2.0 equiv) was added to a solution of C5α-aminomethylminocycline trifluoroacetate 49 (4.0 mg, 0.0067 mmol, 1 equiv) and N,N-diisopropylethylamine (4.6 μL, 0.027 mmol, 4.0 equiv) in methanol (200 μL) at 23° C. The reaction mixture was stirred at this temperature for 2 h, then was concentrated. The product was purified by preparatory HPLC on an AGILENT TECHNOLOGIES® Prep C18 column [10 μm, 250×21.2 mm, UV detection at 350 nm, Solvent A: 0.1% trifluoroacetic acid in water, Solvent B: acetonitrile, injection volume: 5.0 mL (4.0 mL 0.1% trifluoroacetic acid in water, 1.0 mL acetonitrile), gradient elution with 5→40% B over 50 min, flow rate: 7.5 mL/min]. Fractions eluting at 28-30 min were collected and concentrated, affording C5a-N-methoxyacetylaminomethylminocycline trifluoroacetate 53 as a yellow solid (2.0 mg, 45%). $^1$H NMR (600 MHz, CD$_3$OD, trifluoroacetate) δ 7.75 (d, 1H, J=9.0 Hz), 7.00 (d, 1H, J=9.0 Hz), 3.92 (s, 1H), 3.84 (AB quartet, 2H, J=15.0 Hz, Δv=10.2 Hz), 3.59 (d, 1H, J=14.4 Hz), 3.40 (s, 3H), 3.32-3.28 (m, 1H), 3.27 (d, 1H, J=15.6 Hz), 3.10 (s, 6H), 3.10-3.07 (m, 1H), 3.03 (s, 6H), 2.58 (d, 1H, J=16.2 Hz), 2.09 (dd, 1H, J=14.4, 3.0 Hz), 1.69 (t, 1H, J=13.8 Hz); HRMS-ESI (m/z): [M+H]$^+$ calcd for C$_{27}$H$_{34}$N$_4$O$_9$, 559.2399. found 559.2435.

Example 41

Synthesis of C5a-N-3,5-Difluorobenzoylaminomethylminocycline 54

3,5-Difluorobenzoyl chloride (1.9 μL, 0.013 mmol, 2.0 equiv) was added to a solution of C5α-aminomethylminocycline trifluoroacetate 49 (4.0 mg, 0.0067 mmol, 1 equiv) and N,N-diisopropylethylamine (4.6 μL, 0.027 mmol, 4.0 equiv) in methanol (200 μL) at 23° C. The reaction mixture was stirred at this temperature for 2 h, then was concentrated. The product was purified by preparatory HPLC on an AGILENT TECHNOLOGIES® Prep C18 column [10 μm, 250×21.2 mm, UV detection at 350 nm, Solvent A: 0.1% trifluoroacetic acid in water, Solvent B: acetonitrile, injection volume: 5.0 mL (4.0 mL 0.1% trifluoroacetic acid in water, 1.0 mL acetonitrile), gradient elution with 5→40% B over 50 min, flow rate: 7.5 mL/min]. Fractions eluting at 43-45 min were collected and concentrated, affording C5a-N-3,5-difluorobenzoylaminomethylminocycline trifluoroacetate 54 as a yellow solid (1.5 mg, 30%).
$^1$H NMR (600 MHz, CD$_3$OD, trifluoroacetate) δ 7.70 (d, 1H, J=9.0 Hz), 7.37-7.34 (m, 2H), 7.19-7.14 (m, 1H), 6.95 (d, 1H, J=9.0 Hz), 3.95 (s, 1H), 3.74 (d, 1H, J=14.4 Hz), 3.40-3.33 (m, 2H), 3.26 (d, 1H, J=13.8 Hz), 3.13 (s, 6H), 3.01 (s, 6H), 2.62 (d, 1H, J=16.2 Hz), 2.20 (dd, 1H, J=13.8, 2.4 Hz), 1.75 (t, 1H, J=13.8 Hz); HRMS-ESI (m/z): [M+H]$^+$ calcd for C$_{31}$H$_{33}$F$_2$N$_4$O$_8$, 627.2261. found 627.2123.

Example 42

Synthesis of C5a-N-Methanesulfonylaminomethylminocycline 55

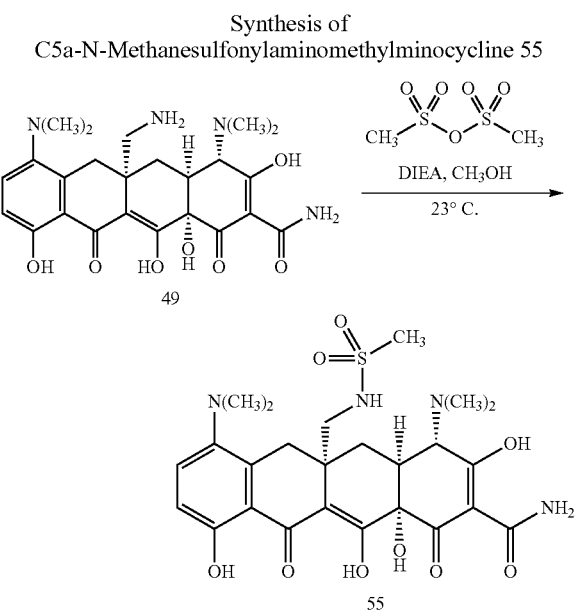

Methanesulfonic anhydride (2.3 mg, 0.013 mmol, 2.0 equiv) was added to a solution of C5a-aminomethylminocycline trifluoroacetate 49 (4.0 mg, 0.0067 mmol, 1 equiv) and N,N-diisopropylethylamine (4.6 μL, 0.027 mmol, 4.0 equiv) in methanol (200 μL) at 23° C. The reaction mixture was stirred at this temperature for 2 h, then was concentrated. The product was purified by preparatory HPLC on an AGILENT TECHNOLOGIES® Prep C18 column [10 μm, 250×21.2 mm, UV detection at 350 nm, Solvent A: 0.1% trifluoroacetic acid in water, Solvent B: acetonitrile, injection volume: 5.0 mL (4.0 mL 0.1% trifluoroacetic acid in water, 1.0 mL acetonitrile), gradient elution with 5→40% B over 50 min, flow rate: 7.5 mL/min]. Fractions eluting at 28-30 min were collected and concentrated, affording C5a-N-methanesulfonylaminomethylminocycline trifluoroacetate 55 as a yellow solid (1.5 mg, 33%).

$^1$H NMR (600 MHz, CD$_3$OD, trifluoroacetate) δ 7.77 (d, 1H, J=9.0 Hz), 7.01 (d, 1H, J=9.0 Hz), 3.91 (s, 1H), 3.34 (d, 1H, J=16.2 Hz), 3.26-3.21 (m, 2H), 3.08 (s, 6H), 3.03 (s, 6H), 2.99 (d, 1H, J=13.8 Hz), 2.86 (s, 3H), 2.60 (d, 1H, J=16.2 Hz), 2.35 (dd, 1H, J=14.4, 3.0 Hz), 1.70 (t, 1H, J=14.4 Hz); HRMS-ESI (m/z): [M+H]$^+$ calcd for C$_{25}$H$_{32}$N$_4$O$_9$S, 565.1963. found 565.1973.

Example 43

Preparation of β-Methylenone 59 from Enone 56

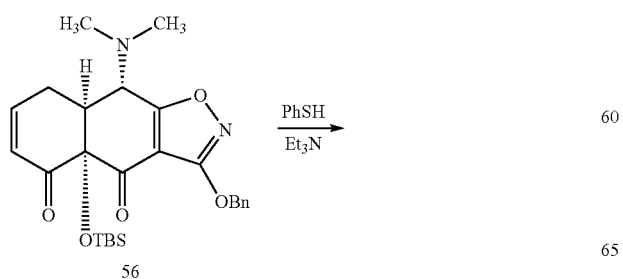

Step 1

Synthesis of β-Phenylthio ketone 57

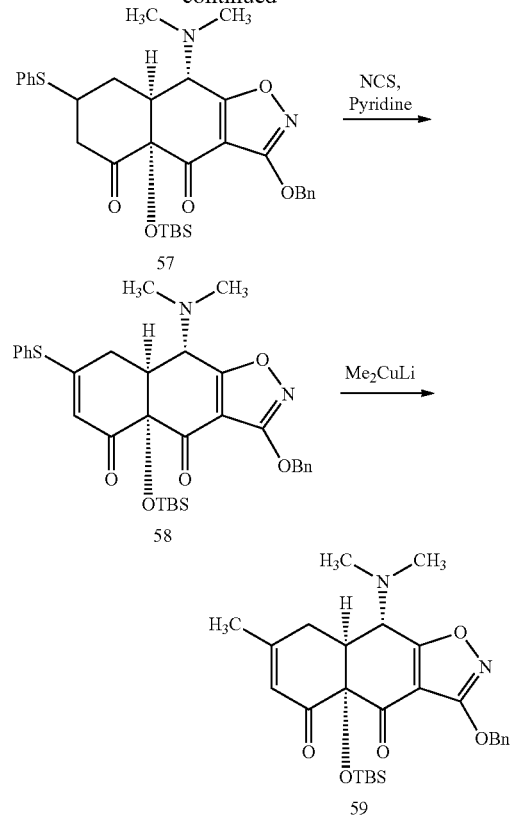

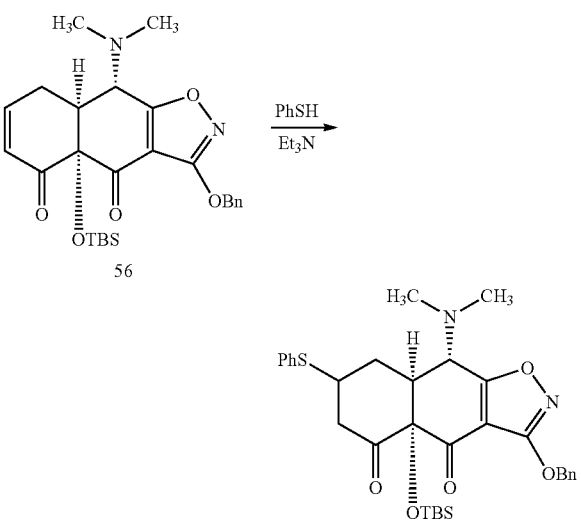

To a solution of enone 56 (1.94 g, 4.03 mmol, 1 equiv) in dichloromethane (9 mL) was added triethylamine (56 μL, 0.40 mmol, 0.1 equiv). The solution was cooled to 0° C. then thiophenol (434 μL, 4.23 mmol, 1.05 equiv) was added dropwise and the reaction was stirred at 0° C. After forty minutes, additional thiophenol was added (40 μL, 0.39 mmol, 0.1 equiv). Seven minutes later, acetic acid (26 μL, 0.40 mmol, 0.1 equiv) was added, and the reaction was concentrated under reduced pressure to remove the solvent. Purification of the resulting crude oil via flash column chromatography on silica gel (BIOTAGE®, 100 g, 5 to 30% EtOAc in hexane gradient) provided enone 57 as a white foam (2.33 g, 97%, 6:1 mixture of diastereomers): $^1$H NMR (400 MHz, CDCl$_3$; mixture of diastereomers, δ: 1H:H') δ 7.43-7.37 (m, 2H+2H'), 7.36-7.19 (m, 8H, 8H'), 5.29 (s, 2H), 5.26 (s, 2H'), 4.31 (d, J=9.2 Hz, 1H), 3.84-3.73 (m, 1H), 3.63 (d, J=11.6 Hz, 1H'), 3.42-3.31 (m, 1H'), 3.25 (dd, J=6.7, 14.0, 1H), 3.12 (t, J=12.8 Hz, 1H'), 2.63-2.47 (m, 2H+2H'), 2.40 (s, 6H), 2.38 (s, 6H'), 2.33-2.21 (m, 2H+2H'), 0.81 (s, 9H'), 0.79 (s, 9H), 0.050 (s, 3H'), 0.037 (s, 3H), 0.02 (s, 3H'), 0.00 (s, 3H); MS (ESI) m/z 591.31 (M−H).

Step 2

Synthesis of β-Phenylthio Enone 58

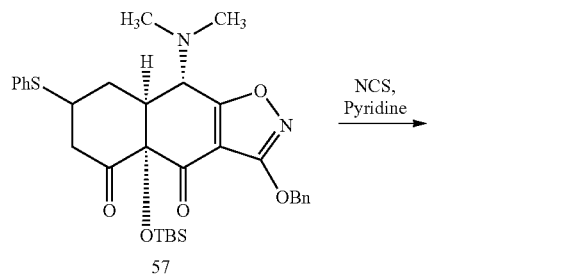

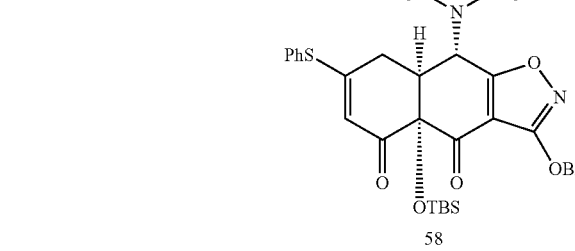

To a solution of enone 57 (2.34 g, 3.94 mmol, 1 equiv) in dichloromethane (12 mL) at 0° C. was added pyridine (476 μL, 5.91 mmol, 1.5 equiv) followed by N-chlorosuccinimide (NCS, 634 mg, 4.75 mmol, 1.2 equiv). The solution was allowed to warm to ambient temperature, during which the NCS dissolved into solution. After 2 h, additional NCS (1.2 equiv, as above) and pyridine (1.5 equiv, as above) were added at ambient temperature. After an additional 3.5 h, the resulting brown solution was poured into aqueous NaOH solution (1 N, 15 mL) and extracted with EtOAc (3×60 mL). The combined organic layers were washed with aqueous NaOH solution (1 N, 10 mL), water (20 mL), and brine (20 mL) then dried (Na$_2$SO$_4$), filtered, and concentrated under reduced pressure. Purification of the resulting oil via flash column chromatography on silica gel (BIOTAGE®, 100 g, 5 to 40% EtOAc in hexane gradient) provided enone 58 as a yellow foam (1.89 g, 81%): $^1$H NMR (400 MHz, CDCl$_3$) δ 7.50-7.39 (m, 7H), 7.38-7.28 (m, 3H), 5.44 (d, J=2.4 Hz, 1H), 5.31 (dd, J=12.2, 15.3 Hz, 2H), 3.80 (d, J=11.0 Hz, 1H), 3.10 (ddd, J=2.44, 4.27, 18.3 Hz, 1H), 2.98 (d, J=1.2 Hz, 18.3 Hz, 1H), 2.73 (ddd, J=1.8, 4.9, 10.4 Hz, 1H), 2.47 (s, 6H), 0.86 (s, 9H), 0.24 (s, 3H), 0.00 (s, 3H); MS (ESI) m/z 589.29 (M−H).

Step 3

Synthesis of O-Methyl Enone 59

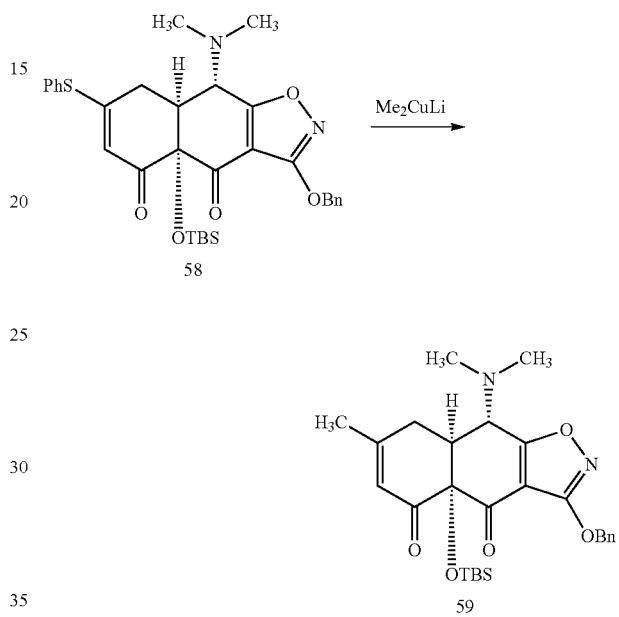

A flame-dried flask was cooled under nitrogen atmosphere and charged with copper iodide (CuI, 242 mg, 1.27 mmol, 1.15 equiv). The flask was evacuated and back-filled with nitrogen three times, then Et$_2$O (10 mL) was added. The resulting gray suspension was cooled to −78° C. and methyllithium (1.6 M in Et$_2$O; 1.51 mL, 2.2 equiv) was added dropwise. After 5 min the solution was removed from the bath and swirled until the solution was homogeneous (5 min, a slight yellow color was also observed). The solution was recooled to −78° C. for 10 min. Vacuum-dried enone 58 (650 mg, 1.10 mmol, 1 equiv) in Et$_2$O (5 mL) under nitrogen was added dropwise via syringe to the cold cuprate solution over 5 min. An orange color develops during the addition, followed by the appearance of an orange-yellow precipitate. After 30 min, excess cuprate was quenched via the addition of saturated aqueous ammonium chloride (3 mL) and warming to ambient temperature. The solution was poured into saturated aqueous ammonium chloride (20 mL) and water (15 mL) and extracted with EtOAc (3×60 mL). The combined organic layers were washed sequentially with water (30 mL) and brine (10 mL), dried (Na$_2$SO$_4$), filtered, and concentrated under reduced pressure. Purification of the resulting oil via flash column chromatography on silica gel (BIOTAGE®, 100 g, 5 to 40% EtOAc in hexane gradient) provided enone 59 as a yellow solid (387 mg, 71%): $^1$H NMR (400 MHz, CDCl$_3$) δ 7.45 (d, J=7.9 Hz, 2H), 7.38-7.26 (m, 3H), 5.89 (s, 1H), 5.31 (s, 2H), 3.68 (d, J=20.1 Hz, 1H), 2.80-2.61 (m, 3H), 2.41 (s, 6H), 1.96 (s, 3H), 0.77 (s, 9H), 0.21 (s, 3H), 0.00 (s, 3H); MS (ESI) m/z 495.33 (M−H).

Example 44

Preparation of Phenyl 2-(benzyloxy)-3-(dibenzylamino)-5-fluoro-6-methylbenzoate 67 from 5-Fluoro-2-methoxybenzoic acid 60

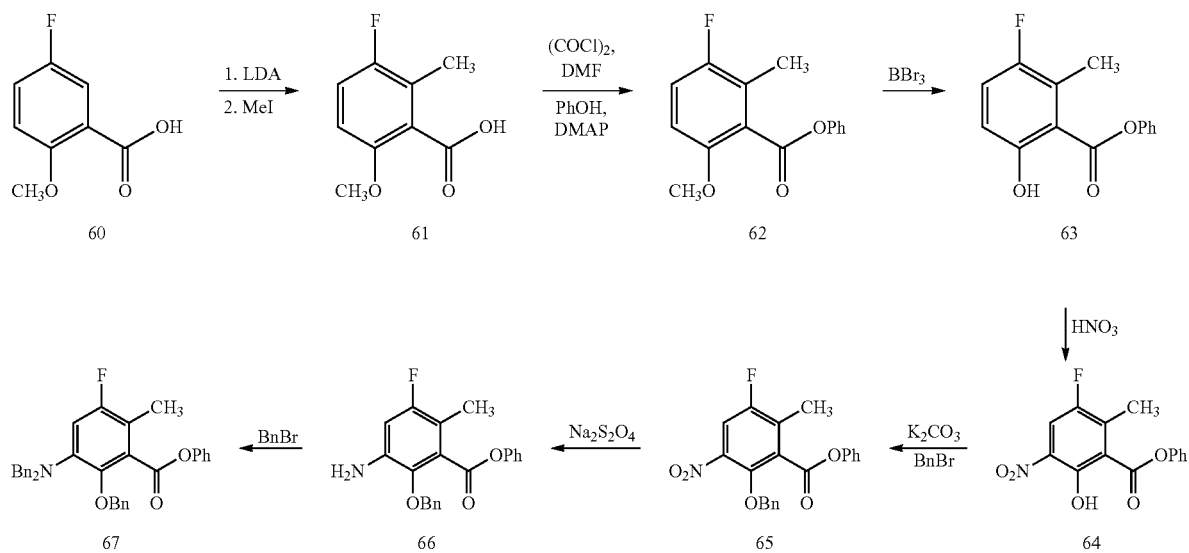

Step 1

Synthesis of 3-fluoro-6-methoxy-2-methylbenzoic acid 61

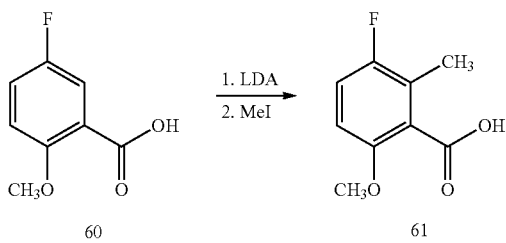

Diisopropyl amine (478 g, 4.725 mol) and anhydrous THF (2.8 L) were charged to a 10 L 4-neck flask equipped with gas inlet, addition funnel, thermometer and mechanical stirrer. The solution was degassed with $N_2$ for 5 min then cooled to −78° C. with dry ice acetone bath under $N_2$ flow. A solution of n-BuLi in n-hexane (1.8 L, 2.5 M, 4.5 mol) was added to the stirring mixture at −20° C.~−10° C. over 40 min. After the addition, the reaction was stirred at −20° C. for 40 min A solution of 5-fluoro-2-methoxybenzoic acid 60 (297.5 g, 1.75 mol) in anhydrous THF (1.3 L) was added to the reaction mixture at −55° C.—45° C. with stirring over 60 min. The resulting brown mixture was stirred at −15~−25° C. for 3.5 h. The reaction mixture turned to red brown. Another para-reaction same with above reaction was set at same time. A 20 L four-neck flask equipped with gas inlet, addition funnel, thermometer and mechanical stirrer was charged with neat MeI (1500 g, 10.5 mol) and anhydrous THF (2.6 L). The mixture was degassed with $N_2$ for 5 min and cooled to −20~−15° C. with dry ice acetone bath under small $N_2$ flow. The obtained solution from the above two para-reactions was transferred to the 20 L flask containing MeI at −15~−5° C. with stirring over 20 min. The resulting cloudy mixture was stirred at −20~−15° C. for 2 h and brought to ambient temperature over 1.5 h. The obtained brown suspension was stirred at 25-30° C. for 16 h. The reaction was then quenched with aqueous HCl (5.0 L, 2N) at 20-25° C. and diluted MTBE (3.0 L). After being stirred for 5 min at 20° C., the two phase mixture was separated, and the upper layer was concentrated to dryness under vacuum to give black oil. The aqueous layer was extracted with EtOAc (5×1.5 L) and all the organic layers were combined with the black oil. The resulting solution was washed with water (2×µL) and brine (3×1 L). The organic layer was dried over $Na_2SO_4$ and filtered. The filtrate was concentrated under reduce pressure to afford crude 3-fluoro-6-methoxy-2-methylbenzoic acid 61 (740 g, >100%) as brown crystal solid that was used in the next step without further purification: $^1$H NMR (400 MHz, CDCl$_3$) δ 7.06 (dd, J=9.8, 8.5 Hz, 1H), 6.75 (dd, J=9.8, 3.7 Hz, 1H), 3.86 (s, 3H), 2.34 (d, J=2.4 Hz, 3H); MS (ESI) m/z 185.12 (M+H).

Step 2

Synthesis of Phenyl 3-fluoro-6-methoxy-2-methylbenzoate 62

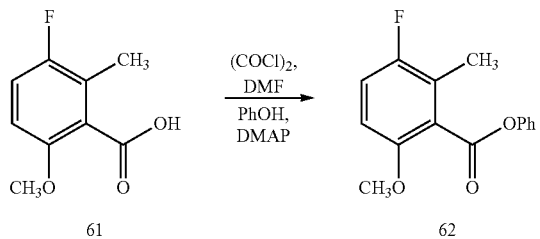

A 20 L 3-neck flask, equipped with mechanical stirrer, addition funnel and thermometer was charged with a solution of compound 61 (740 g, 4.02 mol) in anhydrous CH$_2$Cl$_2$ (8.0 L) followed by several drops of DMF. The solution was degassed with N$_2$ for 3 min (COCl)$_2$ (880 g, 6.93 mol) was added to the stirring reaction mixture slowly and carefully at 25~27° C. over 45 min. A lot of gas was generated. After stirring at 25~27° C. for 60 min, the reaction mixture was concentrated to dryness under reduced pressure. The residual oil was re-dissolved in anhydrous CH$_2$Cl$_2$ (2.0 L), concentrated to dryness again and further dried with under reduced pressure for 40 min to give black oil that was dissolved in anhydrous CH$_2$Cl$_2$ (8.0 L). PhOH (460 g, 4.9 mol) was added to the stirred solution at 25~30° C., followed by Et$_3$N (824 g, 8.16 mol). After DMAP (4.9 g, 0.04 mol) was added to the reaction, the reaction mixture was stirred at 20-30° C. for 16 h. Aqueous HCl (2.0 L, 3N) was added to the reaction mixture below 30° C. The organic layer was separated and washed with 3N aqueous HCl (2×1 L). The organic layer was concentrated to dryness under reduce pressure to give brown oil that was dissolved in EtOAc (4.0 L) and washed with 0.5N aqueous (3×1.0 L) and brine (2×1.0 L). The above acid aqueous layer was extracted with EtOAc (2×1.0 L) and the extracts were combined with the above EtOAc solution. The organic layer was dried over Na$_2$SO$_4$ and filtered. The filtrate was concentrated under reduce pressure to afford crude compound 62 (1100 g) as brown partially crystalline slurry (>100% yield): $^1$H NMR (400 MHz, CDCl$_3$) δ 7.47-7.41 (m, 2H), 7.31-7.24 (m, 3H), 7.08 (dd, J=9.2, 9.2 Hz, 1H), 6.77 (dd, J=9.2, 3.7 Hz, 1H), 3.88 (s, 3H), 2.36 (d, J=2.3 Hz, 3H); MS (ESI) m/z 261.12 (M+H).

Step 3

Synthesis of Phenyl 3-fluoro-6-hydroxy-2-methylbenzoate 63

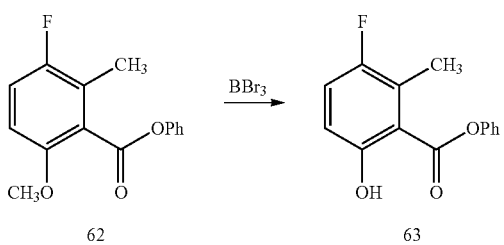

A 30 L 4-neck flask equipped with mechanical stirrer, thermometer and gas inlet was charged with a solution of compound 62 (1140 g, 4.38 mol) in CH$_2$Cl$_2$ (15 L). The brown solution was cooled to −78° C. with dry ice acetone bath under small N$_2$ flow. A solution of BBr$_3$ in CH$_2$Cl$_2$ (4.5 L, 5.26 mol) was added to the reaction at −70~−78° C. with stirring over 74 min. The reaction mixture was the allowed to warm to 20~25° C. over 3 h and stirred at room temperature for 16 h. Saturated aqueous NaHCO$_3$ was added to the reaction mixture slowly to pH 2~3. After stirring for 5 min, the layers were separated and the aqueous layer was extracted with CH$_2$Cl$_2$ (2×1 L). The organic layers were combined and washed with brine (2×2 L). The organic layer was dried over Na$_2$SO$_4$ and filtered and the filtrate was concentrated under reduced pressure to give 1100 g (>100%) of crude compound 63 as brown oil: $^1$H NMR (400 MHz, CDCl$_3$) δ 10.66 (s, 1H), 7.50-7.44 (m, 2H), 7.36-7.31 (m, 1H), 7.26-7.18 (m, 3H), 6.86 (dd, J=9.3, 4.9 Hz, 1H), 2.60 (d, J=2.4 Hz, 3H); MS (ESI) m/z 245.11 (M−H).

Step 4

Synthesis of phenyl 3-fluoro-6-hydroxy-2-methyl-5-nitrobenzoate 64

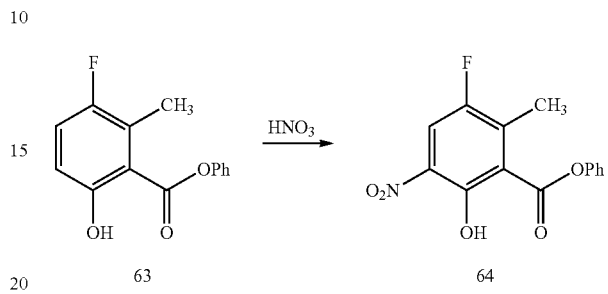

A 30 L 4-neck flask equipped with mechanical stirrer, thermometer and addition funnel was charged with a solution of compound 63 (1100 g, 4.47 mol) in CH$_2$Cl$_2$ (8.0 L) followed by water (8.1 L) and tetrabutyl ammonium bromide (144 g, 0.45 mol). Aqueous HNO$_3$ (591 mL, 68 w %, 8.94 mol) was added to the stirred two-phase reaction mixture at 24~27° C. over 3 min and the mixture was stirred at 24-28° C. for 20 h. The two layers were separated and the aqueous layer was extracted with CH$_2$Cl$_2$ (4×1.0 L). The organic layers were then combined and successively washed with water (3×1.0 L) and brine (2×2 L). The organic layer was dried over Na$_2$SO$_4$ and filtered and concentrated under reduce pressure to give 1423 g (>100%) of compound 64 as dark brown solid.

Step 5

Synthesis of phenyl 2-(benzyloxy)-5-fluoro-6-methyl-3-nitrobenzoate 65

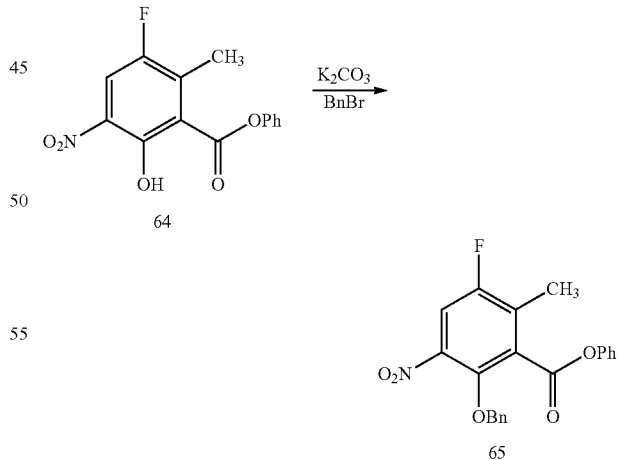

A 30 L 4-neck flask equipped with mechanical stirrer, thermometer, addition funnel and gas inlet was charged with a solution of compound 64 (1423 g, 4.89 mol) in acetone (17 L). K$_2$CO$_3$ (1350 g, 9.8 mol) and KI (81 g, 0.49 mol) were added to the stirring reaction mixture and the resulting suspension was degassed with N$_2$ for 5 min prior to adding BnBr (878.2 g, 5.13 mol) at 27~29° C. over 8 mM. After the addition, the brown suspension was refluxed for 2.5 h, then allowed to cool to 20~30° C. The suspension was filtered, and the filter cake was washed with acetone (3×900 mL). The filtrate was concentrated under reduced pressure and the residual oil was dissolved in MTBE (7.0 L) and successively washed with water (5×1.0 L) and brine (4×1.0 L). The organic layer was dried over Na$_2$SO$_4$ filtered then concentrated to dryness under reduced pressure to afford 1840 g of crude compound 65 (98.7% yield) as brown oil.

Step 6

Synthesis of Phenyl 3-amino-2-(benzyloxy)-5-fluoro-6-methylbenzoate 66

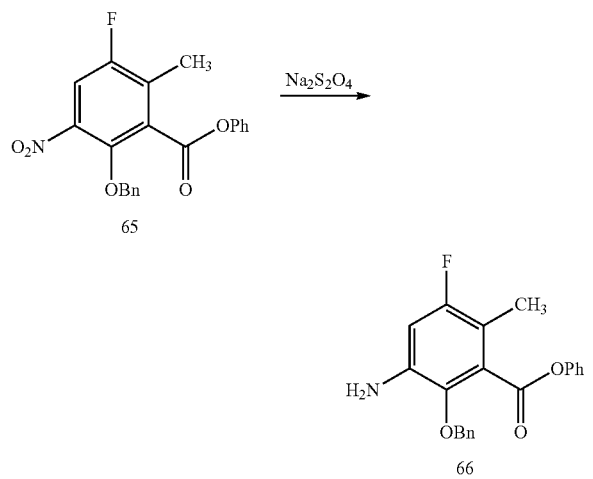 [SMILES: Cc1c(F)cc([N+](=O)[O-])c(OCc2ccccc2)c1C(=O)Oc1ccccc1 ; "Na2S2O4" ; Cc1c(F)cc(N)c(OCc2ccccc2)c1C(=O)Oc1ccccc1]

A solution of compound 65 (700 g, 1.84 mol) in THF (7 L) was cooled to 12° C. and stirred while adding a solution of Na$_2$S$_2$O$_4$ (1599 g, 9.18 mol) in water (7.0 L) was added to the reaction with stirring. The exotherm was controlled by addition rate so that the reaction mixture temperature was below 17° C. The reaction mixture was then allowed to stir for 15 hours prior to adding 15.3 L EtOAc. The layers were separated and the organic layer was washed with successively with water (2×4 L and brine (1×4 L). The organic was dried over Na$_2$SO$_4$ and concentrated to give 699 g of a brownish solid that was recrystallized from heptane/toluene to afford 532 g (82.7%) of desired compound 66 obtained as an off-white solid.

Step 7

Synthesis of Phenyl 2-(benzyloxy)-3-(dibenzylamino)-5-fluoro-6-methylbenzoate 67

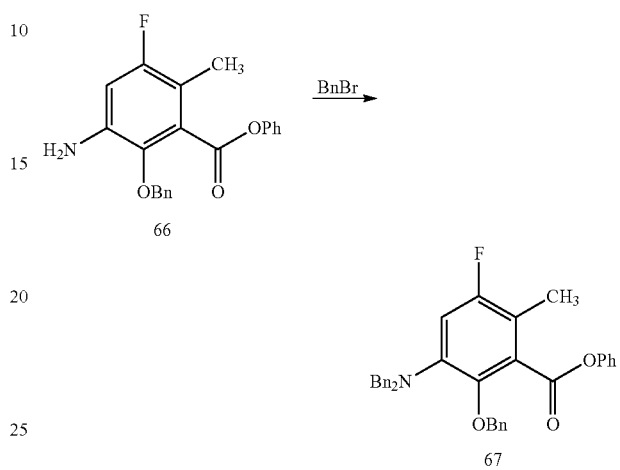

To a solution of 500 g of compound 66 in 4.25 L N-methylpyrrolidinone was added N,N-diisopropylethylamine (620 mL) followed by BnBr (425 mL, 2.5 equiv.). The mixture was heated at 100° C. for 18 h then cooled to 8° C. and treated over 10 min with 25% w/w aqueous triethyl amine aqueous. The mixture was allowed to stir for 25 minutes at ambient temperature before being cooled to 15° C. adding water (10 L) over ca. 3 hours to precipitate product. The obtained pale colored suspension was filtered then washed with 2 L water and dried. The crude product (750 g) was then dissolved in 4.1 L toluene and filtered through silica gel to give 762 g of a yellow solid that was recrystallized from acetone/heptane to afford 606 g of desired compound 67 (80% yield) obtained as an off-white solid: $^1$H NMR (400 MHz, CDCl$_3$) δ 7.48-7.03 (m, 20H), 6.60 (d, J=11.5 Hz, 1H), 5.31 (s, 2H), 4.33 (s, 4H), 2.30 (s, 3H).

Example 45

Preparation of 5a-Methyl-7-amido tetracyclines 70 from Phenyl 2-(benzyloxy)-3-(dibenzylamino)-5-fluoro-6-methylbenzoate 67

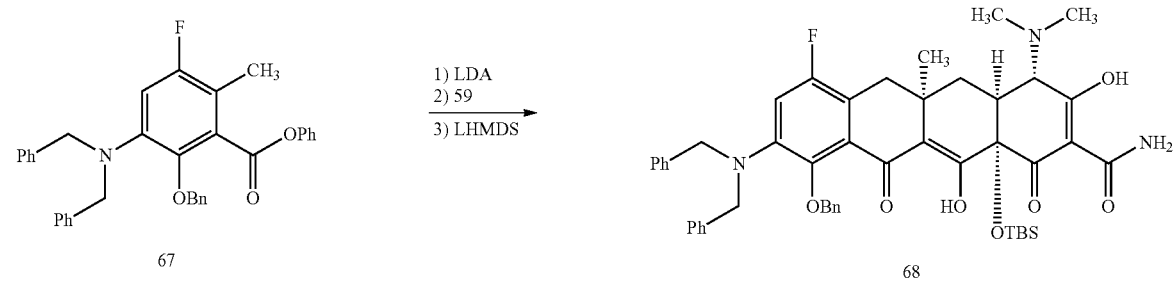

1) HF
2) H$_2$, Pd/C

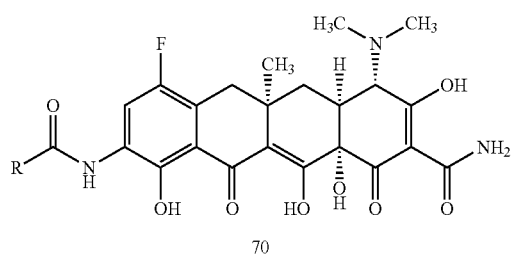

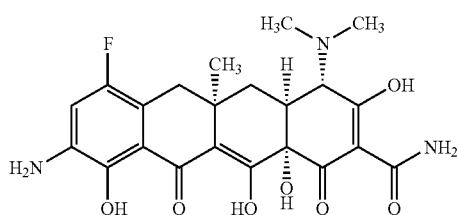

Step 1

Synthesis of 7-Fluoro-9-dibenzyl analog 68

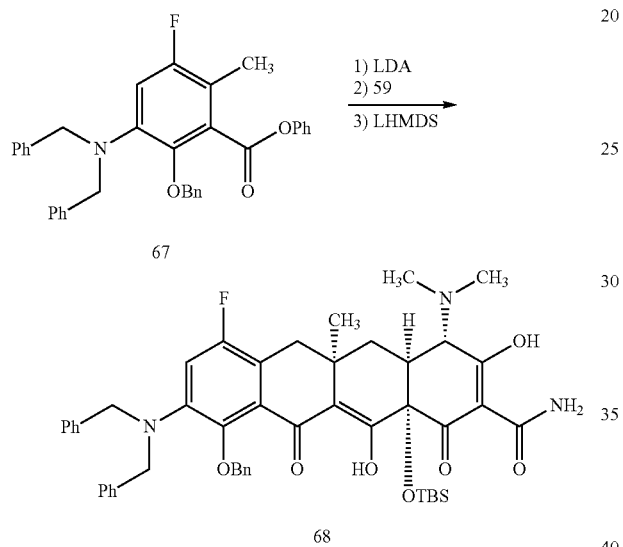

To a solution of lithium diisopropylamide (2.0 M in hexanes, 478 µL, 0.959 mmol, 2 equiv) and TMEDA (144 µL, 0.957 mmol, 2 equiv) in THF (8 mL) at −78° C. was added a solution of compound 67 (509 mg, 0.957 mmol, 2 equiv) in THF (2 mL) by dropwise addition. This resulted in a dark red colored solution. After 10 min, a solution of enone 59 (235 mg, 0.473 mmol, 1 equiv) in THF (1 mL) was added, followed by slow addition of LHMDS (1 M in hexanes; 957 µL, 0.957 mmol, 2 equiv). The reaction mixture was allowed to warm to −15° C. over 80 min. Excess base was quenched by the addition of a saturated, aqueous solution of ammonium chloride (1 mL). The solution was warmed to ambient temperature, poured into a saturated, aqueous solution of ammonium chloride (15 mL) and water (5 mL) and extracted with EtOAc (2×25 mL). The combined organic extracts were dried over Na$_2$SO$_4$, filtered, and concentrated under reduced pressure. Purification of the resulting oil via flash column chromatography on silica gel (SILICYCLE® INC., 40 g, 5 to 12.5% EtOAc in hexanes gradient) provided 7-fluoro-9-dibenzyl analog 68 as a yellow oil (275 mg, 62%): $^1$H NMR (400 MHz, CDCl$_3$) δ 16.59 (s, 1H), 7.53-7.44 (m, 4H), 7.41-7.20 (m, 12H), 7.18-7.10 (m, 4H), 6.65 (d, J=10.4 Hz, 1H), 5.38 (d, J=9.8 Hz, 1H), 5.36 (s, 2H), 5.07 (d, J=9.8 Hz, 1H), 4.36 (d, J=14.0 Hz, 2H), 4.21 (d, J=14.0 Hz, 2H), 4.04 (d, J=9.8 Hz, 1H), 2.89 (d, J=15.9 Hz, 1H), 2.66 (d, J=15.0 Hz, 1H), 2.48 (s, 6H), 2.32-2.22 (m, 1H), 2.15 (dd, J=4.9, 12.7 Hz, 1H), 1.08 (s, 9H), 0.25 (s, 3H), 0.18 (s, 3H); MS (ESI) m/z 934.40 (M+H).

Step 2

Synthesis of 7-Fluoro-9-amino analog 69

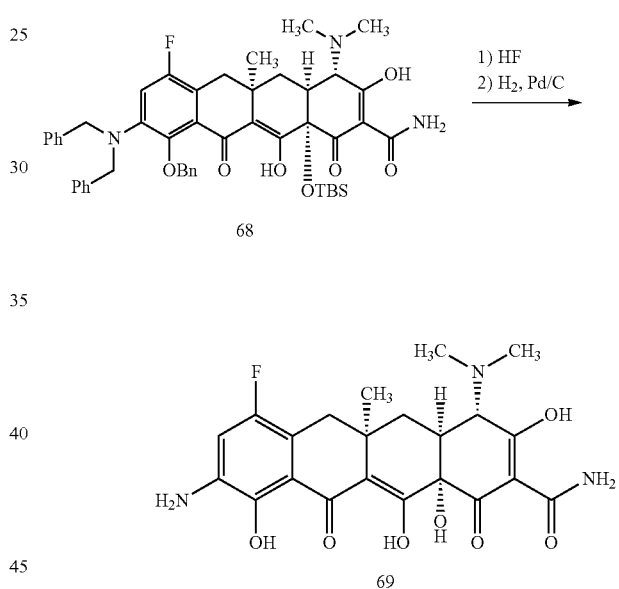

To a solution of 68 (275 mg, 0.294 mmol, 1 equiv) in dioxane (1 mL) was added an aqueous solution of HF (50%, 350 µL). After 75 min, the reaction mixture was poured into an aqueous K$_2$HPO$_4$ solution (4.4 g in 35 mL) and extracted with EtOAc (2×30 mL). The combined organic layers were dried (Na$_2$SO$_4$), filtered, and concentrated under reduced pressure. Palladium on carbon (10%; 168 mg) was added to a solution of this crude oil in dioxane:MeOH (1:1, 6 mL). The flask was fitted with a septum and evacuated and back-filled three times with hydrogen gas. The reaction was stirred under an atmosphere (balloon) of hydrogen gas for 1 h. The reaction mixture was filtered through CELITE® (diatomaceous earth) to remove the palladium catalyst and concentrated under reduced pressure. Preparative reverse phase HPLC of the resulting oil provided 115 mg of the desired compound 69 (73%): $^1$H NMR (400 MHz, CD$_3$OD) δ 7.40 (d, J=9.2 Hz, 1H), 4.11 (s, 1H), 3.10-2.94 (m, 8H), 2.62 (d, J=15.9 Hz, 1H), 2.04 (dd, J=3.1, 14.0 Hz, 1H), 1.97-1.87 (m, 1H), 1.28 (s, 3H); MS (ESI) m/z 462.09 (M+H).

Step 3

Synthesis of 7-Fluoro-9-amido analog 70

Protocols for synthesizing various 7-fluoro-9-amido analogs are described in Examples 46-51.

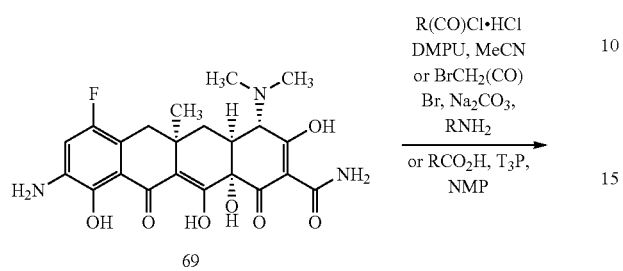

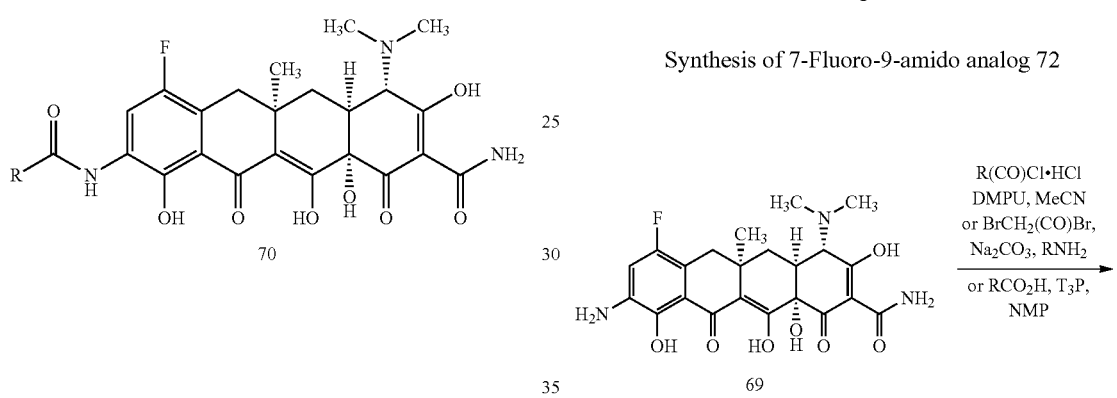

Example 46

Synthesis of 7-Fluoro-9-amido analog 71

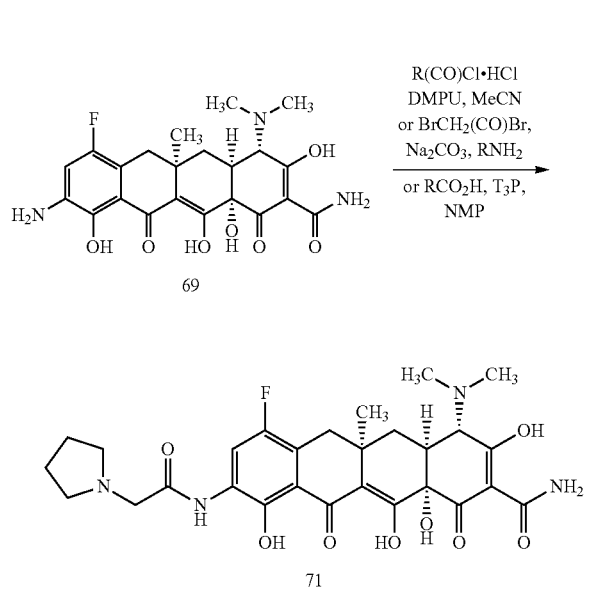

To an orange solution of aniline 69 (10.6 mg, 0.021 mmol, 1 equiv) in DMPU:CH$_3$CN (3:1, 400 μL) was added 2-(pyrrolidin-1-yl)acetyl chloride hydrochloride (5.2 mg, 0.028 mmol, 1.3 equiv). The solution lightens to yellow. After 45 min, the solvent was removed under reduced pressure. Removal of excess DMPU was achieved by precipitation of the desired salt via addition of HCl in MeOH (0.5 M, 200 μL) followed by Et$_2$O (5 mL). The precipitate was filtered off on CELITE® (diatomaceous earth) with Et$_2$O wash, then rinsed off with MeOH and concentrated under reduced pressure. Preparative reverse phase HPLC of the resulting oil afforded 4.55 mg of the desired compound 71 (33%): $^1$H NMR (400 MHz, CD$_3$OD) δ 8.25 (d, J=11.0 Hz, 1H), 4.33 (s, 2H), 4.10 (s, 1H), 3.84-3.73 (m, 2H), 3.26-3.14 (m, 2H), 3.08-2.95 (m, 8H), 2.55 (d, J=15.9 Hz, 1H), 2.25-1.97 (m, 5H), 1.96-1.84 (m, 1H), 1.26 (s, 3H); MS (ESI) m/z 573.13 (M+H).

Example 47

Synthesis of 7-Fluoro-9-amido analog 72

To an orange solution of 69 (11.7 mg, 0.023 mmol, 1 equiv) in DMPU:CH$_3$CN (3:1, 400 μL) was added 2-(tert-butylamino)acetyl chloride hydrochloride (7.3 mg, 0.039 mmol, 1.7 equiv). The solution lightens to yellow. After 1 h, the solvent was removed under reduced pressure. Removal of excess DMPU was achieved by precipitation of the desired salt via addition of HCl in MeOH (0.5 M, 200 μL) followed by Et$_2$O (3.5 mL). The precipitate was filtered off on CELITE® (diatomaceous earth) with Et$_2$O wash, then rinsed off with MeOH and concentrated under reduced pressure. Preparative reverse phase HPLC of the resulting oil afforded 8.68 mg of the desired compound 72 (58%): $^1$H NMR (400 MHz, CD$_3$OD) δ 8.27 (d, J=11.0 Hz, 1H), 4.14-4.06 (m, 3H), 3.10-2.96 (m, 8H), 2.55 (d, J=15.9 Hz, 1H), 2.03 (dd, J=2.4, 14.0 Hz, 1H), 1.95-1.85 (m, 1H), 1.42 (s, 9H), 1.27 (s, 3H); MS (ESI) m/z 575.14 (M+H).

Example 48

Synthesis of 7-Fluoro-9-amido analog 73

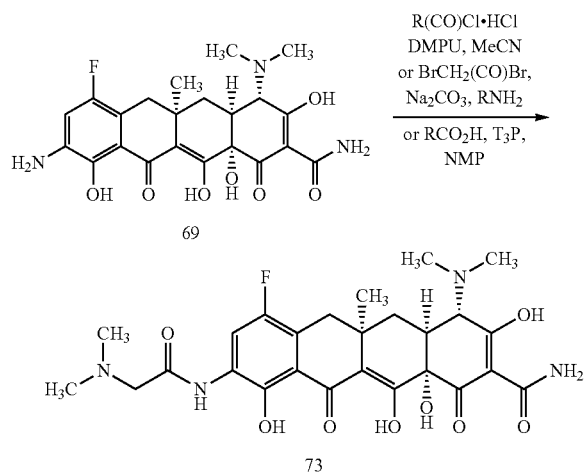

To a solution of compound 69 (10.0 mg, 0.020 mmol, 1 equiv) in DMPU:CH$_3$CN (3:1, 400 µL) was added 2-(dimethylamino)acetyl chloride hydrochloride (5.6 mg, 0.030 mmol, 1.5 equiv). The solution lightens to yellow. After 1.5 h, another 1.5 equiv of the acetyl chloride was added. After 3 h, the solvent was removed under reduced pressure. Removal of excess DMPU was achieved by precipitation of the desired salt via addition of HCl in MeOH (0.5 M, 200 µL) followed by Et$_2$O (3.5 mL). The precipitate was filtered off on CELITE® (diatomaceous earth) with Et$_2$O wash, then rinsed off with MeOH and concentrated under reduced pressure. Preparative reverse phase HPLC of the resulting oil afforded 5.58 mg of the desired compound 73 (45%): $^1$H NMR (400 MHz, CD$_3$OD) δ 8.25 (d, J=11.0 Hz, 1H), 4.23 (s, 2H), 4.10 (s, 1H), 3.09-2.94 (m, 14H), 2.56 (d, 15.9 Hz, 1H), 2.04-1.98 (m, 1H), 1.95-1.85 (m, 1H), 1.26 (s, 3H); MS (ESI) m/z 547.16 (M+H).

Example 49

Synthesis of 7-Fluoro-9-amido analog 74

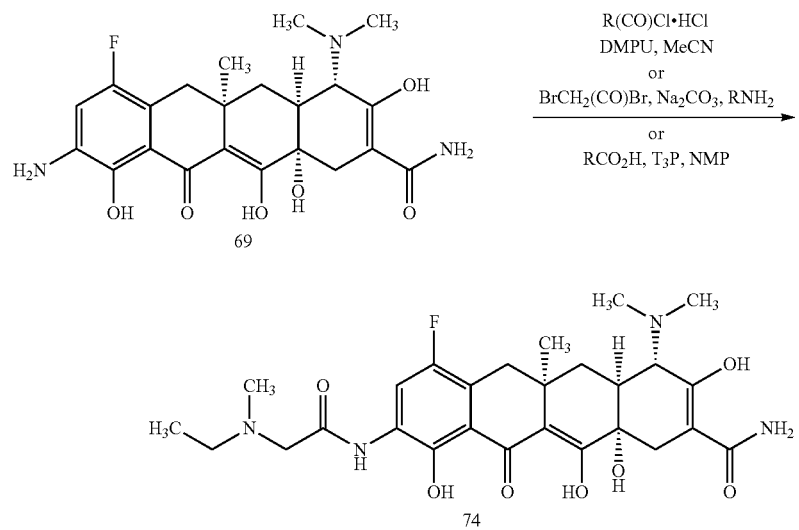 [SMILES: CN(C)[C@@H]1C(O)=C(C(N)=O)C[C@@]2(O)C(O)=C3C(=O)c4c(O)c(N)cc(F)c4C[C@@]3(C)C[C@@H]12 ; "R(CO)Cl·HCl" ; CCN(C)CC(=O)Nc1cc(F)c2c(c1O)C(=O)C1=C(O)[C@]3(O)CC(C(N)=O)=C(O)[C@@H](N(C)C)[C@@H]3C[C@]1(C)C2]

To a solution of 69 (11.8 g, 0.024 mmol, 1 equiv) in DMPU:CH$_3$CN (3:1, 400 µL) was added sodium carbonate (9.6 mg, 0.091 mmol, 3.8 equiv). After seven minutes bromoacetylbromide (2.3 µL, 0.026 mmol, 1.1 equiv) was added. The color lightens to yellow. After 45 min, N-ethylmethylamine (9.5 µL, 0.11 mmol, 4.5 equiv) was added. After an additional 19 h, the sodium carbonate was removed by CELITE® (diatomaceous earth) filtration, followed by concentration under reduced pressure to remove excess amine. Removal of excess DMPU was achieved by precipitation of the desired salt via addition of HCl in MeOH (0.5 M, 200 µL) followed by Et$_2$O (8 mL). The precipitate was filtered off on CELITE® (diatomaceous earth) with Et$_2$O wash, then rinsed off with MeOH and concentrated under reduced pressure. Preparative reverse phase HPLC of the resulting oil afforded 7.89 mg of the desired compound 74 (53%): $^1$H NMR (400 MHz, CD$_3$OD) δ 8.25 (d, J=11.0 Hz, 1H), 4.30 (d, J=15.9 Hz, 1H), 4.18 (d, J=16.4 Hz, 1H), 4.10 (s, 1H), 3.43-3.21 (m, 2H), 3.09-2.95 (m, 11H), 2.56 (d, J=15.9 Hz, 1H), 2.05-1.99 (m, 1H), 1.95-1.86 (m, 1H), 1.38 (t, J=7.3 Hz, 3H), 1.26 (s, 3H); MS (ESI) m/z 561.13 (M+H).

Example 50

Synthesis of 7-Fluoro-9-amido analog 75

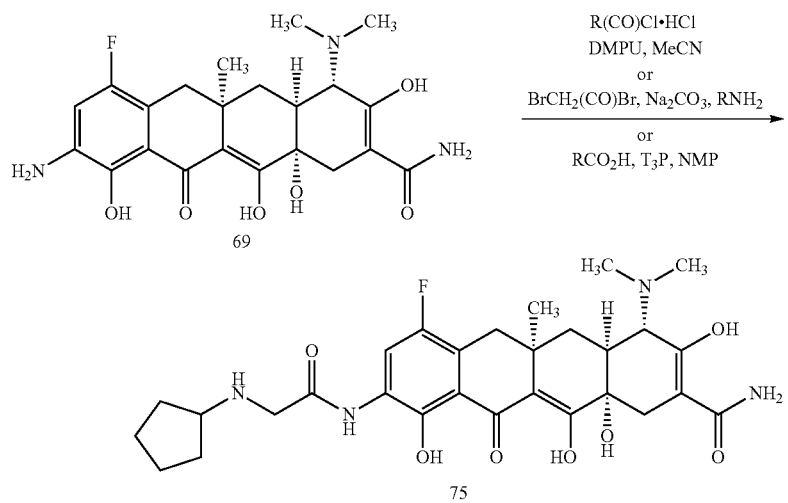

To a solution of compound 69 (10.1 g, 0.020 mmol, 1 equiv) in DMPU:CH$_3$CN (3:1, 400 μL) was added sodium carbonate (10.5 mg, 0.099 mmol, 5 equiv). After 15 min bromoacetylbromide (2.0 μL, 0.022 mmol, 1.1 equiv) was added. The color lightens to yellow. After 45 min, cyclopentylamine (9.4 μL, 0.095 mmol, 4.8 equiv) was added. After an additional 19 h, the sodium carbonate was removed by CELITE® (diatomaceous earth) filtration, followed by concentration under reduced pressure to remove excess amine. Removal of excess DMPU was achieved by precipitation of the desired salt via addition of HCl in MeOH (0.5 M, 200 μL) followed by Et$_2$O (8 mL). The precipitate was filtered off on CELITE® (diatomaceous earth) with Et$_2$O wash, then rinsed off with MeOH and concentrated under reduced pressure. Preparative reverse phase HPLC of the resulting oil provided 1.07 mg of the desired compound 75 (8%; 3.64 mg impure, 28%): $^1$H NMR (400 MHz, CD$_3$OD) δ 8.26 (d. J=11.0 Hz, 1H), 4.09 (s, 3H), 3.69-3.56 (m, 1H), 3.08-2.95 (m, 8H), 2.56 (d, J=15.9 Hz, 1H), 2.21-2.09 (m, 2H), 2.04-1.97 (m, 1H), 1.95-1.78 (m, 3H), 1.76-1.63 (m, 4H), 1.26 (s, 3H); MS (ESI) m/z 587.16 (M+H).

Example 51

Synthesis of 7-Fluoro-9-amido analog 76

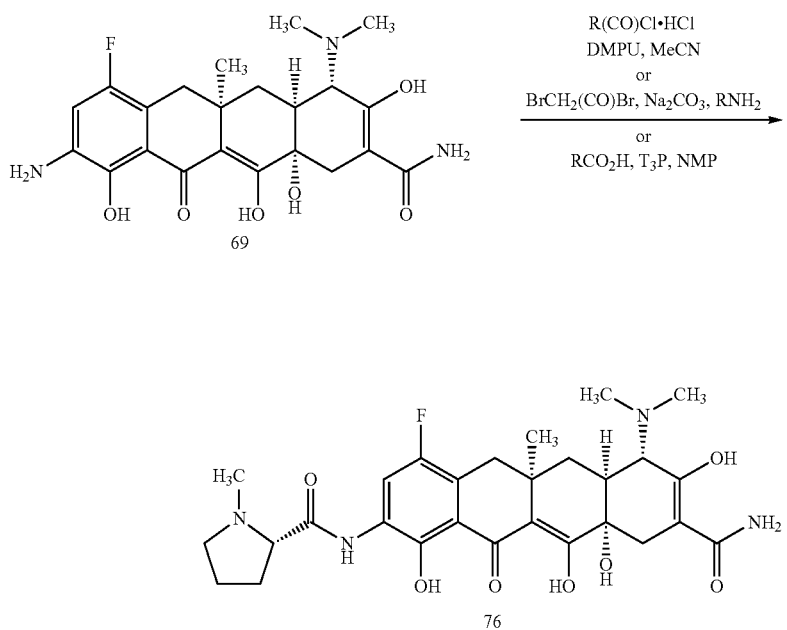

To a suspension of methylated N-methylproline hydrochloride (34.6 mg, 0.21 mmol, 5 equiv) in NMP (500 μL) at 0° C. was added 1-propanephosphonic acid cyclic anhydride (150 μL, 0.25 mmol, 6 equiv). The solution was warmed to ambient temperature over twenty minutes, then compound 69 (21.1 mg, 0.042 mmol, 1 equiv) was added. The solution turned dark orange. After 55 min, removal of excess NMP was achieved by precipitation of the desired salt via addition of HCl in MeOH (0.5 M, 250 μL) followed by Et$_2$O (10 mL). The precipitate was filtered off on CELITE® (diatomaceous earth) with Et$_2$O wash, then rinsed off with MeOH and concentrated under reduced pressure. Preparative reverse phase HPLC of the resulting oil provided 9.01 mg of the desired compound 76 (33%): $^1$H NMR (400 MHz, CD$_3$OD) δ 8.19 (d, J=11.0 Hz, 1H), 4.37 (t, J=7.9 Hz, 1H), 4.10 (s, 1 H), 3.82-3.73 (m, 1H), 3.09-2.95 (m, 11H), 2.77-2.66 (m, 1H), 2.57 (d, J=15.9 Hz, 1H), 2.31-1.98 (m, 5H), 1.96-1.85 (m, 1H), 1.27 (s, 3H); MS (ESI) m/z 573.08 (M+H).

Example 52

Preparation of phenyl 4-(benzyloxy)-2-tert-butyl-7-fluoro-6-methylisoindoline-5-carboxylate 83 from Phenyl 3-fluoro-6-hydroxy-2-methylbenzoate 63

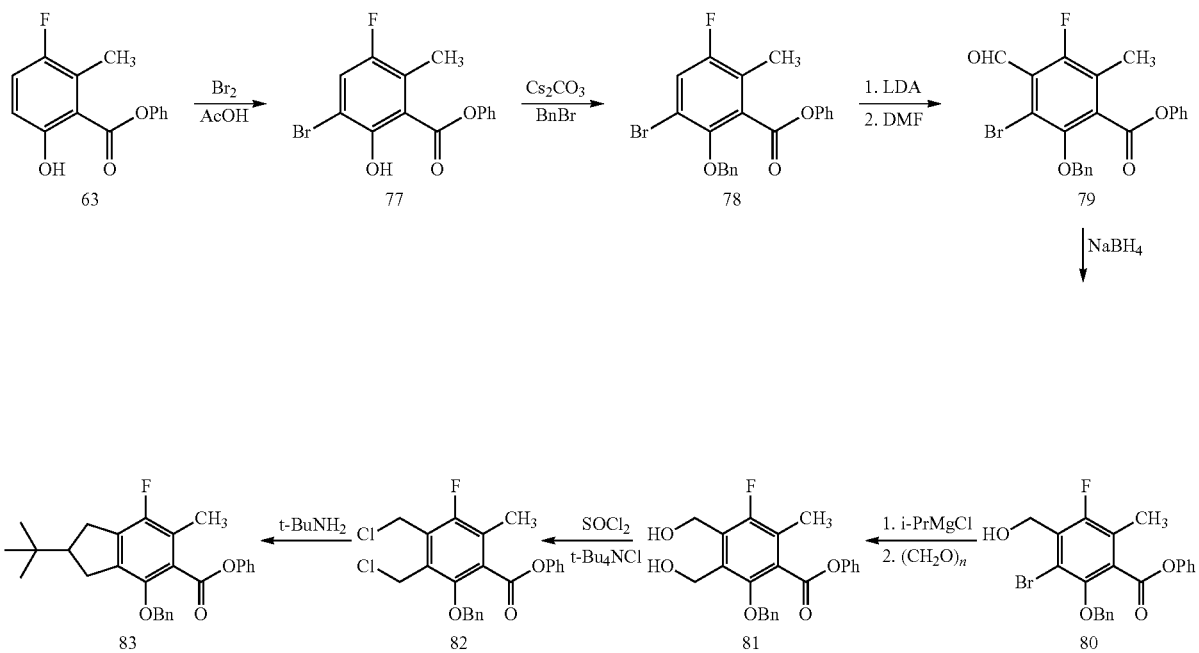

Step 1

Synthesis of Phenyl 3-bromo-5-fluoro-2-hydroxy-6-methylbenzoate 77 from Phenyl 3-fluoro-6-hydroxy-2-methylbenzoate 63

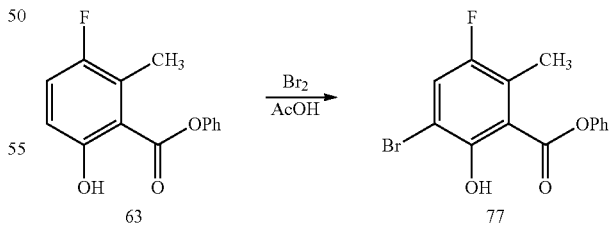

Compound 63 (4.92 g, 95% purity, 20 mmol) was dissolved in acetic acid (50 mL) and bromine (1.54 mL, 30 mmol) was added via syringe at room temp. After stirred at room temp for 2 hour, LC/MS indicated that the starting material was consumed. This reaction mixture was diluted with ethyl acetate, washed with water (3×100 mL) and brine. The organics were dried over Na$_2$SO$_4$, filtered, and concentrated under reduced pressure. This gave 7.06 g of compound 77 as light yellow solid: $^1$H NMR (400 MHz, CDCl$_3$) δ 11.14

(s, 1H), 7.52 (d, J=9.2 Hz, 1H), 7.49-7.43 (m, 2H), 7.36-7.30 (m, 1H), 7.21-7.16 (m, 2H), 2.55 (d, J=2.3 Hz, 3H).

Step 2

Synthesis of Phenyl 2-(benzyloxy)-3-bromo-5-fluoro-6-methylbenzoate 78 from Phenyl 3-bromo-5-fluoro-2-hydroxy-6-methylbenzoate 77

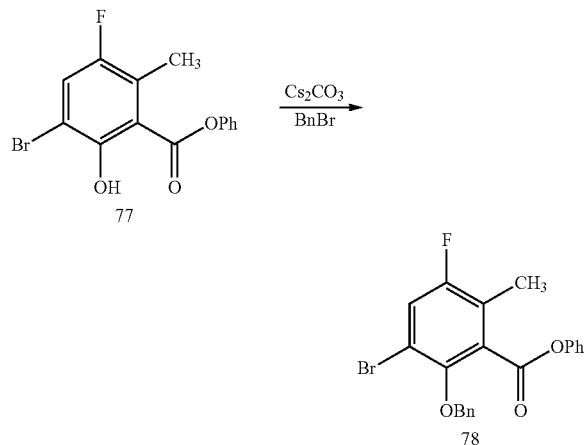

Compound 77 (crude, 1.06 g, 2.97 mmol) was dissolved in acetone (20 mL) containing potassium carbonate (821 mg, 5.94 mmol, 2.0 equiv.) and the mixture was cooled to 0° C. in an ice-bath. Benzyl bromide (540 μL, 4.45 mmol, 1.5 equiv.) was added dropwise. After 2 hrs, LC/MS indicated that the starting material was consumed 40%. The reaction mixture was heated to 50° C. for another hour the cooled and diluted with ethyl acetate (100 mL), and successively washed with water and brine. The organics were dried over $Na_2SO_4$, filtered, and concentrated under reduced pressure to afford 2.2 g of crude 78, which was purified by column chromatography (BIOTAGE® 10 g column, 2 to 5% ethyl acetate in hexane gradient), yielding 1.03 g (84% for two steps) of the pure compound 78 as a colorless oil: $^1$H NMR (400 MHz, $CDCl_3$) δ 7.50-7.47 (m, 2H), 7.40-7.33 (m, 6H), 7.25 (t, J=7.3 Hz, 1H), 7.04 (d, J=8.6 Hz, 2H), 5.09 (s, 2H), 2.32 (d, J=1.8 Hz, 3H).

Step 3

Synthesis of Phenyl 2-(benzyloxy)-3-bromo-5-fluoro-4-formyl-6-methylbenzoate 79 from Phenyl 2-(benzyloxy)-3-bromo-5-fluoro-6-methylbenzoate 78

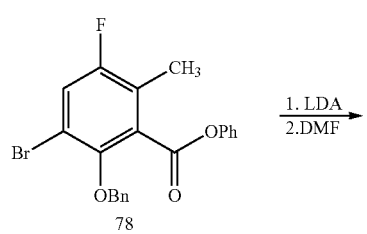

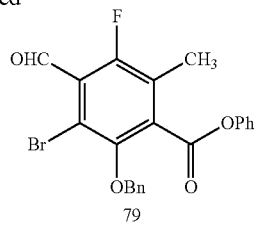

A LDA solution was prepared by adding n-BuLi (1.6 M in hexane, 5.1 mL, 8.16 mmol, 1.5 equiv) to a solution of diisopropylamine (1.15 mL, 8.16 mmol) in THF (15 mL) at −78° C. The reaction mixture was warmed up to −20° C. and stirred for 15 min. Thr LDA solution was cooled again to −78° C. to which was added dropwise a solution of compound 78 (2.26 g, 5.44 mmol) in THF (5 mL), forming an orange-red solution. After 10 min, DMF (1.26 mL, 16.3 mmol, 3 equiv) was added dropwise. The reaction solution was allowed to warm up to −20° C. over 1 hour and was then quenched with $NH_4Cl$ (saturated aqueous solution). The reaction mixture was diluted with ethyl acetate (100 mL) and washed with water and brine. The organics were dried over $Na_2SO_4$, filtered, and concentrated under reduced pressure. This gave 2.42 g of the crude compound 79, which was purified by column chromatography (BIOTAGE® 24 g column, 5 to 10% ethyl acetate in hexane gradient), yielding 2.23 g (92%) of the pure compound 79 as light yellow solid. $^1$H NMR (400 MHz, $CDCl_3$) δ 10.37 (s, 1H), 7.51-7.47 (m, 2H), 7.40-7.33 (m, 5H), 7.27 (t, J=7.3 Hz, 1H), 7.06-7.02 (m, 2H), 5.12 (s, 2H), 2.37 (d, J=2.3 Hz, 3H).

Step 4

Synthesis of Phenyl 2-(benzyloxy)-3-bromo-5-fluoro-4-(hydroxymethyl)-6-methylbenzoate 80 from Phenyl 2-(benzyloxy)-3-bromo-5-fluoro-4-formyl-6-methylbenzoate 79

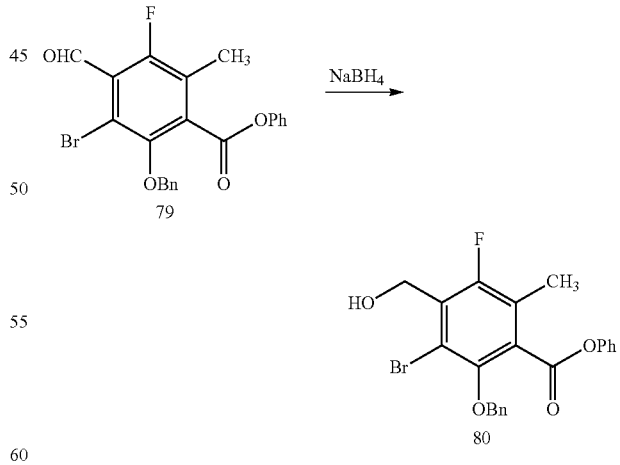

Compound 79 (416 mg, 0.94 mmol) was dissolved in methanol (5 mL) and sodium borohydride (75.6 mg, 2 mmol) was added in several portions. After stirring at ambient temperature for 30 min, the reaction mixture was diluted with ethyl acetate and washed with water (2×20 mL) and brine. The organics were dried over $Na_2SO_4$, filtered, and concentrated under reduced pressure. The crude material was purified by column chromatography (BIOTAGE® 10 g column, 5 to 20% ethyl acetate in hexane gradient), yielding 367 mg (87.7%) of the pure compound 80 as a colorless oil. $^1$H NMR (400 MHz, CDCl$_3$) δ 10.37 (s, 1H), 7.49 (dd, J=7.8, 2.3 Hz, 2H), 7.40-7.33 (m, 5H), 7.25 (t, J=7.8 Hz, 1H), 7.07-7.02 (m, 2H), 5.10 (s, 2H), 4.91 (dd, J=6.9, 2.3 Hz, 2H), 2.35 (d, J=2.3 Hz, 3H); MS (ESI) m/z 467.10, 469.08 (M+Na).

Step 5

Synthesis of Phenyl 2-(benzyloxy)-5-fluoro-3,4-bis(hydroxymethyl)-6-methylbenzoate 81 from Phenyl 2-(benzyloxy)-3-bromo-5-fluoro-4-(hydroxymethyl)-6-methylbenzoate 80

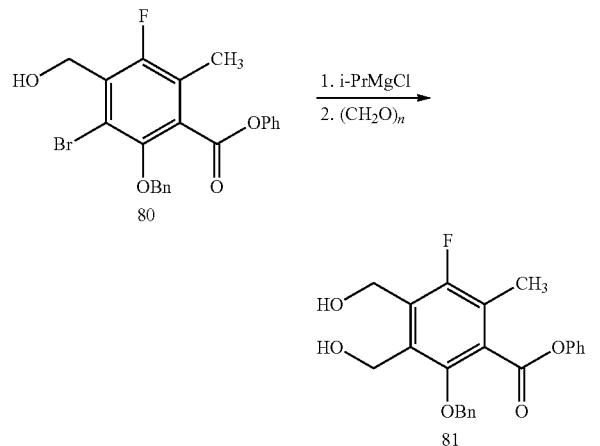

i-Propyl magnesium chloride/lithium chloride solution (1.2 M in THF, 4.4 mL, 5.3 mmol) was added to a −78° C. solution of compound 80 (472 mg, 1.06 mmol) in THF (10 mL). The reaction mixture was allowed to warm to 0° C. over 1 hour. Paraformaldehyde (318 mg, 10.6 mmol) was added, and the reaction was allowed to warm to ambient temperature. After 1 hour, the reaction mixture was heated to 40° C. then cooled, quenched with ammonium chloride (saturated aqueous solution) and extracted with EtOAc (2×). The combined extracts were dried over Na$_2$SO$_4$, filtered, and concentrated under reduced pressure. The crude material was purified by column chromatography (BIOTAGE® 10 g column, 10 to 35% EtOAc in hexane gradient), yielding 337 mg (80%) of compound 81 as a thick oil. $^1$H NMR (400 MHz, CDCl$_3$) δ 7.45-7.34 (m, 7H), 7.30-7.23 (m, 1H), 7.10 (d, J=7.8 Hz, 2H), 5.08 (s, 2H), 4.85 (s, 2H), 4.76 (s, 2H), 2.39 (d, J=2.3 Hz, 3H); MS (ESI) m/z 419.19 (M+Na).

Step 6

Synthesis of Phenyl 2-(benzyloxy)-3,4-bis(chloromethyl)-5-fluoro-6-methylbenzoate 82 from Phenyl 2-(benzyloxy)-5-fluoro-3,4-bis(hydroxymethyl)-6-methylbenzoate 81

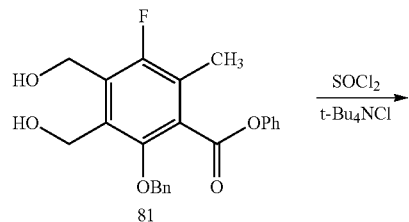

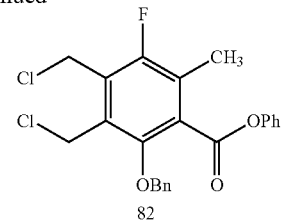

To a solution of compound 81 (2.98 g, 7.52 mmol, 1 equiv) in dichloroethane (20 mL) was added thionyl chloride (2.18 mL, 30.1 mmol, 4 equiv) and tetrabutylammonium chloride (174 mg, 0.76 mmol, 0.1 equiv). The reaction vessel was sealed and the mixture was heated to 80° C. for 2 h before being concentrated under reduced pressure. Purification of the resulting crude oil via flash column chromatography on silica gel (REDISEP®, 80 g, 4 to 6% EtOAc in hexane gradient) provided 2.66 g of compound 82 (81%) as a waxy white solid: $^1$H NMR (400 MHz, CDCl$_3$) δ 7.48-7.42 (m, 2H), 7.41-7.34 (m, 4H), 7.29-7.24 (m, 1H), 7.10-7.05 (m, 2H), 5/13 (s, 2H), 4.81 (s, 4H), 2.44-2.39 (m, 3H); MS (ESI) m/z 431.14, 433.16 (M+H).

Step 7

Synthesis of Phenyl 4-(benzyloxy)-2-tert-butyl-7-fluoro-6-methylisoindoline-5-carboxylate 83 from Phenyl 2-(benzyloxy)-3,4-bis(chloromethyl)-5-fluoro-6-methylbenzoate 82

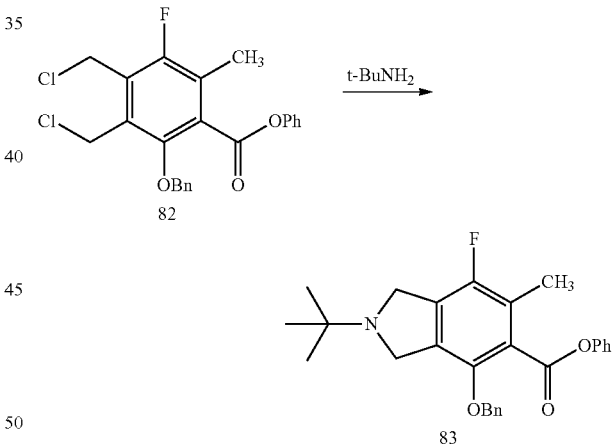

Compound 82 (120 mg, 0.277 mmol), t-butylamine (0.032 mL, 0.305 mmol) and N,N-diisopropylethylamine (0.096 mL, 0.554 mmol) were heated to 110° C. in 1,2-dimethoxyethane (1 mL). After 2 hours, additional t-butylamine (0.100 mL, 0.95 mmol) was added. After 2 more hours, additional t-butylamine (0.500 mL, 4.75 mmol) was added, and the reaction mixture was heated overnight. The reaction mixture was concentrated under reduced pressure and was purified by column chromatography (BIOTAGE® 10 g column, 5 to 20% EtOAc in hexane gradient), yielding 64.1 mg (53%) of desired compound 83. R$_f$=0.25 in 20% EtOAc in hexane; $^1$H NMR (400 MHz, CDCl$_3$) δ 7.42-7.30 (m, 7H), 7.27-7.20 (m, 1H), 7.04 (d, J=7.8 Hz, 2H), 5.02 (s, 2H), 4.08 (s, 2H), 4.04 (s, 2H), 2.33 (d, J=1.8 Hz, 3H), 1.15 (s, 9H); MS (ESI) m/z 434.29 (M+H).

Example 53

Preparation of Indoline analog 85 from Phenyl 4-(benzyloxy)-2-tert-butyl-7-fluoro-6-methylisoindoline-5-carboxylate 83

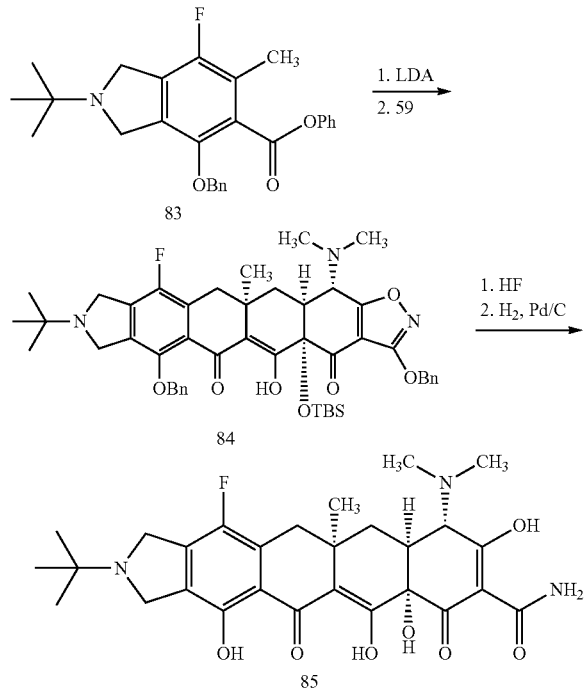

Step 1

Synthesis of protected indoline analog 84 from Phenyl 4-(benzyloxy)-2-tert-butyl-7-fluoro-6-methyl-isoindoline-5-carboxylate 83

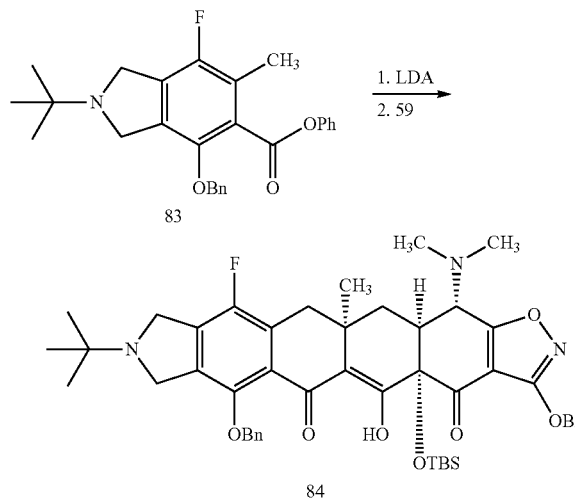

To a solution of lithium diisopropylamide (2.0 M in hexanes, 125 µL, 0.25 mmol, 3.8 equiv) and TMEDA (49 µL, 0.33 mmol, 5 equiv) in THF (3 mL) at −70° C. was added dropwise a solution of compound 83 (54.0 mg, 0.125 mmol, 1.2 equiv) in THF (750 µL). After 20 min, a solution of compound 59 (32.2 mg, 0.065 mmol, 1 equiv) in THF (750 µL) was added, followed by slow warming to −5° C. over 1.5 h. Excess base was quenched by the addition of a saturated, aqueous solution of ammonium chloride (1 mL). The solution was warmed to ambient temperature, poured into a saturated, aqueous solution of ammonium chloride (5 mL) and water (3 mL) and extracted with EtOAc (2×30 mL). The combined organic extracts were dried over $Na_2SO_4$, filtered, and concentrated under reduced pressure. Purification of the resulting oil via flash column chromatography on silica gel (BIOTAGE® 10 g, 3 to 25% EtOAc in hexanes gradient) provided compound 84 as a yellow oil: $^1$H NMR (400 MHz, CDCl$_3$) δ 16.4 (s, 1H), 7.49-7.38 (m, 4H), 7.38-7.26 (m, 6H), 5.34 (s, 2H), 5.03 (d, J=10.4 Hz, 1H), 4.88 (d, J=10.4 Hz, 1H), 3.00-2.91 (m, 1H), 2.74-2.64 (m, 1H), 4.05-3.99 (m, 1H), 3.98-3.84 (m, 2H), 3.93-3.56 (m, 1H), 2.47 (s, 6H), 1.22 (s, 9H), 1.23 (t, J=7.3 Hz, 3H), 0.87 (s, 9H), 0.23 (s, 3H), 0.16 (s, 3H); MS (ESI) m/z 836.54 (M−H).

Step 2

Synthesis of indoline analog 85 from protected indoline analog 84

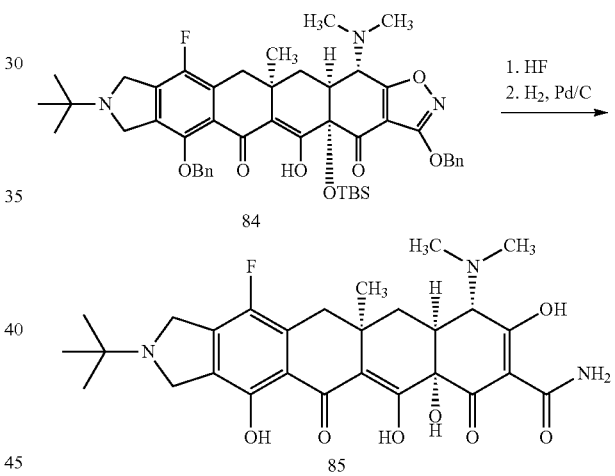

To a solution of compound 84 (25 mg, 70% pure, ~0.020 mmol, 1 equiv) in dioxane (750 µL) was added an aqueous solution of HF (50%, 200 µL). After 16 h, the reaction mixture was poured into an aqueous $K_2HPO_4$ solution (2.4 g in 25 mL) and extracted with EtOAc (2×30 mL). The combined organic layers were dried ($Na_2SO_4$), filtered, and concentrated under reduced pressure. Palladium on carbon (10%; 11 mg) was added to a solution of this crude oil in dioxane:MeOH:0.5 N HCl in MeOH (1:1:1, 1.5 mL). The flask was fitted with a septum and evacuated and back-filled three times with hydrogen gas. The reaction was stirred under an atmosphere of hydrogen gas for 85 min. The reaction mixture was filtered through CELITE® (diatomaceous earth) to remove the palladium catalyst and then concentrated under reduced pressure. Preparative reverse phase HPLC of the resulting oil provided 4.2 mg of the desired compound 85: $^1$H NMR (400 MHz, CD$_3$OD) δ 4.91-4.85 (m, 2H), 4.79-4.74 (m, 2H), 4.10 (s, 1H), 3.10-2.89 (m, 8H), 2.60 (d, J=16.5 Hz, 1H), 2.03 (dd, J=3.05, 14.0 Hz, 1H), 1.95-1.86 (m, 1H), 1.53 (s, 9H), 1.27 (d, J=4.9 Hz, 3H); MS (ESI) m/z 544.35 (M+H).

Example 54

Preparation of Pyridine analog 91 from 3,5-Dichloropyridine-4-carboxylic 86

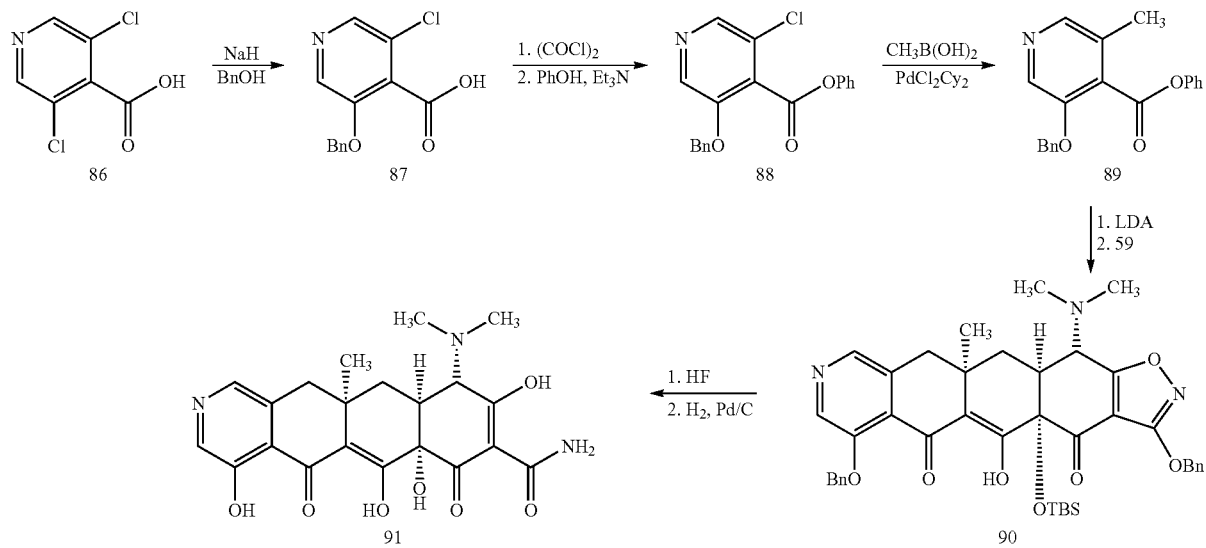

Step 1

Synthesis of 3-(Benzyloxy)-5-chloropyridine-4-carboxylic acid 87 from 3,5-Dichloropyridine-4-carboxylic 86

Step 2

Synthesis of Phenyl 3-(benzyloxy)-5-chloropyridine-4-carboxylate 88 from 3-(Benzyloxy)-5-chloropyridine-4-carboxylic acid 87

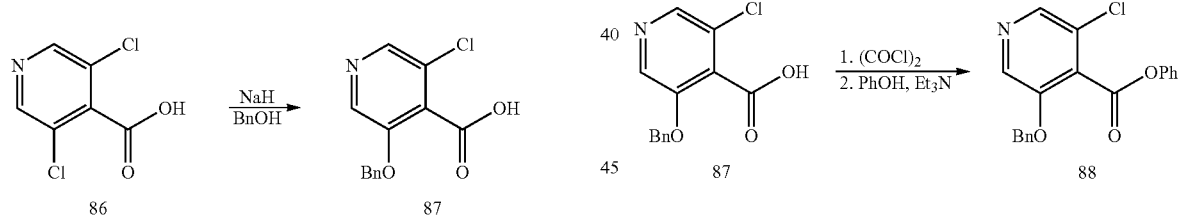

Sodium hydride (60% dispersion in mineral oil, 4.37 g, 109 mmol) was added portionwise to a solution of 3,5-dichloroisonicotinic acid (10.24 g, 53.3 mmol) in NMP (100 mL). After gas evolution ceased, benzyl alcohol (5.52 mL, 53.3 mmol) was added dropwise. After gas evolution ceased, the reaction mixture was heated to 80° C. After 1 hour, the reaction was complete and was allowed to cool to RT and stand overnight. The reaction mixture was diluted with water (300 mL) and was washed with Et$_2$O (2×100 mL, discarded). The aqueous layer was brought to pH ~2 with conc. HCl, causing a precipitate to form. The mixture was diluted with brine (100 mL) and was allowed to stand for 30 minutes. The solid was collected by filtration, washed with water (3×), and was dried in a 45° C. vacuum oven overnight. This gave 9.36 g (67%) of the product 87 as a white solid. $^1$H NMR (400 MHz, DMSO-d6) δ 14.30-14.10 (bs, 1H), 8.52 (s, 1H), 8.34 (s, 1H), 7.50-7.30 (m, 5H), 5.33 (s, 2H); MS (ESI) m/z 264.20 (M+H).

Oxalyl chloride (4.9 mL, 56 mmol) was added to a suspension of compound 86 (3.71 g, 14.1 mmol) in CH$_2$Cl$_2$ (50 mL) over ~2 minutes. DMF was added dropwise in 20 µL portions every 5 minutes until complete solution was achieved. After stirring for an additional 30 minutes, the reaction mixture was concentrated under reduced pressure. The resulting solid was dissolved in CH$_2$Cl$_2$ (50 mL) and phenol (2.65 g, 28.1 mmol), DMAP (0.172 g, 1.41 mmol), and Et$_3$N (9.76 mL, 70.4 mmol) were added sequentially. After 1 hour, the reaction mixture was diluted with CH$_2$Cl$_2$ (50 mL) and was washed with water (2×100 mL) and NaHCO$_3$ (saturated, aqueous, 100 mL). The organics were dried over Na$_2$SO$_4$, filtered, and concentrated under reduced pressure. The material was purified by column chromatography (BIOTAGE® 50 g column, 0 to 25% EtOAc in Hexanes gradient), yielding 4.20 g (88%) of compound 88 as an off-white solid. R$_f$=0.43 in 30% EtOAC/Hexanes. $^1$H NMR (400 MHz, DMSO-d6) δ 8.70 (s, 1H), 8.48 (s, 1H), 7.52-7.30 (m, 8H), 7.15-7.08 (m, 2H), 5.44 (s, 2H); MS (ESI) m/z 340.25 (M+H).

195

Step 3

Synthesis of Phenyl 3-(benzyloxy)-5-methylpyridine-4-carboxylate 89 from Phenyl 3-(benzyloxy)-5-chloropyridine-4-carboxylate 88

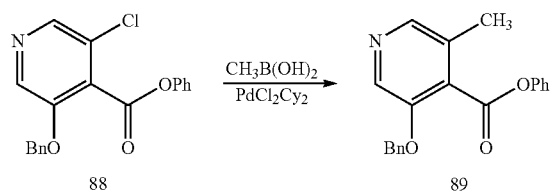 [SMILES: O=C(Oc1ccccc1)c1c(Cl)cncc1OCc1ccccc1 ; "CH3B(OH)2" ; Cc1cncc(OCc2ccccc2)c1C(=O)Oc1ccccc1 ; "PdCl2Cy2"]

Compound 88 (2.01 g, 5.92 mmol), methyl boronic acid (1.06 g, 17.7 mmol), dichlorobis(tricyclohexylphosphine)palladium(II) (102 mg, 0.296 mmol), and $K_3PO_4$ (3.76 g, 17.7 mmol) were heated to 100° C. in toluene (20 mL) and water (2 mL). After 16 hours, the reaction mixture was allowed to cool to ambient temperature, diluted with EtOAc (20 mL) and washed with water (20 mL) and brine (20 mL) before being dried over $Na_2SO_4$, filtered, and concentrated under reduced pressure. The material was purified by column chromatography (BIOTAGE® 50 g column, 0 to 40% EtOAc/Hexanes gradient), yielding 1.66 g (88%) of the compound 89 as a white solid. $R_f$=0.18 in 30% EtOAc/Hexanes. $^1$H NMR (400 MHz, DMSO-d6) δ 8.50 (s, 1H), 8.26 (s, 1H), 7.52-7.30 (m, 8H), 7.20-7.10 (m, 2H), 5.37 (s, 2H), 2.38 (s, 3H); MS (ESI) m/z 320.27 (M+H).

Step 4

Synthesis of protected pyridine analog 90 from Phenyl 3-(benzyloxy)-5-methylpyridine-4-carboxylate 89

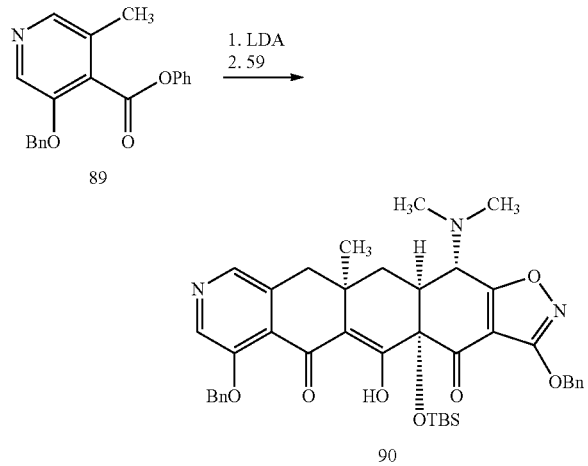

To a cooled (−70° C.) solution of lithium diisopropylamide (2.0 M in hexanes, 104 μL, 0.20 mmol, 4 equiv) and TMEDA (45 μL, 0.30 mmol, 6 equiv) in THF (1 mL) was added a solution of compound 89 (33.4 mg, 0.104 mmol, 2 equiv) in THF (500 μL). After 45 min, a solution of compound 59 (25 mg, 0.050 mmol, 1 equiv) in THF (500 μL) and the solution was allowed to warm up to −20° C. over 75 min. Excess base was quenched by the addition of a saturated, aqueous solution of ammonium chloride (1 mL). The solution was warmed to ambient temperature, poured into a saturated, aqueous solution of ammonium chloride (10 mL) and water (3 mL) and extracted with EtOAc (2×25 mL). The combined organic extracts were dried over $Na_2SO_4$, filtered, and concentrated under reduced pressure. Purification of the resulting oil via flash column chromatography on silica gel (BIOTAGE® 10 g, 9 to 80% EtOAc in hexanes gradient) provided compound 90 as a yellow oil (5 mg). MS (ESI) m/z 720.42 (M−H).

Step 5

Synthesis of Pyridine analog 91 from Phenyl 3-(benzyloxy)-5-methylpyridine-4-carboxylate 89

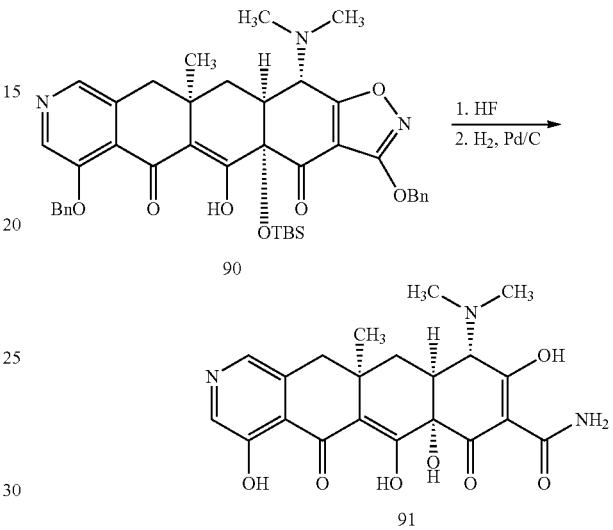

To a solution of compound 90 (5 mg) in dioxane (700 μL) was added an aqueous solution of HF (50%, 200 μL). After 4.5 h, the reaction mixture was poured into an aqueous $K_2HPO_4$ solution (2.4 g in 25 mL) and extracted with EtOAc (2×30 mL). The combined organic layers were dried ($Na_2SO_4$), filtered, and concentrated under reduced pressure. Palladium on carbon (10%; 11 mg) was added to a solution of this crude oil in dioxane:MeOH:0.5 N HCl in MeOH (1:1:1, 900 μL). The flask was fitted with a septum and evacuated and back-filled three times with hydrogen gas. The reaction was stirred under an atmosphere of hydrogen gas for 80 min. The reaction mixture was filtered through CELITE® (diatomaceous earth) and concentrated under reduced pressure. Preparative reverse phase HPLC of the resulting oil using provided 0.79 mg of the desired compound 91: $^1$H NMR (400 MHz, CD$_3$OD) δ 8.54 (s, 1H), 8.28 (s, 1H), 4.13 (s, 1H), 3.19-2.93 (m, 9H), 2.13-2.05 (m, 1H), 2.01-1.92 (m, 1H), 1.30 (s, 3H); MS (ESI) m/z 430.06 (M+H).

Example 55

Synthesis of silyl dienol ether 92

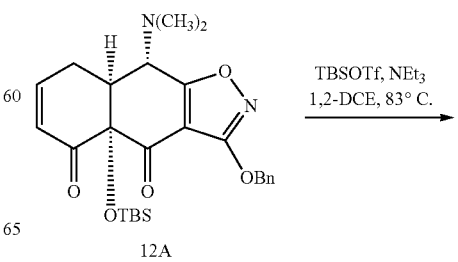

-continued

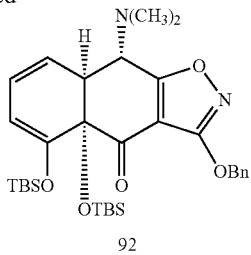

92

To a stirred solution of the AB enone 12A (1.055 g, 2.19 mmol) in dry 1,2-dichloroethane (25 mL) under an atmosphere of Ar was added triethylamine (2.44 mL, 8.0 eq.) and t-butyldimethylsilyl trifluoromethanesulfonate (2.0 mL, 4.0 eq.). The resultant solution was heated to relux and stirred 16 h under an inert atmosphere. The reaction mixture was poured over NaHCO$_3$ sat. aq. (60 mL) and extracted with ethyl acetate (2×70 mL). The combined organics were washed with NaHCO$_3$ sat. aq., brine (60 mL), dried (Na$_2$SO$_4$), and concentrated in vacuo. Flash column chromatography (SiO$_2$, 10% ethyl acetate in hexanes) of the residue provided the silyl dienol ether 92 ((4aS,8aS,9S)-3-(benzyloxy)-5-((tert-butyldimethylsilyl)oxy)-9-(dimethylamino)-4-a-hydroxy-8a,9-dihydronaphthol-[2,3-d]isoxazol-4(4aH)-one) as a waxy off-white solid (1.12 g, 86%): R$_f$=0.68 (20% ethyl acetate in hexanes); R$_f$=0.79 (20% ethyl acetate in hexanes); IR (neat) 2929, 1716, 1510, 1247 cm$^{-1}$; $^1$H NMR (500 MHz, CDCl$_3$) δ 7.48 (d, J=7.8 Hz, 2H), 7.35 (m, 3H), 5.98 (dd, J=9.3, 5.9 Hz, 1H), 5.87 (dd, J=9.3, 5.9 Hz, 1H), 5.32 (m, 2H), 5.25 (d, J=5.8 Hz, 1H), 3.78 (d, J=10.3 Hz, 1H), 2.83 (dd, J=9.8, 5.9 Hz, 1H), 2.48 (s, 6H), 0.82 (s, 9H), 0.77 (s, 9H), 0.15 (s, 6H), 0.13 (s, 3H), −0.04 (s, 3H); $^{13}$C NMR (500 MHz, CDCl$_3$) δ 188.7, 181.8, 167.7, 151.0, 139.3, 135.1, 128.9, 128.5, 128.4, 123.0, 122.9, 107.9, 103.4, 94.7, 81.7, 72.3, 64.2, 48.1, 42.4, 25.8, 25.4, 18.9, 17.8, −2.8, −3.4, −4.5, −5.3; HRMS for C$_{32}$H$_{48}$N$_2$O$_5$Si$_2$ [MH+] m/z calc. 597.31745. found 596.31789.

Example 56

Synthesis of C5-Bromoenone 93

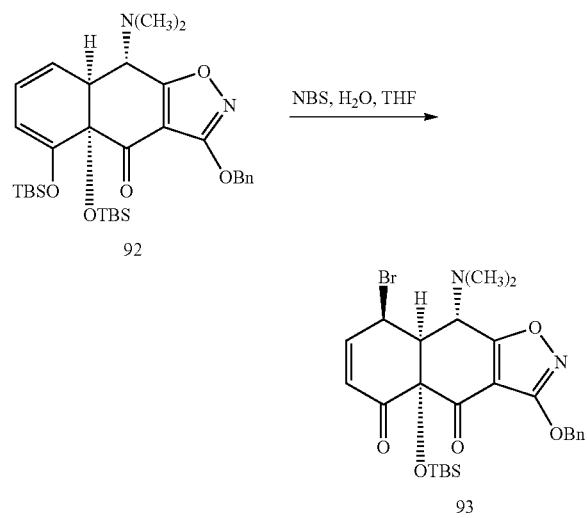

To a stirred solution of the silyl dienol ether 92 (3.048 g, 5.11 mmol) in THF (40 mL) with H$_2$O (10 mL) was added N-bromosuccinimide (1.09 g, 6.13 mmol, 1.2 eq.) which dissolved over approximately two minutes, at which point the reaction was determined to be complete (TLC monitoring). The reaction mixture was poured over NaHCO$_3$ sat. aq. (100 mL) and extracted with ethyl acetate (2×120 mL). The combined organics were washed with brine (100 mL), dried (Na$_2$SO$_4$), and concentrated in vacuo. Flash column chromatography (SiO$_2$, 20% ethyl acetate in hexanes) of the residue provided the bromoenone 93 ((4aS,8R,8aS,9S)-3-(benzyloxy)-8-bromo-4-a-((tert-butyldimethylsilyl)oxy)-9-(dimethylamino)-8a,9-dihydronaphtho[2,3-d]isoxazole-4,5(4aH,8H)-dione) as a yellow solid (2.456 g, 86%): R$_f$=0.50 (20% ethyl acetate in hexanes); IR (neat) 2935, 1722, 1688, 1616, 1514, 1473 cm$^{-1}$; $^1$H NMR (500 MHz, CDCl$_3$) δ 7.50 (d, J=6.8 Hz, 2H), 7.37 (m, 3H), 6.88 (m, 1H), 6.10 (d, J=10.2 Hz, 1H), 5.37 (s, 2H), 5.34 (d, J=4.4 Hz, 1H), 3.55 (d, J=10.7 Hz, 1H), 3.22 (d, J=10.7 Hz, 1H), 2.52 (s, 6H), 0.94 (s, 9H), 0.22 (s, 3H), 0.06 (s, 3H); $^{13}$C NMR (500 MHz, CDCl$_3$) δ 193.3, 186.3, 179.4, 167.4, 145.1, 134.9, 128.6, 128.6, 128.4, 127.3, 82.7, 72.7, 60.8, 53.0, 42.0, 38.2, 26.4, 19.3, 17.8, 12.3, −2.4, −2.7; HRMS for C$_{26}$H$_{33}$N$_2$O$_5$SiBr [MH+] m/z calc. 561.14149. found 561.14899.

Example 57

Synthesis of azidoenone 94

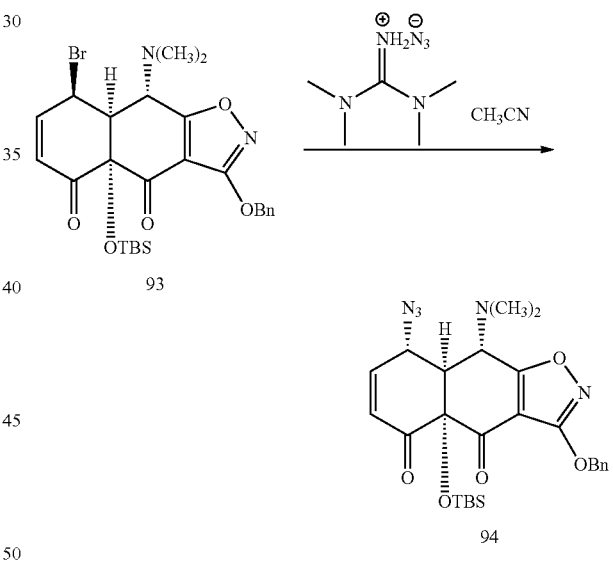

To a stirred solution of the bromoenone 93 (790 mg, 1.41 mmol) in dry acetonitrile (12 mL) under an atmosphere of Ar at room temperature was added tetramethylguanidinium azide (660 mg, 5.64 mmol, 4.0 eq.). After 30 min, the mixture was added dropwise via cannula to methyl t-butyl ether (200 mL). The mixture was dried (Na$_2$SO$_4$), filtered over CELITE® (diatomaceous earth), and the filtrate was concentrated in vacuo. Flash column chromatography (SiO$_2$, 10% ethyl acetate in hexanes) of the residue provided the azidoenone 94 ((4aS,8S,8aR,9S)-8-azido-3-(benzyloxy)-4-a-((tert-butyldimethylsilyl)oxy)-9-(dimethylamino)-8a,9-dihydronaphtho[2,3-d]isoxazole-4,5(4aH,8H)-dione) as a pink powder which could be recrystallized from hot hexanes (412 mg, 60%) to off-white needles: R$_f$=0.68 (20% ethyl acetate in hexanes); $^1$H NMR (500 MHz, CDCl$_3$) δ 7.49 (d, J=7.0 Hz, 2H), 7.37 (m, 3H), 6.72 (dd, J=8.0, 6.5 Hz, 1H), 6.10 (dd, J=10.5, 3.0 Hz, 1H), 5.34 (s, 2H), 5.18 (m, 1H), 4.04 (d, J=8.5 Hz, 1H), 3.12 (m, 1H), 2.44 (s, 6H), 0.86 (s, 9H), 0.30 (s, 3H), 0.05 (s, 3H); $^{13}$C NMR (500 MHz, CDCl$_3$) δ 190.9, 185.6, 179.8, 166.9, 147.9, 134.8, 128.6, 128.5, 128.5, 128.4, 108.9, 83.4, 72.6, 58.0, 57.9, 51.5, 41.2, 31.2, 29.7, 26.0, 18.9, 1.0, −2.4, −3.9; HRMS for C$_{26}$H$_{33}$N$_5$O$_5$Si [MH+] m/z calc. 524.23237. found 524.23489.

Example 58

Synthesis of C5-Michael-Claisen product 96

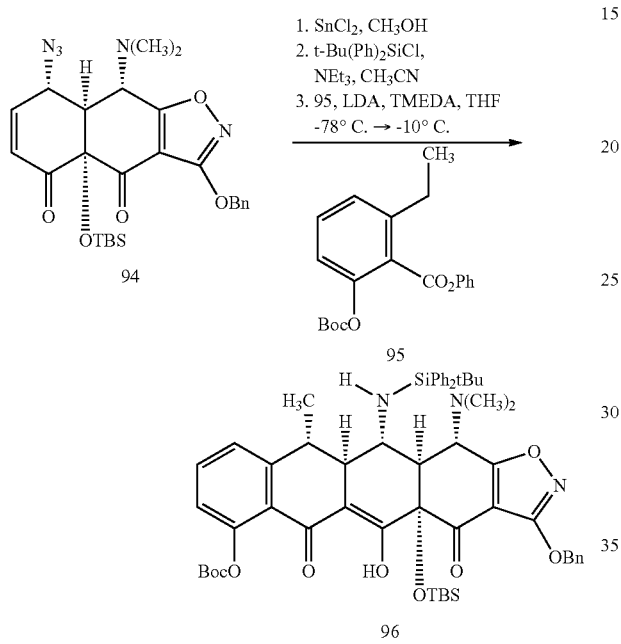

To a stirred suspension of azidoenone 94 (345 mg, 0.659 mmol) in methanol (10 mL) was added anhydrous stannous chloride (375 mg, 1.97 mmol, 3.0 eq.). The mixture was stirred 12 h at 23° C. and concentrated in vacuo. The residue was suspended between methyl t-butyl ether (10 mL) and 0.5 M NaOH aq. (15 mL) and stirred vigorously until both layers were clear. The organic layer was collected and the aqueous layer was further extracted with methyl t-butyl ether (3×10 mL). The combined organics were dried (Na$_2$SO$_4$) and concentrated to provide the intermediate aminoenone as a gray solid, pure by $^1$H NMR. The intermediate amine was dissolved in dry acetonitrile (4 mL) under an atmosphere of Ar. To this was added triethylamine (450 μL, 3.23 mmol, 5.0 eq.) and t-butyldiphenylsilyl chloride (339 μL, 1.30 mmol, 2.02 eq.) and the mixture stirred 1 h. The reaction mixture was diluted in methyl t-butyl ether (25 mL) and washed with 0.5M NaOH aq. (2×20 mL), brine (20 mL), dried (Na$_2$SO$_4$) and concentrated in vacuo to the desired bis-silylated aminoenone as a brown oil, pure by $^1$H NMR, and was used without further purification.

A solution of lithium diisopropylamide (LDA, 0.5M in THF) was prepared immediately prior to its use and kept under an atmosphere of Ar (g). To a stirred solution of compound 95 (880 mg, 2.58 mmol, 4.0 eq.) in dry THF (12 mL) with dry TMEDA (distilled from CaH$_2$, 423 μL, 2.84 mmol, 4.4 eq.) under an atmosphere of Ar (g) at −78° C. was added LDA (5.7 mL, 2.84 mmol, 4.4 eq.). After allowing to stir 30 min at −78° C., during which time the solution became a deep red color, the crude bis-silylated aminoenone (0.645 mmol, 1.0 eq.) was added as a solution in dry THF (4 mL) and the mixture was stirred an additional 40 min. The reaction was slowly warmed to −10° C. over 2 hrs, at which point it was quenched by the addition of pH=7 buffer. The aqueous layer was adjusted to pH=7, then extracted with dichloromethane (2×20 mL) and the organic layer dried (Na$_2$SO$_4$) and concentrated. Flash column chromatography (SiO$_2$, 20% ethyl acetate in hexanes) of the residue provided the Michael-Claisen product 96 ((4aS,11R,11aR,12S,12aR,13S)-3-(benzyloxy)-4-a-((tert-butyldimethylsilyl)oxy)-12-((tert-butyldiphenylsilyl)amino)-13-(dimethylamino)-5-hydroxy-11-methyl-4,6-dioxo-4,4-a,6,11,11a,12,12a,13-octahydrotetraceno[2,3-d]isoxazol-7-yl tert-butyl carbonate) (411 mg, 65% for three steps) as a bright yellow foam: R$_f$=0.57 (30% ethyl acetate in hexanes); IR (neat) 2929, 1759, 1716, 1604, 1510, 1147 cm$^{-1}$; $^1$H NMR (500 MHz, CDCl$_3$) δ 17.33 (s, 1H), 7.28-7.54 (m, 16H), 7.05 (dd, J=7.8, 6.4 Hz, 2H), 5.44 (q, J=8.2 Hz, 2H), 3.60 (s, 1H), 3.35 (d, J=12.2 Hz, 1H), 3.16 (m, 1H), 2.75 (dd, J=8.3, 3.0 Hz, 1H) 2.35 (s, 1H), 2.21 (s, 6H), 1.60 (m, 1H), 1.58 (s, 9H), 0.81 (s, 9H), 0.70 (bs, 3H), 0.60 (s, 3H), −0.10 (s, 3H); $^{13}$C NMR (500 MHz, CDCl$_3$) δ 193.4, 188.2, 184.3, 180.7, 167.8, 151.6, 150.4, 147.7, 146.8, 136.3, 136.3, 135.2, 134.9, 134.0, 133.7, 129.9, 129.3, 128.4, 128.4, 127.9, 127.3, 124.0, 122.7, 121.9, 114.3, 108.3, 105.6, 97.4, 83.4, 72.1, 61.3, 54.2, 52.6, 45.1, 42.2, 31.9, 27.7, 27.2, 25.7, 18.9, 18.8, 17.0, −3.1, −3.2; HRMS for C$_{56}$H$_{69}$N$_3$O$_9$Si$_2$ [MH+] m/z calc. 984.46451. found 984.46680.

Example 59

Synthesis of C$_{5-5}$-amino-6-deoxytetracycline 97

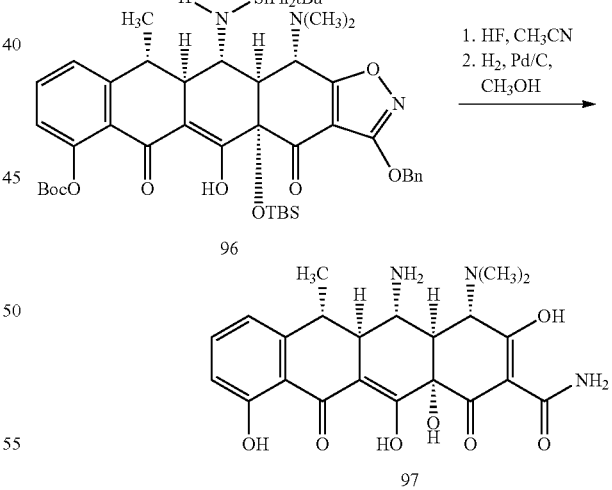

Concentrated aqueous hydrofluoric acid solution (48 wt %, 1.5 mL) was degassed with bubbling Ar and added to a degassed (Ar) solution of the Michael-Claisen product 96 (9.1 mg, 0.0089 mmol) in acetonitrile (1.5 mL) in a polypropylene reaction vessel at 23° C. The reaction solution was stirred vigorously under an atmosphere of Ar at 23° C. for 36 h. To this mixture was added a suspension of palladium on activated carbon (10 wt %, 22 mg) in methanol (degassed with bubbling Ar) in one portion at 23° C. An atmosphere of hydrogen was introduced by briefly evacuating the flask, then flushing with pure hydrogen (1 atm). The yellow reaction mixture was stirred at 23° C. for 1 h, then was cooled in a 4° C. bath and quenched by the dropwise addition of methoxytrimethylsilane until bubbling ceased. The mixture was filtered through a syringe filter and the filtrate concentrated, providing a yellow solid. The product was purified by preparatory HPLC using an AGILENT TECHNOLOGIES® C18 column [10 μM, 250×21.2 mm, UV detection at 350 nm, Solvent A: 0.1% TFA aq., Solvent B: acetonitrile, isochratic elution 15% B, flow rate: 15 mL/min]. Fractions eluting at 39 min were collected and concentrated, affording 5-aminodoxycycline trifluoracetate 97 as a pale yellow powder (2.2 mg, 57% for two steps): $^1$H NMR (500 MHz, CD$_3$OD) δ 7.47 (t, J=8.0, 7.5 Hz, 1H), 7.00 (d, J=7.5 Hz, 1H), 6.82 (d, J=8.0 Hz, 1H), 4.49 (s, 1H), 4.18 (d, J=10.0 Hz, 1H), 2.8-3.12 (m, 3H), 3.10 (s, 6H), 1.49 (d, J=6.0 Hz, 3H); HRMS for C$_{22}$H$_{25}$N$_3$O$_7$ [MH+] m/z calc. 444.17653. found 444.17616.

Example 60

Synthesis of C5-substituted Enones 98 and 99

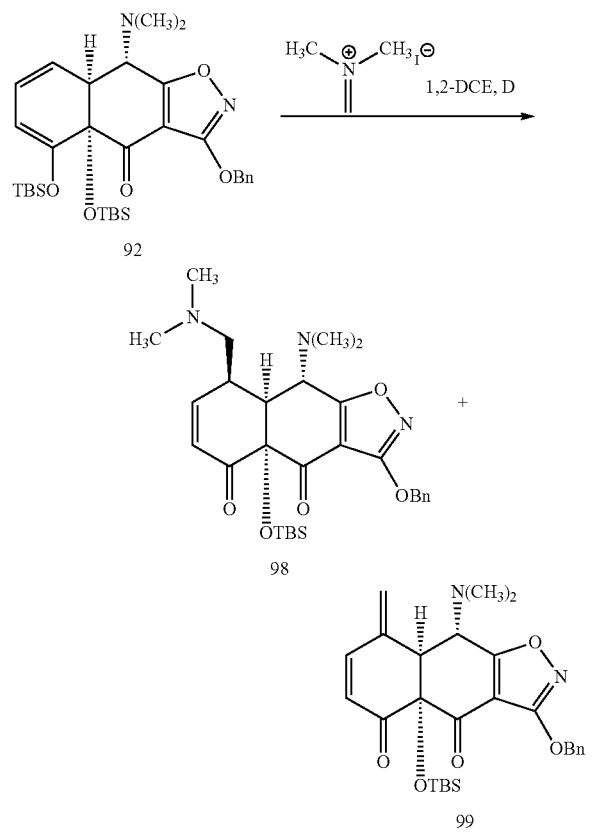

((tert-butyldimethylsilyl)oxy)-9-(dimethylamino)-8-methylene-8a,9-dihydronaphtho[2,3-d]isoxazole-4,5(4aH,8H)-dione (B)), and flushing with ethyl acetate to elute enone 98 ((4aS,8R,8aS,9S)-3-(benzyloxy)-4-a-((tert-butyldimethylsilyl)oxy)-9-(dimethylamino)-8-((dimethylamino)methyl)-8a, 9-dihydronaphtho[2,3-d]isoxazole-4,5(4aH,8H)-dione (A)) of the residue provided the products 98 (139 mg, 40%) as a bright yellow oil and 99 (154 mg, 48%) as an orange solid: Enone 98: R$_f$=0.05 (20% ethyl acetate in hexanes); $^1$H NMR (500 MHz, CDCl$_3$) δ 7.52 (d, J=6.9 Hz, 2H), 7.41 (dd, J=7.8, 6.8 Hz, 2H), 7.36 (d, J=7.3 Hz, 1H), 6.92 (m, 1H), 6.10 (dd, J=10.2, 1.9 Hz, 1H), 5.38 (s, 2H), 3.59 (d, J=11.3 Hz, 1H), 3.21 (m, 1H), 2.92 (d, J=12.2 Hz, 1H), 2.80 (dd, J=11.7, 8.8 Hz, 1H), 2.56 (dd, J=12.2, 6.3 Hz, 1H), 2.50 (s, 6H), 2.28 (s, 6H), 0.90 (s, 9H), 0.26 (s, 3H), 0.03 (s, 3H); Enone 99: R$_f$=0.52 (20% ethyl acetate in hexanes); $^1$H NMR (500 MHz, CDCl$_3$) δ 7.52 (d, J=7.4 Hz, 2H), 7.41 (dd, J=7.4, 5.9 Hz, 2H), 7.37 (d, J=5.9 Hz, 1H), 7.13 (d, J=10.3 Hz, 1H), 6.00 (d, J=10.3 Hz, 1H), 5.64 (s, 1H), 5.52 (s, 1H), 5.38 (s, 2H), 3.74 (d, J=10.3 Hz, 1H), 3.27 (d, J=10.3 Hz, 1H), 2.48 (s, 6H), 0.80 (s, 9H), 0.24 (s, 3H), 0.07 (s, 3H).

Example 61

Synthesis of C5-Michael-Claisen Product 100

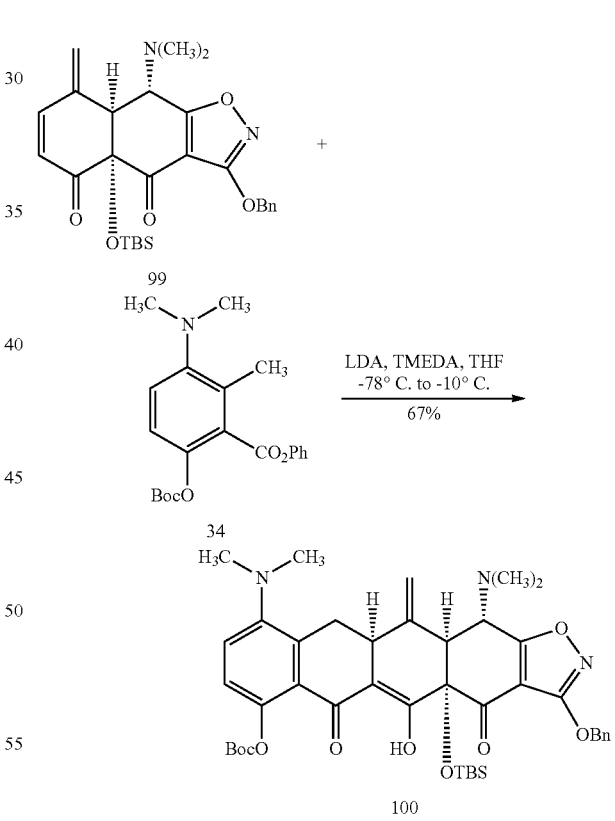

To a stirred solution of the silyl dienol ether 92 (362 mg, 0.652 mmol) in 1,2-dichloroethane (10 mL) was added Eschenmoser's salt (150 mg, 0.80 mmol, 1.2 eq.). The mixture was heated to reflux and stirred 14 h. After cooling to room temperature, the solution was diluted in CH$_2$Cl$_2$ (25 mL) and washed with sat. aq. NaHCO$_3$ (2×25 mL), the organic layer was dried (Na$_2$SO$_4$) and concentrated in vacuo. Flash column chromatography (SiO$_2$, 20% ethyl acetate in hexanes to elute enone 99 ((4aS,8aS,9S)-3-(benzyloxy)-4-a-

A solution of lithium diisopropylamide (LDA, 0.5M in THF) was prepared immediately prior to its use and kept under an atmosphere of Ar (g). To a stirred solution of phenylester 34 (59 mg, 0.160 mmol, 4.0 eq.) in dry THF (3 mL) with dry TMEDA (distilled from CaH$_2$, 26 μL, 0.176 mmol, 4.4 eq.) under an atmosphere of Ar (g) at −78° C. was added LDA (352 μL, 0.176 mmol, 4.4 eq.). After allowing to stir 30 min at −78° C., during which time the solution became a deep red color, enone 99 (20 mg, 0.040 mmol, 1.0 eq.) was added as a solution in dry THF (1 mL) and the mixture was stirred an additional 40 min. The reaction was slowly warmed to −10° C. over 1.5 hrs, at which point it was quenched by the addition of pH 7 buffer. The pH of the aqueous layer was adjusted to 7, which was then extracted with dichloromethane (3×25 mL) and the organic layer dried ($Na_2SO_4$) and concentrated. Flash column chromatography ($SiO_2$, 20% ethyl acetate in hexanes, then 50% ethyl acetate in hexanes) of the residue provided the Michael-Claisen product 100 ((4aS,11aS,12aS,13S)-3-(benzyloxy)-4-a-((tert-butyldimethylsilyl)oxy)-10,13-bis(dimethylamino)-5-hydroxy-12-methylene-4,6-dioxo-4,4-a,6,11,11a,12,12a,13-octahydrotetraceno[2,3-d]isoxazol-7-yl tert-butyl carbonate) (17.0 mg, 57%) as a bright yellow oil: $R_f$=0.17 (15% ethyl acetate in hexanes); $^1$H NMR (500 MHz, $CDCl_3$) δ 15.65 (s, 1H), 7.50 (d, J=7.4 Hz, 2H), 7.40 (dd, J=7.4, 6.8 Hz, 2H), 7.35 (d, J=7.4 Hz, 1H), 7.25 (d, J=8.8 Hz, 1H), 7.05 (d, J=8.8 Hz, 1H), 5.42 (s, 1H), 5.37 (s, 2H), 5.22 (s, 1H), 4.18 (d, J=10.7 Hz, 1H), 3.51-3.62 (m, 2H), 3.49 (s, 1H), 3.15 (d, J=10.3 Hz, 1H), 2.66 (s, 6H), 2.53 (s, 6H), 1.55 (s, 9H), 0.77 (s, 9H), 0.26 (s, 3H), 0.10 (s, 3H). $^{13}$C NMR (500 MHz, $CDCl_3$) 6186.4, 184.4, 181.6, 180.4, 167.7, 152.1, 149.8, 145.3, 140.6, 136.6, 134.9, 128.5, 128.4, 128.4, 124.1, 123.9, 122.2, 119.1, 108.3, 106.7, 83.7, 81.9, 72.5, 61.0, 6.0, 53.4, 44.1, 41.6, 36.4, 34.5, 30.8, 27.6, 25.8, 18.9, −2.6, −3.9.

Example 62

Synthesis of C5-methylene-minocycline 101

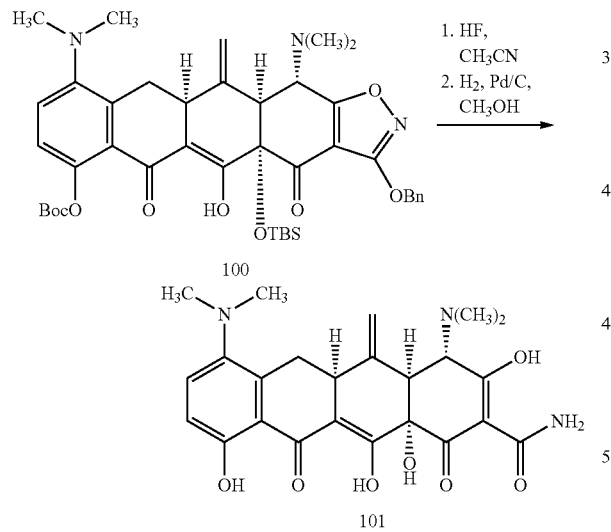

Concentrated aqueous hydrofluoric acid solution (48 wt %, 1.5 mL) was added to a solution of the Michael-Claisen product 100 (17 mg, 0.022 mmol) in acetonitrile (1.5 mL) in a polypropylene reaction vessel at 23° C. The reaction solution was stirred vigorously at 23° C. for 30 h, then was poured into aq. $K_2HPO_4$ and adjusted to pH=7. The resulting mixture was extracted with ethyl acetate (3×25 mL). The organic extracts were combined and the combined solution was dried ($Na_2SO_4$) and concentrated, affording a yellow solid. Methanol (4 mL) was added to the crude product, forming a yellow solution. Palladium on activated carbon (10 wt %, 22 mg) was added in one portion at 23° C. An atmosphere of hydrogen was introduced by briefly evacuating the flask, then flushing with pure hydrogen (1 atm). The yellow reaction mixture was stirred at 23° C. for 20 min, then was filtered through a syringe filter plug. The filtrate was concentrated, providing a yellow solid. The product was purified by preparatory HPLC in using an AGILENT TECHNOLOGIES® C18 column [10 μM, 250×21.2 mm, UV detection at 350 nm, Solvent A: 0.1% TFA aq., Solvent B: acetonitrile, gradient elution 5→35% B over 40 min, flow rate: 10 mL/min]. Fractions eluting at 24-25 min were collected and concentrated, affording 5-methylenemi-nocycline trifluoracetate 101 as a pale yellow powder (1.7 mg, 17% for two steps): $^1$H NMR (500 MHz, $CD_3OD$) δ 7.67 (d, J=8.8 Hz, 1H), 6.95 (d, J=9.3 Hz, 1H), 5.62 (bs, 1H), 5.45 (bs, 1H), 4.65 (bs, 1H), 3.78 (bs, 1H), 3.57 (d, J=5.4 Hz, 1H), 3.07 (s, 6H), 3.02-3.17 (m, 2H), 2.93 (s, 6H); HRMS for $C_{24}H_{27}N_3O_7$ [MH+] m/z calc. 470.19218. found 470.19163.

Example 63

Synthesis of C5-Michael-Claisen Product 102

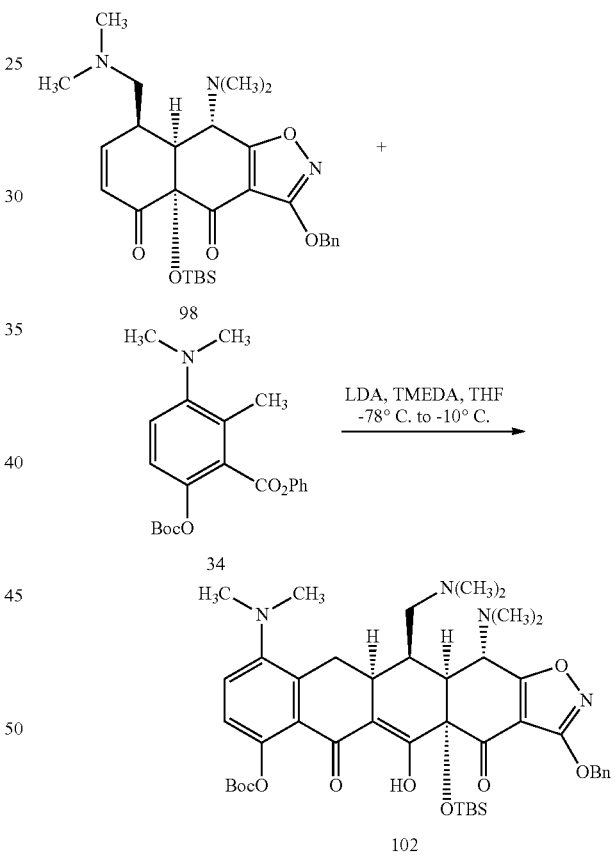

A solution of lithium diisopropylamide (LDA, 0.5M in THF) was prepared immediately prior to its use and kept under an atmosphere of Ar (g). To a stirred solution of phenylester 34 (59 mg, 0.160 mmol, 4.0 eq.) in dry THF (3 mL) with dry TMEDA (distilled from $CaH_2$, 26 μL, 0.176 mmol, 4.4 eq.) under an atmosphere of Ar (g) at −78° C. was added LDA (352 μL, 0.176 mmol, 4.4 eq.). After allowing to stir 30 min at −78° C., during which time the solution became a deep red color, enone 98 (22 mg, 0.040 mmol, 1.0 eq.) was added as a solution in dry THF (1 mL) and the mixture was stirred an additional 40 min. The reaction was slowly warmed to −10°

C. over 1.5 hrs, at which point it was quenched by the addition of pH 7 buffer. The pH of the aqueous layer was adjusted to 7, which was then extracted with dichloromethane (3×25 mL) and the organic layer dried (Na$_2$SO$_4$) and concentrated. Flash column chromatography (SiO$_2$, 20% ethyl acetate in hexanes, then 50% ethyl acetate in hexanes) of the residue provided the Michael-Claisen product 102 ((4aS,11aS,12R,12aS,13S)-3-(benzyloxy)-4-a-((tert-butyldimethylsilyl)oxy)-10,13-bis(dimethylamino)-12-((dimethylamino)methyl)-5-hydroxy-4,6-dioxo-4,4-a,6,11,11a,12,12a,13-octahydrotetraceno[2,3-d]isoxazol-7-yl tert-butyl carbonate) (25.0 mg, 78%) as a bright yellow oil: R$_f$=0.55 (50% ethyl acetate in hexanes); $^1$H NMR (500 MHz, CDCl$_3$) δ 15.69 (s, 1H), 7.52 (d, J=6.9 Hz, 2H), 7.42 (dd, J=7.4, 6.9 Hz, 2H), 7.38 (d, J=7.4 Hz, 1H), 7.25 (d, J=8.8 Hz, 1H), 7.03 (d, J=8.8 Hz, 1H), 5.39 (s, 2H), 3.71 (d, J=11.2 Hz, 1H), 3.54 (dd, J=15.1, 5.4 Hz, 1H), 2.99 (d, J=11.2 Hz, 1H), 2.82 (d, J=10.7 Hz, 1H), 2.71 (s, 6H), 2.67 (m, 1H), 2.51 (s, 6H), 2.38 (m, 1H), 2.29 (t, J=5.4 Hz, 1H), 2.26 (s, 6H), 1.55 (s, 9H), 0.91 (s, 9H), 0.25 (s, 3H), −0.01 (s, 3H).

Example 64

Synthesis of C5-dimethylaminomethylminocycline 103

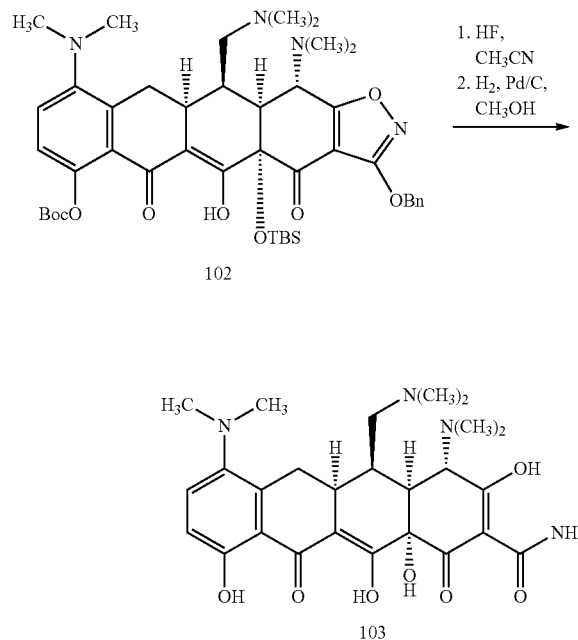

102

103

Concentrated aqueous hydrofluoric acid solution (48 wt %, 1.5 mL) was added to a solution of the Michael-Claisen product 102 (25 mg, 0.031 mmol) in acetonitrile (1.5 mL) in a polypropylene reaction vessel at 23° C. The reaction solution was stirred vigorously at 23° C. for 30 h, then was poured into aq. K$_2$HPO$_4$ and adjusted to pH=7. The resulting mixture was extracted with ethyl acetate (3×25 mL). The organic extracts were combined and the combined solution was dried (Na$_2$SO$_4$) and concentrated, affording a yellow solid. Methanol (4 mL) was added to the crude product, forming a yellow solution. Palladium on activated carbon (10 wt %, 22 mg) was added in one portion at 23° C. An atmosphere of hydrogen was introduced by briefly evacuating the flask, then flushing with pure hydrogen (1 atm). The yellow reaction mixture was stirred at 23° C. for 20 min, then was filtered through a syringe filter plug. The filtrate was concentrated, providing a yellow solid. The product was purified by preparatory HPLC in using an AGILENT TECHNOLOGIES® C18 column [10 μM, 250×21.2 mm, UV detection at 350 nm, Solvent A: 0.1% TFA aq., Solvent B: acetonitrile, gradient elution 5-35% B over 40 min, flow rate: 10 mL/min]. Fractions eluting at 30-32 min were collected and concentrated, affording 5-dimethylaminomethylminocycline trifluoracetate 103 as a pale yellow powder (13.7 mg, 70% for two steps): $^1$H NMR (500 MHz, CD$_3$OD) δ 7.86 (d, J=9.3 Hz, 1H), 7.04 (d, J=9.3 Hz, 1H), 5.62 (bs, 1H), 5.45 (bs, 1H), 4.65 (bs, 1H), 3.74 (dd, J=11.2, 10.7 Hz, 1H), 3.65 (d, J=10.7 Hz, 1H), 3.60 (dd, J=11.3, 6.9 Hz, 1H), 3.39 (dd, J=13.2, 4.9 Hz, 1H), 3.23 (s, 6H), 3.00 (bs, 6H), 2.89 (m, 1H), 2.62 (s, 6H), 2.61 (m, 1H), 2.32 (m, 1H); HRMS for C$_{26}$H$_{34}$N$_4$O$_7$ [MH+] m/z calc. 515.25003. found 515.24919.

Example 65

Antibacterial Activity

The antibacterial activities for the compounds of the invention were studied according to the following protocols, and are shown in FIGS. 1-7.

Minimum Inhibitory Concentration (MIC) Assay

MICs were determined according to the Clinical and Laboratory Standards Institute (CLSI) guidances (e.g., CLSI. Performance standards for antimicrobial susceptibility testing; nineteenth information supplement. CLSI document M100-S19, CLSI, 940 West Valley Road, Suite 1400, Wayne, Pa. 19087-1898, USA, 2009). Briefly, frozen bacterial strains were thawed and subcultured onto Mueller Hinton Broth (MHB) or other appropriate media (Streptococcus requires blood and Haemophilus requires hemin and NAD). Following incubation overnight, the strains were subcultured onto Mueller Hinton Agar and again incubated overnight. Colonies were observed for appropriate colony morphology and lack of contamination. Isolated colonies were selected to prepare a starting inoculum equivalent to a 0.5 McFarland standard. The starting inoculum was diluted 1:125 using MHB for further use. Test compounds were prepared by dilution in sterile water to a final concentration of 5.128 mg/mL. Antibiotics (stored frozen, thawed and used within 3 hours of thawing) and compounds were further diluted to the desired working concentrations.

The assays were run as follows. Fifty μL of MHB was added to wells 2-12 of a 96-well plate. One hundred μL of appropriately diluted antibiotics was added to well 1. Fifty μL of antibiotics was removed from well 1 and added to well 2 and the contents of well 2 mixed by pipetting up and down five times. Fifty μL of the mixture in well 2 was removed and added to well 3 and mixed as above. Serial dilutions were continued in the same manner through well 12. Fifty μL was removed from well 12 so that all contained 50 μL. Fifty μL of the working inoculum was then added to all test wells. A growth control well was prepared by adding 50 μL of working inoculum and 50 μL of MHB to an empty well. The plates were then incubated at 37° C. overnight, removed from the incubator and each well was read on a plate reading mirror. The lowest concentration (MIC) of test compound that inhibited the growth of the bacteria was recorded.

Example:

| | 1 | 2 | 3 | 4 | 5 | 6 | 7 | 8 | 9 | 10 | 11 | 12 |
|---|---|---|---|---|---|---|---|---|---|---|---|---|
| [Abt] | 32 | 16 | 8 | 4 | 2 | 1 | 0.5 | 0.25 | 0.125 | 0.06 | 0.03 | 0.015 |
| grow | − | − | − | − | − | + | + | + | + | + | + | + |

[abt] = antibiotic concentration in the well
Grow = bacterial growth (cloudiness)
Interpretation: MIC = 2 µg/mL

Example 66

Protocol for Determining Inoculum Concentration (Viable Count)

Ninety µl of sterile 0.9% NaCl was pipetted into wells 2-6 of a 96-well microtiter plate. Fifty 50 µL of the inoculum was pipetted into well 1. Ten µL from was removed from well 1 and added it to well 2 followed by mixing. Ten µL was removed from well two and mixed with the contents of well 3 and so on creating serial dilutions through well 6. Ten µL was removed from each well and spotted onto an appropriate agar plate. The plate was placed into an incubator overnight. The colonies in spots that contain distinct colonies were counted.

Viable count was calculated by multiplying the number of colonies by the dilution factor.

| | Spot from Well | | | | | |
|---|---|---|---|---|---|---|
| | 1 | 2 | 3 | 4 | 5 | 6 |
| Dilution Factor | $10^2$ | $10^3$ | $10^4$ | $10^5$ | $10^6$ | $10^7$ |

Bacterial Strains

The following bacterial strains, listed below and in FIGS. 2-7, were examined in minimum inhibitory concentration (MIC) assays.

| ORGANISM | STRAIN DESIGNATION | KEY PROPERTIES |
|---|---|---|
| Staphylococcus aureus | SA100 | ATCC 13709, MSSA, Smith strain |
| Staphylococcus aureus | SA101 | ATCC 29213, CLSI quality control strain, MSSA |
| Staphylococcus aureus | SA191 | HA-MRSA, tetracycline-resistant, lung infection model isolate |
| Staphylococcus aureus | SA161 | HA-MRSA, tetracycline-resistant, tet(M) |
| Staphylococcus aureus | SA158 | Tetracycline-resistant tet(K) |
| Staphylococcus epidermidis | SE164 | ATCC 12228, CLSI quality control strain, tetracycline-resistant |
| Enterococcus faecalis | EF103 | ATCC 29212, tet-I/R, control strain |
| Enterococcus faecalis | EF159 | Tetracycline-resistant, tet(M) |
| Enterococcus faecalis | EF327 | Wound isolate (US) tet(M) |
| Enterococcus faecium | EF404 | Blood isolate (US) tet(M) |
| Streptococcus pneumoniae | SP106 | ATCC 49619, CLSI quality control strain |
| Streptococcus pneumoniae | SP160 | Tetracycline-resistant, tet(M) |
| Streptococcus pyogenes | SP312 | 2009 clinical isolate, tet(M) |
| Streptococcus pyogenes | SP193 | S. pyogenes for efficacy models; tetS; sensitive to sulfonamides |
| Haemophilus influenzae | HI262 | Tetracycline-resistant, ampicillin-resistant |
| Moraxella catarrhalis | MC205 | ATCC 8176, CLSI quality control strain |
| Escherichia coli | EC107 | ATCC 25922, CLSI quality control strain |
| Escherichia coli | EC155 | Tetracycline-resistant, tet(A) |
| Escherichia coli | EC878 | MG1655 tolC::kan |
| Escherichia coli | EC880 | lpxA |
| Escherichia coli | EC882 | impA |
| Escherichia coli | EC200 | MDR uropathogenic; serotype O17:K52:H18; UMN 026; trimeth/sulfa-R; BAA-1161 |
| Enterobacter cloacae | EC108 | ATCC 13047, wt |
| Enterobacter cloacae | EC603 | Urine isolate (Spain) |
| Klebsiella pneumoniae | KP109 | ATCC 13883, wt |
| Klebsiella pneumoniae | KP153 | Tetracycline-resistant, tet(A), MDR, ESBL+ |
| Klebsiella pneumoniae | KP457 | 2009 ESBL+, CTX-M, OXA |
| Proteus mirabilis | PM112 | ATCC 35659 |
| Proteus mirabilis | PM385 | Urine ESBL+ isolate |
| Pseudomonas aeruginosa | PA111 | ATCC 27853, wt, control strain |
| Pseudomonas aeruginosa | PA169 | Wt, parent of PA170-173 |
| Pseudomonas aeruginosa | PA173 | PA170 ΔmexX; MexXY-(missing a functional efflux pump) |
| Pseudomonas aeruginosa | PA555 | ATCC BAA-47, wild type strain PAO1 |
| Pseudomonas aeruginosa | PA556 | Multiple-Mex efflux pump knockout strain |
| Pseudomonas aeruginosa | PA689 | Blood isolate (US) |
| Acinetobacter baumannii | AB110 | ATCC 19606, wt |
| Acinetobacter baumannii | AB250 | Cystic fibrosis isolate, MDR |

-continued

| ORGANISM | STRAIN DESIGNATION | KEY PROPERTIES |
|---|---|---|
| *Stenotrophomonas maltophilia* | SM256 | Cystic fibrosis isolate, MDR |
| *Burkholderia cenocepacia* | BC240 | Cystic fibrosis isolate, MDR |

*MDR, multidrug-resistant; MRSA, methicillin-resistant *S. aureus*; MSSA, methicillin-sensitive *S. aureus*; HA-MRSA, hospital-associated MRSA; tet(K), major gram-positive tetracycline efflux mechanism; tet(M), major gram-positive tetracycline ribosome-protection mechanism; ESBL⁺, extended spectrum β-lactamase Other Embodiments The foregoing has been a description of certain non-limiting preferred embodiments of the invention. Those of ordinary skill in the art will appreciate that various changes and modifications to this description may be made without departing from the spirit or scope of the present invention, as defined in the following claims.

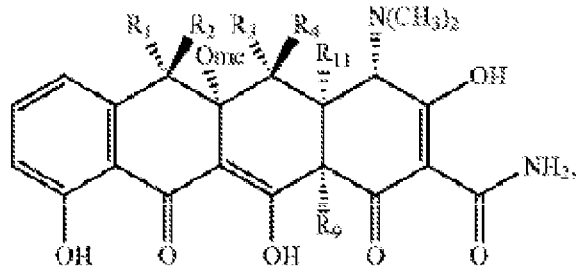 should be replaced with the formula: 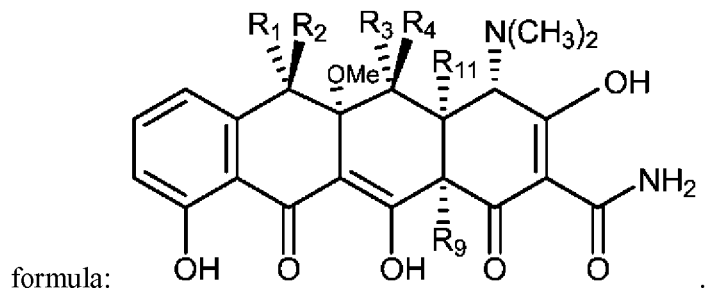

What is claimed is:
1. A compound of formula:

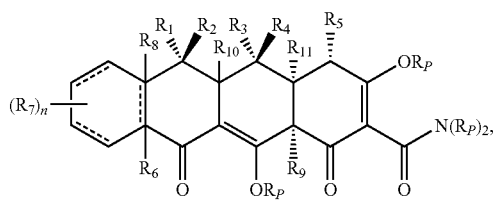

or a pharmaceutically acceptable salt thereof;
wherein:
---- represents a single or double bond;
$R_1$ and $R_2$ are each independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR_A$; —$CH_2OR_A$; —$CH_2R_A$; —$CH_2N(R_A)_2$; —$C(=O)R_A$; —$CO_2R_A$; —CN; —SCN; —$SR_A$; —$SOR_A$; —$SO_2R_A$; —$N_3$; —$NO_2$; —$N(R_A)_2$; —$NHC(O)R_A$; —$NHSO_2R_A$; or —$C(R_A)_3$; wherein each occurrence of $R_A$ is independently hydrogen, halogen, azido, a protecting group, aliphatic, heteroaliphatic, haloaliphatic, acyl, aryl, heteroaryl, alkoxy, aryloxy, alkylthio, arylthio, amino, alkylamino, dialkylamino, heteroaryloxy, or heteroarylthio; or $R_1$ and $R_2$ are taken together to form =O or =$C(R_A)_2$;

$R_3$ and $R_4$ are each independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR_B$; —$CH_2OR_B$; —$CH_2R_B$; $CH_2N(R_B)_2$; —$C(=O)R_B$; —$CO_2R_B$; —CN; —SCN; —$SR_B$; —$SOR_B$; —$SO_2R_B$; —$N_3$; —$NO_2$; —$N(R_B)_2$; —$NHC(O)R_B$; —$NHSO_2R_B$; or —$C(R_B)_3$; wherein each occurrence of $R_B$ is independently hydrogen, halogen, azido, a protecting group, aliphatic, heteroaliphatic, haloaliphatic, acyl, aryl, heteroaryl, alkoxy, aryloxy, alkylthio, arylthio, amino, alkylamino, dialkylamino, heteroaryloxy, or heteroarylthio; or $R_3$ and $R_4$ are taken together to form =O or =$C(R_B)_2$;

$R_5$, $R_9$, and $R_{11}$ are each independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR_C$; —$CH_2OR_C$; —$CH_2R_C$; —$CH_2N(R_C)_2$; —$C(=O)R_C$; —$CO_2R_C$; —CN; —SCN; —$SR_C$; —$SOR_C$; —$SO_2R_C$; —$N_3$; —$NO_2$; —$N(R_C)_2$; —$NHC(O)R_C$; —$NHSO_2R_C$; or —$C(R_C)_3$;

each $R_7$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR_C$; —$CH_2OR_C$; —$CH_2R_C$; —$CH_2N(R_C)_2$; —$C(=O)R_C$; —$CO_2R_C$; —CN; —SCN; —$SR_C$; —$SOR_C$; —$SO_2R_C$; —$N_3$; —$NO_2$; —$N(R_C)_2$; —$NHC(O)R_C$; —$NHSO_2R_C$; or —$C(R_C)_3$;

$R_{10}$ is halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR_C$; —$CH_2OR_C$; —$CH_2R_C$; —$CH_2N(R_C)_2$; —$C(=O)R_C$; —$CO_2R_C$; —CN; —SCN; —$SR_C$; —$SOR_C$; —$SO_2R_C$; —$N_3$; —$NO_2$; —$N(R_C)_2$; —$NHC(O)R_C$; —$NHSO_2R_C$; or —$C(R_C)_3$;

each occurrence of $R_C$ is independently hydrogen, halogen, azido, a protecting group, aliphatic, heteroaliphatic, haloaliphatic, acyl, aryl, heteroaryl, alkoxy, aryloxy, alkylthio, arylthio, amino, alkylamino, dialkylamino, heteroaryloxy, or heteroarylthio;

$R_6$ and $R_8$ are absent if the dashed line between the carbon atoms which $R_6$ and $R_8$ are attached to represents a bond, or are each independently hydrogen, halogen, substituted or unsubstituted aliphatic, substituted or unsubstituted heteroaliphatic, haloaliphatic, substituted or unsubstituted alkoxy, —OH, —CN, —SCN, —SH, alkylthio, —$N_3$; —$NO_2$, amino, alkylamino, or dialkylamino;

each $R_P$ is independently hydrogen, substituted or unsubstituted aliphatic, substituted or unsubstituted heteroaliphatic, haloaliphatic, a protecting group, substituted or unsubstituted acyl, substituted or unsubstituted aryl, or substituted or unsubstituted heteroaryl; and n is an integer in the range of 0 to 8, inclusive.

2. The compound of claim 1 of formula:

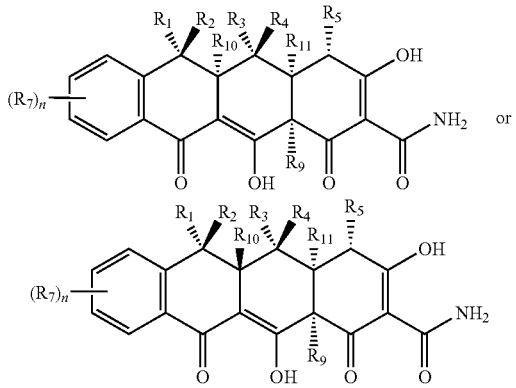

or a pharmaceutically acceptable salt thereof, wherein n is an integer in the range of 0 to 4, inclusive.

3. The compound of claim 1 of formula:

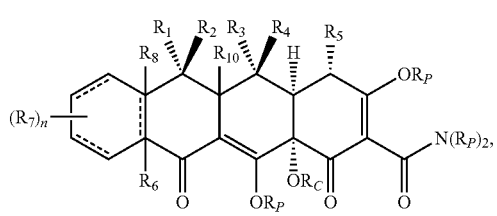

or a pharmaceutically acceptable salt thereof.

4. The compound of claim 1, wherein $R_1$ is hydrogen or $C_{1-6}$ alkyl.

5. The compound of claim 1, wherein $R_2$ is hydrogen, —$OR_4$, or $C_{1-6}$ alkyl.

6. The compound of claim 1 of the formula:

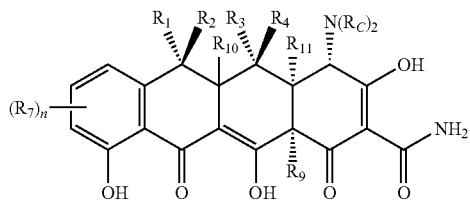

or a pharmaceutically acceptable salt thereof; wherein $R_C$ is hydrogen or $C_1$-$C_6$ alkyl; and n is an integer in the range of 0 to 3, inclusive.

7. The compound of claim 1 of the formula:

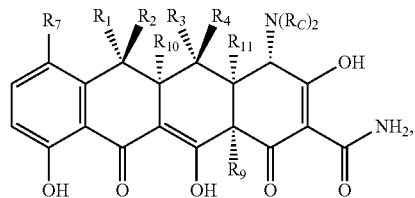

-continued

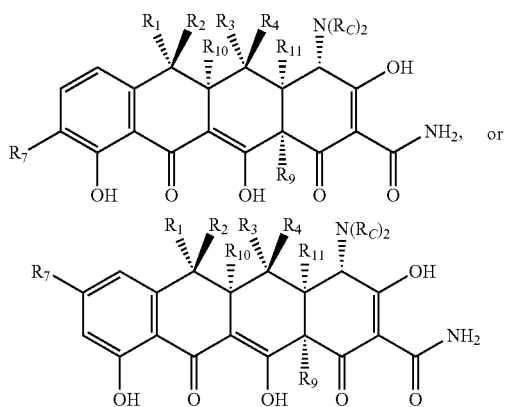

or a pharmaceutically acceptable salt thereof.

8. The compound of claim 1 selected from the group consisting of:

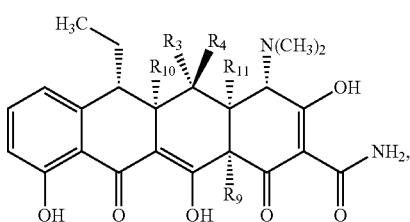

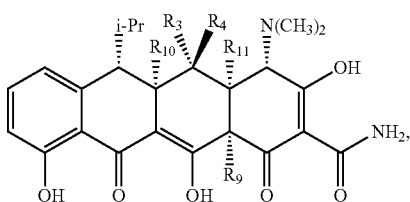

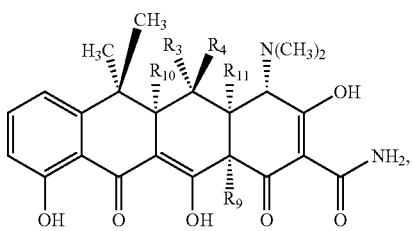

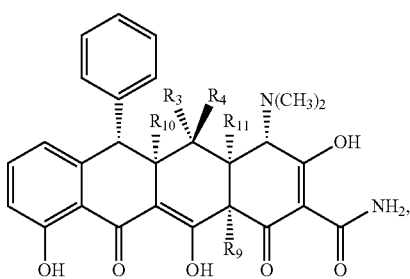

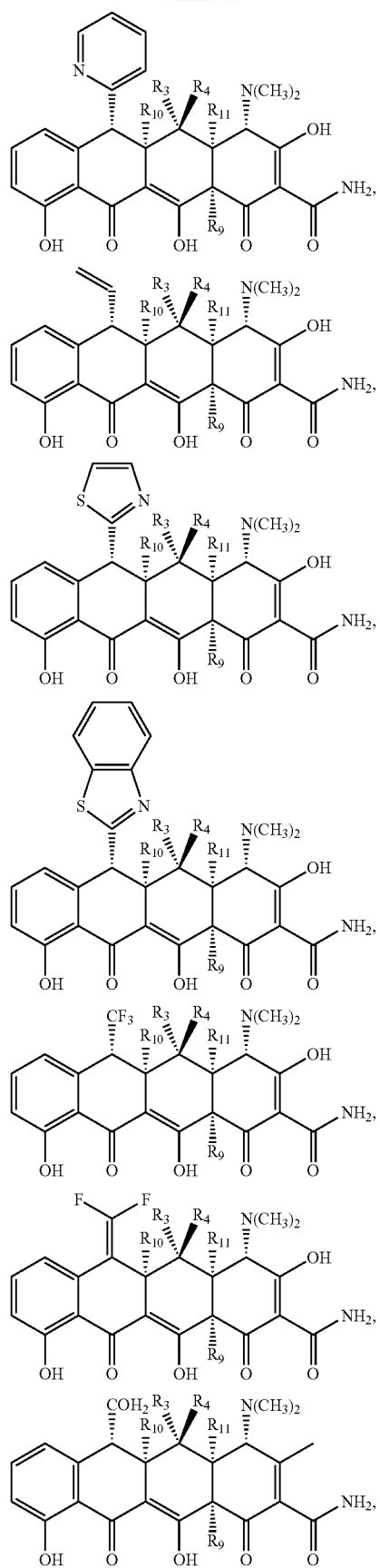
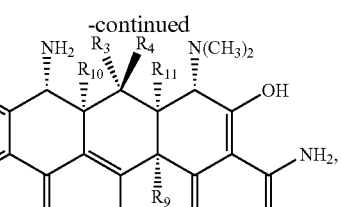
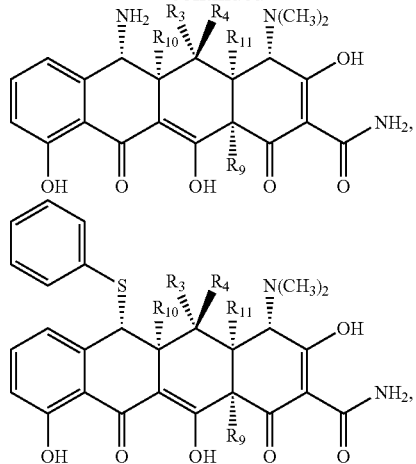
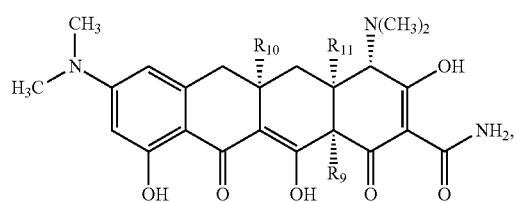
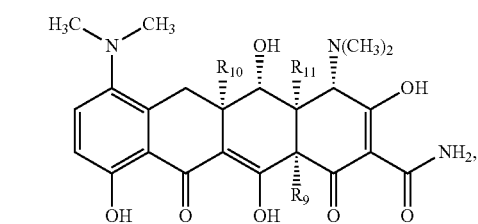
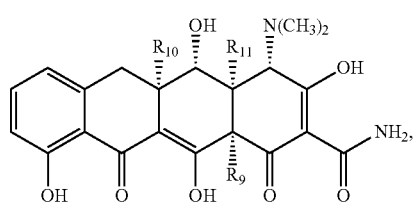
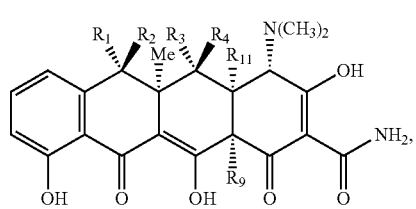
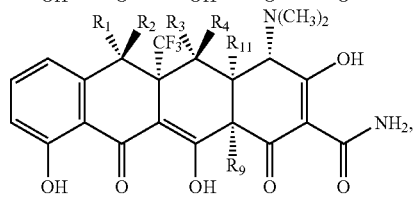

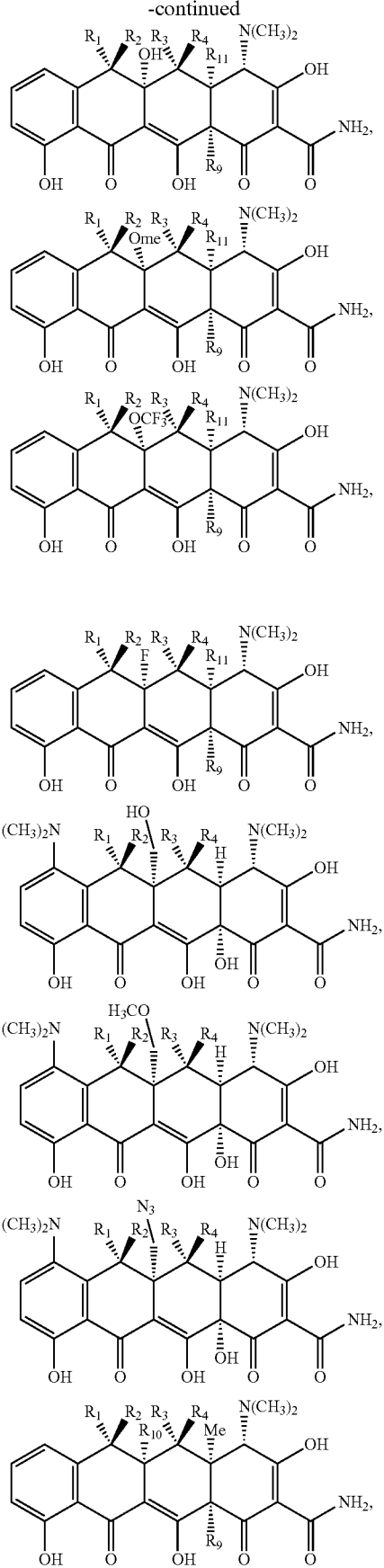
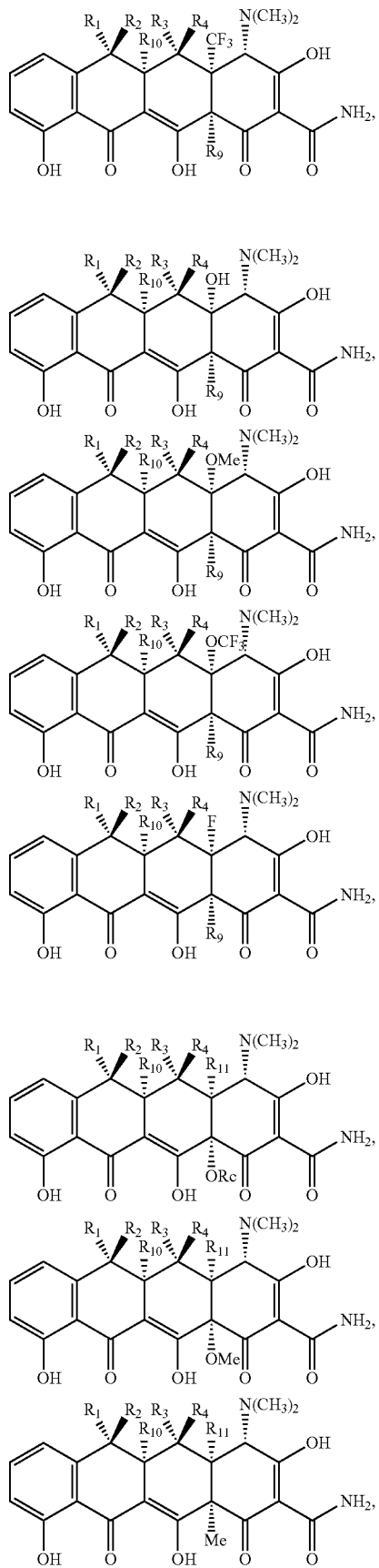

-continued

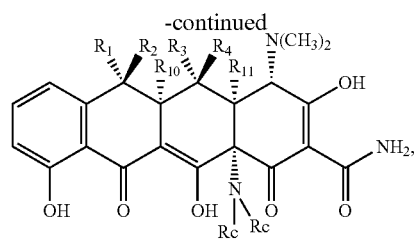

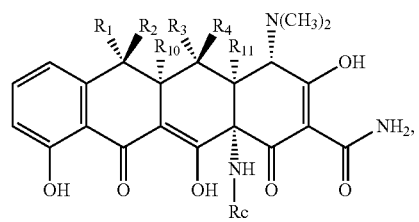

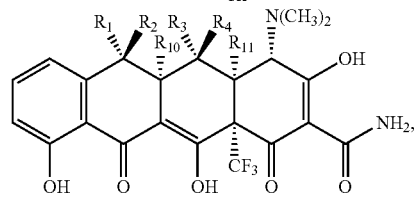

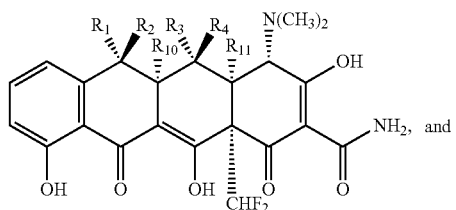

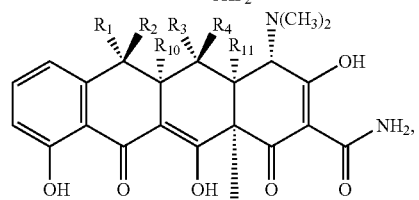

and pharmaceutically acceptable salts thereof.

9. The compound of claim 1, wherein $R_1$ and $R_2$ are each hydrogen.

10. The compound of claim 1, wherein $R_3$ is hydrogen, halogen, —$OR_B$, or $C_{1-6}$ alkyl.

11. The compound of claim 1, wherein $R_4$ is hydrogen, halogen, —$OR_B$, or $C_{1-6}$ alkyl.

12. The compound of claim 1, wherein $R_5$ is —$N(R_C)_2$.

13. The compound of claim 1, wherein $R_6$ and $R_8$ are absent, and ---- represents a double bond.

14. The compound of claim 1, wherein each $R_7$ is independently selected from the group consisting of —$OR_C$, —$SR_C$, —$N(R_C)_2$, —$NHC(O)R_C$, —$C(R_C)_3$, —$CH_2R_C$, and halogen.

15. The compound of claim 1, wherein $R_9$ is —$OR_C$.

16. The compound of claim 1, wherein $R_{10}$ is substituted or unsubstituted alkyl, —$OR_C$, or halogen.

17. The compound of claim 1, wherein $R_{11}$ is hydrogen.

18. The compound of claim 1, wherein the compound is selected from the group consisting of:

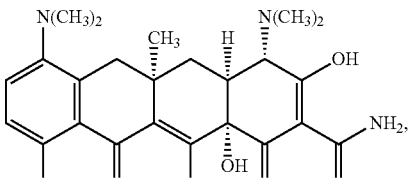

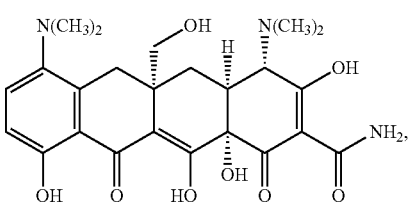

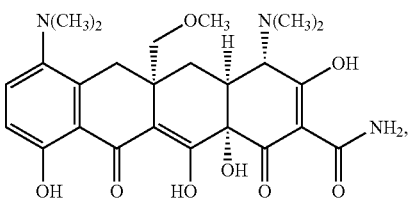

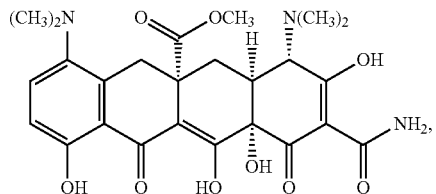

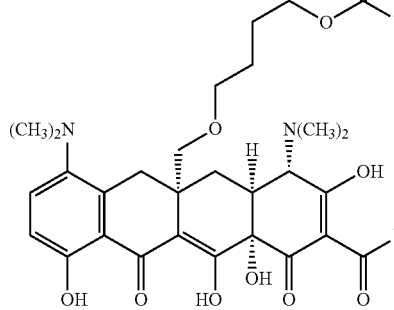

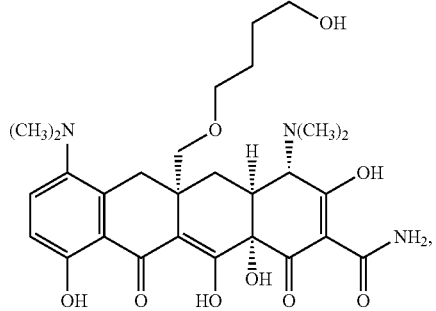

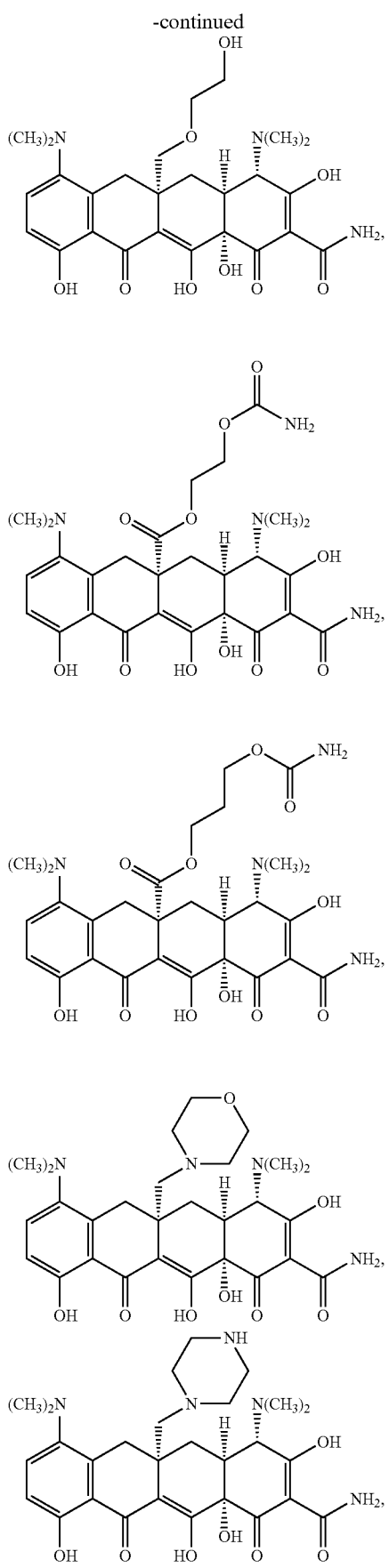
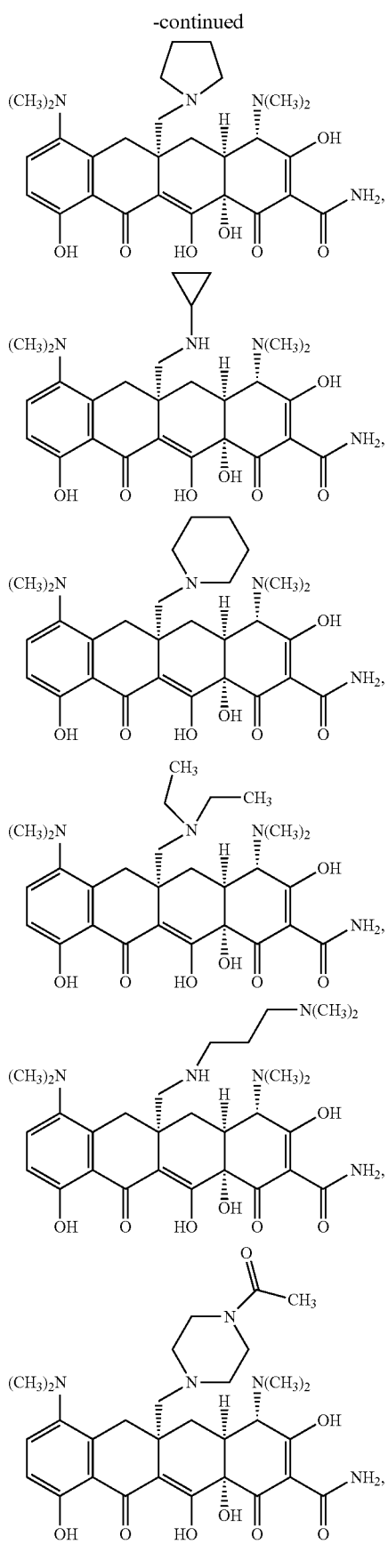

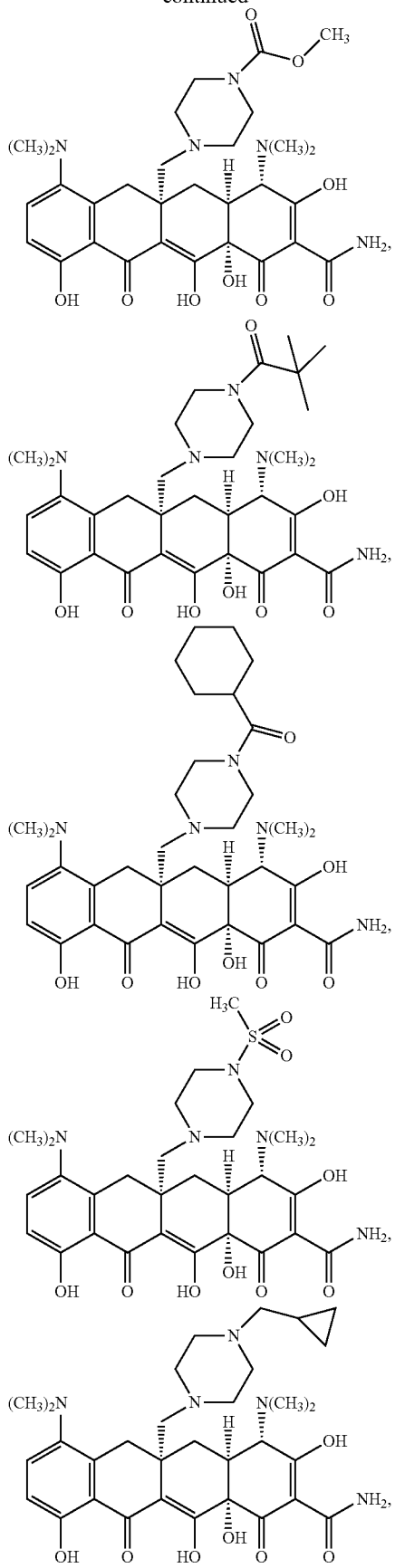
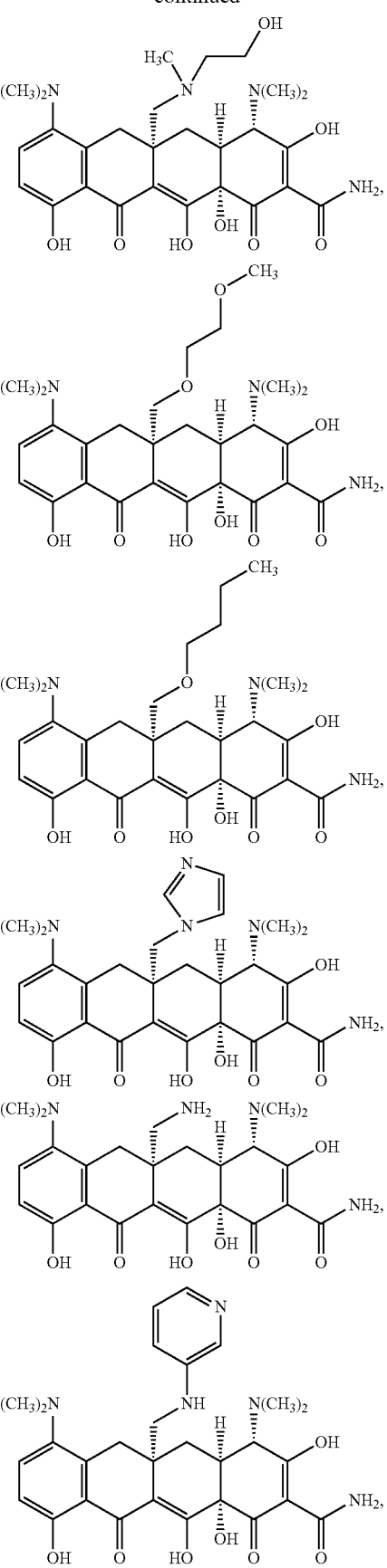

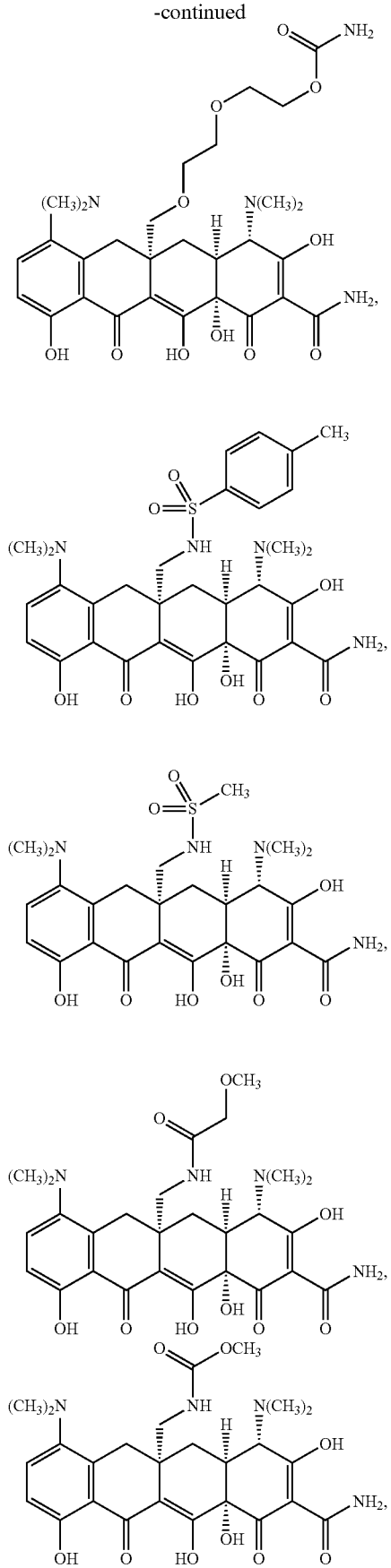
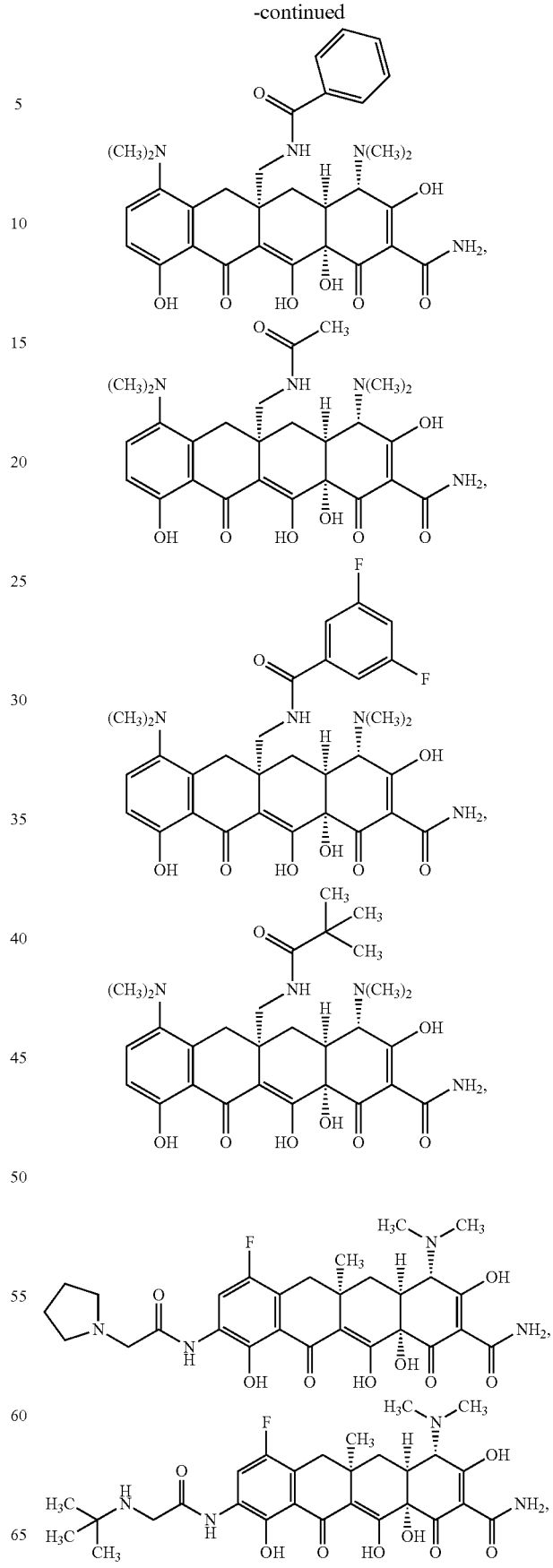

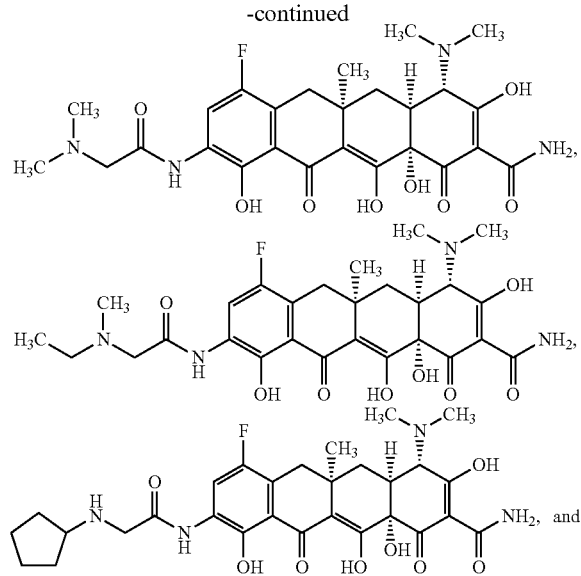

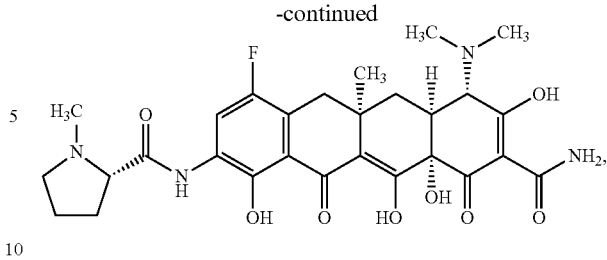

and pharmaceutically acceptable salts thereof.

19. A pharmaceutical composition comprising a compound of claim 1, or a pharmaceutically acceptable salt thereof, and a pharmaceutically acceptable excipient.

20. A method of treating a bacterial infection, the method comprising administering the compound of claim 1, or a pharmaceutically acceptable salt thereof, to a subject in need thereof in an amount effective to kill or inhibit the growth of the bacteria.

* * * * *

UNITED STATES PATENT AND TRADEMARK OFFICE
CERTIFICATE OF CORRECTION

PATENT NO. : 9,073,829 B2
APPLICATION NO. : 13/266788
DATED : July 7, 2015
INVENTOR(S) : Andrew G. Myers et al.

Page 1 of 2

It is certified that error appears in the above-identified patent and that said Letters Patent is hereby corrected as shown below:

In the claims

In claim 6, at column 211, lines 42-51, formula:

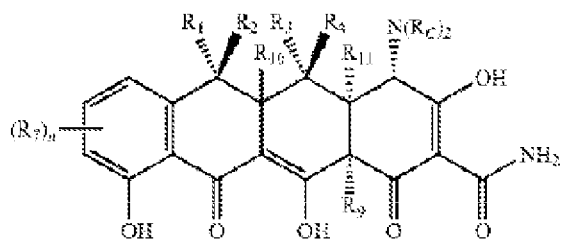 should be replaced with the formula: 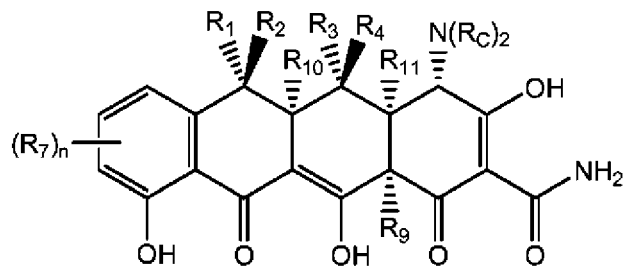 .

In claim 8, at column 213, lines 59-66, formula:

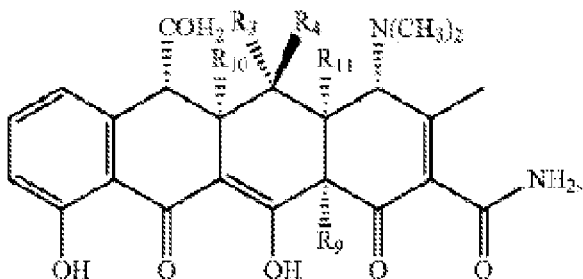 should be replaced with the

Signed and Sealed this
Third Day of May, 2016

Michelle K. Lee
*Director of the United States Patent and Trademark Office*

CERTIFICATE OF CORRECTION (continued)
U.S. Pat. No. 9,073,829 B2

Page 2 of 2 formula: 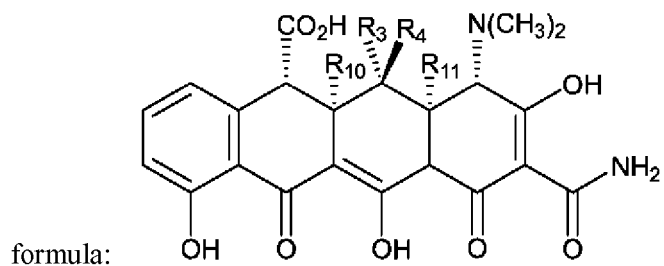

In claim 8, at column 215, lines 10-17, formula: